United States Patent
Neagu et al.

(10) Patent No.: US 7,919,490 B2
(45) Date of Patent: **\*Apr. 5, 2011**

(54) 6-SUBSTITUTED 2-(BENZIMIDAZOLYL)PURINE AND PURINONE DERIVATIVES FOR IMMUNOSUPPRESSION

(75) Inventors: Irina Neagu, Plainsboro, NJ (US); David Diller, East Windsor, NJ (US); Celia Kingsbury, Cream Ridge, NJ (US); Adolph C. Bohnstedt, Burlington, NJ (US); Michael J. Ohlmeyer, Plainsboro, NJ (US); Vidyadhar Paradkar, Sommerville, NJ (US); Nasrin Ansari, Monmouth Junction, NJ (US)

(73) Assignee: Wyeth LLC, Madison, NJ (US)

( * ) Notice: Subject to any disclaimer, the term of this patent is extended or adjusted under 35 U.S.C. 154(b) by 205 days.

This patent is subject to a terminal disclaimer.

(21) Appl. No.: 11/867,562

(22) Filed: Oct. 4, 2007

(65) Prior Publication Data
US 2008/0214580 A1 Sep. 4, 2008

Related U.S. Application Data

(60) Provisional application No. 60/828,165, filed on Oct. 4, 2006, provisional application No. 60/828,169, filed on Oct. 4, 2006.

(51) Int. Cl.
*C07D 473/32* (2006.01)
*C07D 473/18* (2006.01)
*A61K 31/52* (2006.01)
*A61K 31/522* (2006.01)
*A61P 37/06* (2006.01)
*A61P 11/06* (2006.01)
*A61P 35/02* (2006.01)
*C07D 239/48* (2006.01)
*C07D 239/50* (2006.01)
*C07D 405/12* (2006.01)
*C07D 405/14* (2006.01)

(52) U.S. Cl. ............. 514/228.5; 514/234.2; 514/211.15; 514/217.06; 514/252.16; 514/263.2; 514/263.21; 514/263.22; 514/263.24; 540/575; 540/600; 544/61; 544/81; 544/276; 544/277; 544/321; 544/323; 544/324; 544/326; 544/328; 544/332; 549/396; 549/399; 549/404

(58) Field of Classification Search .......... 544/276, 544/277; 514/263.37, 263.38, 263.23, 263.24, 514/252.16, 263.21, 263.2, 263.22
See application file for complete search history.

(56) References Cited

U.S. PATENT DOCUMENTS

| | | | |
|---|---|---|---|
| 4,247,556 | A | 1/1981 | von Bebenburg et al. |
| 4,813,998 | A | 3/1989 | Van Lommen et al. |
| 5,493,011 | A | 2/1996 | Jung et al. |
| 5,705,625 | A | 1/1998 | Civin et al. |
| 5,916,792 | A | 6/1999 | Civin et al. |
| 6,313,129 | B1 | 11/2001 | Uckun et al. |
| 6,372,740 | B1 | 4/2002 | Murata et al. |
| 6,432,947 | B1 | 8/2002 | Arnaiz et al. |
| 6,452,005 | B1 | 9/2002 | Uckun et al. |
| 6,506,738 | B1 | 1/2003 | Yu et al. |
| 6,582,357 | B2 | 6/2003 | Ouchi et al. |

(Continued)

FOREIGN PATENT DOCUMENTS

| | | |
|---|---|---|
| CA | 2238689 | 5/1997 |
| DE | 2841209 | 4/1979 |
| DE | 10 2005 042742 | 3/2007 |
| EP | 0 277 384 | 8/1988 |
| EP | 0 807 629 | 11/1997 |

(Continued)

OTHER PUBLICATIONS

Cetkovic-Cvrlje et al., "Dual Targeting of Burton's Tyrosine Kinase and Janus Kinase 3 with Rationally Designed Inhibitors Prevents Graft-Versus-Host Disease (GVHD)," *British Journal of Haematology*, vol. 126, pp. 821-827 (2004).

(Continued)

*Primary Examiner* — Mark L Berch
(74) *Attorney, Agent, or Firm* — Ram W. Sabnis

(57) ABSTRACT

The present invention provides novel purinones and purines useful for the prevention and treatment of autoimmune diseases, inflammatory disease, mast cell mediated disease and transplant rejection. The compounds are of the general formulae I and II shown below, in which Q is selected from the group consisting of CX and nitrogen; and A is chosen from the group consisting of H, $(C_1-C_6)$ alkyl, heteroaryl, and aryl:

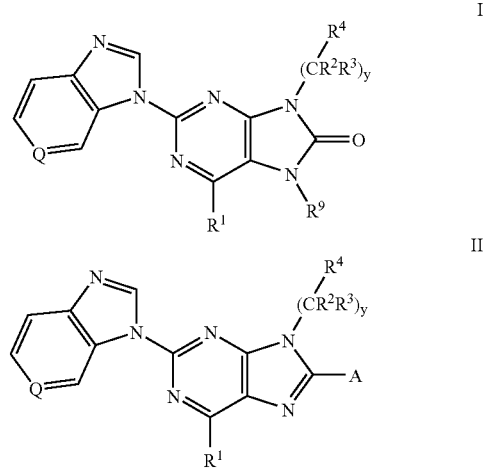

24 Claims, No Drawings

U.S. PATENT DOCUMENTS

| | | | |
|---|---|---|---|
| 2004/0116435 A1 | 6/2004 | Eriksson et al. | |
| 2004/0116449 A1 | 6/2004 | Changelian | |
| 2004/0157739 A1 | 8/2004 | Ahrens et al. | |
| 2005/0032725 A1 | 2/2005 | Rao et al. | |
| 2007/0021443 A1* | 1/2007 | Ohlmeyer et al. | 514/263.22 |
| 2007/0253896 A1* | 11/2007 | Le Brazidec et al. | 424/1.11 |
| 2008/0076752 A1* | 3/2008 | Becker et al. | 514/211.07 |
| 2008/0085898 A1* | 4/2008 | Lu et al. | 514/234.2 |
| 2008/0085909 A1* | 4/2008 | Roughton et al. | 514/263.22 |
| 2008/0119496 A1* | 5/2008 | Ohlmeyer et al. | 514/263.21 |
| 2008/0207613 A1 | 8/2008 | Styles et al. | |
| 2008/0214580 A1 | 9/2008 | Neagu et al. | |
| 2008/0220256 A1* | 9/2008 | Bhattacharya et al. | 428/408 |
| 2008/0254029 A1* | 10/2008 | Yanni et al. | 424/133.1 |
| 2008/0287468 A1* | 11/2008 | Ohlmeyer et al. | 514/263.2 |
| 2009/0023723 A1* | 1/2009 | Cole et al. | 514/234.2 |
| 2009/0036449 A1* | 2/2009 | Mederski et al. | 514/236.5 |
| 2009/0069289 A1* | 3/2009 | Neagu et al. | 514/234.2 |
| 2009/0088569 A1* | 4/2009 | Eckhardt et al. | 544/118 |
| 2009/0118220 A1* | 5/2009 | Cavero-Tomas et al. | 514/45 |
| 2009/0281075 A1 | 11/2009 | Roughton et al. | |
| 2010/0035916 A1* | 2/2010 | Ben Ayad et al. | 514/299 |

FOREIGN PATENT DOCUMENTS

| | | |
|---|---|---|
| EP | 1043324 | 10/2000 |
| EP | 1221444 | 7/2002 |
| JP | 07075798 | 3/1995 |
| JP | 2004 217582 | 8/2004 |
| WO | 99/41248 | 8/1999 |
| WO | 00/12089 | 3/2000 |
| WO | 01/19828 | 3/2001 |
| WO | WO 02/055521 | 7/2002 |
| WO | 03/051277 | 6/2003 |
| WO | 2004/043386 | 5/2004 |
| WO | 2004/099204 | 11/2004 |
| WO | WO 2005/023761 | 3/2005 |
| WO | 2005/066156 | 7/2005 |
| WO | 2006/069080 | 6/2006 |
| WO | WO 2006/074985 | 7/2006 |
| WO | WO 2006/087538 | 8/2006 |
| WO | WO 2006/091737 | 8/2006 |
| WO | 2006/096270 | 9/2006 |
| WO | 2006/108103 | 10/2006 |
| WO | 2007/035873 | 3/2007 |
| WO | WO 2007/058990 | 5/2007 |
| WO | WO 2007/140222 | 12/2007 |
| WO | WO 2007/146712 | 12/2007 |
| WO | WO 2008/043019 | 4/2008 |
| WO | WO 2008/043031 | 4/2008 |
| WO | WO 2008/051493 | 5/2008 |
| WO | WO 2008/051494 | 5/2008 |
| WO | WO 2008/143674 | 11/2008 |
| WO | WO 2009/062059 | 5/2009 |

OTHER PUBLICATIONS

Cetkovic-Cvrlje et al., "Targeting Janus kinase 3 in the treatment of leukemia and inflammatory diseases," *Arch. Immunol. Ther. Exp.*, vol. 52, pp. 69-82 (2004.).
Changelian et al., "Prevention of Organ Allograft Rejection by a Specific Janus Kinase 3 Inhibitor," *Science*, vol. 302, pp. 875-878 (2003).
O'Shea, J.J., "Cytokine signaling: new insights and new opportunities for therapeutic intervention?", *Arthristis Res.*, vol. 3(Suppl A): L018 (2001).
Ortmann et al., "Janus kinases and signal transducers and activators of transcription: their roles in cytokine signaling, development and immunoregulation," *Arthritis Res.*, vol. 2, pp. 16-32 (2000).
Yamaoka et al., "The Janus kinases (Jaks)," *Genome Biology*, vol. 5:253, pp. 253.1-253.6 (2004).
Uckun et al., "Structure-based Design of Novel Anticancer Agents," *Current Cancer Drug Targets*, vol. 1(1), pp. 59-71 (2001).
Kawahara et al., "Critical role of the interleukin 2 (IL-2) receptor γ-chain associated Jak3 in the IL-2-induced c-*fos* and c-*myc*, but not bcl-2, gene induction," *Proc. Natl. Acad. Sci.*, vol. 92, pp. 8724-8728 (1995).

O'Shea et al., "A New Modality for Immunosuppression: Targeting the Jak/Stat Pathway," *Nature Reviews*, vol. 3, pp. 555-564 (2004).
Papageorgiou et al., "Is Jak3 a new drug target for immunomodulation-based therapies?" *TRENDS in Pharmacological Sciences*, vol. 25(11), pp. 558-562 (2004).
Lin et al., "Constitutive Activation of Jak3/Stat3 in Colon Carcinoma Tumors and Cell Lines", *American Journal of Pathology*, vol. 167(4), pp. 969-980 (2005).
Dana et al, "Role of Immunity and Inflammation in Corneal and Ocular Surface Disease Associated with Dry Eye," *Lacrimal Gland, Tear Film and Dry Eye Syndromes 3*, pp. 729-738 (2002).
Nagelhout et al., "Preservation of Tear Film Integrity and Inhibition of Corneal Injury by Dexamethasone in a Rabbit Model of Lacrimal Gland Inflammation-Induced Dry Eye," *Journal of Ocular Pharmacology and Therapeutics*, vol. 21(2), pp. 139-148 (2005).
Pflugfelder, S., "Perspective Anti-inflammatory Therapy for Dry Eye," *American Journal of Ophthalmology*, vol. 137(2), pp. 337-342 (2004).
Amin et al., "Inhibition of Jak3 induces apoptosis and decreases anaplastic lymphoma kinase activity in anaplastic large cell lymphoma," *Oncogene*, vol. 22, pp. 5399-5407 (2003).
Harrington et al., "VX-680, a potent and selective small-molecule inhibitor of the Aurora kinases, suppresses tumor growth in vivo," *Nature Medicine*, vol. 10(3), pp. 262-267 (2004).
Jung et al., "Discovery of Novel and Potent Thiazoloquinazolines as Selective Aurora A and B Kinase," American Chem Soc., pp. 1-16 (2005).
Frantz, S., "Playing Dirty", *Nature*, vol. 437, pp. 942-943 (2005).
Martinez-Lostao et al., "Role of the STAT 1 pathway in apoptosis induced by fludarabine and JAK kinase inhibitors in B-cell chronic lymphocytic leukemia," *Leuk Lymphoma*, vol. 46(3), pp. 435-442 (2005), Abstract only (PMID: 15621835).
Lai et al., "Jak3 activation is significantly associated with ALK expression in anaplastic large cell lymphoma," *Human Pathology*, vol. 36, pp. 939-944 (2005).
Pearson, H., "Designer transplant drug shows promise in monkeys," *News & Nature* (2003).
Goldberg. et. al., "Optimization of 2-Phenylaminoimidazo [4,5-*h*]isoquinolin-9-ones: Orally Active Inhibitors of Ick Kinase," *Journal of Medical Chem.*, vol. 46, pp. 1337-1349, 2003.
International Search Report from International Application No. PCT/US2006/012824.
International Search Report from International Application No. PCT/US2006/061004.
Beijersbergen van Henegouwen GM et al., Hydrolysis of RRR0alpha-tocopheryl acetate (vitamin # acetate) in the skin and its UV protecting activity (an in vivo study with the rat) *J Photochem Photobiol*, Jul. 29, 2005, vol. 1, pp. 45-51.
Cetkovic-Cvrlje et al., "Targeting Janus kinase 3 in the treatment of leukemia and inflammatory diseases," *Arch. Immunol. Ther. Exp.*, vol. 52, pp. 69-82 (2004.).
Ortmann et al., "Janus kinases and signal transducers and activators of transcription: their roles in cytokine signaling, development and immunoregulation," *Arthritis Res.*, ,vol. 2, pp. 16-32 (2000).
Yamaoka et al., "The Janus kinases (Jaks)," *Genome Biology*, vol. 5:253, pp. 253.1-253.6 (2004).
Kawahara et al., "Critical role of the interleukin 2 (IL-2) receptor γ-chain associated Jak3 in the IL-2-induced c-*fos* and c-*myc*, but not bcl-2, gene induction," *Proc. Natl. Acad. Sci.*, vol. 92, pp. 8724-8728 (1995).
Amin et al., "Inhibition of Jak3 induces apoptosis and decreases anaplastic lymphoma kinase activity in anaplastic large cell lymphoma," *Oncogene*, vol. 22, pp. 5399-5407 (2003).
International Search Report from International Application No. PCT/US2007/080447.
International Search Report from International Application No. PCT/US2007/080464.
International Search Report and Written Opinion from International Application No. PCT/US2007/081232.
International Search Report and Written Opinion from International Application No. PCT/US2007/069530.

Hirota et all, "Synthesis and Biological Evaluation of 2,8-Disubstituted 9-Benzyladenines: Discovery of 8-Mercaptoadenines as Potent Interferon-Inducers," *Bioorganic & Medicinal Chemistry 11*, 2003, pp. 2715-2722.
Written Opinion corresponding to PCT/US2007/080447.
Written Opinion corresponding to PCT/US2007/080464.
Written Opinion corresponding to PCT/US2006/012824.
Written Opinion corresponding to PCT/US2006/061004.
Cadena-Amaro et al., Synthesis and incorporation into DNA fragments of the artificial nucleobase, 2-amino-8-oxopurine, Bioorganic & Medicinal Chemistry Letters, 2005, vol. 15, Issue 4, pp. 1069-1073.
Chem Abstracts Search # 1 1996:496070 CAPLUS: Bakavoli et al., Synthesis of 4, 4'-bis-pyrimidines and some related bis-fused pyrimidines, Journal of Sciences, Islamic Republic of Iran, 1995, vol. 6, Issue 3, pp. 158-162.
Chem Abstracts Search #2 1980:604652 CAPLUS: Brazilian patent No. BR 7806210, Apr. 1, 1980.

Frankowski, Synthesis of imidazo [4,5-c]pyridine and imidazo [4,5-d][1,2] diazepine systems and their ribonucleosides, Tetrahedron, 1986, vol. 42, Issue 5, pp. 1511-1528.
Gaulon et al., A General and Facile Route to New Trisubstituted Purin-8-ones, Synthesis, Jul. 2005, vol. 13, pp. 2227-2233.
International Search Report dated Mar. 20, 2009 for International Application No. PCT/US2008/082832 filed Nov. 7, 2008.
International Search Report dated Jan. 9, 2007 in International Application No. PCT/US2006/036833, filed Sep. 21, 2006.
Lum et al., 2,5-Diaminopyrimidines and 3,5-disubstituted azapurines as inhibitors of glycogen synthase kinase-3 (GSK-3), Bioorganic & Medicinal Chemistry Letters, 2008, vol. 18, Issue 12, pp. 3578-3581.
Pochet et al., Construction of a self-complementary nucleoside from deoxyguanosine, Comptes Rendus de I'Academie des Sciences, Serie III: Sciences de la Vie, 1996, vol. 319, Issue 1, pp. 1-7.
Rokos et al., 8.2-Anhydro-8-Hydroxypurine α-D-Ribosides, J. Carbohydrates, Necleosides, Nucleotides, 1976, Issue 77-91.

* cited by examiner

6-SUBSTITUTED 2-(BENZIMIDAZOLYL)PURINE AND PURINONE DERIVATIVES FOR IMMUNOSUPPRESSION

CROSS-REFERENCE TO RELATED APPLICATIONS

This application claims priority from U.S. Provisional Application Ser. No. 60/828,165, filed Oct. 4, 2006, and U.S. Provisional Application Ser. No. 60/828,169 filed Oct. 4, 2006, the entire contents of both are incorporated herein by reference.

FIELD OF THE INVENTION

The invention relates to 6-substituted 2-(benzimidazolyl) purine or purinone derivatives and 6-substituted 2-(imidazolo [4,5-c]pyridinyl)purine or purinone derivatives useful as immunosuppressants.

BACKGROUND OF THE INVENTION

Immunosuppression is an important clinical approach in treating autoimmune disease and in preventing organ and tissue rejection. The clinically available immunosuppressants, including azathioprine, cyclosporine and tacrolimus, although effective, often cause undesirable side effects including nephrotoxicity, hypertension, gastrointestinal disturbances and gum inflammation. Inhibitors of the tyrosine kinase Jak3 are known to be useful as immunosuppressants (see U.S. Pat. No. 6,313,129).

The members of the Janus kinase (Jak) family of non-receptor intracellular tyrosine kinases are components of cytokine signal transduction. Four family members have been identified to date: Jak1, Jak2, Jak3, and Tyk2. The Jaks play a key role in the intracellular signaling mediated through cytokine receptors. Upon binding of cytokines to their receptors, Jaks are activated and phosphorylate the receptors, creating docking sites for other signaling molecules, in particular members of the signal transducer and activator of transcription (STAT) family. While expression of Jak1, Jak2 and Tyk2 is relatively ubiquitous, Jak3 expression is temporally and spatially regulated. Jak3 is predominantly expressed in cells of hematopoietic lineage; it is constitutively expressed in natural killer (NK) cells and thymocytes and is inducible in T cells, B cells and myeloid cells (reviewed in Ortmann, et al., 1999 and Yamaoka, et al., 2004). Jak3 is also expressed in mast cells, and its enzymatic activity is enhanced by IgE receptor/FcεRI cross-linking (Malaviya and Uckun, 1999).

A specific, orally active Jak3 inhibitor, CP-690,550, has been shown to act as an effective immunosuppressant and prolong animal survival in a murine model of heart transplantation and a primate model of kidney transplantation (Changelian, et al., 2003). Furthermore, aberrant Jak3 activity has been linked to a leukemic form of cutaneous T-cell lymphoma (Sezary's syndrome) and acute lymphoblastic leukemia (ALL), the most common form of childhood cancer. The identification of Jak3 inhibitors has provided the basis for new clinical approaches in treating leukemias and lymphomas (reviewed in Uckun, et al, 2005). Two dimethoxyquinazoline derivatives, WHI-P131 (JANEX-1) and WHI-P154 (JANEX-2), have been reported to be selective inhibitors of Jak3 in leukemia cells (Sudbeck et al., 1999).

Jak3 has also been shown to play a role in mast-cell mediated allergic reactions and inflammatory diseases and serves as a target in indications such as asthma and anaphylaxis.

Therefore, compounds that inhibit Jak3 are useful for indications such as leukemias and lymphomas, organ and bone marrow transplant rejection, mast cell-mediated allergic reactions and inflammatory diseases and disorders.

SUMMARY OF THE INVENTION

It has now been found that compounds of general formula I and II are potent and selective inhibitors of Jak3:

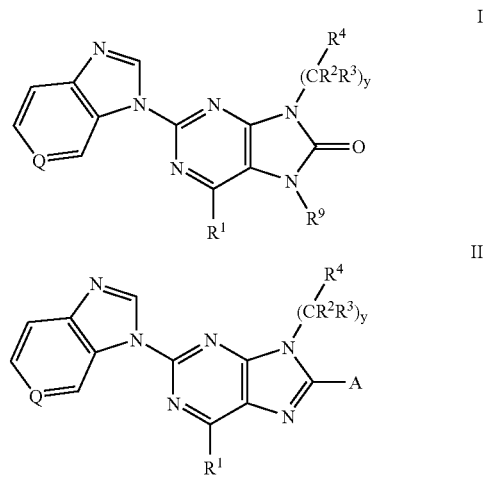

In these compounds,

Q is selected from the group consisting of CX and nitrogen;

X is selected from the group consisting of hydrogen, halogen, and electron-withdrawing groups;

A is chosen from the group consisting of H, $(C_1-C_6)$ alkyl, heteroaryl and aryl;

$R^1$ is selected from the group consisting of halogen, CN, $(C_2-C_6)$ alkyl, substituted $(C_1-C_6)$ alkyl, aryl, substituted aryl, heterocyclyl, substituted heterocyclyl and $-V-R^7$;

$R^2$ and $R^3$ are selected independently for each occurrence of $(CR^2R^3)$ from the group consisting of hydrogen and $(C_1-C_6)$ alkyl;

$R^4$ is selected from a group consisting of alkyl, OH, alkoxy, heterocyclyl, aryl, substituted alkyl, substituted heterocyclyl, and substituted aryl;

$R^7$ is chosen from H, $(C_1-C_6)$ alkyl, substituted $(C_1-C_6)$ alkyl, aryl, substituted aryl, heterocyclyl, and substituted heterocyclyl;

V is chosen from $-C(=O)O-$, $-C(=O)NR^8-$, $-O-$ and $-NR^8-$;

$R^8$ is chosen from H and $(C_1-C_6)$ alkyl, or, when taken together with the nitrogen to which they are attached, $R^1$ and $R^8$ form a 4-7 membered nitrogen heterocycle;

$R^9$ is chosen from hydrogen, alkyl, and substituted alkyl; and y is zero or an integer selected from 1, 2, and 3.

The members of this genus are useful in inhibiting Jak3 activity and as such are useful in indications where clinical immunosuppression is desired and in the treatment of hematological cancers.

In another aspect, the invention relates to pharmaceutical compositions comprising a therapeutically effective amount of at least one compound of general formula I or II, or a pharmaceutically acceptable salt thereof, and a pharmaceutically acceptable carrier.

In another aspect, the invention relates to a method for treating a disease by altering a response mediated by Jak3 tyrosine kinase. The method comprises bringing into contact with Jak3 at least one compound of general formula I or II.

In yet another aspect the present invention relates to a method of suppressing the immune system in a subject in need thereof comprising administering to the subject a therapeutically effective amount of at least one compound of general formula I or II. Suppression of immune system activity is desirable for preventing or treating tissue or organ rejection following transplant surgery and for preventing and treating diseases and disorders arising from aberrant activity of the immune system, in particular autoimmune disorders and diseases. Exemplary autoimmune disorders include graft versus host disease (GVHD), insulin-dependent diabetes (Type I), Hashimoto's thyroiditis and Graves' disease, pernicious anemia, Addison's disease, chronic active hepatitis, Crohn's disease, ulcerative colitis, rheumatoid arthritis, multiple sclerosis, systemic lupus erythematosus, psoriasis, scleroderma and myasthenia gravis.

The compounds of the present invention are useful in preventing and treating diseases and disorders related to mast cell-mediated allergic reactions and inflammation.

Other indications in which the Jak3 inhibitors are useful include leukemias and lymphomas.

DETAILED DESCRIPTION OF THE INVENTION

Throughout this specification the substituents are defined when introduced and retain their definitions.

In a first aspect the invention relates to purines and purinones of the formulae:

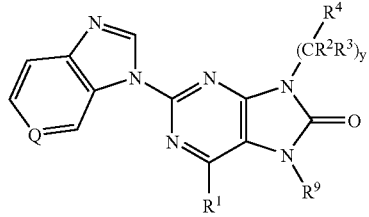

I

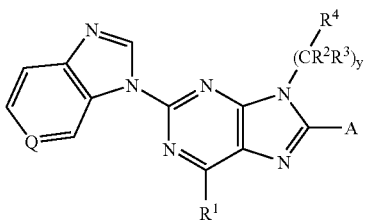

II

The members of the genus I may be conveniently divided into two subgenera based on the values of Q. When Q is nitrogen, a subgenus of purinones having an attached imidazo [5,4-c]pyridine arises. When Q is carbon, a subgenus of purinones having an attached benzimidazole arises. The structures of these subgenera are shown below:

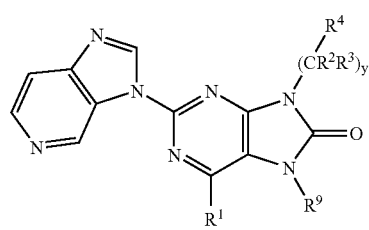

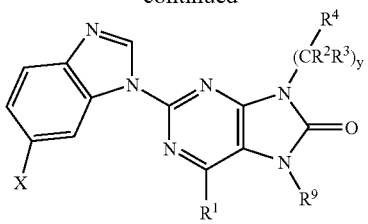

Similarly, the members of the genus II may be conveniently divided into two subgenera based on the values of Q. When Q is nitrogen, a subgenus of purines having an attached imidazo [5,4-c]pyridine arises. When Q is carbon, a subgenus of purines having an attached benzimidazole arises. The structures of these subgenera are shown below:

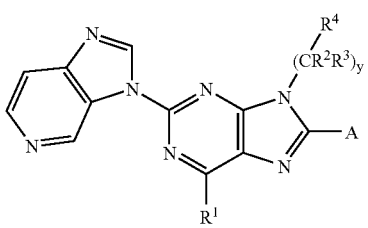

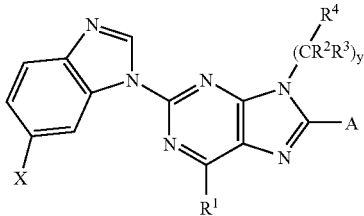

In certain embodiments, X may be hydrogen, halogen, or an electron-withdrawing group containing one or fewer carbons. Examples include: H, F, Cl, CN, $CF_3$, or $OCF_3$. In some embodiments, y is 1 or 2, and $R^2$ and $R^3$ are hydrogen or methyl, and in particular, y may be one, both of $R^2$ and $R^3$ may be hydrogen, $R^9$ may be hydrogen, and $R^4$ may be aryl, heteroaryl, and their substituted counterparts. In other embodiments, y may be 1 to 3, $R^2$ and $R^3$ may be hydrogen in all occurrences, $R^9$ may be hydrogen, and $R^4$ may be alkoxy or OH. These embodiments have the formulae Ib or IIb:

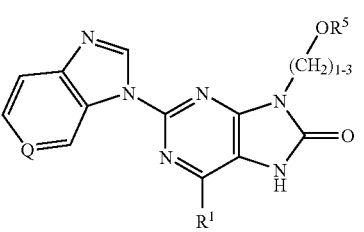

Ib

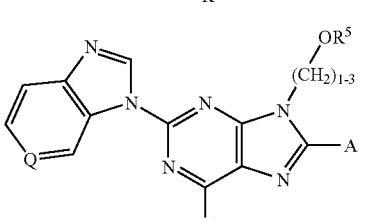

IIb wherein $R^5$ is hydrogen or $(C_1$-$C_6)$ alkyl.

In yet other embodiments, $R^9$ is hydrogen, y is zero, and $R^4$ is a residue selected from an optionally substituted monocycle or bicycle. The $R^4$ residue in this case contains at least one oxygen atom. More particularly, $R^4$ may be an oxygen heterocycle, an amide, a substituted alkyl amide, a halogen-substituted oxygen heterocycle, a hydroxyl-substituted cycloalkyl, a hydroxyl-substituted aryl, or an alkoxy-substituted cycloalkyl, such as methoxycyclohexyl, particularly trans 4-methoxycyclohexyl, or

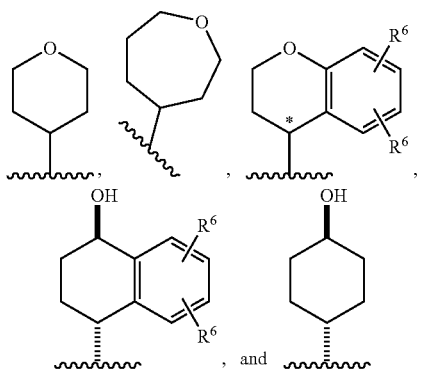

wherein $R^6$ is hydrogen or fluorine. In the chroman, the carbon marked with an asterisk may be of the R absolute configuration:

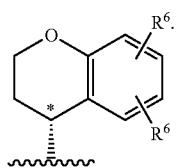

In the 4-substituted-1,23,4-tetrahydronaphthalen-1-ol, the carbon atoms marked with an asterisk may both be of the R absolute configuration:

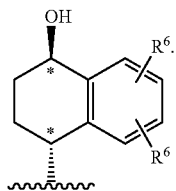

In other embodiments, A is hydrogen or $(C_1-C_6)$ alkyl. For example, A may be hydrogen or methyl.

In other embodiments, $R^1$ is (1) heteroaryl, substituted heteroaryl, heterocyclyl, or substituted heterocyclyl, e.g. pyridinyl, pyrazolyl, pyrimidinyl, isoquinolinyl, azetidinyl, piperidinyl, piperizinyl, pyrrolidinyl, morpholinyl, azepanyl, and diazepanyl; (2) aryl, substituted aryl, $(C_2-C_6)$ alkyl or substituted $(C_1-C_6)$ alkyl; (3) halogen or CN; or (4)-V—$R^7$. The foregoing are typically optionally substituted with hydroxy, halogen, carboxamide, alkyl, carboxy, sulfone, alkoxy, and cyano.

In the embodiment in which $R^1$ is $VR^7$, V may be —C(=O)O— or —C(=O)$NR^8$— and $R^7$ may be —$CH_2CN$, $(C_1-C_6)$ alkyl, or H. Alternatively, $VR^7$ may be

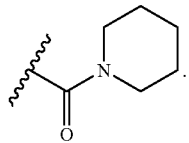

Also when $R^1$ is $VR^7$, V may be —O— or —$NR^8$—, $R^7$ may be $(C_1-C_6)$ alkyl, and $R^8$ may be H.

All of the compounds falling within the foregoing parent genera and their subgenera are useful as Jak3 inhibitors.

In additional embodiments, $R^9$ may be H, Q may be CX and Y may be zero as shown in formulae Ic and IIc:

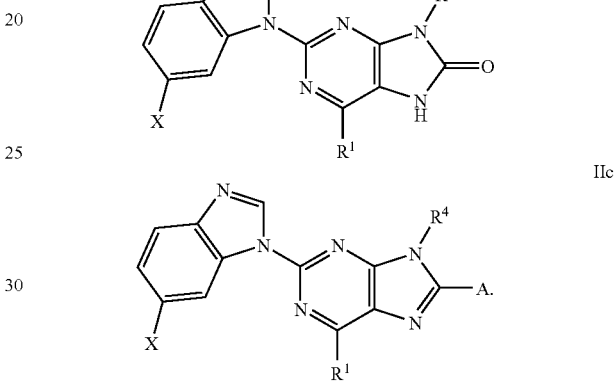

In some embodiments of formulae Ic and IIc, $R^1$ is chosen from halogen, $(C_2-C_6)$ alkyl, substituted $(C_1-C_6)$ alkyl, heterocyclyl, substituted heterocyclyl, aryl, substituted aryl, or —V—$R^7$ wherein V is —$NR^8$—, —C(=O)O—, —C(=O)$NR^8$, or O; $R^7$ is H, $(C_1-C_6)$ alkyl, substituted $(C_1-C_6)$ alkyl, heterocyclyl, substituted heterocyclyl, or aryl; and $R^8$ is hydrogen or $(C_1-C_6)$ alkyl, or when taken together with the nitrogen to which they are attached, $R^7$ and $R^8$ form a 4-7 membered nitrogen heterocycle.

Examples of compounds that fall within the scope of the foregoing embodiments include but are not limited to:

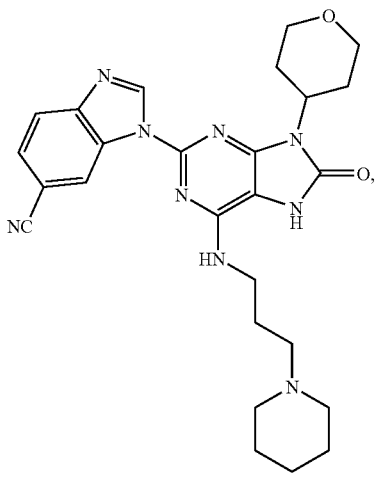

-continued
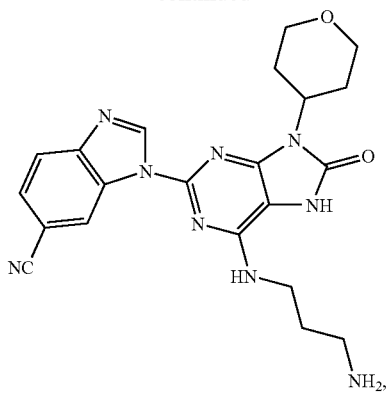
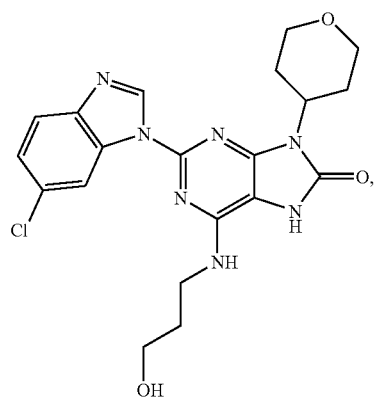
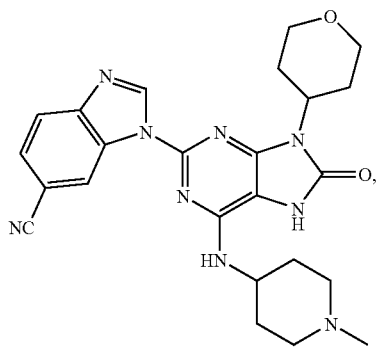
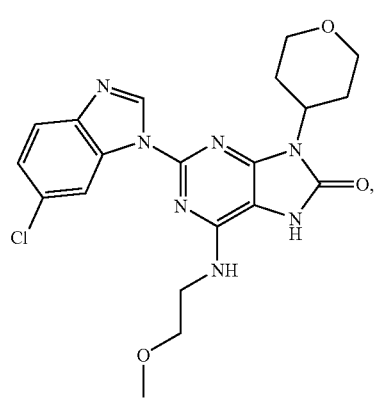
-continued
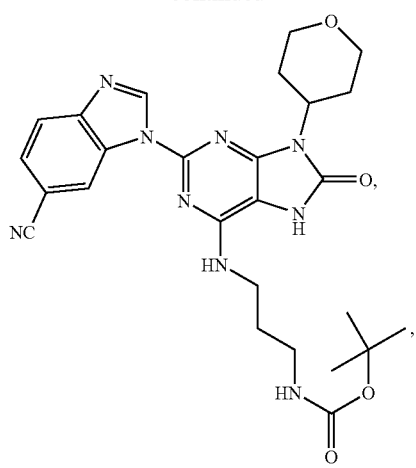
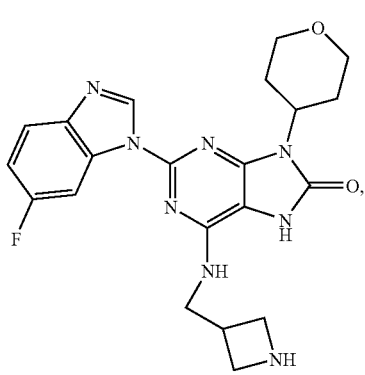
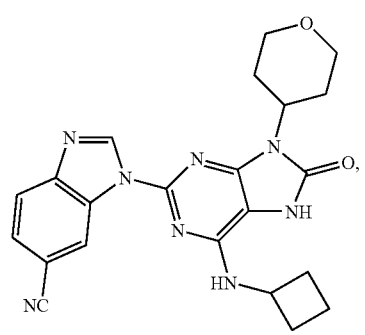
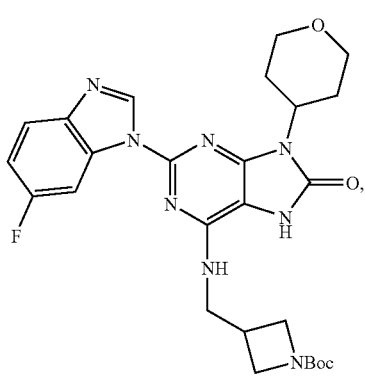

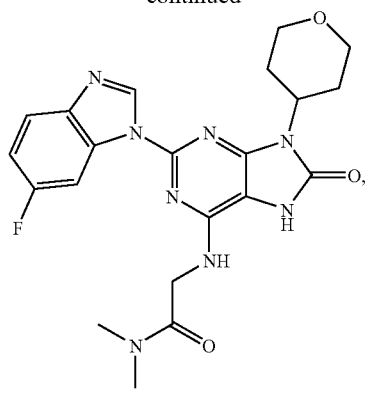
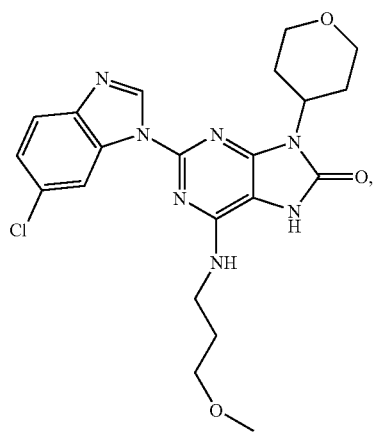
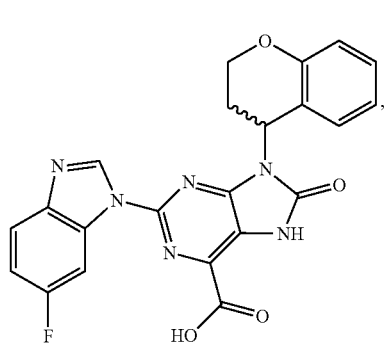
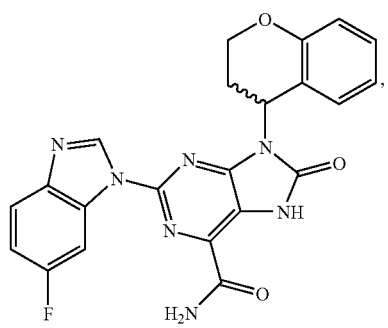
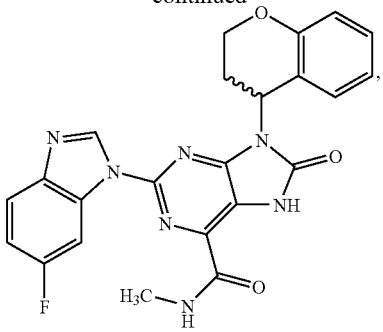
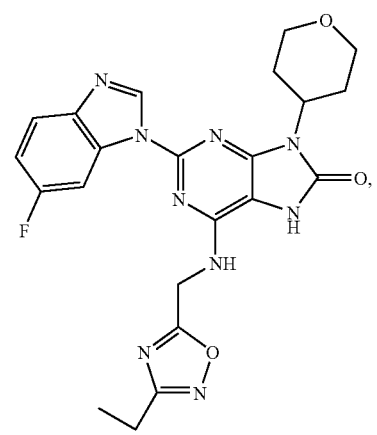
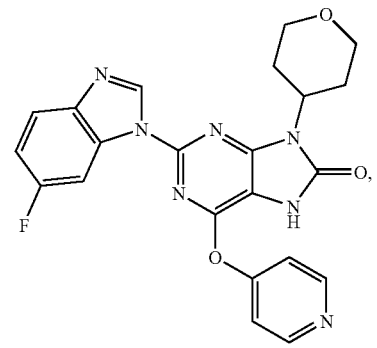
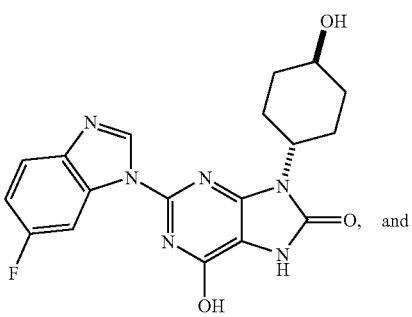

-continued

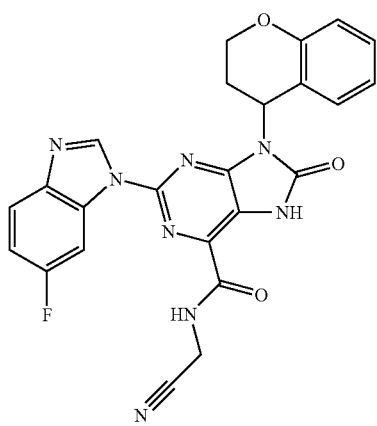

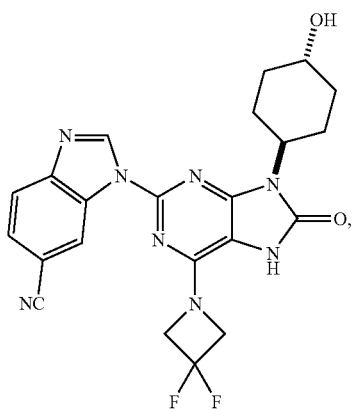

In other embodiments R⁴ is chosen from substituted alkyl, heterocyclyl, substituted heterocyclyl, and substituted aryl, e.g. tetrahydrofuranyl, pyranyl, benzopyranyl, hydroxytetralinyl, oxepanyl, hydroxycyclohexyl, and their halogenated congeners; R¹ is chosen from halogen, $(C_2-C_6)$ alkyl, substituted $(C_1-C_6)$ alkyl, phenyl, azetidinyl, piperidinyl, piperizinyl, pyrrolidinyl, morpholinyl, azepanyl, diazepanyl, pyridinyl, pyrimidinyl, and pyrazolyl optionally substituted with hydroxy, halogen, carboxamide, carboxy, sulfone, alkoxy, and cyano; and X is chosen from halogen, cyano, and hydrogen.

Examples of compounds that fall within the scope of the foregoing embodiments include but are not limited to:

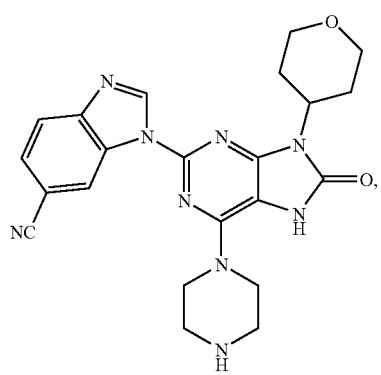

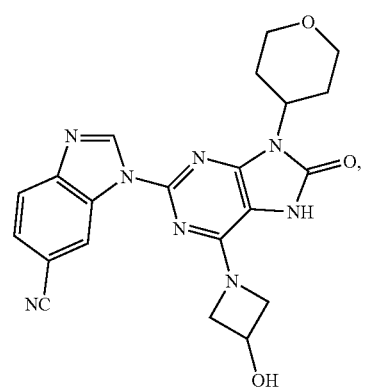

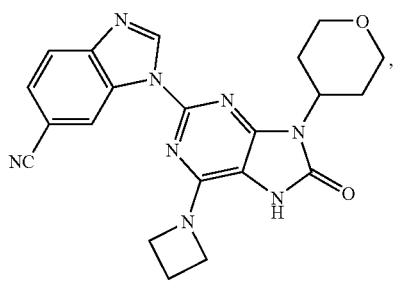

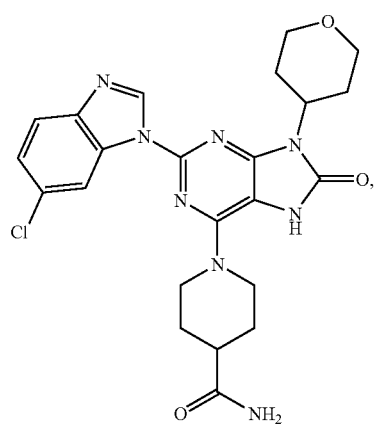

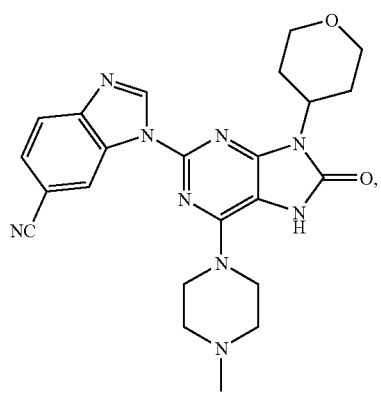

-continued
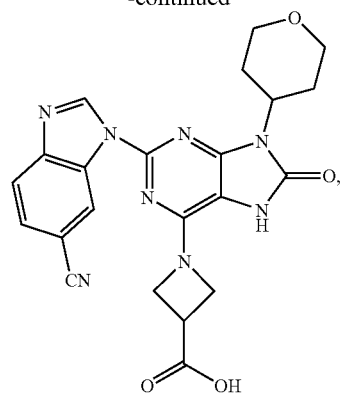
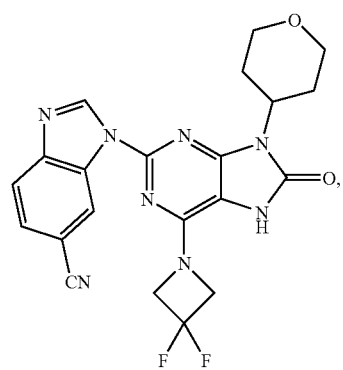
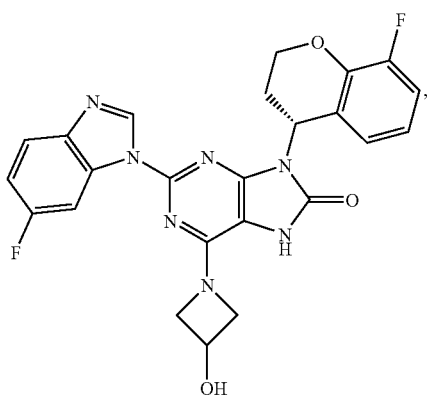
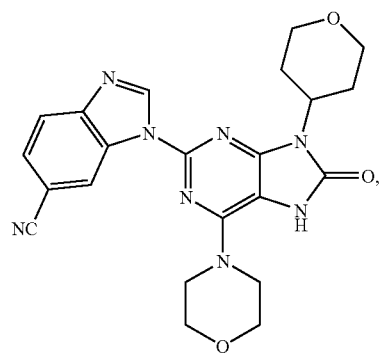
-continued
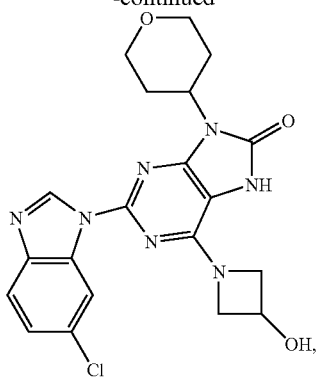
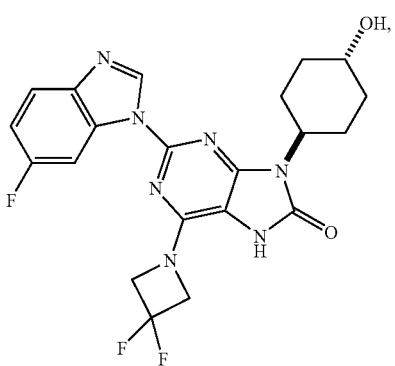
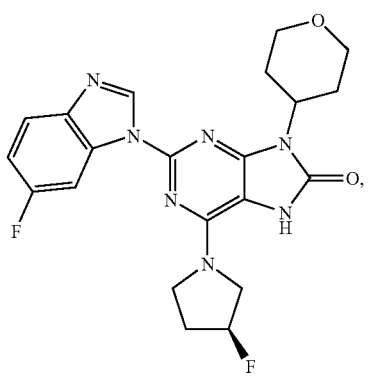
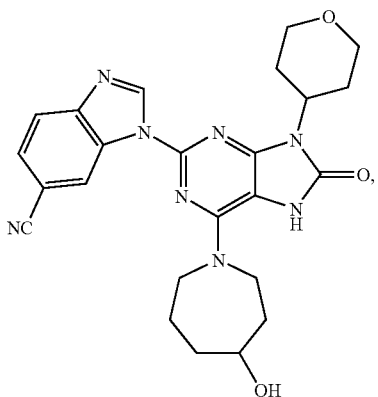

-continued
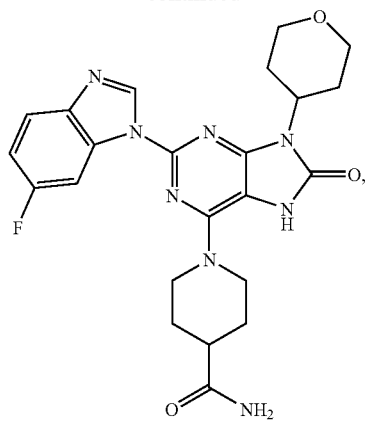
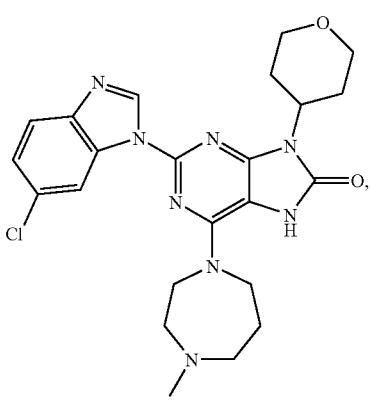
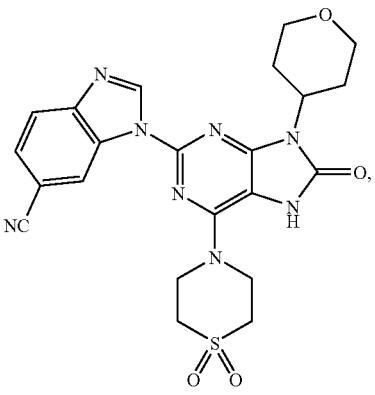
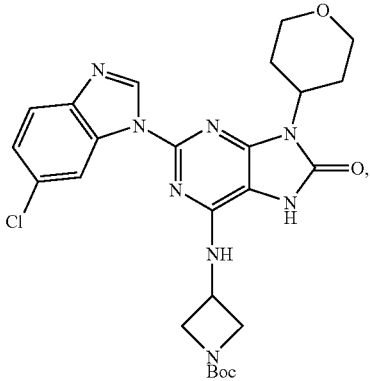
-continued
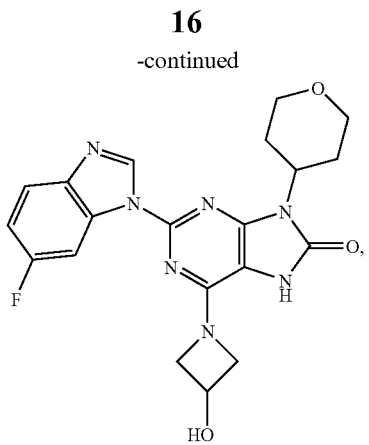
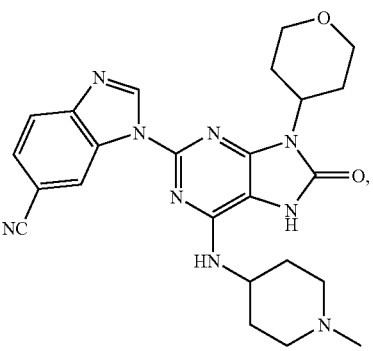
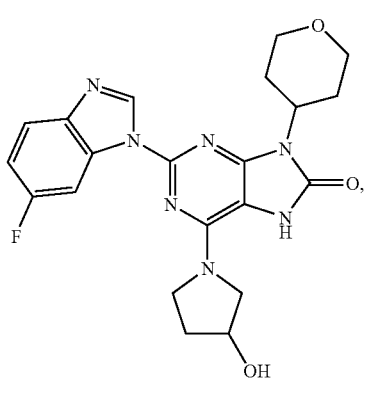
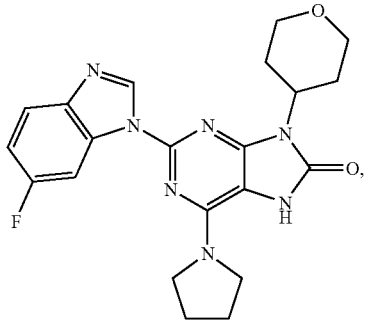

17
-continued
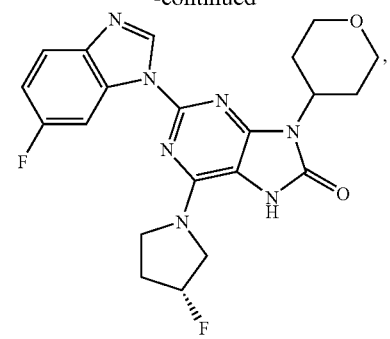
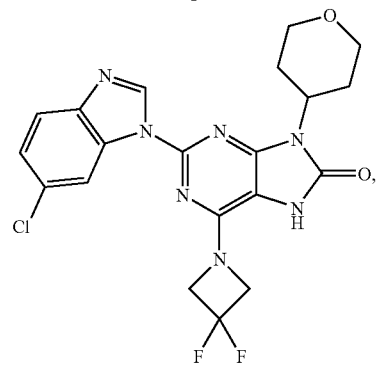
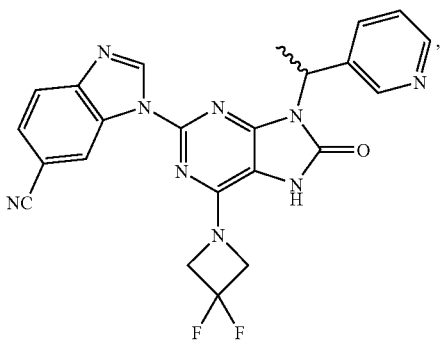
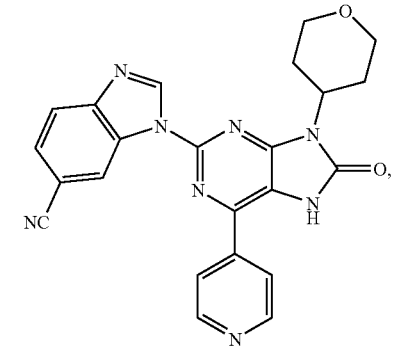
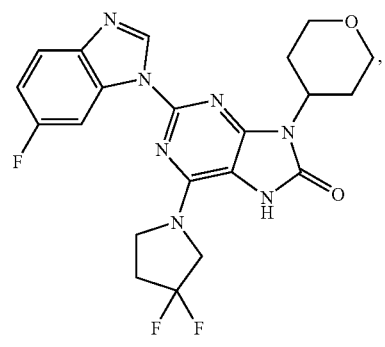
18
-continued
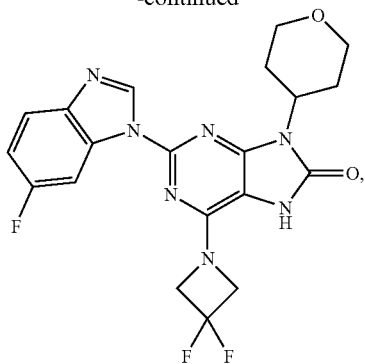
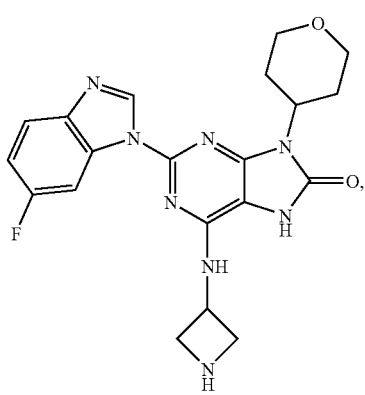
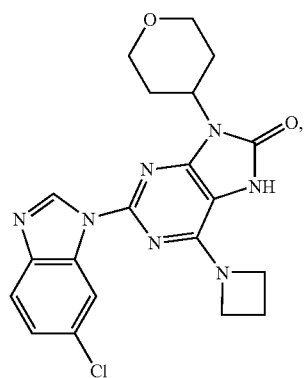
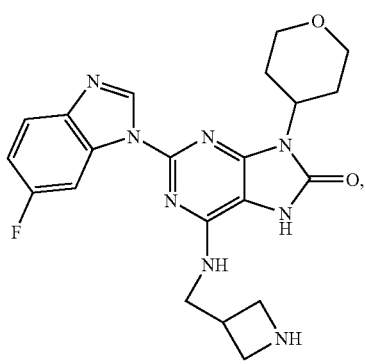

-continued
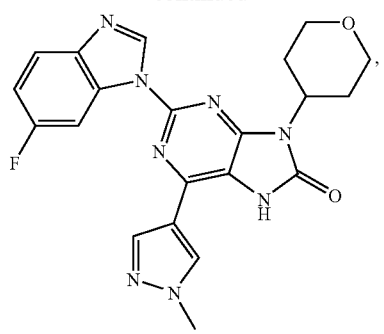
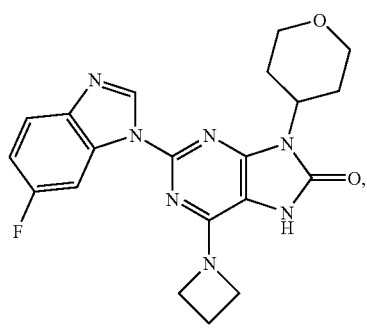
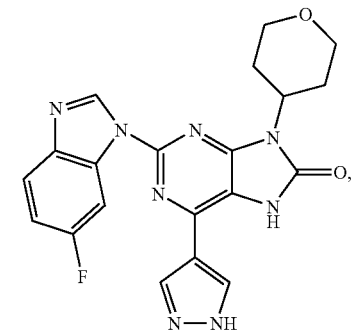
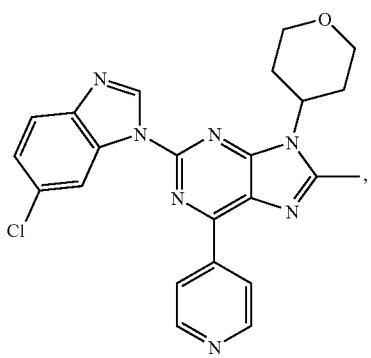
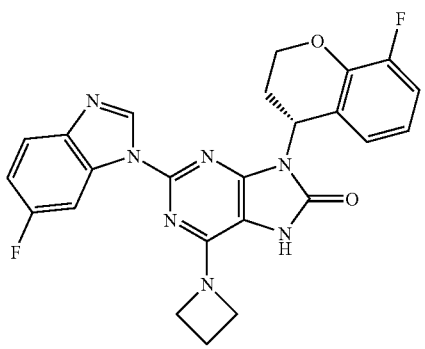
-continued
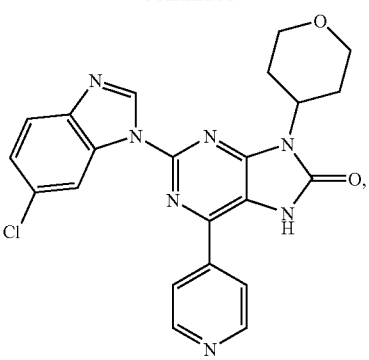
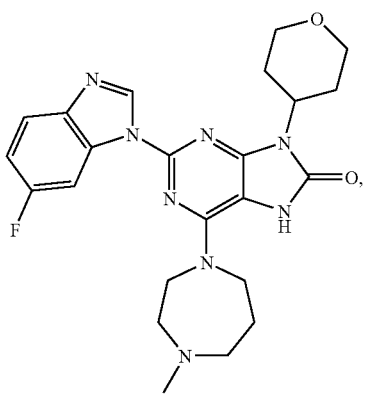
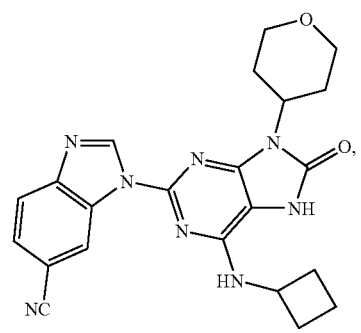
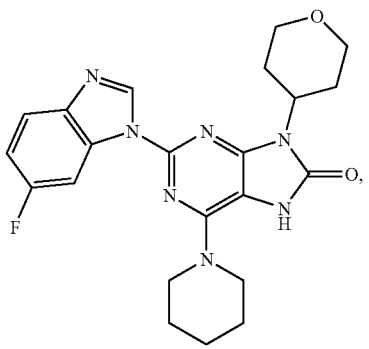

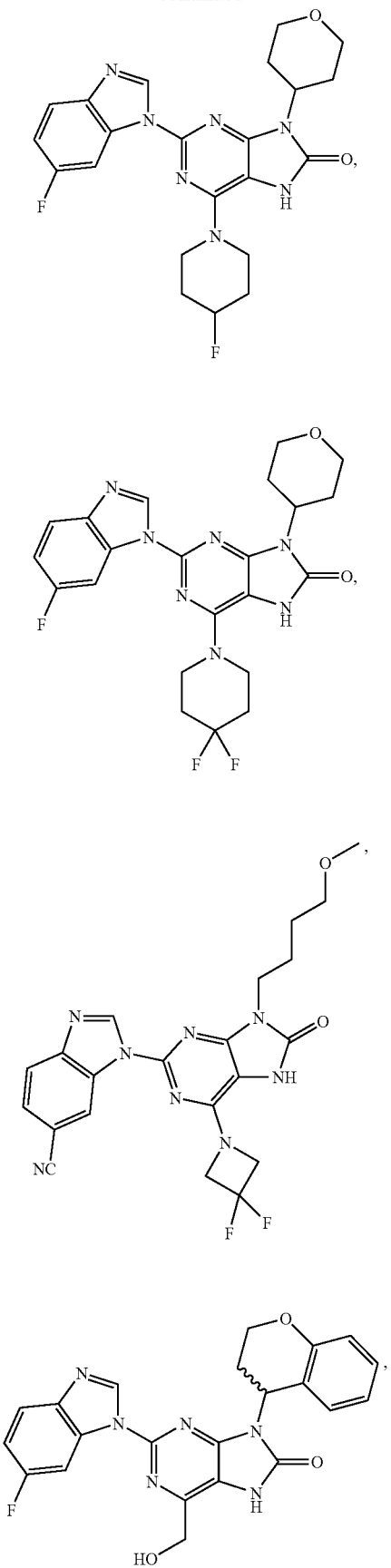
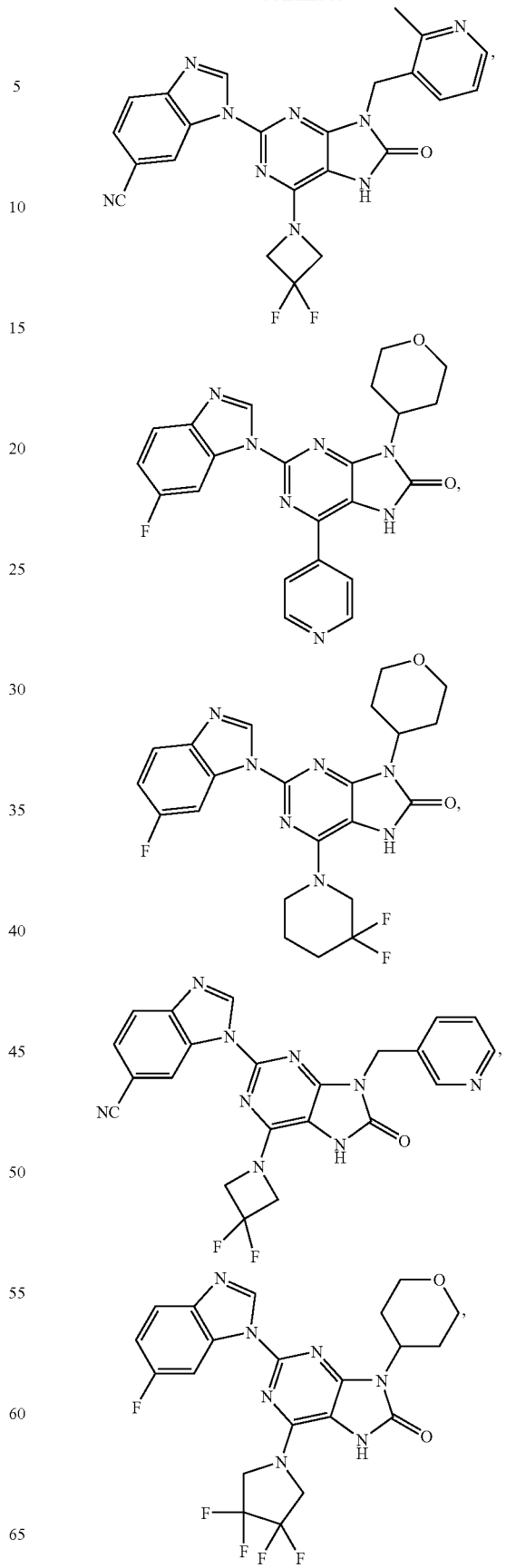

23
-continued
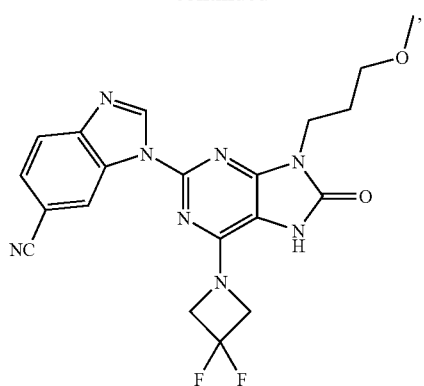
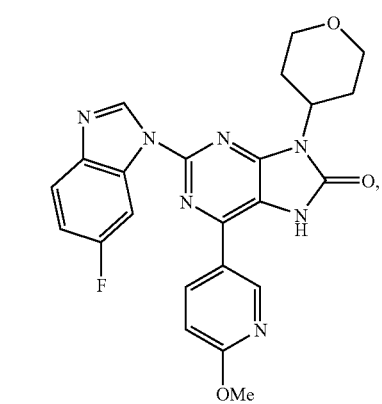
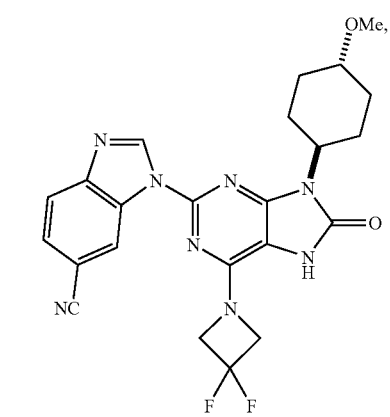
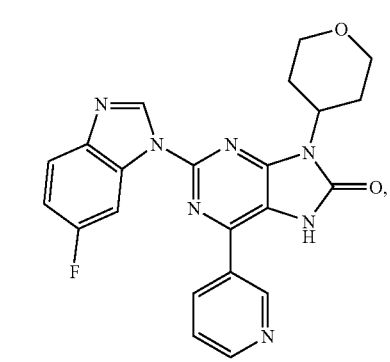
24
-continued
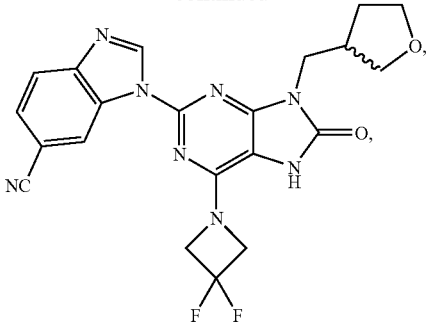
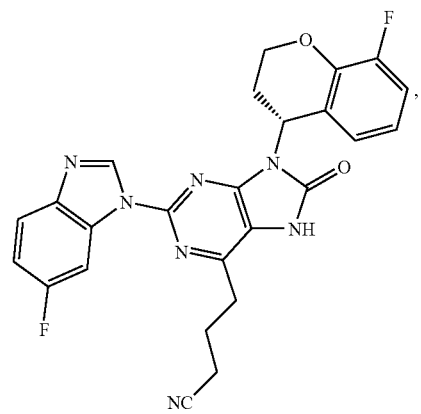
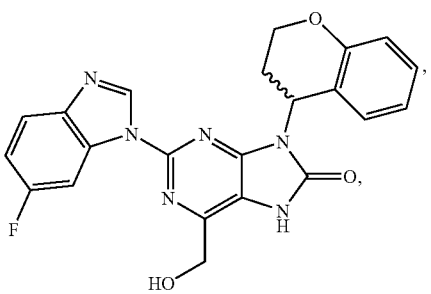
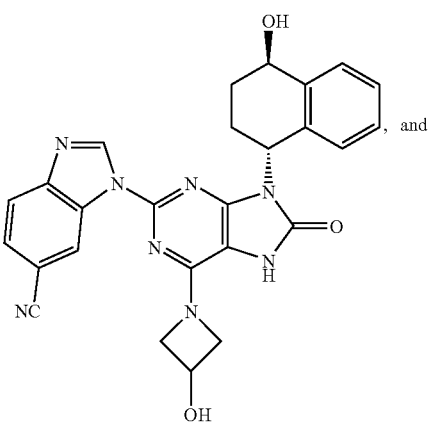

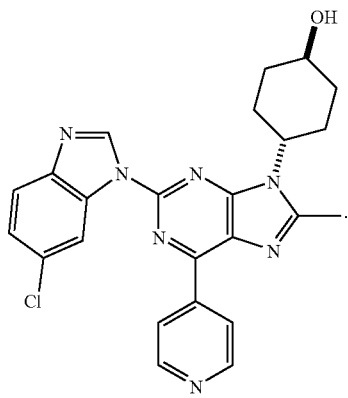

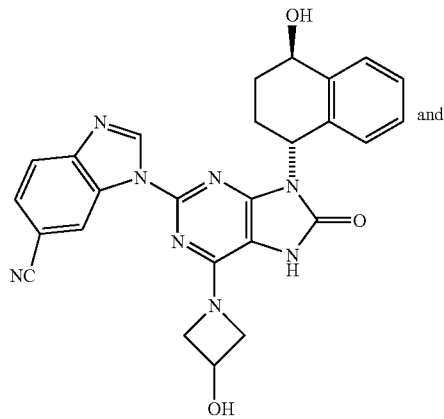

In a further embodiment, $R^9$ may be H, Q may be CX, y may be zero, and $R^4$ is a hydroxytetralin and hydroxycyclohexyl of formulae Id and IId:

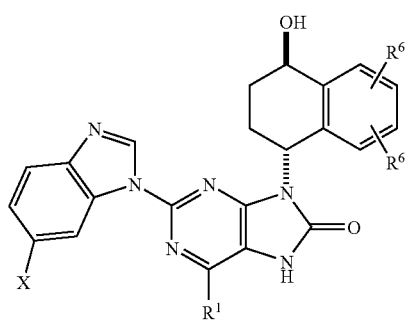

Id

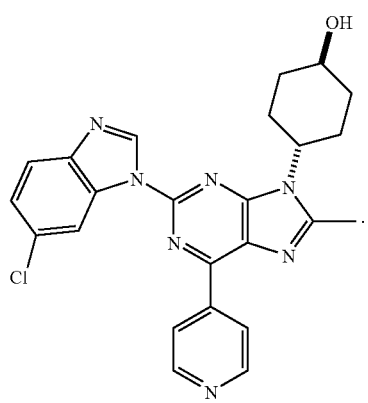

In certain embodiments, $R^9$ may be alkyl or substituted alkyl, Q may be CX, and y may be zero, and of formula Ie:

IId

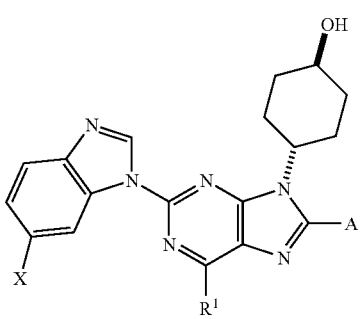

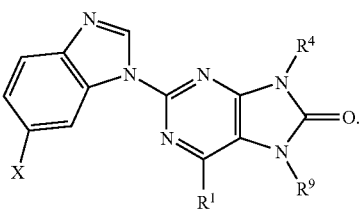

Ie wherein $R^6$ is H or halogen. $R^1$ may be selected from ($C_2$-$C_6$) alkyl, substituted ($C_1$-$C_6$) alkyl, halogen, azetidinyl, piperidinyl, piperizinyl, pyrrolidinyl, phenyl, morpholinyl, azepanyl, diazepanyl, pyridinyl, pyrimidinyl, and pyrazolyl optionally substituted with hydroxy, halogen, carboxamide, alkyl, carboxy, sulfone, alkoxy, and cyano; and X is halogen, cyano, substituted alkoxy, and hydrogen.

Examples of compounds that are within the scope of the foregoing embodiments include but are not limited to:

In further embodiments, $R^4$ may be chosen from tetrahydrofuran, benzopyran, hydroxytetralin, oxepane, hydroxycyclohexane, and their halogenated congeners; $R^1$ may be chosen from halogen, heterocyclyl, substituted heterocyclyl, ($C_2$-$C_6$) alkyl, substituted ($C_1$-$C_6$) alkyl, aryl, substituted aryl, cyano, carboxy, carboalkoxy, carboxamide, and amidino; and X may be chosen from halogen, cyano, hydrogen, alkoxy, or substituted alkoxy.

Compounds that fall within the scope of the foregoing embodiments include but are not limited to:

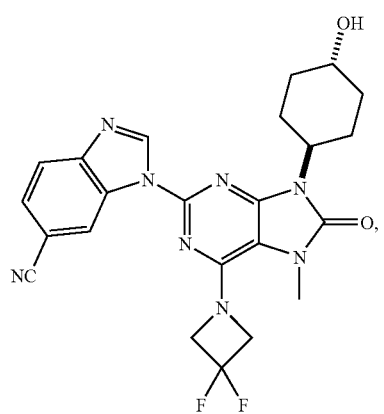
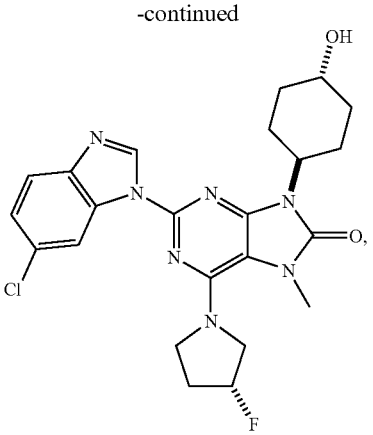
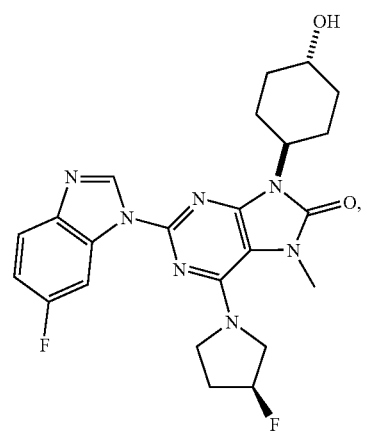
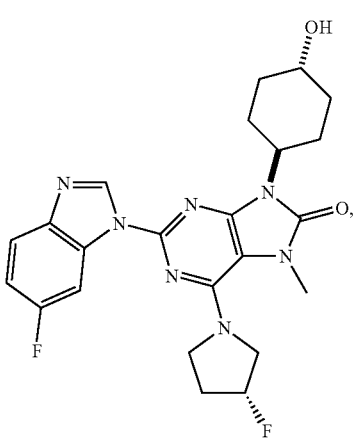
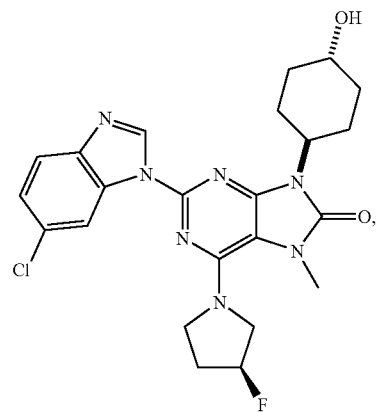
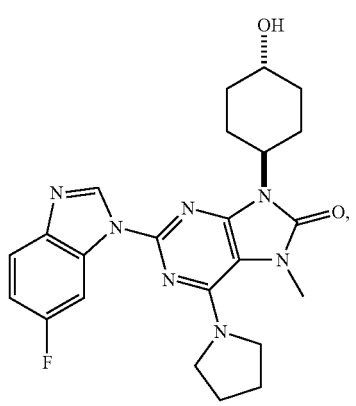
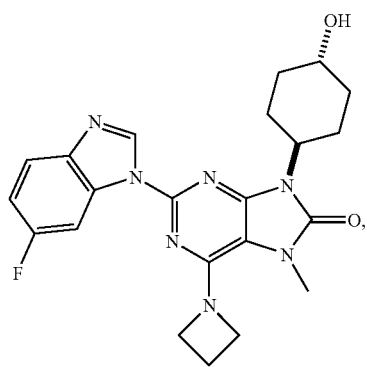
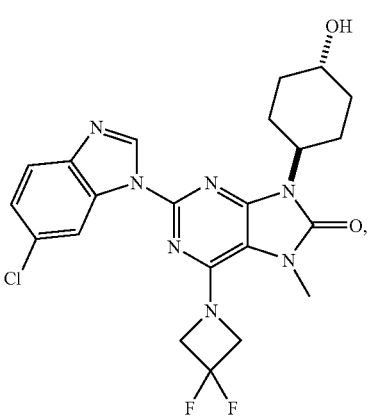

-continued

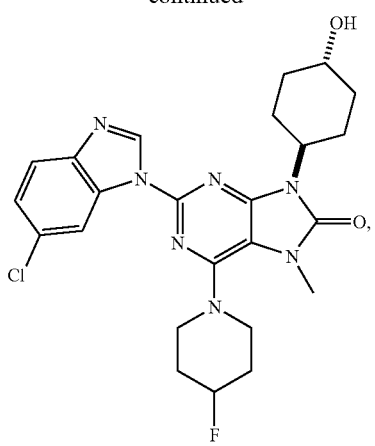

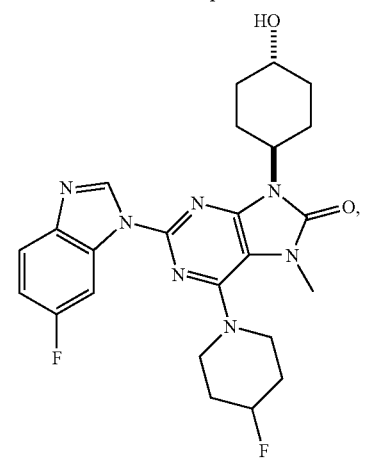

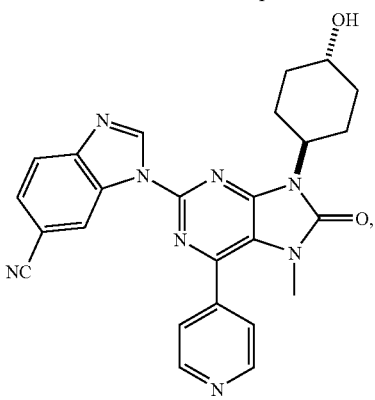

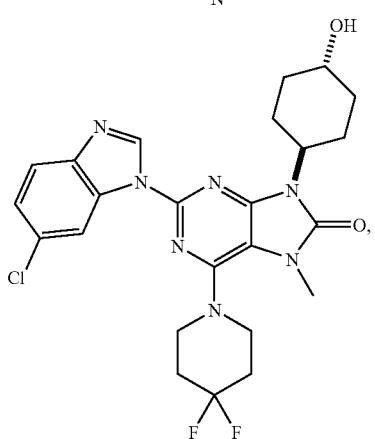

-continued

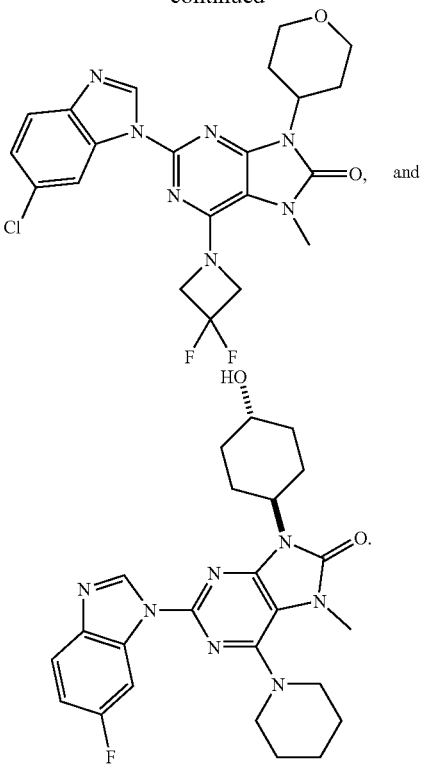

DEFINITIONS

For convenience and clarity certain terms employed in the specification, examples and claims are described herein.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below; more preferred are $C_1$-$C_8$ alkyl. Cycloalkyl is a subset of alkyl and includes cyclic hydrocarbon groups of from 3 to 8 carbon atoms. Examples of cycloalkyl groups include cyclopropyl, cyclobutyl, cyclopentyl, cyclohexyl, norbornyl, and the like.

$C_1$ to $C_{20}$ hydrocarbon includes alkyl, cycloalkyl, alkenyl, alkynyl, aryl and combinations thereof. Examples include phenethyl, cyclohexylmethyl, camphoryl and naphthylethyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Loweralkoxy refers to groups containing one to four carbons. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds); it does not refer to doubly bonded oxygen, as would be found in carbonyl groups.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene and naphthalene, and for the purposes of the present invention, fused moieties such as tetrahydronaphthalene (tetralin), indane and fluorine, in which one or more rings are aromatic, but not all need be. The 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl refers to a substituent in which an aryl residue is attached to the parent structure through alkyl. Examples are benzyl, phenethyl and the like.

Heteroarylalkyl refers to a substituent in which a heteroaryl residue is attached to the parent structure through alkyl. Examples include, e.g., pyridinylmethyl, pyrimidinylethyl and the like.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic.

Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl. A nitrogenous heterocycle is a heterocycle containing at least one nitrogen in the ring; it may contain additional nitrogens, as well as other heteroatoms.

Substituted alkyl, aryl, cycloalkyl, heterocyclyl etc. refer to alkyl, aryl, cycloalkyl, or heterocyclyl wherein up to three H atoms in each residue are replaced with halogen, haloalkyl, hydroxy, loweralkoxy, hydroxyloweralkyl, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzenesulfonyl, benzyloxy, or heteroaryloxy. When the parent is a heterocycle that allows such substitution, the term also includes oxides, for example pyridine-N-oxide, thiopyran sulfoxide and thiopyran-S,S-dioxide. As mentioned above, two hydrogens on a single carbon may be replaced by a carbonyl to form an oxo derivative. Noteworthy oxo-substituted aryl residues include tetralone (3,4-dihydronaphthalen-1(2H)-one) and indanone (2,3-dihydroinden-1-one).

The terms "halogen" and "halo" refer to fluorine, chlorine, bromine or iodine.

The term "electron-withdrawing group" refers to substituents which have a Hammett $\sigma_{meta}$ greater than 0.2. Examples of such substituents include cyanide, trifluoromethoxy, trifluoromethyl, chlorine, and fluorine.

Some of the compounds described herein may contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, as well as, their racemic and optically pure forms. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

Likewise, all tautomeric forms are also intended to be included. When the enol-form of a tautomeric compound is present, the keto-form of the compound is also within the scope of the present invention. An example of a keto-enol tautomerization of a 6-substituted 2-(benzimidazolyl) purinone and subsequently a tautomer of the foregoing that is in accordance with the present invention are depicted below.

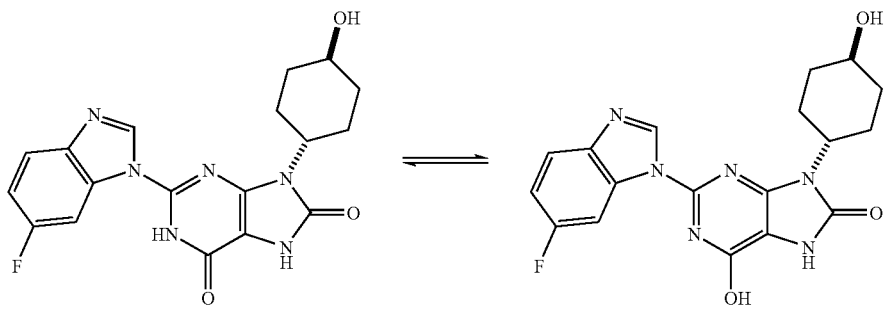

The graphic representations of racemic, ambiscalemic and scalemic or enantiomerically pure compounds used herein are taken from Maehr J. Chem. Ed. 62, 114-120 (1985): solid and broken wedges are used to denote the absolute configuration of a chiral element; wavy lines indicate disavowal of any stereochemical implication which the bond it represents could generate; solid and broken bold lines are geometric descriptors indicating the relative configuration shown; and wedge outlines and dotted or broken lines denote enantiomerically pure compounds of indeterminate absolute configuration. For example, the graphic representation

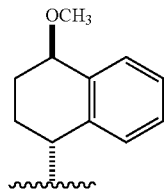

indicates either, or both, of the two trans enantiomers

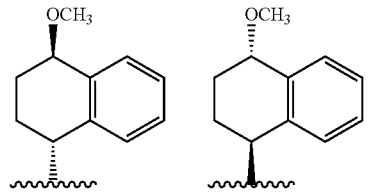

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, chlorine and iodine include $^3H$, $^{14}C$, $^{35}S$, $^{18}F$, $^{36}Cl$ and $^{125}I$, respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectability. Radiolabeled compounds of this invention can generally be prepared by methods well known to those skilled in the art. Conveniently, such radiolabeled compounds can be prepared by carrying out the procedures disclosed in the Examples by substituting a readily available radiolabeled reagent for a non-radiolabeled reagent. Because of the high affinity for the JAK3 enzyme active site, radiolabeled compounds of the invention are useful for JAK3 assays.

An oxygenous heterocycle is a heterocycle containing at least one oxygen in the ring; it may contain additional oxygens, as well as other heteroatoms. Exemplary oxygenous heterocycles include tetrahydropyran, chroman and their variously substituted derivatives, such as:

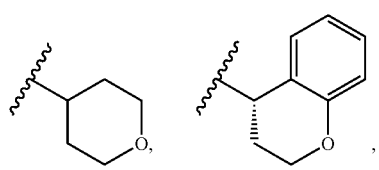

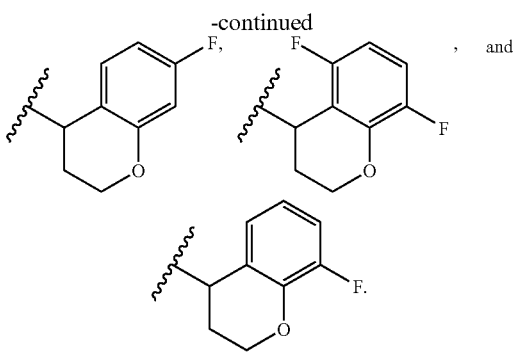

Chemical Synthesis

Terminology related to "protecting", "deprotecting" and "protected" functionalities occurs throughout this application. Such terminology is well understood by persons of skill in the art and is used in the context of processes that involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

A comprehensive list of abbreviations utilized by organic chemists appears in the first issue of each volume of the Journal of Organic Chemistry. The list, which is typically presented in a table entitled "Standard List of Abbreviations", is incorporated herein by reference.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here. The starting materials, for example in the case of suitably substituted benzimidazole ring compounds, are either commercially available, synthesized as described in the examples or may be obtained by the methods well known to persons of skill in the art.

The present invention further provides pharmaceutical compositions comprising as active agents, the compounds described herein.

As used herein a "pharmaceutical composition" refers to a preparation of one or more of the compounds described herein, or physiologically acceptable salts or solvents thereof, with other chemical components such as physiologically suitable carriers and excipients. Pharmaceutical compositions for use in accordance with the present invention thus may be formulated in conventional manner using one or more physiologically acceptable carriers comprising excipients and auxiliaries, which facilitate processing of the active compounds into preparations which, can be used pharmaceutically. Proper formulation is dependent upon the route of administration chosen.

Compounds that inhibit Jak-3 can be formulated as pharmaceutical compositions and administered to a mammalian subject, such as a human patient in a variety of forms adapted to the chosen route of administration, i.e., orally or parenterally, by intravenous, intramuscular, topical, transdermal or subcutaneous routes.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar or alginic acid or a salt thereof such as sodium alginate.

In addition, enteric coating may be useful as it is may be desirable to prevent exposure of the compounds of the invention to the gastric environment. Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers.

In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For injection, the compounds of the invention may be formulated in aqueous solutions, preferably in physiologically compatible buffers such as Hank's or Ringer's solution or physiological saline buffer. For transmucosal and transdermal administration, penetrants appropriate to the barrier to be permeated may be used in the composition. Such penetrants, including for example DMSO or polyethylene glycol, are known in the art.

For administration by inhalation, the compounds for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Pharmaceutical compositions for parenteral administration include aqueous solutions of the active ingredients in water-soluble form. Additionally, suspensions of the active compounds may be prepared as appropriate oily injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the compounds, to allow for the preparation of highly concentrated solutions.

The compounds of the present invention may also be formulated in rectal compositions such as suppositories or retention enemas, using, e.g., conventional suppository bases such as cocoa butter or other glycerides.

Depending on the severity and responsiveness of the condition to be treated, dosing can also be a single administration of a slow release composition, with course of treatment lasting from several days to several weeks or until cure is effected or diminution of the disease state is achieved. The amount of a composition to be administered will, of course, be dependent on many factors including the subject being treated, the severity of the affliction, the manner of administration, the judgment of the prescribing physician. The compounds of the invention may be administered orally or via injection at a dose from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

As used herein, and as would be understood by the person of skill in the art, the recitation of "a compound" is intended to include salts, solvates and inclusion complexes of that compound. The term "solvate" refers to a compound of Formula I or II in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Inclusion complexes are described in Remington: The Science and Practice of Pharmacy 19th Ed. (1995) volume 1, page 176-177, which is incorporated herein by reference. The most commonly employed inclusion complexes are those with cyclodextrins, and all cyclodextrin complexes, natural and synthetic, are specifically encompassed within the claims.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

The term "preventing" as used herein refers to administering a medicament beforehand to forestall or obtund an attack. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended herein.

It should be understood that in addition to the ingredients particularly mentioned above, the formulations of this invention may include other agents conventional in the art having regard to the type of formulation in question, for example those suitable for oral administration may include flavoring agents.

The compositions may be presented in a packaging device or dispenser, which may contain one or more unit dosage forms containing the active ingredient. Examples of a packaging device include metal or plastic foil, such as a blister pack and a nebulizer for inhalation. The packaging device or dispenser may be accompanied by instructions for administration. Compositions comprising a compound of the present invention formulated in a compatible pharmaceutical carrier may also be placed in an appropriate container and labeled for treatment of an indicated condition.

Indications

The compounds of the present invention are useful in inhibiting the activity if Jak3 or in inhibiting Jak3 mediated activity and are useful as immunosuppressive agents for tissue and organ transplants, including bone marrow transplant and in the treatment of autoimmune and inflammatory diseases and of complications arising therefrom. Hyperacute, acute and chronic organ transplant rejection may be treated. Hyperacute rejection occurs within minutes of transplantation. Acute rejection generally occurs within six to twelve months of the transplant. Hyperacute and acute rejections are typically reversible where treated with immunosuppressant agents. Chronic rejection, characterized by gradual loss of organ function, is an ongoing concern for transplant recipients because it can occur anytime after transplantation.

There are about 75 different autoimmune disorders known that may be classified into two types, organ-specific (directed mainly at one organ) and non-organ-specific (affecting multiple organs).

Examples of organ-specific autoimmune disorders are insulin-dependent diabetes (Type I) which affects the pancreas, Hashimoto's thyroiditis and Graves' disease which affect the thyroid gland, pernicious anemia which affects the stomach, Cushing's disease and Addison's disease which affect the adrenal glands, chronic active hepatitis which affects the liver; polycystic ovary syndrome (PCOS), celiac disease, psoriasis, inflammatory bowel disease (IBD) and ankylosing spondylitis.

Examples of non-organ-specific autoimmune disorders are rheumatoid arthritis, multiple sclerosis, systemic lupus and myasthenia gravis.

Type I diabetes ensues from the selective aggression of autoreactive T-cells against insulin secreting β cells of the islets of Langerhans. Targeting Jak3 in this disease is based on the observation that multiple cytokines that signal through the Jak pathway are known to participate in the T-cell mediated autoimmune destruction of β cells. Indeed, a Jak3 inhibitor, JANEX-1 was shown to prevent spontaneous autoimmune diabetes development in the NOD mouse model of type I diabetes.

Graft-versus-host disease (GVHD) is a donor T-cell initiated pathological condition that frequently follows allogeneic bone marrow transplantation (BMT). Substantial experimental and clinical research have demonstrated that donor T-cells are the principal mediators and effectors of GVHD. Jak3 plays a key role in the induction of GVHD and treatment with a Jak3 inhibitor, JANEX-1, was shown to attenuate the severity of GVHD (reviewed in Cetkovic-Cvrlje and Ucken, 2004).

Mast cells express Jak3 and Jak3 is a key regulator of the IgE mediated mast cell responses including the release of inflammatory mediators. Jak3 was shown to be a valid target in the treatment of mast cell mediated allergic reaction.

Allergic disorders associated with mast cell activation include Type I immediate hypersensitivity reactions such as allergic rhinitis (hay fever), allergic urticaria (hives), angioedema, allergic asthma and anaphylaxis, i.e., "anaphylatic shock." These disorders are treated or prevented by inhibition of Jak3 activity, for example, by administration of a Jak3 inhibitor according to the present invention. According to the present invention, the Jak3 inhibitors may be administered prophylactically, i.e., prior to onset of acute allergic reaction, or they may be administered after onset of the reaction, or at both times.

Inflammation of tissues and organs occurs in a wide range of disorders and diseases and in certain variations, results from activation of the cytokine family of receptors. Exemplary inflammatory disorders associated with activation of Jak3 include, in a non-limiting manner, skin inflammation due radiation exposure, asthma, allergic inflammation and chronic inflammation.

The Jak3 inhibitors of the present invention are also useful in treating certain malignancies, including skin cancer and hematological malignancy such as lymphomas and leukemias.

The following examples will further describe the invention, and are used for the purposes of illustration only, and should not be considered as limiting the invention being disclosed.

EXAMPLES

The following abbreviations and terms have the indicated meaning throughout:

Ac=acetyl
Bu=butyl
DCM=dichloromethane=methylene chloride=$CH_2Cl_2$
DEAD=diethyl azodicarboxylate
DIC=diisopropylcarbodiimide
DIEA=N,N-diisopropylethyl amine
DMF=N,N-dimethylformamide
DMSO=dimethyl sulfoxide
EA (EtOAc)=Ethyl Acetate
GC=gas chromatography
h=hours
HOAc=acetic acid
HOBt=hydroxybenzotriazole
Me=methyl
Pd(dppf)$_2$Cl$_2$=dichloro[1,1'-bis(diphenylphosphinoferrocene]palladium
Ph=phenyl PhOH=phenol
RT=room temperature
sat'd=saturated
s-=secondary
t-=tertiary
TBDMS=t-butyldimethylsilyl
TFA=trifluoroacetic acid
THF=tetrahydrofuran
TMOF=trimethyl orthoformate
TMS=trimethylsilyl
tosyl=p-toluenesulfonyl
Trt=triphenylmethyl Examples below describe syntheses of compounds, precursors and intermediates of the invention.

Experimental Part complete (by HPLC), the reaction mixture was cooled to room temperature and the solvent was removed in vacuo. The residue was purified by flash chromatography (silica gel, gradual elution with 95/5 methylene chloride/methanol to 90/10 methylene chloride/methanol) to give 7.1 g (87% yield) of the desired product as a pink solid. In an alternative procedure, water (300 mL) was added to the residue (before chromatographic purification) and the mixture stirred for 30 min at room temperature. Filtration under vacuum, thorough washing of the precipitate with water, followed by thorough drying of the pink solid in vacuum oven at 60° C., provided high purity desired product in 78% yield. $^1$H NMR (300 MHz, CD$_3$OD) δ, ppm: 4.21-4.12 (m, 1H), 4.01-3.96 (m, 2H), 3.53 (td, J=11.7, 2.2 Hz, 2H), 2.01-1.96 (m, 2H), 1.60 (tdd, J=12.1, 11.7, 4.6 Hz, 2H); MS (EI) m/z 244.3 (MH)$^+$.

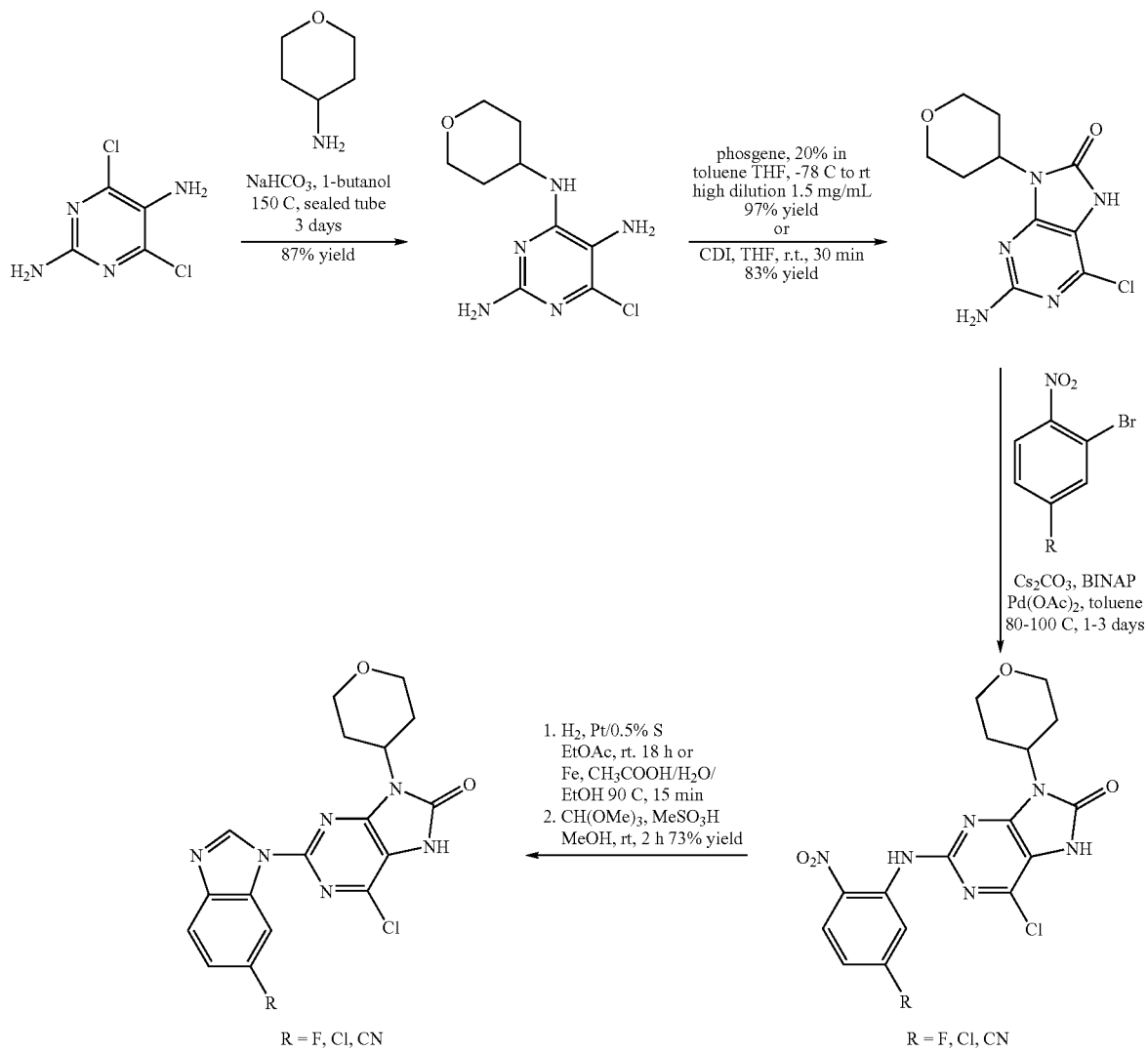

Route A

R = F, Cl, CN 6-chloro-N$^4$-(tetrahydro-2H-pyran-4-yl)pyrimidine-2,4,5-triamine. 2,5-diamino-4,6-dichloropyrimidine (6 g, 33.5 mmol), 4-aminotetrahydropyran (3.39 g, 33.5 mmol, 1 equiv.), sodium bicarbonate (9.85 g, 117.2 mmol, 3.5 equiv.) and 1-butanol (120 mL) were heated together at 150° C. in a sealed tube. After 3 days, when the reaction appeared to be 2-amino-6-chloro-9-(tetrahydro-2H-pyran-4-yl)-7H-purin-8(9H)-one. To a solution of 6-chloro-N$^4$-(tetrahydro-2H-pyran-4-yl)pyrimidine-2,4,5-triamine (1 g, 4.1 mmol) in 900 mL of anhydrous THF at −78° C. under Ar was added dropwise, over 40 min, a solution of phosgene in THF (3.8 mL of a 20% solution of phosgene in toluene, 7 mmol, 1.7 equiv., diluted with 26 mL of anhydrous THF). The reaction mixture was left to gradually warm up to room temperature over 16 h. It was purged with air for 30 min, then the solvent was removed in vacuo to give 1.2 g (97% yield) of the desired product (HCl salt) as a white solid. $^1$H NMR (300 MHz, d$_6$-DMSO) δ, ppm: 11.40 (s, 1H), 7.00 (br s, 2H), 4.50-4.37 (m, 1H), 4.12-4.04 (m, 2H), 3.50 (app t, 2H), 2.68-2.55 (m, 2H), 1.78-1.71 (m, 2H); MS (EI) m/z 270.3 (MH)$^+$.

Alternative route to 2-amino-6-chloro-9-(tetrahydro-2H-pyran-4-yl)-7H-purin-8(9H)-one. To a solution of 6-chloro-N$^4$-(tetrahydro-2H-pyran-4-yl)pyrimidine-2,4,5-triamine (5.1 g, 20.9 mmol) in 170 mL of anhydrous THF was added 1,1-carbonyldiimidazole (20.4 g, 126 mmol) as a solid, in portions. The reaction mixture was stirred at room temperature for 20-30 min (completion of the reaction checked by HPLC and MS). The solvent was removed in vacuo. Water (250 mL) was added to the residue and the mixture stirred at room temperature for 10 min. The solid formed was filtered under vacuum, and thoroughly dried to give 4.67 g (83% yield) of the desired product as a pink solid. $^1$H NMR (300 MHz, d$_6$-DMSO) δ, ppm: 11.40 (s, 1H), 7.00 (br s, 2H), 4.50-4.37 (m, 1H), 4.12-4.04 (m, 2H), 3.50 (app t, 2H), 2.68-2.55 (m, 2H), 1.78-1.71 (m, 2H); MS (EI) m/z 270.3 (MH)$^+$.

General procedure for the Buchwald-Hartwig Palladium-catalyzed C—N cross coupling. All glassware was dried in vacuum oven at 60° C. for one day prior to reaction. Cesium carbonate and 2-amino-6-chloro-9-(tetrahydro-2H-pyran-4-yl)-7H-purin-8(9H)-one were dried at 60° C. under high vacuum for one day prior to experiment. An oven-dried vial was charged with 2-amino-6-chloro-9-(tetrahydro-2H-pyran-4-yl)-7H-purin-8(9H)-one (1 equiv.), freshly grounded cesium carbonate (1.4 equiv.), Pd(OAc)$_2$ (0.1 equiv.), racemic BINAP (0.15 equiv.) and an aryl bromide (1.3 equiv.), followed by anhydrous toluene (0.25 M solution). The vial was purged with Ar for 3 min, then closed and heated at 80-100° C. for 17-22 h. The reaction mixture was cooled to room temperature, and the solvent removed in vacuo. Column chromatography of the residue afforded the desired product.

6-chloro-2-(5-fluoro-2-nitrophenylamino)-9-(tetrahydro-2H-pyran-4-yl)-7H-purin-8(9H)-one. To an oven-dried vial was added 2-amino-6-chloro-9-(tetrahydro-2H-pyran-4-yl)-7H-purin-8(9H)-one (50 mg of HCl salt, 0.186 mmol, 1 equiv.) in anhydrous toluene (3 mL), then freshly grounded cesium carbonate (85 mg, 0.26 mmol, 1.4 equiv.) with stirring at room temperature under Ar. After 20 min, Pd(OAc)$_2$ (12.5 mg, 0.019 mmol, 0.1 equiv.), racemic BINAP (17.3 mg, 0.028 mmol, 0.15 equiv.) and 1-bromo-5-fluoro-2-nitrobenzene (Oakwood) (53 mg, 0.24 mmol, 1.3 equiv.) were added as solids, followed by DIEA (50 μL, 1.5 equiv.). The vial was purged with Ar for 3 min, then closed and heated at 80° C. for 18 h. The reaction mixture was cooled to room temperature, diluted with 5% methanol in methylene chloride, filtered through a Nylon 0.45 μm filter, and the filter repeatedly washed with 5% methanol in methylene chloride. The filtrate was concentrated in vacuo and the resulting residue was purified using preparative TLC (silica gel, 4.25% methanol in methylene chloride) to give the desired product as a yellow solid (45.3 mg, 60% yield). $^1$H NMR (300 MHz, CDCl$_3$) δ, ppm: 10.90 (s, 1H), 8.89 (dd, 1H), 8.45 (dd, 1H), 8.10 (br s, 1H), 6.92-6.83 (m, 1H), 4.75-4.60 (m, 1H), 4.28 (dd, 2H), 3.65 (app t, 2H), 2.82 (tdd, 2H), 1.90 (br d, 2H); MS (EI) m/z 409.1 (MH)$^+$.

6-chloro-2-(5-chloro-2-nitrophenylamino)-9-(tetrahydro-2H-pyran-4-yl)-7H-purin-8(9H)-one. To an oven-dried 2-neck flask under Ar was added racemic BINAP (2.27 g, 3.64 mmol, 0.35 equiv.) followed by anhydrous toluene (20 mL) and Pd(OAc)$_2$ (1.05 g, 1.56 mmol, 0.15 equiv.) and the mixture was stirred under Ar, at room temperature for 15 min. A deep yellow paste is formed. Then, 2-bromo-4-chloro-1-nitrobenzene (3.19 g, 13.52 mmol, 1.3 equiv.), 2-amino-6-chloro-9-(tetrahydro-2H-pyran-4-yl)-7H-purin-8(9H)-one (2.80 g, 10.4 mmol, 1.0 equiv.) and cesium carbonate (5.08 g, 15.6 mmol, 1.5 equiv.) were added as solids, under Ar, followed by anhydrous toluene (22 mL), and the reaction mixture was stirred at room temperature for 10 min, then stirred at 100° C. for 17 h. The reaction mixture was cooled to room temperature, diluted with toluene (450 mL) and passed through Celite. The filtrate was concentrated in vacuo to give a dark brown residue. Flash chromatographic purification (silica gel, gradual elution with 1 to 5% methanol in methylene chloride), followed by recrystallization from hot ethyl acetate gave the desired product as a bright yellow solid (1.63 g, 37% yield) in high purity. $^1$H NMR (300 MHz, CDCl$_3$+CD$_3$OD) δ, ppm: 9.05 (s, 1H), 8.24 (d, 1H), 7.06 (d, 1H), 4.56-4.52 (m, 1H), 4.16 (dd, 2H), 3.58 (app t, 2H), 2.72 (tdd, 2H), 1.81 (br d, 2H); MS (EI) m/z 425.2 (MH)$^+$.

3-(6-chloro-8-oxo-9-(tetrahydro-2H-pyran-4-yl)-8,9-dihydro-7H-purin-2-ylamino)-4-nitrobenzonitrile. To an oven-dried 2-neck flask under Ar was added racemic BINAP (2.59 g, 4.17 mmol, 0.35 equiv.) followed by anhydrous toluene (20 mL) and Pd(OAc)$_2$ (1.20 g, 1.79 mmol, 0.15 equiv.) and the mixture was stirred under Ar, at room temperature for 15 min. A deep yellow paste is formed. Then, 3-bromo-4-nitro-benzonitrile (3.51 g, 15.47 mmol, 1.3 equiv.), 2-amino-6-chloro-9-(tetrahydro-2H-pyran-4-yl)-7H-purin-8(9H)-one (3.2 g, 11.9 mmol, 1.0 equiv.) and cesium carbonate (5.81 g, 17.8 mmol, 1.5 equiv.) were added as solids, under Ar, followed by anhydrous toluene (27 mL), and the reaction mixture was stirred at room temperature for 10 min, then stirred at 100° C. for 22 h (LC-MS shows reaction to be complete). The reaction mixture was cooled to room temperature, diluted with toluene (450 mL) and passed through Celite. The filtrate was concentrated in vacuo to give a dark brown residue. The desired product was recrystallized as a bright orange solid from the residue using mixtures of 100 mL acetonitrile/100 mL water. Repeated recrystallizations resulted in isolation of 1.49 g of desired product (30% yield) in high purity. $^1$H NMR (300 MHz, CDCl$_3$) δ, ppm: 10.40 (s, 1H), 9.33 (s, 1H), 8.35 (d, 1H), 7.85 (br s, 1H), 7.31 (d, 1H), 4.65-4.50 (m, 1H), 4.19 (dd, 2H), 3.55 (app t, 2H), 2.70 (tdd, 2H), 1.90 (br d, 2H); MS (EI) m/z 416.2 (MH)$^+$.

General procedure for the reduction of the nitrophenyl group in 6-chloro-2-(5-substituted-2-nitrophenylamino)-9-(tetrahydro-2H-pyran-4-yl)-7H-purin-8(9H)-one with iron powder. To 6-chloro-2-(5-substituted-2-nitrophenylamino)-9-(tetrahydro-2H-pyran-4-yl)-7H-purin-8(9H)-one (1 equiv.) was added glacial acetic acid, water and ethanol (ratio 1/2.5/5 vol), followed by iron powder (10 equiv.) and the resulting mixture heated at 90° C. for 15 min (HPLC monitoring). The reaction mixture was left to cool down to room temperature, concentrated ammonium hydroxide solution was added to bring the pH to basic, and the mixture was stirred for 10 min. The aqueous layer diluted with water, was extracted with ethyl acetate, the combined organic layers were washed with brine, dried (anhydrous Na$_2$SO$_4$), and the solvent removed in vacuo to give the desired product. This material was used in the next step without further purification.

2-(2-amino-5-chlorophenylamino)-6-chloro-9-(tetrahydro-2H-pyran-4-yl)-7H-purin-8(9H)-one. Pale yellow solid. Synthesized from 6-chloro-2-(5-chloro-2-nitrophenylamino)-9-(tetrahydro-2H-pyran-4-yl)-7H-purin-8(9H)-one, using glacial acetic acid, water and ethanol (57 mL/142 mL/285 mL). MS (EI) m/z 395.2 (MH)$^+$.

General procedure for the reduction of the nitrophenyl group in 6-chloro-2-(5-substituted-2-nitrophenylamino)-9-(tetrahydro-2H-pyran-4-yl)-7H-purin-8(9H)-one by catalytic hydrogenation. To 6-chloro-2-(5-substituted-2-nitrophenylamino)-9-(tetrahydro-2H-pyran-4-yl)-7H-purin-8 (9H)-one (1 equiv.) was added ethyl acetate and Pt catalyst, 0.5% sulfur (Alfa Aesar) (5% on activated carbon, 0.05 equiv.) with stirring at room temperature under hydrogen (1 atm) for 18 h (HPLC monitoring). Filtration of the reaction mixture over a small plug of Celite, thorough washing with ethyl acetate and methanol, evaporation of solvent and drying provided the desired product, which was used in the next step without further purification.

2-(2-amino-5-fluorophenylamino)-6-chloro-9-(tetrahydro-2H-pyran-4-yl)-7H-purin-8(9H)-one. 160 mg on 0.49 mmol scale, 86% yield. Synthesized from 6-chloro-2-(5-fluoro-2-nitrophenylamino)-9-(tetrahydro-2H-pyran-4-yl)-7H-purin-8(9H)-one. MS (EI) m/z 379.3 $(MH)^+$.

4-amino-3-(6-chloro-8-oxo-9-(tetrahydro-2H-pyran-4-yl)-8,9-dihydro-7H-purin-2-ylamino)benzonitrile. Pale yellow solid. 86% yield on 0.49 mmol scale. In a typical procedure, to 3-(6-chloro-8-oxo-9-(tetrahydro-2H-pyran-4-yl)-8,9-dihydro-7H-purin-2-ylamino)-4-nitrobenzonitrile (0.49 mmol) was added ethyl acetate (20 mL) and Pt catalyst, 0.5% sulfur (Alfa Aesar) (95.5 mg 5% on activated carbon, 4.8 mg, 0.025 mmol, 0.05 equiv.) with stirring at room temperature under hydrogen (1 atm) for 18 h (HPLC monitoring). Filtration of the reaction mixture over a small plug of celite, thorough washing with ethyl acetate and methanol, evaporation of solvent and drying provided the desired product, which was used in the next step without further purification. Yield quantitative on 2.95 mmol scale. The catalyst was washed with 12-15 portions of 100 mL of a 1/1 (v) solution of methylene chloride/isopropanol to recover desired product. MS (EI) m/z 386.1 $(MH)^+$.

General procedure for closing the benzimidazole ring. To a flask containing crude 2-(2-amino-5-substituted-phenylamino)-6-chloro-9-(tetrahydro-2H-pyran-4-yl)-7H-purin-8 (9H)-one (1 equiv.) was added anhydrous methanol, followed by anhydrous trimethylorthoformate (excess) and methane sulfonic acid (catalytic amount) and the reaction mixture was stirred under Ar at room temperature for 2 h (HPLC monitoring). The solvent was removed in vacuo and the residue purified by column chromatography to afford the desired product.

6-chloro-2-(6-fluoro-1H-benzo[d]imidazol-1-yl)-9-(tetrahydro-2H-pyran-4-yl)-7H-purin-8(9H)-one. Pale yellow solid. Synthesized from 2-(2-amino-5-fluorophenylamino)-6-chloro-9-(tetrahydro-2H-pyran-4-yl)-7H-purin-8(9H)-one (160 mg, 0.42 mmol) in anhydrous methanol (10 mL), using anhydrous trimethylorthoformate (1 mL) and methane sulfonic acid (5 drops) with stirring under Ar at room temperature for 2 h (HPLC monitoring). The solvent was removed in vacuo and the residue purified by column chromatography (silica gel, gradual elution with 2% methanol in methylene chloride to 10% methanol in methylene chloride) to afford the desired product (120 mg, 73% yield). $^1$H NMR (300 MHz, CDCl$_3$+CD$_3$OD) δ, ppm: 9.03 (s, 1H), 8.40-8.20 (m, 1H), 7.82-7.72 (m, 1H), 7.17-7.11 (m, 1H), 4.72-4.58 (m, 1H), 4.28-4.13 (m, 2H), 3.70-3.62 (m, 2H), 2.90-2.72 (m, 2H), 1.90-1.78 (m, 2H); MS (EI) m/z 389.2 $(MH)^+$.

6-chloro-2-(6-chloro-1H-benzo[d]imidazol-1-yl)-9-(tetrahydro-2H-pyran-4-yl)-7H-purin-8(9H)-one. Pale yellow solid. 46% yield on 2 steps (reduction and benzimidazole closing), on 2.47 mmol scale. Synthesized from 2-(2-amino-5-chlorophenylamino)-6-chloro-9-(tetrahydro-2H-pyran-4-yl)-7H-purin-8(9H)-one. $^1$H NMR (300 MHz, CDCl$_3$+CD$_3$OD) δ, ppm: 9.08 (s, 1H), 8.61 (s, 1H), 7.74 (d, 1H), 7.40 (d, 1H), 4.65-4.58 (m, 1H), 4.23-4.19 (m, 2H), 3.62 (appt, 2H), 2.82-2.76 (m, 2H), 1.93 (br d, 2H); MS (EI) m/z 405.2 $(MH)^+$.

3-(6-chloro-8-oxo-9-(tetrahydro-2H-pyran-4-yl)-8,9-dihydro-7H-purin-2-yl)-3H-benzo[d]imidazole-5-carbonitrile. Pale yellow solid. 73% yield (0.42 mmol scale). Synthesized from 4-amino-3-(6-chloro-8-oxo-9-(tetrahydro-2H-pyran-4-yl)-8,9-dihydro-7H-purin-2-ylamino)benzonitrile. $^1$H NMR (300 MHz, CDCl$_3$+CD$_3$OD) δ, ppm: 9.27 (s, 1H), 8.99 (s, 1H), 7.93 (d, 1H), 7.71 (d, 1H), 4.72-4.58 (m, 1H), 4.23-4.19 (m, 2H), 3.64-3.62 (m, 2H), 2.82-2.78 (m, 2H), 1.90-1.85 (m, 2H); MS (EI) m/z 396.2 $(MH)^+$.

Method 1

General procedure for cross-coupling reactions of 6-chloropurinones with (hetero)arylboronic acids. Ethanol (2 mL) was added to an argon-purged vial containing 6-chloro-2-(6-fluoro-1H-benzo[d]imidazol-1-yl)-9-(tetrahydro-2H-pyran-4-yl)-7H-purin-8(9H)-one (25 mg, 0.064 mmol), (hetero)aryl boronic acid (0.128 mmol, 2 equiv.), Pd(PPh$_3$)$_4$ (7 mg, 0.006 mmol, 0.1 equiv.) and a 2M aqueous solution of Na$_2$CO$_3$ (200 µL), and the mixture was heated for 30 min in the microwave oven at 150° C. After cooling to ambient temperature, the reaction mixture was diluted with ethanol, filtered through a Nylon 0.45 µm filter and the filtrate concentrated in vacuo. Preparative HPLC purification of the residue afforded, after evaporation and drying, the desired compound.

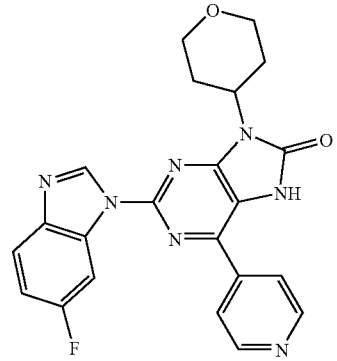

2-(6-fluoro-1H-benzo[d]imidazol-1-yl)-6-(pyridin-4-yl)-9-(tetrahydro-2H-pyran-4-yl)-7H-purin-8(9H)-one. White solid. TFA salt. 56% yield. Prepared from pyridine-4-yl boronic acid. $^1$H NMR (300 MHz, CDCl$_3$+CD$_3$OD) δ, ppm: 9.22 (br s, 1H), 8.97 (br m, 2H), 8.37 (d, 1H), 8.22 (br m, 2H), 7.91-7.82 (m, 1H), 7.28-7.19 (m, 1H), 4.83-4.71 (m, 1H), 4.35-4.23 (m, 2H), 3.69 (app t, 2H), 3.01-2.82 (m, 2H), 1.92 (br d, 2H); MS (EI) m/z 432.2 $(MH)^+$.

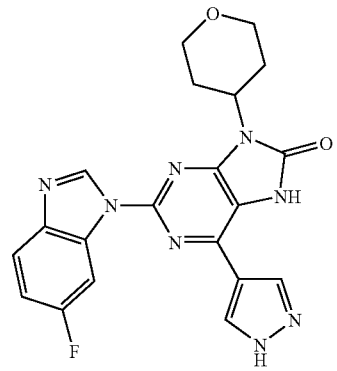

2-(6-fluoro-1H-benzo[d]imidazol-1-yl)-6-(1H-pyrazol-4-yl)-9-(tetrahydro-2H-pyran-4-yl)-7H-purin-8(9H)-one. TFA salt. 10% yield. Prepared from 1H-pyrazole-4-boronic acid. ¹H NMR (300 MHz, CDCl₃+CD₃OD) δ, ppm: 9.22 (br s, 1H), 8.47-8.30 (m, 3H), 7.83-7.72 (m, 1H), 7.23-7.11 (m, 1H), 4.73-4.61 (m, 1H), 4.25-4.13 (m, 2H), 3.61 (app t, 2H), 2.92-2.73 (m, 2H), 1.83 (br d, 2H); MS (EI) m/z 421.4 (MH)⁺.

Method 2

General procedure for displacement reactions of 6-chloropurinones with aliphatic benzylic amine. To 0.049 mmol of 6-chloro-2-(6-substituted-1H-benzo[d]imidazol-1-yl)-9-(tetrahydro-2H-pyran-4-yl)-7H-purin-8(9H)-one dissolved in 1 mL of DMSO was added 1 mL of 1-butanol, followed by an aliphatic/benzylic amine (0.2 mmol, 4 equiv.), and the reaction mixture was stirred at 110° C. for 18 h (HPLC monitoring). Upon completion of the reaction, the mixture was left to cool to room temperature, was diluted with acetonitrile and filtered through a Nylon 0.45 μm filter. Preparative HPLC purification afforded, after solvent evaporation and drying, the desired product.

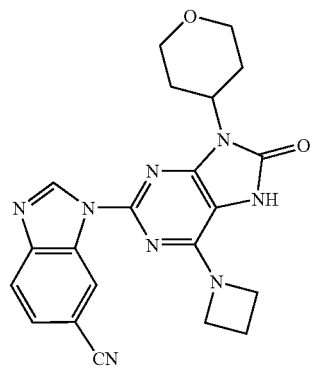

3-(6-(azetidin-1-yl)-8-oxo-9-(tetrahydro-2H-pyran-4-yl)-8,9-dihydro-7H-purin-2-yl)-3H-benzo[d]imidazole-5-carbonitrile. White solid. ¹H NMR (300 MHz, d₆-DMSO) δ, ppm: 11.13 (br s, 1H), 9.24 (s, 1H), 8.86 (d, J=0.9 Hz, 1H), 7.96 (d, J=8.4 Hz, 1H), 7.75 (dd, 1H), 4.60-4.40 (m, 1H), 4.34 (t, 4H), 4.05-4.00 (dd, 2H), 3.51-3.38 (dd, 2H), 2.61-2.42 (m, 4H), 1.72 (br d, 2H); MS (EI) m/z 417.1 (MH)⁺.

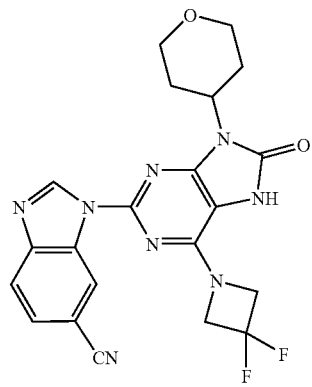

3-(6-(3,3-difluoroazetidin-1-yl)-8-oxo-9-(tetrahydro-2H-pyran-4-yl)-8,9-dihydro-7H-purin-2-yl)-3H-benzo[d]imidazole-5-carbonitrile. White solid. TFA salt. ¹H NMR (300 MHz, CDCl₃+CD₃OD) δ, ppm: 9.17 (s, 1H), 8.87 (br s, 1H), 7.88 (d, 1H), 7.64 (dd, 1H), 4.71 (t, 4H), 4.62-4.52 (m, 1H), 4.17 (dd, 2H), 3.58 (app t, 2H), 2.84-2.68 (m, 2H), 1.79 (br d, 2H); MS (EI) m/z 453.1 (MH)⁺.

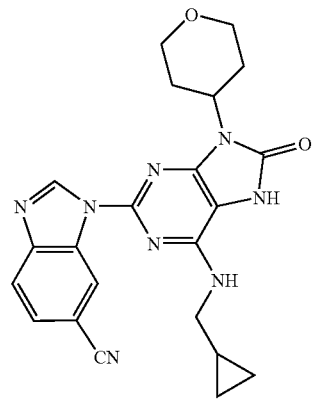

3-(6-(cyclopropylmethylamino)-8-oxo-9-(tetrahydro-2H-pyran-4-yl)-8,9-dihydro-7H-purin-2-yl)-3H-benzo[d]imidazole-5-carbonitrile. Pale yellow solid. TFA salt. ¹H NMR (300 MHz, CDCl₃+CD₃OD) δ, ppm: 9.23 (s, 1H), 9.01 (s, 1H), 7.88 (d, 1H), 7.63 (dd, 1H), 4.62-4.44 (m, 1H), 4.18 (dd, 2H), 3.60 (app t, 2H), 3.52 (d, 2H), 2.87-2.73 (m, 2H), 1.83 (br d, 2H), 1.26-1.20 (m, 1H), 0.67-0.61 (dd, 2H), 0.37 (d, 2H); MS (EI) m/z 431.2 (MH)⁺.

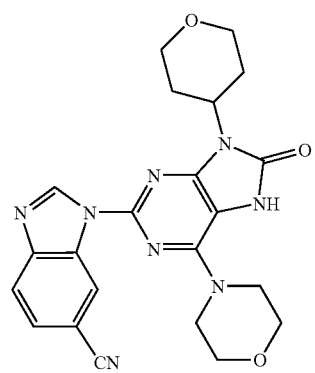

3-(6-morpholino-8-oxo-9-(tetrahydro-2H-pyran-4-yl)-8,9-dihydro-7H-purin-2-yl)-3H-benzo[d]imidazole-5-carbonitrile. White solid. ¹H NMR (300 MHz, CDCl₃+CD₃OD) δ, ppm: 9.19 (s, 1H), 8.91 (s, 1H), 7.89 (d, 1H), 7.65 (d, 1H), 4.72-4.58 (m, 1H), 4.19 (dd, 2H), 3.91-3.87 (m, 4H), 3.79-3.75 (m, 4H), 3.60 (app t, 2H), 2.99-2.78 (m, 2H), 1.83 (br d, 2H); MS (EI) m/z 447.1 (MH)⁺.

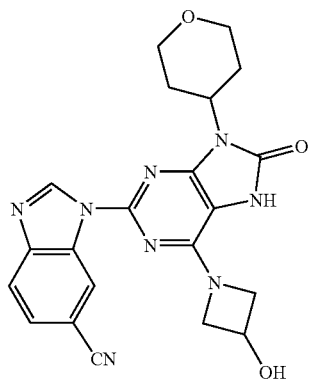

2-(6-chloro-1H-benzo[d]imidazol-1-yl)-6-(3-hydroxyazetidin-1-yl)-9-(tetrahydro-2H-pyran-4-yl)-7H-purin-8(9H)-one. Pale yellow solid (TFA salt). $^1$H NMR (300 MHz, CDCl$_3$+CD$_3$OD) δ, ppm: 9.17 (s, 1H), 8.68 (s, 1H), 7.71 (d, 1H), 7.37 (d, 1H), 4.85-4.64 (m, 1H), 4.78-4.53 (m, 3H), 4.23-4.17 (m, 4H), 3.62 (appt, 2H), 2.88-2.76 (m, 2H), 1.83 (br d, 2H); MS (EI) m/z 442.1 (MH)$^+$.

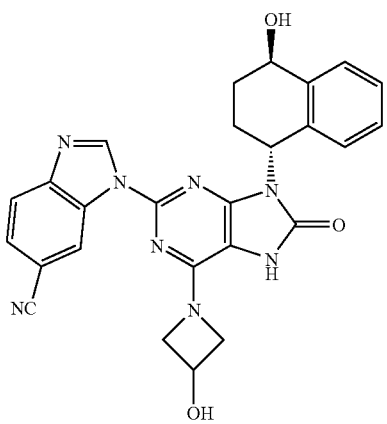

3-(9((1R,4R)-4-hydroxy-1,2,3,4-tetrahydronaphthalen-1-yl)-6-(3-hydroxyazetidin-1-yl)-8-oxo-8,9-dihydro-7H-purin-2-yl)-3H-benzo[d]imidazole-5-carbonitrile. Synthesis of the foregoing purinone is accomplished according to the reaction sequence presented in Route A with the modification that the first step involves the reaction of 2,5-diaminio-4,6-dichloropyrimidine with (1R,4R)-4-amino-1,2,3,4-tetrahydronaphthalen-1-ol) to give (1R,4R)-4-(2,5-diamino-6-chloropyrimidin-4-ylamino)-1,2,3,4-tetrahydronaphthalen-1-ol. A suitable protection for the alcohol is to be used. The subsequent reaction sequence is then carried out as presented to give, after deprotection of the alcohol, the desired product.

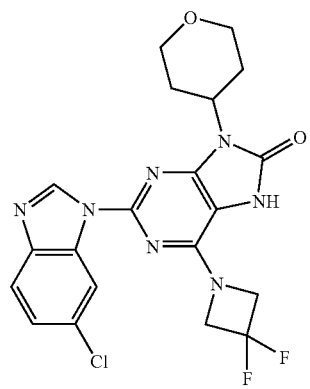

2-(6-chloro-1H-benzo[d]imidazol-1-yl)-6-(3,3-difluoroazetidin-1-yl)-9-(tetrahydro-2H-pyran-4-yl)-7H-purin-8(9H)-one. White solid (HCl salt). Yield 57%. $^1$H NMR (300 MHz, CDCl$_3$+CD$_3$OD) δ, ppm: 10.07 (s, 1H), 8.83 (s, 1H), 7.87 (d, 1H), 7.66 (d, 1H), 4.79 (app t, 4H), 4.65-4.60 (m, 1H), 4.23-4.17 (m, 2H), 3.63 (appt, 2H), 2.85-2.78 (m, 2H), 1.86 (br d, 2H); MS (EI) m/z 462.1 (MH)$^+$.

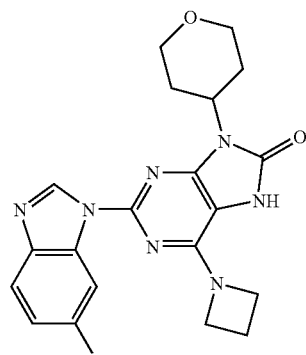

6-(azetidin-1-yl)-2-(6-chloro-1H-benzo[d]imidazol-1-yl)-9-(tetrahydro-2H-pyran-4-yl)-7H-purin-8(9H)-one. White solid (TFA salt). $^1$H NMR (300 MHz, CDCl$_3$+CD$_3$OD) δm, ppm: 9.07 (s, 1H), 8.67 (s, 1H), 7.70 (d, 1H), 7.35 (d, 1H), 4.65-4.60 (m, 1H), 4.43 (app t, 4H), 4.23-4.17 (m, 2H), 3.62 (appt, 2H), 2.85-2.78 (m, 2H), 2.68-2.53 (m, 2H), 1.83 (br d, 2H); MS (EI) m/z 426.1 (MH)$^+$.

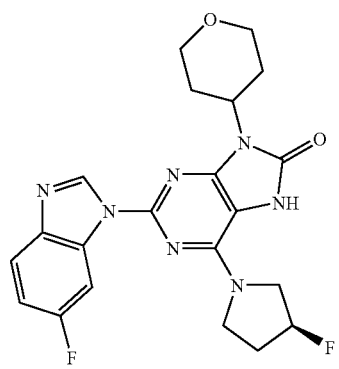

2-(6-fluoro-1H-benzo[d]imidazol-1-yl)-6-((S)-3-fluoro-pyrrolidin-1-yl)-9-(tetrahydro-2H-pyran-4-yl)-7H-purin-8(9H)-one. White solid. TFA salt. $^1$H NMR (300 MHz, CDCl$_3$+CD$_3$OD) δ, ppm: 9.20 (br s, 1H), 8.40-8.31 (m, 1H), 7.78-7.68 (m, 1H), 7.20-7.15 (m, 1H), 5.46 (d, $J_{H-C-F}$=52.6 HZ, 1H), 4.67-4.57 (m, 1H), 4.21-3.90 (m, 6H), 3.61 (appt, 2H), 2.84-2.76 (m, 2H), 2.48-2.16 (m, 2H), 1.81 (br d, 2H); MS (EI) m/z 442.1 (MH)$^+$.

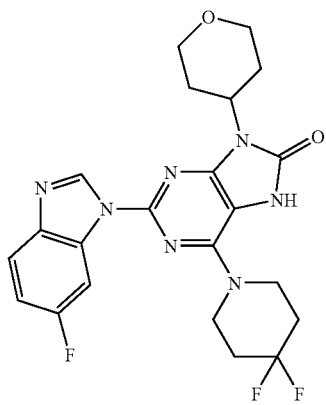

6-(4,4-difluoropiperidin-1-yl)-2-(6-fluoro-1H-benzo[d]imidazol-1-yl)-9-(tetrahydro-2H-pyran-4-yl)-7H-purin-8(9H)-one. White solid. TFA salt. $^1$H NMR (300 MHz, CDCl$_3$+CD$_3$OD) δ, ppm: 9.34 (s, 1H), 8.31-8.27 (m, 1H), 7.81-7.76 (m, 1H), 7.27-7.20 (m, 1H), 4.67-4.57 (m, 1H), 4.20 (dd, 2H), 3.91 (t, 4H), 3.63 (appt, 2H), 2.91-2.76 (m, 2H), 2.25-2.11 (m, 4H), 1.84 (br d, 2H); MS (EI) m/z 474.0 (MH)$^+$.

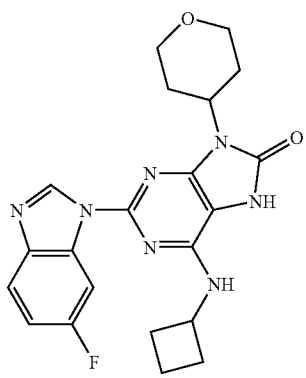

6-(cyclobutylamino)-2-(6-fluoro-1H-benzo[d]imidazol-1-yl)-9-(tetrahydro-2H-pyran-4-yl)-7H-purin-8(9H)-one. Pale yellow solid. TFA salt. $^1$H NMR (300 MHz, CDCl$_3$+CD$_3$OD) δ, ppm: 9.09 (s, 1H), 8.37-8.33 (m, 1H), 7.75-7.69 (m, 1H), 7.17-7.14 (m, 1H), 4.73-4.67 (m, 1H), 4.64-4.57 (m, 1H), 4.19 (dd, 2H), 3.62 (appt, 2H), 2.87-2.76 (m, 2H), 2.59-2.55 (m, 2H), 2.09-1.81 (m, 6H); MS (EI) m/z 424.2 (MH)$^+$.

Method 3

Typical procedure for cross-coupling reactions of 6-chloropurinones with organozinc halides. THF (3 mL) was added to an argon-purged vial containing 6-chloro-2-(6-fluoro-1H-benzo[d]imidazol-1-yl)-9-(tetrahydro-2H-pyran-4-yl)-7H-purin-8(9H)-one (0.2 mmol) and Pd(PPh$_3$)$_4$ (0.05 equiv.). The mixture was stirred at room temperature for 10 min, and then a 0.5 M solution of an organozinc reagent in THF (15 equiv.) was added dropwise at room temperature. The stirring at room temperature was continued for 15 min, followed by stirring at 50° C. for 3 h. The reaction mixture was left to cool to room temperature, the solvent was removed in vacuo, acetonitrile was added to the residue and the mixture filtered through a Nylon 0.45 µm filter. Preparative HPLC purification afforded, after evaporation and drying, the desired compound.

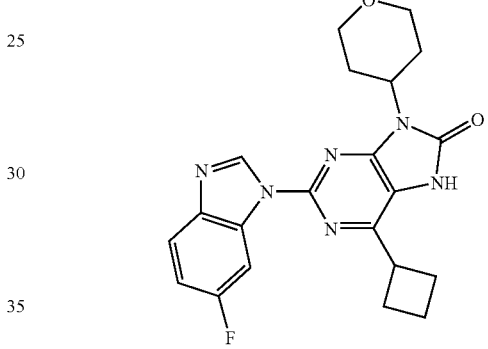

6-cyclobutyl-2-(6-fluoro-1H-benzo[d]imidazol-1-yl)-9-(tetrahydro-2H-pyran-4-yl)-7H-purin-8(9H)-one. White semi-solid, prepared using a 0.5 M solution of cyclobutylzinc bromide in THF. $^1$H NMR (300 MHz, CDCl$_3$+CD$_3$OD) δ, ppm: 9.26 (s, 1H), 8.49 (d, 1H), 7.79-7.73 (m, 1H), 7.22-7.16 (m, 1H), 4.73-4.67 (m, 1H), 4.19 (dd, 2H), 3.94-3.82 (m, 1H), 3.63 (appt, 2H), 2.90-2.76 (m, 2H), 2.70-2.57 (m, 2H), 2.53-2.42 (m, 2H), 2.31-2.08 (m, 2H), 1.98-1.83 (m, 2H); MS (EI) m/z 409.1 (MH)$^+$.

Method 4

General procedure for displacement reactions of 6-chloropurinones with alcohols. 6-chloro-2-(6-fluoro-1H-benzo[d]imidazol-1-yl)-9-(tetrahydro-2H-pyran-4-yl)-7H-purin-8(9H)-one (0.128 mmol) was taken in a dry microwave vial. To it was added an aliphatic or aromatic alcohol (1-10 equiv), cesium carbonate (10 equiv.) and DMF. The sealed reaction tube was subjected to microwave heating at 200° C. for 4 h. Completion of the reaction was checked by LC-MS. Solvent was removed under high vacuum, the residue was dissolved in MeOH and filtered through a Nylon 0.45 µm filter. Preparative HPLC purification afforded, after solvent evaporation and drying, the desired product.

2-(6-fluoro-1H-benzo[d]imidazol-1-yl)-6-pyridin-3-yloxy)-9-(tetrahydro-2H-pyran-4-yl)7H-purin-8(9H)-one

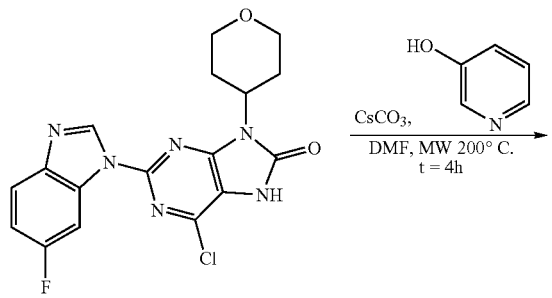

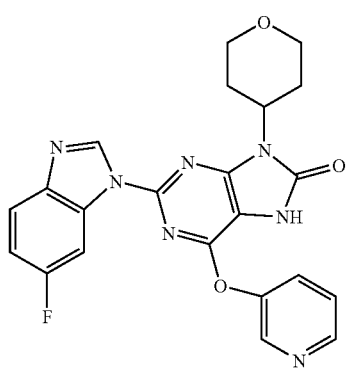

Synthesized using 3-hydroxypyridine (12.2 mg, 0.128 mmol, 1 equiv). ¹H NMR (300 MHz, CD₃OD) δ, ppm: 9.20 (br s, 2H), 8.10 (d, 2H), 7.80 (br m, 2H), 7.45 (br m, 1H), 7.15 (br m, 1H), 4.80-4.63 (m, 1H), 4.18 (dd, 2H), 3.65 (app t, 2H), 2.90-2.72 (m, 2H), 1.92-1.82 (m, 2H); MS (EI) m/z 448.1 (MH)⁺.

6-cyclobutoxy-2-(6-fluoro-1H-benzo[d]imidazol-1-yl)-9-(tetrahydro-2H-pyran-4-yl)-7H-purin-8(9H)-one

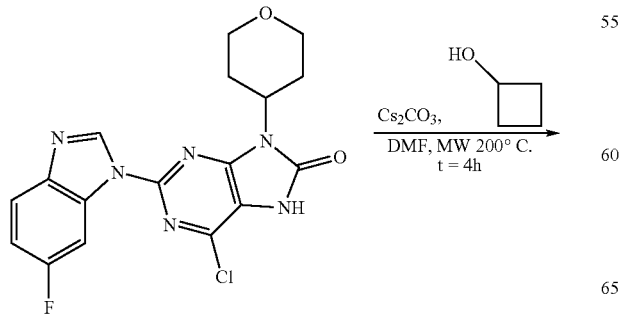

-continued

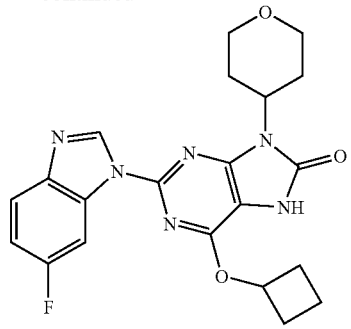

Synthesized using cyclobutanol (10 μL, 1.28 mmol, 10 equiv.). ¹H NMR (300 MHz, CDCl₃+CD₃OD) δ, ppm: 9.01 (s, 1H), 8.26 (dd, 1H), 7.77 (dd, 1H), 7.16 (td, 1H), 5.54-5.44 (m, 1H), 4.68-4.56 (m, 1H), 4.22 (dd, 2H), 3.62 (appt, 2H), 2.89-2.72 (m, 2H), 2.70-2.58 (m, 2H), 2.40-2.24 (m, 2H), 2.06-1.92 (m, 1H), 1.92-1.80 (m, 3H); MS (EI) m/z 425.1 (MH)⁺.

Variant B

Typical Procedure for N-7 alkylation/methylation. To a solution of 2-(6-chloro-1H-benzo[d]imidazol-1-yl)-6-(3,3-difluoroazetidin-1-yl)-9-(tetrahydro-2H-pyran-4-yl)-7H-purin-8(9H)-one (15 mg, 0.033 mmol) in CH₃CN (5 mL) was added polystyrene supported BEMP (2-tert.butylimino-2-diethylamino-1,3-dimethyl-perhydro-1,3,2-diazaphosphorine (Fluka, loading 2.2 mmol/g) (4 equiv.), followed by alkyl iodide/iodomethane (6 equiv.). The reaction mixture was stirred at room temperature for 1 h. Completion of the reaction mixture was checked by HPLC and MS. The reaction mixture was filtered and the resin was washed with CH₃CN (5 mL×2) and MeOH (5 mL×2). The washings and the filtrate were combined and concentrated in vacuo to give the desired compound.

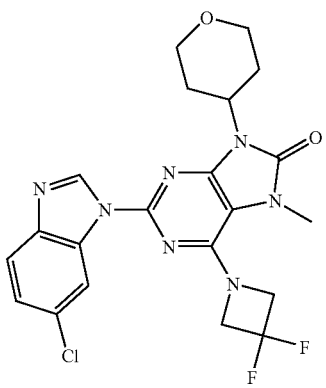

2-(6-chloro-1H-benzo[d]imidazol-1-yl)-6-(3,3-difluoroazetidin-1-yl)-7-methyl-9-(tetrahydro-2H-pyran-4-yl)-7H-purin-8(9H)-one. White solid. ¹H NMR (300 MHz, CDCl₃+CD₃OD) δ, ppm: 9.22 (s, 1H), 8.63 (s, 1H), 7.73 (br d, 1H), 7.37 (br d, 1H), 4.79 (app t, 4H), 4.65-4.60 (m, 1H), 4.23-4.13 (m, 2H), 3.65 (appt, 2H), 3.57 (s, 3H), 2.85-2.78 (m, 2H), 1.82 (br d, 2H); MS (EI) m/z 476.2 (MH)⁺.

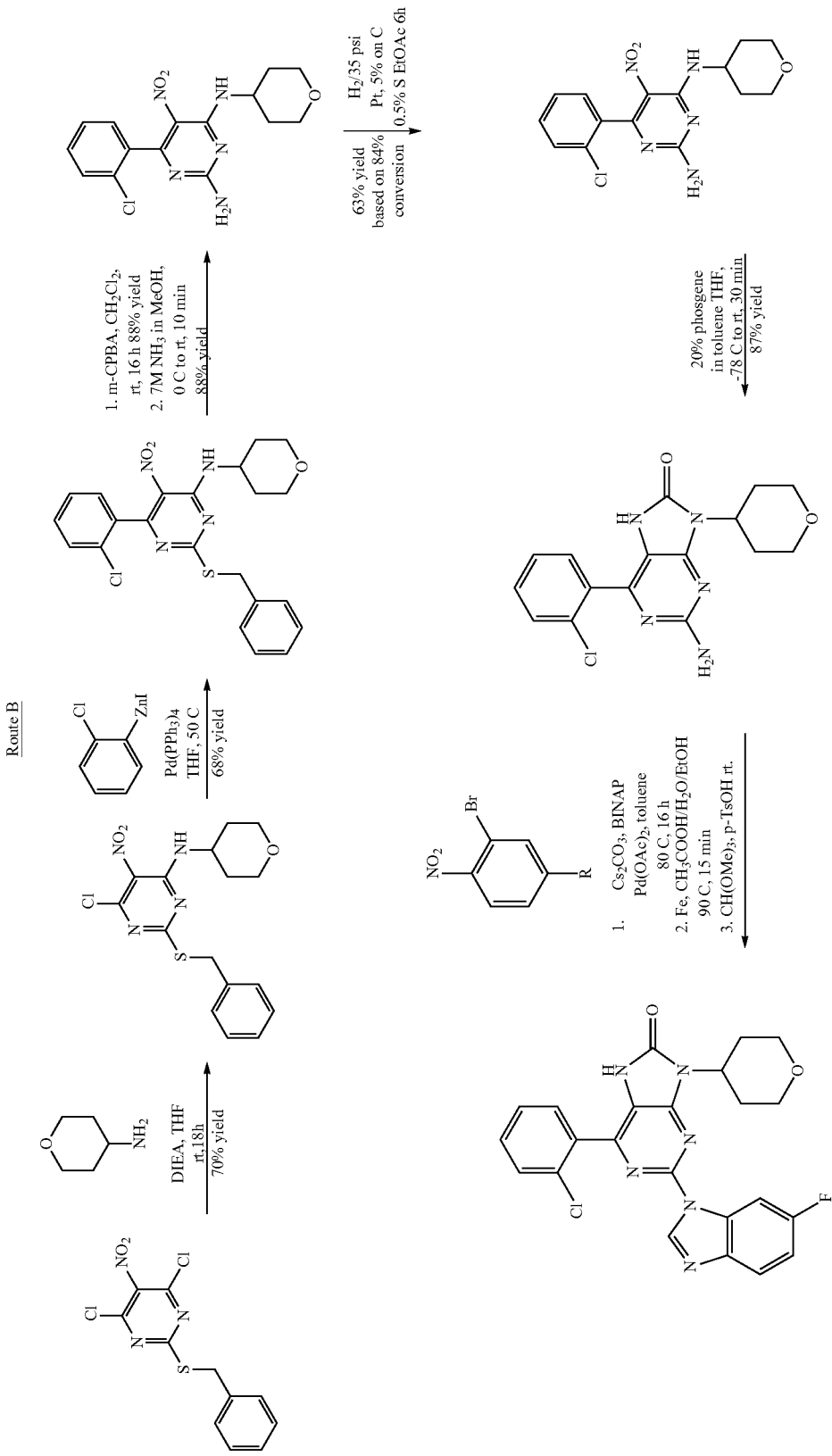

2-(benzylthio)-6-chloro-5-nitro-N-(tetrahydro-2H-pyran-4-yl)pyrimidin-4-amine. To a solution of 2-(benzylthio)-4,6-dichloro-5-nitropyrimidine (WO 01/58906 A1) (9 g, 28.5 mmol) in THF (60 mL) and DIEA (9.9 mL, 7.36 g, 57 mmol, 2 equiv.) was added drop wise a solution of 4-aminotetrahydropyran (2.77 g, 27.4 mmol, 0.96 equiv.) in THF (20 mL) over 15 min. The reaction mixture was stirred at room temperature for 18 h. The solvent was then removed in vacuo and the residue purified by column chromatography (silica gel, elution with 4/1 hexanes/ethyl acetate) to afford, after evaporation and drying, the desired product as a yellow solid (7.59 g, 70% yield). $^1$H NMR (300 MHz, CDCl$_3$) δ, ppm: 7.86 (br d, J=6.8 Hz, 1H), 7.42-7.36 (m, 2H), 7.36-7.27 (m, 3H), 4.38 (s, 2H), 4.31-4.20 (m, 1H), 3.96 (dt, J=11.7, 3.5 Hz, 2H), 3.47 (ddd, J=11.7, 11.3, 2.2 Hz, 2H), 1.92 (br dd, J=12.4, 2.2 Hz, 2H), 1.66-1.52 (m, 2H).

General procedure for cross-coupling reactions of 2-(benzylthio)-6-chloro-5-nitro-N-(tetrahydro-2H-pyran-4-yl)pyrimidin-4-amine with organozinc halides. In an oven dried flask under Ar, Pd(PPh$_3$)$_4$ (152 mg, 0.13 mmol, 0.05 equiv.) was added to a solution of 2-(benzylthio)-6-chloro-5-nitro-N-(tetrahydro-2H-pyran-4-yl)pyrimidin-4-amine (1 g, 2.63 mmol, 1.0 equiv.) in THF (26 mL). The mixture was stirred under Ar for 10 min, then it was cooled to 0° C. and the organozinc halide reagent (0.5 M solution in THF, 1.5 equiv.) was added drop wise, under Ar, within 30 min. The reaction mixture was then warmed up to room temperature, and subsequently heated to 50° C. for 3 days. Upon completion of the reaction, the mixture was poured into a saturated aqueous NH$_4$Cl solution. Extraction into ethyl acetate (3×100 mL), washing of the combined organic layers with brine (1×100 mL), drying (Na$_2$SO$_4$), and solvent removal in vacuo afforded a brown residue, which was purified by column chromatography to give the desired product.

2-(benzylthio)-6-(2-chlorophenyl)-5-nitro-N-(tetrahydro-2H-pyran-4-yl)pyrimidin-4-amine. Yellow solid. 0.81 g, 68% yield. Synthesized using 2-chlorophenylzinc iodide, 0.5 M in THF (7.9 mL, 3.95 mmol, 1.5 equiv.). Column chromatography purification: silica gel, elution with 6/1 hexanes/ethyl acetate. $^1$H NMR (300 MHz, CDCl$_3$) δ, ppm: 8.20 (br d, 1H), 7.42-7.27 (m, 9H), 4.41 (s, 2H), 4.41-4.32 (m, 1H, overlapping with 4.41 ppm), 4.02-3.94 (m, 2H), 3.55-3.47 (m, 2H), 1.99-1.94 (m, 2H), 1.64-1.56 (m, 2H); MS (EI) m/z 457.1 (MH)$^+$.

4-(2-(benzylthio)-5-nitro-6-(tetrahydro-2H-pyran-4-ylamino)pyrimidin-4-yl)benzonitrile. 0.39 g, 33% yield. Synthesized using 4-cyanophenylzinc bromide, 0.5 M in THF (8 mL, 4 mmol, 1.5 equiv.). Column chromatography purification: silica gel, gradual elution with 9/1 to 4/1 hexanes/ethyl acetate. $^1$H NMR (300 MHz, CDCl$_3$) δ, ppm: 7.88 (br d, 1H), 7.73 (d, 2H), 7.54 (d, 2H), 7.41-7.27 (m, 5H), 4.41 (s, 2H), 4.41-4.32 (m, 1H, overlapping with 4.41 ppm), 4.02-3.96 (m, 2H), 3.55-3.46 (m, 2H), 1.99-1.94 (m, 2H), 1.64-1.55 (m, 2H); MS (EI) m/z 448.1 (MH)$^+$.

General procedure for the oxidation of 2-(benzylthio)-6-substituted-5-nitro-N-(tetrahydro-2H-pyran-4-yl)pyrimidin-4-amine to 2-(benzylsulfonyl)-6-substituted-5-nitro-N-(tetrahydro-2H-pyran-4-yl)pyrimidin-4-amine. A solution of mCPBA (4.11 mmol, 2.3 equiv.) in methylene chloride (20 mL) was dried over anhydrous Na$_2$SO$_4$ and added dropwise, under Ar, to a solution of 2-(benzylthio)-6-substituted-5-nitro-N-(tetrahydro-2H-pyran-4-yl)pyrimidin-4-amine (1.78 mmol, 1.0 equiv.) in 50 mL of anhydrous methylene chloride at 0° C. The reaction mixture was then stirred at room temperature for 18 h. Upon completion of the reaction, the mixture was washed repeatedly with a saturated aqueous solution of NaHCO$_3$ (6×100 mL), the organic layer was washed with water (1×100 mL), dried (Na$_2$SO$_4$), and the solvent removed in vacuo.

2-(benzylsulfonyl)-6-(2-chlorophenyl)-5-nitro-N-(tetrahydro-2H-pyran-4-yl)pyrimidin-4-amine. Orange solid. 0.87 g, yield quantitative. Synthesized from 2-(benzylthio)-6-(2-chlorophenyl)-5-nitro-N-(tetrahydro-2H-pyran-4-yl)pyrimidin-4-amine. $^1$H NMR (300 MHz, CDCl$_3$) δ, ppm: 7.92 (br d, 1H), 7.50-7.27 (m, 9H), 4.74 (s, 2H), 4.51-4.41 (m, 1H), 4.02-3.98 (m, 2H), 3.61-3.52 (m, 2H), 2.07-2.01 (m, 2H), 1.71-1.57 (m, 2H); MS (EI) m/z 489.2 (MH)$^+$.

4-(2-(benzylsulfonyl)-5-nitro-6-(tetrahydro-2H-pyran-4-ylamino)pyrimidin-4-yl)benzonitrile. Yield quantitative. Synthesized from 4-(2-(benzylthio)-5-nitro-6-(tetrahydro-2H-pyran-4-ylamino)pyrimidin-4-yl)benzonitrile. $^1$H NMR (300 MHz, CDCl$_3$) δ, ppm: 7.96 (br d, 1H), 7.78 (d, 2H), 7.62 (d, 2H), 7.47-7.28 (m, 5H), 4.75 (s, 2H), 4.51-4.41 (m, 1H), 4.04-3.98 (m, 2H), 3.61-3.55 (m, 2H), 2.04-2.00 (m, 2H), 1.71-1.57 (m, 2H); MS (EI) m/z 480.2 (MH)$^+$.

General procedure for the displacement of 2-(benzylsulfonyl)-6-substituted-5-nitro-N-(tetrahydro-2H-pyran-4-yl)pyrimidin-4-amine with ammonia. To a solution of 2-(benzylsulfonyl)-6-substituted-5-nitro-N-(tetrahydro-2H-pyran-4-yl)pyrimidin-4-amine (1.58 mmol) in 80 mL anhydrous methylene chloride at 0° C. was added dropwise 4 mL of a 7 M solution of ammonia in methanol. Upon completion of the reaction (5-10 min), the solvent was removed in vacuo. The residue was taken in ethyl acetate/ethyl ether 100 mL/100 mL, washed with a saturated aqueous solution of ammonium chloride (2×100 mL), followed by a saturated aqueous solution of sodium carbonate (2×100 mL), and brine (1×100 mL). The organic layer was dried (Na$_2$SO$_4$), then concentrated in vacuo.

6-(2-chlorophenyl)-5-nitro-N$^4$-(tetrahydro-2H-pyran-4-yl)pyrimidine-2,4-diamine. Pale yellow solid. 0.48 g, 87% yield. Synthesized from 2-(benzylsulfonyl)-6-(2-chlorophenyl)-5-nitro-N-(tetrahydro-2H-pyran-4-yl)pyrimidin-4-amine. $^1$H NMR (300 MHz, CDCl$_3$+CD$_3$OD) δ, ppm: 7.52-7.29 (m, 4H), 4.51-4.41 (m, 1H), 4.04-3.90 (m, 2H), 3.78-3.52 (m, 2H), 2.07-2.01 (m, 2H), 1.71-1.64 (m, 2H); MS (EI) m/z 350.3 (MH)$^+$.

4-(2-amino-5-nitro-6-(tetrahydro-2H-pyran-4-ylamino)pyrimidin-4-yl)benzonitrile. Pale yellow solid. 75% yield. Synthesized from 4-(2-(benzylsulfonyl)-5-nitro-6-(tetrahydro-2H-pyran-4-ylamino)pyrimidin-4-yl)benzonitrile. MS (EI) m/z 341.2 (MH)$^+$.

General procedure for the reduction of 6-substituted-5-nitro-N$^4$-(tetrahydro-2H-pyran-4-yl)pyrimidine-2,4-diamine. To 6-substituted-5-nitro-N$^4$-(tetrahydro-2H-pyran-4-yl)pyrimidine-2,4-diamine (1.57 mmol, 1.0 equiv.) was added ethyl acetate (75 mL), followed by Pt catalyst, 0.5% sulfur, 5% on activated carbon (Alfa Aesar) (304 mg, 0.078 mmol, 0.05 equiv.) with stirring at room temperature under hydrogen (35 psi) for 6 h (HPLC monitoring). Filtration of the reaction mixture over a small plug of celite, thorough washing with ethyl acetate and methanol, evaporation of solvent and column chromatography of the residue afforded the desired product.

6-(2-chlorophenyl)-N$^4$-(tetrahydro-2H-pyran-4-yl)pyrimidine-2,4,5-triamine. Yellow solid. 0.26 g, 63% yield based on 84% conversion. Synthesized from 6-(2-chlorophenyl)-5-nitro-N$^4$-(tetrahydro-2H-pyran-4-yl)pyrimidine-2,4-diamine. Column chromatography on silica gel, elution with 9/1 methylene chloride/ethyl acetate to 4/1 methylene chloride/ethyl acetate with up to 10% methanol. $^1$H NMR (300 MHz, CD$_3$OD) δ, ppm: 7.52-7.42 (m, 1H), 7.35-7.27 (m, 3H), 4.21-4.10 (m, 1H), 3.93-3.77 (m, 2H), 3.51-3.42 (m, 2H), 1.97-1.91 (m, 2H), 1.55-1.50 (m, 2H); MS (EI) m/z 320.2 (MH)$^+$.

General procedure for the selective formation of the purinone from 6-substituted-N$^4$-(tetrahydro-2H-pyran-4-yl)pyrimidine-2,4,5-triamine. A solution of 6-substituted-N$^4$-(tetrahydro-2H-pyran-4-yl)pyrimidine-2,4,5-triamine (0.5 mmol, 1.0 equiv.) in 90 mL of anhydrous THF was added dropwise, over 30 min, to a solution of phosgene in THF (0.5 mL of a 20% solution of phosgene in toluene, 0.95 mmol, 1.9 equiv., diluted with 10 mL of anhydrous THF) at −78° C. under Ar. The reaction mixture was left to gradually warm up to room temperature, then stirred at room temperature for 30 min. It was purged with air for 30 min. The solvent was then removed in vacuo, and the residue was taken in ethyl acetate/saturated aqueous NaHCO$_3$. The layers were separated, and the aqueous layer extracted with ethyl acetate three times. The combined organic extracts were put together, dried (anhydrous Na$_2$SO$_4$) and the solvent removed in vacuo. Chromatographic purification afforded the desired product.

2-amino-6-(2-chlorophenyl)-9-(tetrahydro-2H-pyran-4-yl)-7H-purin-8(9H)-one. White solid. 150 mg, 87% yield. Synthesized from 6-(2-chlorophenyl)-N$^4$-(tetrahydro-2H-pyran-4-yl)pyrimidine-2,4,5-triamine. Preparative TLC purification on silica gel, elution with 3% methanol in methylene chloride. $^1$H NMR (300 MHz, CDCl$_3$+CD$_3$OD) δ, ppm: 7.57-7.41 (m, 4H), 4.58-4.47 (m, 1H), 4.15 (ddd, 2H), 3.58 (appt, J=11.7 Hz, 2H), 2.82 (ddd, 2H), 1.74 (br d, J=10.6 Hz, 2H); MS (EI) m/z 346.3 (MH)$^+$.

4-(2-amino-8-oxo-9-(tetrahydro-2H-pyran-4-yl)-8,9-dihydro-7H-purin-6-yl)benzonitrile. Synthesized from 4-(2,5-diamino-6-(tetrahydro-2H-pyran-4-ylamino)pyrimidin-4-yl)benzonitrile. $^1$H NMR (300 MHz, CDCl$_3$) δ, ppm: 7.98 (d, 2H), 7.82 (d, 2H), 7.42 (br d, 1H), 4.58-4.47 (m, 1H), 4.18-4.09 (m, 2H), 3.56 (app t, 2H), 2.93 (br s, 2H), 2.88-2.70 (m, 2H), 1.78-1.67 (m, 2H); MS (EI) m/z 337.3 (MH)$^+$.

General procedure for the Buchwald-Hartwig Palladium-catalyzed C—N cross coupling. An oven-dried vial was charged with 2-amino-6-substituted-9-(tetrahydro-2H-pyran-4-yl)-7H-purin-8(9H)-one (0.29 mmol, 1 equiv.), freshly grounded cesium carbonate (132 mg, 0.41 mmol, 1.4 equiv.), Pd(OAc)$_2$ (20 mg, 0.003 mmol, 0.1 equiv.), racemic BINAP (27 mg, 0.04 mmol, 0.15 equiv.) and 1-bromo-5-fluoro-2-nitrobenzene (83 mg, 0.38 mmol, 1.3 equiv.), followed by anhydrous toluene (2 mL). The vial was purged with Ar for 3 min, then closed and heated at 80° C. for 3 days. The reaction mixture was allowed to stand overnight at room temperature and poured into saturated aqueous NH$_4$Cl (10 mL). To this mixture, saturated aqueous Na$_2$EDTA (10 mL) was added and the mixture was stirred for 10 min. The mixture was extracted with ethyl acetate (3×20 mL), the collected organic layers were washed with brine, dried (anhydrous Na$_2$SO$_4$) and the solvent evaporated in vacuo. Column chromatography of the residue on silica gel, elution with 1% methanol in 4/2/1 hexane/methylene chloride/ethyl acetate afforded, after evaporation and drying, the desired product.

6-(2-chlorophenyl)-2-(5-fluoro-2-nitrophenylamino)-9-(tetrahydro-2H-pyran-4-yl)-7H-purin-8(9H)-one. Yellow solid. 22 mg, 16% yield. Synthesized from 2-amino-6-(2-chlorophenyl)-9-(tetrahydro-2H-pyran-4-yl)-7H-purin-8 (9H)-one. $^1$H NMR (300 MHz, CDCl$_3$) δ, ppm: 10.77 (s, 1H), 8.98 (dd, 1H), 8.34 (dd, 1H), 7.99 (s, 1H), 7.69-7.65 (m, 1H), 7.60-7.48 (m, 3H), 6.75-6.68 (m, 1H), 4.66-4.57 (m, 1H), 4.19 (dd, 2H), 3.59 (app t, J=11.7 Hz, 2H), 2.81 (ddd, 2H), 1.81 (br d, J=10.3 Hz, 2H); MS (EI) m/z 485.3 (MH)$^+$.

4-(2-(5-fluoro-2-nitrophenylamino)-8-oxo-9-(tetrahydro-2H-pyran-4-yl)-8,9-dihydro-7H-purin-6-yl)benzonitrile. Yellow solid. 15% yield. Synthesized from 4-(2-amino-8-oxo-9-(tetrahydro-2H-pyran-4-yl)-8,9-dihydro-7H-purin-6-yl)benzonitrile. MS (EI) m/z 476.2 (MH)$^+$.

General procedure for the reduction of the nitrophenyl group in 6-substituted-2-(5-fluoro-2-nitrophenylamino)-9-(tetrahydro-2H-pyran-4-yl)-7H-purin-8(9H)-one with iron powder. To a vial containing 6-substituted-2-(5-fluoro-2-nitrophenylamino)-9-(tetrahydro-2H-pyran-4-yl)-7H-purin-8 (9H)-one (0.045 mmol) was added glacial acetic acid (1 mL), water (2.5 mL) and ethanol (5 mL), followed by iron powder (26 mg, 0.45 mmol, 10 equiv.) and the resulting mixture heated at 90° C. for 15 min (HPLC monitoring). The reaction mixture was left to cool down to room temperature, concentrated ammonium hydroxide solution was added to bring the pH to basic, and the mixture was stirred for 10 min. The aqueous layer diluted with water (10 mL) was extracted with ethyl acetate (3×20 mL), the combined organic layers were washed with brine, dried (anhydrous Na$_2$SO$_4$), and the solvent removed in vacuo to give the desired product. This material was used in the next step without further purification.

2-(2-amino-5-fluorophenylamino)-6-(2-chlorophenyl)-9-(tetrahydro-2H-pyran-4-yl)-7H-purin-8(9H)-one. Pale yellow solid. 21 mg, yield quantitative. Synthesized from 6-(2-chlorophenyl)-2-(5-fluoro-2-nitrophenylamino)-9-(tetrahydro-2H-pyran-4-yl)-7H-purin-8(9H)-one. MS (EI) m/z 455.3 (MH)$^+$.

4-(2-(2-amino-5-fluorophenylamino)-8-oxo-9-(tetrahydro-2H-pyran-4-yl)-8,9-dihydro-7H-purin-6-yl)benzonitrile. Yield quantitative. Synthesized from 4-(2-(5-fluoro-2-nitrophenylamino)-8-oxo-9-(tetrahydro-2H-pyran-4-yl)-8,9-dihydro-7H-purin-6-yl)benzonitrile. MS (EI) m/z 446.3 (MH)$^+$.

General procedure for closing the benzimidazole ring. To a vial containing crude 2-(2-amino-5-fluorophenylamino)-6-substituted-9-(tetrahydro-2H-pyran-4-yl)-7H-purin-8(9H)-one (0.045 mmol) was added anhydrous methanol (4 mL), followed by anhydrous trimethylorthoformate (0.1 mL) and methane sulfonic acid (catalytic amount) and the reaction mixture was stirred under Ar at room temperature for 3 h (HPLC monitoring). Preparative TLC purification (silica gel, elution with 2.5% methanol in methylene chloride) afforded, after evaporation of solvent and drying, the desired product.

6-(2-chlorophenyl)-2-(6-fluoro-1H-benzo[d]imidazol-1-yl)-9-(tetrahydro-2H-pyran-4-yl)-7H-purin-8(9H)-one. White solid. 12 mg, 57% yield on two steps. Synthesized from 2-(2-amino-5-fluorophenylamino)-6-(2-chlorophenyl)-9-(tetrahydro-2H-pyran-4-yl)-7H-purin-8(9H)-one. $^1$H NMR (300 MHz, CDCl$_3$) δ, ppm: 9.12 (s, 1H), 8.32 (br d, 1H), 7.82-7.71 (m, 3H), 7.62-7.51 (m, 3H), 7.16-7.09 (m, 1H), 4.72-4.64 (m, 1H), 4.24-4.21 (m, 2H), 3.61 (app t, J=11.7 Hz, 2H), 2.87-2.79 (m, 2H), 1.88 (br d, J=11.4 Hz, 2H); MS (EI) m/z 465.2 (MH)$^+$.

4-(2-(6-fluoro-1H-benzo[d]imidazol-1-yl)-8-oxo-9-(tetrahydro-2H-pyran-4-yl)-8,9-dihydro-7H-purin-6-yl)benzonitrile. 11% yield on two steps. Synthesized from 4-(2-(2-amino-5-fluorophenylamino)-8-oxo-9-(tetrahydro-2H-pyran-4-yl)-8,9-dihydro-7H-purin-6-yl)benzonitrile. $^1$H NMR (300 MHz, CDCl$_3$+CD$_3$OD) δ, ppm: 9.12 (s, 1H), 8.32 (br d, 1H), 8.18 (d, 2H), 7.93 (d, 2H), 7.85-7.72 (m, 1H), 7.22-7.13 (m, 1H), 4.68-4.62 (m, 1H), 4.27-4.16 (m, 2H), 3.62 (app t, 2H), 2.92-2.77 (m, 2H), 1.86 (br dd, 2H); MS (EI) m/z 456.2 (MH)$^+$.

Route C

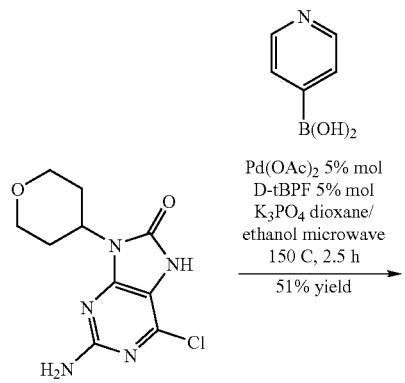

Pd(OAc)$_2$ 5% mol
D-tBPF 5% mol
K$_3$PO$_4$ dioxane/
ethanol microwave
150 C, 2.5 h
51% yield

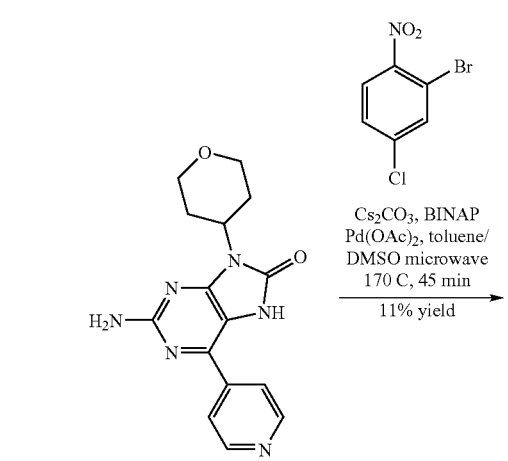

Cs$_2$CO$_3$, BINAP
Pd(OAc)$_2$, toluene/
DMSO microwave
170 C, 45 min
11% yield

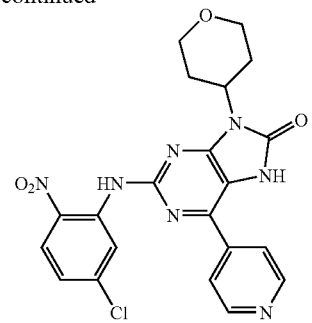

1. Fe, CH$_3$COOH/H$_2$O/EtOH
   90 C, 15 min
2. CH(OMe)$_3$, p-TsOH rt.

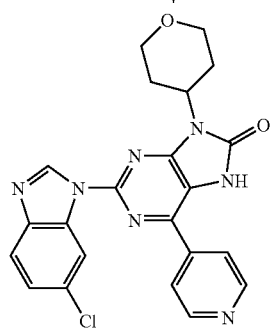

2-amino-6-(pyridin-4-yl)-9-(tetrahydro-2H-pyran-4-yl)-7H-purin-8(9H)-one. Anhydrous ethanol (2 mL) and anhydrous 1,4-dioxane (2 mL) were added to an argon-purged vial containing 2-amino-6-chloro-9-(tetrahydro-2H-pyran-4-yl)-7H-purin-8(9H)-one (see preparation Route A, 100 mg, 0.37 mmol), pyridine-4-boronic acid (69 mg, 0.56 mmol, 1.5 equiv.), K$_3$PO$_4$ (157 mg, 0.74 mmol, 2.0 equiv.), Pd(OAc)$_2$ (12.5 mg, 0.018 mmol, 0.05 equiv.) and D-tBPF 1,1'-bis(di-tbutylphosphino)ferrocene (8.8 mg, 0.018 mmol, 0.05 equiv.) and the mixture was heated for 2.5 h in the microwave oven at 150° C. After cooling to ambient temperature, the reaction mixture was diluted with methanol (20 mL), filtered through a Nylon 0.45 μm filter and the filtrate concentrated in vacuo. Preparative HPLC purification of the residue afforded, after evaporation and drying, the desired compound as a yellow solid (59.2 mg, 51% yield) TFA salt. $^1$H NMR (300 MHz, CD$_3$OD) δ, ppm: 8.92 (d, J=6.4 Hz, 2H), 8.17 (dd, J=5.1, 1.5 Hz, 2H), 4.87-4.55 (m, 1H), 4.10 (dd, J=11.4, 4.3 Hz, 2H), 3.56 (ddd, J=11.3, 6.5, 4.7 Hz, 2H), 2.74 (tdd, J=12.6, 12.5, 4.6 Hz, 2H), 1.77 (dd, J=12.4, 2.4 Hz, 2H); MS (EI) m/z 313.3 (MH)$^+$.

2-(5-chloro-2-nitrophenylamino)-6-(pyridin-4-yl)-9-(tetrahydro-2H-pyran-4-yl)-7H-purin-8(9H)-one. To an oven-dried vial was added 2-amino-6-(pyridin-4-yl)-9-(tetrahydro-2H-pyran-4-yl)-7H-purin-8(9H)-one (68 mg, 0.22 mmol, 1 equiv.) in anhydrous toluene (1 mL), then freshly grounded cesium carbonate (99.4 mg, 0.31 mmol, 1.4 equiv.) with stirring at room temperature under Ar. After 20 min, Pd(OAc)$_2$ (15 mg, 0.02 mmol, 0.1 equiv.), racemic BINAP (20.5 mg, 0.03 mmol, 0.15 equiv.) and 1-bromo-5-chloro-2-nitrobenzene (WO 02/053545 A1) (67.6 mg, 0.29 mmol, 1.3 equiv.) were added as solids, followed by anhydrous DMSO (1 mL). The vial was purged with Ar for 3 min, then closed and heated in a microwave oven at 170° C. for 45 min. The reaction mixture was cooled to room temperature, diluted with ethyl acetate/methylene chloride, filtered through a Nylon 0.45 μm filter, and the filtrate was concentrated in vacuo. The resulting residue was purified using preparative TLC (silica gel, 7.5% methanol in methylene chloride) to give the desired product as a brown solid (11 mg, 11% yield). $^1$H NMR (300 MHz, CDCl$_3$+CD$_3$OD) δ, ppm: 9.13 (s, 1H), 8.63 (br m, 2H), 8.13 (d, J=8.9 Hz, 1H), 7.83 (br m, 2H), 6.91 (d, J=8.6 Hz, 1H), 4.70-4.50 (m, 1H), 4.10-4.03 (m, 2H), 3.51-3.43 (m, 2H), 2.68-2.65 (m, 2H), 1.71-1.66 (m, 2H); MS (EI) m/z 468.4 (MH)$^+$.

2-(2-amino-5-chlorophenylamino)-6-(pyridin-4-yl)-9-(tetrahydro-2H-pyran-4-yl)-7H-purin-8(9H)-one. To a vial containing 2-(5-chloro-2-nitrophenylamino)-6-(pyridin-4-yl)-9-(tetrahydro-2H-pyran-4-yl)-7H-purin-8(9H)-one (7 mg, 0.015 mmol) was added glacial acetic acid (0.5 mL), water (1.25 mL) and ethanol (2.5 mL), followed by iron powder (8.4 mg, 0.15 mmol, 10 equiv.) and the resulting mixture heated at 90° C. for 15 min (HPLC monitoring). The reaction mixture was left to cool down to room temperature, concentrated ammonium hydroxide solution was added to bring the pH to basic, and the mixture was stirred for 10 min. The aqueous layer was extracted with ethyl acetate, the combined organic layers were washed with brine, dried (anhydrous Na$_2$SO$_4$), and the solvent removed in vacuo to give the desired product as a pale yellow solid (yield quantitative). This material was used in the next step without further purification. MS (EI) m/z 438.3 (MH)$^+$.

2-(6-chloro-1H-benzo[d]imidazol-1-yl)-6-(pyridin-4-yl)-9-(tetrahydro-2H-pyran-4-yl)-7H-purin-8(9H)-one. To a vial containing crude 2-(2-amino-5-chlorophenylamino)-6-(pyridin-4-yl)-9-(tetrahydro-2H-pyran-4-yl)-7H-purin-8(9H)-one (0.015 mmol) was added anhydrous methanol (2.5 mL), followed by anhydrous trimethylorthoformate (0.5 mL) and p-toluene sulfonic acid (1 mg) and the reaction mixture was stirred under Ar at room temperature for 4 h (HPLC monitoring). Preparative HPLC purification, after evaporation of solvent and drying, provided the desired product (1.2 mg, 18% yield on two steps), as a yellow solid. TFA salt. $^1$H NMR (300 MHz, CD$_3$OD) δ, ppm: 9.18 (s, 1H), 8.83 (br m, 2H), 8.71 (s, 1H), 8.07 (br m, 2H), 7.76 (d, J=8.6 Hz, 1H), 7.41 (d, J=8.9 Hz, 1H), 4.76-4.72 (m, 1H), 4.26-4.23 (m, 2H), 3.66 (app t, J=11.5 Hz, 2H), 2.90-2.87 (m, 2H), 1.91 (br d, J=12.8 Hz, 2H); MS (EI) m/z 448.3 (MH)$^+$.

Modification of the General Procedure to allow access to 6-(pyridin-4-yl)-9-(tetrahydro-2H-pyran-4-yl)-2-(6-(trifluoromethoxy)-1H-benzo[d]imidazol-1-yl)-7H-purin-8(9H)-one

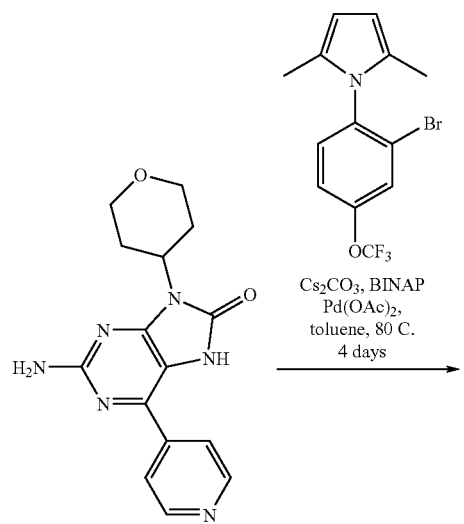

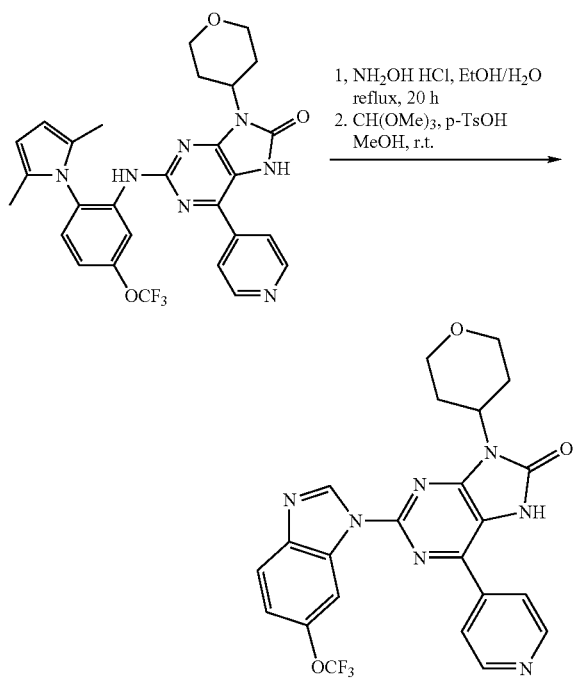

2-(2-(2,5-dimethyl-1H-pyrrol-1-yl)-5-(trifluoromethoxy)phenylamino)-6-(pyridin-4-yl)-9-(tetrahydro-2H-pyran-4-yl)-7H-purin-8(9H)-one. Pale yellow solid. Synthesized following the general procedure for the Buchwald-Hartwig Palladium-catalyzed C—N cross coupling using 2-amino-6-(pyridin-4-yl)-9-(tetrahydro-2H-pyran-4-yl)-7H-purin-8(9H)-one (86 mg, 0.27 mmol) and commercially available 1-[2-bromo-4-(trifluoromethoxy)phenyl-2,5-dimethyl-1H-pyrrole] (Maybridge, 1.3 equiv.) as the aryl bromide. 11 mg (12% yield based on 58% conversion). MS (EI) m/z 566.4 (MH)$^+$.

2-(2-amino-5-(trifluoromethoxy)phenylamino)-6-(pyridin-4-yl)-9-(tetrahydro-2H-pyran-4-yl)-7H-purin-8(9H)-one. 2-(2-(2,5-dimethyl-1H-pyrrol-1-yl)-5-(trifluoromethoxy)phenylamino)-6-(pyridin-4-yl)-9-(tetrahydro-2H-pyran-4-yl)-7H-purin-8(9H)-one (0.018 mmol) was reacted with hydroxylamine hydrochloride (5 equiv.) in a mixture of ethanol and water (1.6 mL/0.6 mL) at reflux for 20 h. Upon completion of the reaction (monitoring by HPLC and MS), the solvent was removed in vacuo, the material thoroughly dried and used in the next step without further purification. MS (EI) m/z 488.4 (MH)$^+$.

6-(pyridin-4-yl)-9-(tetrahydro-2H-pyran-4-yl)-2-(6-(trifluoromethoxy)-1H-benzo[d]imidazol-1-yl)-7H-purin-8(9H)-one. Yellow oil. TFA salt. Synthesized from 2-(2-amino-5-(trifluoromethoxy)phenylamino)-6-(pyridin-4-yl)-9-(tetrahydro-2H-pyran-4-yl)-7H-purin-8(9H)-one following the general procedure for closing the benzimidazole ring. $^1$H NMR (300 MHz, CD$_3$OD+CDCl$_3$) δ, ppm: 9.30 (br s, 1H), 9.00-8.85 (br m, 1H), 8.67 (s, 1H), 8.20-8.10 (m, 2H), 7.84-7.67 (m, 1H), 7.40-7.22 (m, 2H), 4.76-4.72 (m, 1H), 4.26-4.13 (m, 2H), 3.62 (app t, 2H), 2.90-2.80 (m, 2H), 1.90 (br d, 2H); MS (EI) m/z 498.3 (MH)$^+$.

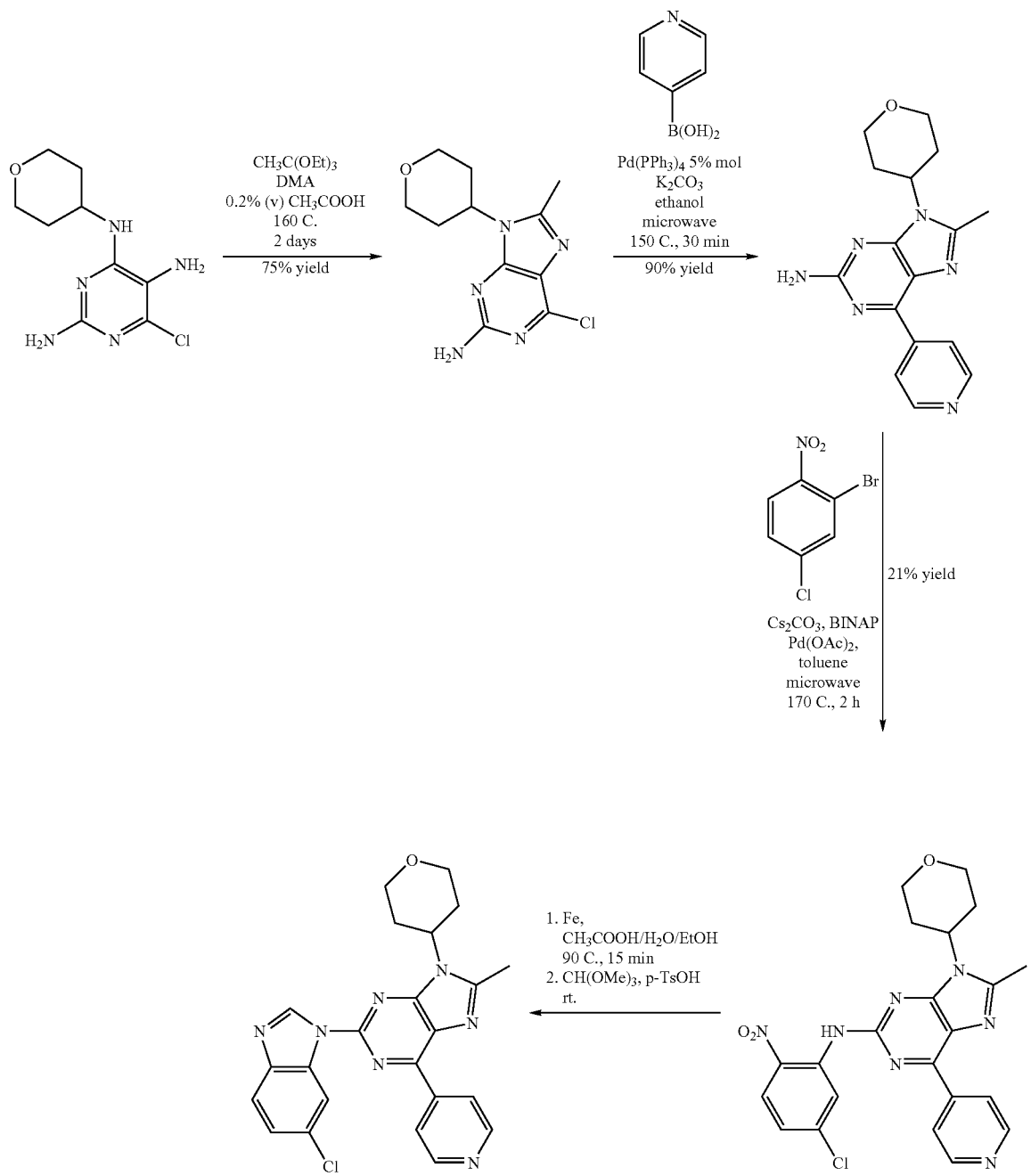

Route D 6-chloro-8-methyl-9-(tetrahydro-2H-pyran-4-yl)-9H-purin-2-amine. N,N-Dimethylacetamide (8 mL) containing 0.2% (v) glacial acetic acid was added to 6-chloro-$N^4$-(tetrahydro-2H-pyran-4-yl)pyrimidine-2,4,5-triamine (preparation Route A) (400 mg, 1.64 mmol), followed by triethylorthoacetate (0.8 mL, 5.32 mmol, 3.2 equiv.), and the reaction mixture was heated at 160° C. in a closed vial for two days. The mixture was then poured into water, and the pH was brought to basic using a saturated solution of sodium bicarbonate. Multiple extractions with methylene chloride, washing of the combined organic layers with water, and evaporation of the solvent in vacuo gave a dark brown residue, which was purified by column chromatography (silica gel, gradual elution with 2% methanol in 4/2/1 hexanes/methylene chloride/ethyl acetate to 3% methanol in 4/2/1 hexanes/methylene chloride/ethyl acetate) to give 330 mg (75% yield) of desired product as a pale yellow solid. $^1$H NMR (300 MHz, CD$_3$OD) δ, ppm: 4.67-4.57 (m, 1H), 4.11 (dd, J=11.5, 4.6 Hz, 2H), 3.61

(td, J=12.0, 1.5 Hz, 2H), 2.91-2.76 (m, 2H), 2.72 (s, 3H), 1.86 (br dd, J=12.5, 2.4 Hz, 2H); MS (EI) m/z 268.1 (MH)+.

In an alternative procedure, the reaction was carried out in parallel using 10 vials. To each vial was added 6-chloro-N4-(tetrahydro-2H-pyran-4-yl)pyrimidine-2,4,5-triamine (preparation Route A) (400 mg, 1.64 mmol), N,N-dimethyl acetamide (8 mL), glacial acetic acid (16 μL, 0.2% vol) and triethylorthoacetate (0.8 mL, 5.32 mmol) and the mixture was stirred at 160° C. After 3 days, the reaction was complete (by LC-MS) and the reaction mixture, containing desired product MS (EI) m/z 268.1 (MH)+, as well as acetylated product MS (EI) m/z 310.2 (MH)+, was cooled to room temperature. To each vial was then added 1 mL of a 1 M aqueous solution of HCl, with stirring at 100° C. After 1 h at 100° C., LC-MS analysis indicated only desired product, in a clean reaction. Upon cooling to room temperature, a white precipitate formed. Filtration under vacuum, followed by washing of the precipitate with portions of methanol provided the desired product (combined yield 2.98 g for 10 vials, 68% yield) as a white solid in pure form. $^1$H NMR (300 MHz, $d_6$-DMSO) δ, ppm: 6.76 (s, 2H), 4.41 (m, 1H), 3.97 (m, 2H), 3.45 (m, 2H), 3.33 (s, 3H), 2.63 (m, 2H), 1.74 (m, 2H); MS (EI) m/z 268.1 (MH)+.

8-methyl-6-(pyridin-4-yl)-9-(tetrahydro-2H-pyran-4-yl)-9H-purin-2-amine. Anhydrous ethanol (4 mL) was added to an argon-purged vial containing 6-chloro-8-methyl-9-(tetrahydro-2H-pyran-4-yl)-9H-purin-2-amine (140 mg, 0.52 mmol), pyridine-4-yl-boronic acid (97 mg, 0.79 mmol, 1.5 equiv.), $K_2CO_3$ (109 mg, 0.79 mmol, 1.5 equiv.), and Pd(PPh$_3$)$_4$ (30 mg, 0.026 mmol, 0.05 equiv.) and the mixture was heated for 30 min in the microwave oven at 150° C. After cooling to ambient temperature, the reaction mixture was diluted with methanol (8 mL), filtered through a Nylon 0.45 μm filter and the filtrate concentrated in vacuo. Preparative HPLC purification of the residue afforded, after evaporation and drying, the desired compound as an orange solid (160 mg, 99% yield). TFA salt. $^1$H NMR (300 MHz, CD$_3$OD) δ, ppm: 9.09 (d, J=6.6 Hz, 2H), 8.95 (d, J=6.2 Hz, 2H), 4.61-4.52 (m, 1H), 4.11 (dd, J=11.5, 4.5 Hz, 2H), 3.61 (app t, J=11.3 Hz, 2H), 2.96-2.82 (m, 2H), 2.68 (s, 3H), 1.84 (dd, J=12.7, 2.3 Hz, 2H); MS (EI) m/z 311.3 (MH)+.

N-(5-chloro-2-nitrophenyl)-8-methyl-6-(pyridin-4-yl)-9-(tetrahydro-2H-pyran-4-yl)-9H-purin-2-amine. To an oven-dried vial was added 8-methyl-6-(pyridin-4-yl)-9-(tetrahydro-2H-pyran-4-yl)-9H-purin-2-amine (56 mg, 0.18 mmol, 1 equiv.) in anhydrous toluene (1 mL), then freshly grounded cesium carbonate (82 mg, 0.25 mmol, 1.4 equiv.) with stirring at room temperature under Ar. After 10 min, Pd(OAc)$_2$ (13.5 mg, 0.02 mmol, 0.1 equiv.), racemic BINAP (17 mg, 0.03 mmol, 0.15 equiv.) and 1-bromo-5-chloro-2-nitrobenzene (WO 02/053545 A1) (55 mg, 0.23 mmol, 1.3 equiv.) were added as solids. The vial was purged with Ar for 3 min, then closed and heated in a microwave oven at 170° C. for 2 h. The reaction mixture was cooled to room temperature, diluted with ethyl acetate/methylene chloride, filtered through a Nylon 0.45 μm filter, and the filtrate was concentrated in vacuo. The resulting residue was purified using preparative TLC (silica gel, 7.5% methanol in methylene chloride) to give the desired product as a yellow solid (18 mg, 21% yield). $^1$H NMR (300 MHz, CDCl$_3$+CD$_3$OD) δ, ppm: 9.30 (s, 1H), 8.77 (br m, 2H), 8.64 (br m, 2H), 8.26 (d, J=8.9 Hz, H), 7.05 (d, J=7.9 Hz, 1H), 4.60-4.56 (m, 1H), 4.26-4.22 (m, 2H), 3.64 (app t, J=11.9 Hz, 2H), 2.94-2.90 (m, 2H), 2.76 (s, 3H), 1.91 (br d, J=11.2 Hz, 2H); MS (EI) m/z 466.3 (MH)+.

5-chloro-N$^1$-(8-methyl-6-(pyridin-4-yl)-9-(tetrahydro-2H-pyran-4-yl)-9H-purin-2-yl)benzene-1,2-diamine. To a vial containing N-(5-chloro-2-nitrophenyl)-8-methyl-6-(pyridin-4-yl)-9-(tetrahydro-2H-pyran-4-yl)-9H-purin-2-amine (16.3 mg, 0.035 mmol) was added glacial acetic acid (1 mL), water (2.5 mL) and ethanol (5 mL), followed by iron powder (20 mg, 0.35 mmol, 10 equiv.) and the resulting mixture heated at 90° C. for 15 min (HPLC monitoring). The reaction mixture was left to cool down to room temperature, concentrated ammonium hydroxide solution was added to bring the pH to basic, and the mixture was stirred for 10 min. The aqueous layer was extracted with ethyl acetate, the combined organic layers were washed with brine, dried (anhydrous Na$_2$SO$_4$), and the solvent removed in vacuo to give the desired product as a pale yellow solid (yield quantitative). This material was used in the next step without further purification. MS (EI) m/z 436.4 (MH)+.

2-(6-chloro-1H-benzo[d]imidazol-1-yl)-8-methyl-6-(pyridin-4-yl)-9-(tetrahydro-2H-pyran-4-yl)-9H-purine. To a vial containing crude 5-chloro-N$^1$-(8-methyl-6-(pyridin-4-yl)-9-(tetrahydro-2H-pyran-4-yl)-9H-purin-2-yl)benzene-1,2-diamine (0.035 mmol) was added anhydrous methanol (2.5 mL), followed by anhydrous trimethylorthoformate (0.5 mL) and methane sulfonic acid (catalytic amount) and the reaction mixture was stirred under Ar at room temperature for 4 h (HPLC monitoring). Preparative HPLC purification, after evaporation of solvent and drying, provided the desired product (3.5 mg, 22% yield on two steps), as a yellow oil. TFA salt. $^1$H NMR (300 MHz, CD$_3$OD+CDCl$_3$) δ, ppm: 9.32 (s, 1H), 8.91 (br m, 4H), 8.79 (s, 1H), 7.78 (d, J=8.6 Hz, 1H), 7.43 (d, J=8.6 Hz, 1H), 4.76-4.72 (m, 1H), 4.32-4.29 (m, 2H), 3.72 (app t, J=11.7 Hz, 2H), 3.08-3.05 (m, 2H), 2.87 (s, 3H), 2.02 (br d, J=10.9 Hz, 2H); MS (EI) m/z 446.3 (MH)+.

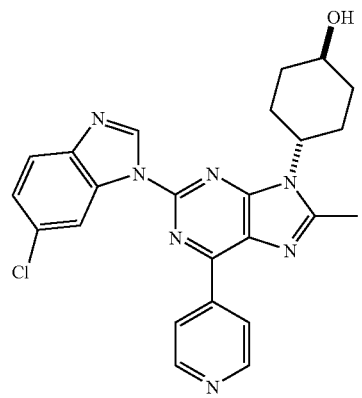

Trans-4-(2-(6-chloro-1H-benzo[d]imidazol-1-yl)-8-methyl-6-(pyridine-4-yl)-9H-purin-9-yl)cyclohexanol. Synthesis of the foregoing purine is accomplished according to the reaction sequence presented in Route D with the modification that the first step involves the reaction of trans-4-(2,5-diamino-6-chloropyrimidin-4-ylamino)cyclohexanol instead of 6-chloro-N$^4$-(tetrahydro-2H-pyran-4-yl)pyrimidine-2,4,5-triamine. Trans-4-(2,5-diamino-6-chloropyrimidin-4-ylamino)cyclohexanol is prepared as described in Route J.

Route E

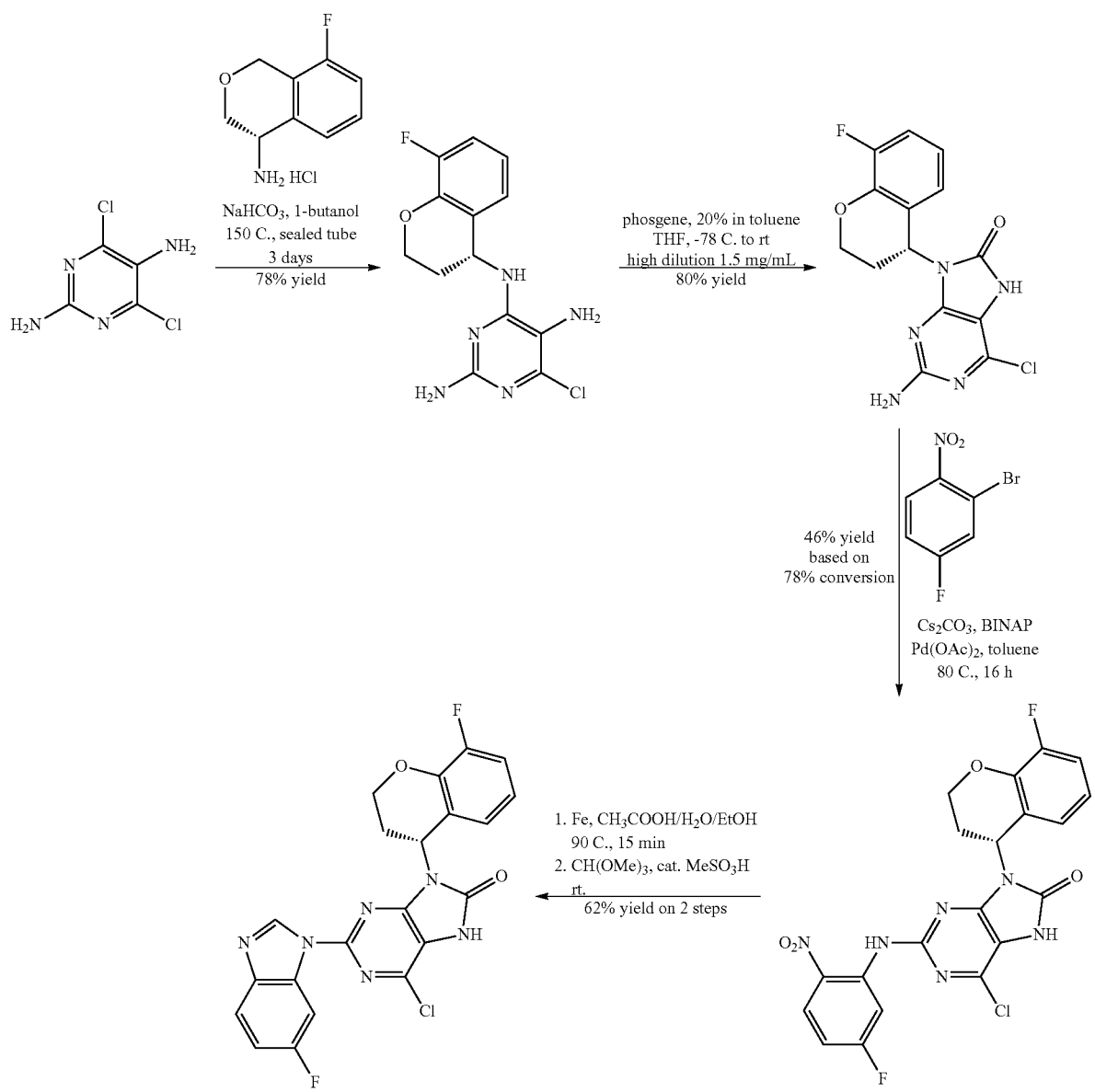

(R)-6-chloro-N⁴-(8-fluorochroman-4-yl)pyrimidine-2,4,5-triamine. 2,5-diamino-4,6-dichloropyrimidine (1.5 g, 8.37 mmol), (R)-8-fluorochroman-4-amine hydrochloride (see preparation below) (1.7 g, 8.37 mmol, 1 equiv.), sodium bicarbonate (2.46 g, 29.3 mmol, 3.5 equiv.) and 1-butanol (30 mL) were heated together at 150° C. in a sealed tube. After 3 days, when the reaction appeared to be complete (by HPLC), the reaction mixture was cooled to room temperature and the solvent was removed in vacuo. The residue was purified by flash chromatography (silica gel, elution with 1/1 ethyl acetate/methylene chloride) to give 2.01 g (78% yield) of the desired product as a yellow solid. $^1$H NMR (300 MHz, CD$_3$OD) δ, ppm: 6.97-6.86 (m, 2H), 6.77-6.72 (m, 1H), 5.36 (m, 1H), 4.25 (m, 2H), 2.10 (m, 2H); MS (EI) m/z 310.1 (MH)⁺.

Synthesis and optical resolution of 8-fluorochroman-4-amine was performed as described in WO 2006/108103 A1

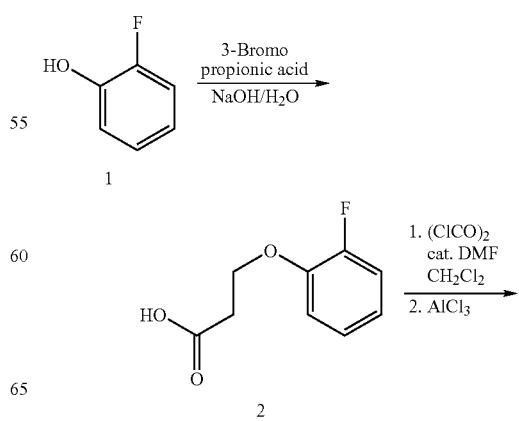

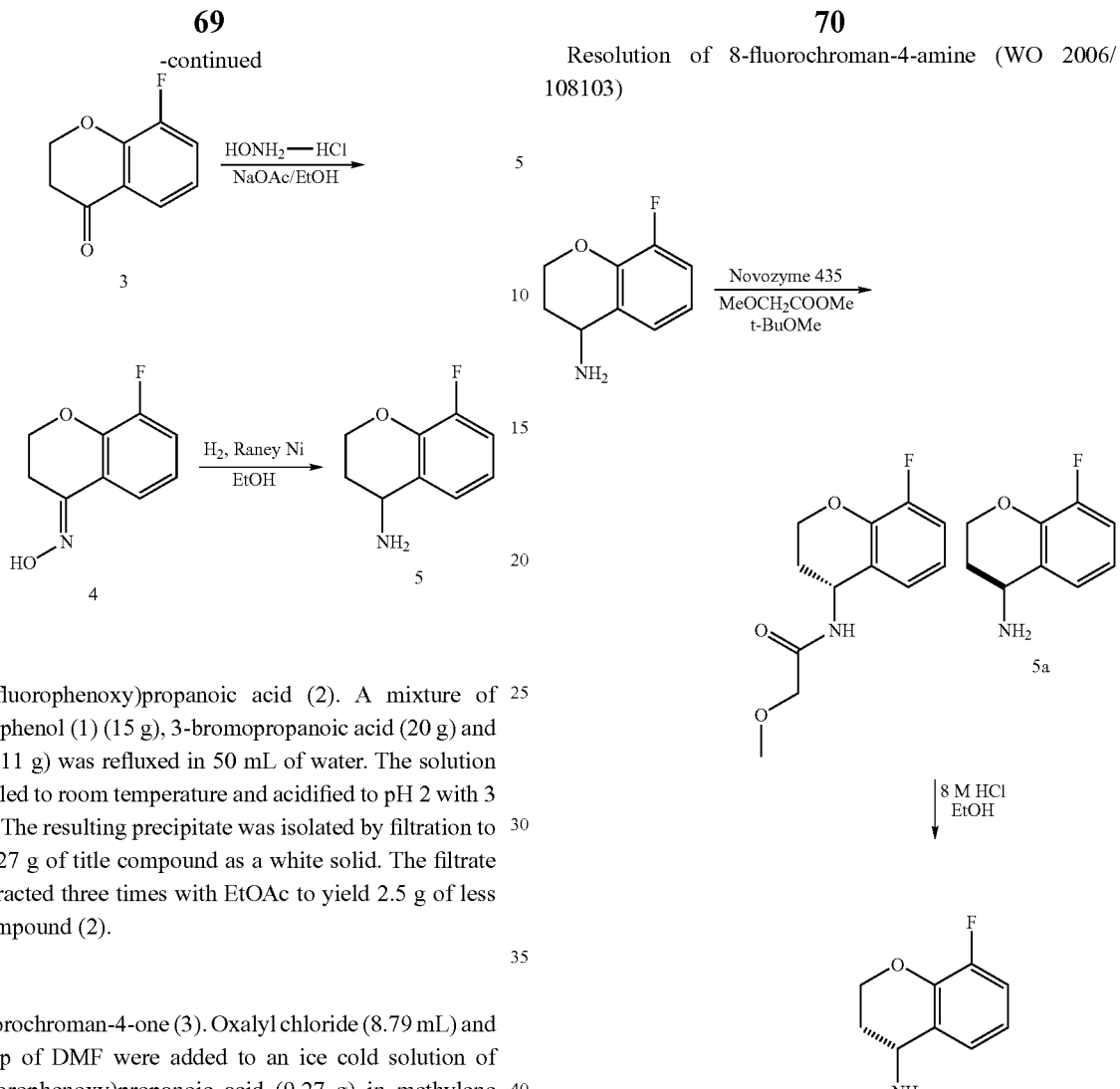

3-(2-fluorophenoxy)propanoic acid (2). A mixture of 2-fluorophenol (1) (15 g), 3-bromopropanoic acid (20 g) and NaOH (11 g) was refluxed in 50 mL of water. The solution was cooled to room temperature and acidified to pH 2 with 3 M HCl. The resulting precipitate was isolated by filtration to yield 9.27 g of title compound as a white solid. The filtrate was extracted three times with EtOAc to yield 2.5 g of less pure compound (2).

8-fluorochroman-4-one (3). Oxalyl chloride (8.79 mL) and one drop of DMF were added to an ice cold solution of 3-(2-fluorophenoxy)propanoic acid (9.27 g) in methylene chloride (50 mL). The solution was stirred at 0° C. for two hours, aluminum chloride (7.39 g, 55.42 mM) was added and the solution was stirred for 16 hours at room temperature. The mixture was poured onto ice water, and extracted three times with methylene chloride. The combined organics were washed with 0.5M NaOH and brine, dried, evaporated, and purified by column chromatography (eluting with 20% EtOAc/Hex) to give 8-fluorochroman-4-one (3) (8.20 g, 98%).

8-fluorochroman-4-amine (5). A round bottom flask was charged with 8-fluorochroman-4-one (8.2 g), hydroxylamine hydrochloride (3.78 g) and sodium acetate (4.46 g). A reflux condenser was added, the flask was purged with argon, dry EtOH (20 mL) was added, and the mixture was stirred at reflux for 18 hours. The solution was cooled to room temperature, diluted with EtOAc, and washed with water. The organic phase was dried, and evaporated to give the intermediate 8-fluorochroman-4-one oxime (4), which was reduced with Raney Nickel in EtOH at 50 PSI to yield the title amine (5) (4.69 g, 57%).

Resolution of 8-fluorochroman-4-amine (WO 2006/108103)

A mixture of 8-fluorochroman-4-amine (3.40 g), methyl 2-methoxyacetate (2.44 g) and Novozyme 435 (Aldrich, 0.68 g) in anhydrous tert-butyl methyl ether (75 mL) was heated at reflux under argon for two hours (at which time the ratio of acylated to unacylated product was 1:1 by HPLC). The solid that formed upon cooling was collected via filtration and dissolved in EtOAc. The mixture was filtered to remove the biocatalyst and washed once with 0.5M HCl to remove any lingering (S)-amine. The solvent was evaporated and the product was recrystallized from tert-butyl methyl ether to yield (R)—N-(8-fluorochroman-4-yl)-2-methoxyacetamide (0.78 g). The reaction solvent and recrystallization mother liquor was washed three times with 0.5 M HCl and concentrated to yield additional (R)-N-(8-fluorochroman-4-yl)-2-methoxyacetamide (0.83 g). The combined acidic aqueous layers were made basic by NaOH and extracted with methylene chloride to yield (S)-8-fluorochroman-4-amine (5a) (1.6 g). A solution of (R)-N-(8-fluorochroman-4-yl)-2-methoxyacetamide (0.78 g) in 8M HCl in EtOH (50 mL) was heated at reflux for four hours. The solvents were removed from the cooled reaction mixture, the resulting solid was taken up in 50 mL of 0.5M NaOH, salted out with NaCl$_{(s)}$, and extracted four times with methylene chloride to yield (R)-8-fluorochroman-4-amine (0.48 g (87%)) (5b). The % ee was checked via chiral HPLC: Chiralcel OD-H (0.46×25 cm analytical column, Daicel Chemical Industries) method: isocratic 5% (0.05% TFA/EtOH) 95% (0.05% TFA/Hex), Rt=7.2 min (S)-enantiomer, Rt=9.2 min (R)-enantiomer.

(R)-2-amino-6-chloro-9-(8-fluorochroman-4-yl)-7H-purin-8(9H)-one. To a solution of (R)-6-chloro-N$^4$-(8-fluorochroman-4-yl)pyrimidine-2,4,5-triamine (0.9 g, 2.91 mmol) in 900 mL of anhydrous THF at −78° C. under Ar was added dropwise, over 20 min, a solution of phosgene in THF (2.6 mL of a 20% solution of phosgene in toluene, 4.94 mmol, 1.7 equiv., diluted with 26 mL of anhydrous THF). The reaction mixture was left to gradually warm up to room temperature over 16 h. It was purged with air for 30 min. The solvent was then removed in vacuo, and the residue was taken in ethyl acetate/saturated aqueous NaHCO$_3$. The layers were separated, and the aqueous layer extracted with ethyl acetate three times. The combined organic extracts were put together, dried (anhydrous Na$_2$SO$_4$) and the solvent removed in vacuo. The residue was purified by flash chromatography (silica gel, gradual elution with 6/1 to 4/1 methylene chloride/ethyl acetate) to give 0.78 g (80% yield) of the desired product as a pale yellow solid. $^1$H NMR (300 MHz, CD$_3$OD) δ, ppm: 7.13-7.06 (m, 1H), 6.90-6.82 (m, 1H), 6.75-6.72 (m, 1H), 5.92-5.82 (m, 1H), 4.80-4.73 (m, 1H), 4.50-4.42 (m, 1H), 3.20-3.05 (m, 1H), 2.42-2.30 (m, 1H); MS (EI) m/z 336.3 (MH)$^+$.

(R)-6-chloro-2-(5-fluoro-2-nitrophenylamino)-9-(8-fluorochroman-4-yl)-7H-purin-8(9H)-one. To an oven-dried vial was added (R)-2-amino-6-chloro-9-(8-fluorochroman-4-yl)-7H-purin-8(9H)-one (152 mg, 0.45 mmol, 1 equiv.) in anhydrous toluene (2.5 mL), followed by freshly grounded cesium carbonate (207 mg, 0.64 mmol, 1.4 equiv.) with stirring at room temperature under Ar. After 10 min, Pd(OAc)$_2$ (30.3 mg, 0.045 mmol, 0.1 equiv.), racemic BINAP (42 mg, 0.067 mmol, 0.15 equiv.) and 1-bromo-5-fluoro-2-nitrobenzene (130 mg, 0.59 mmol, 1.3 equiv.) were added as solids. The vial was purged with Ar for 3 min, then closed and heated at 80° C. for three days. The reaction mixture was cooled to room temperature, then poured into saturated aqueous NH$_4$Cl (10 mL). To this mixture, saturated aqueous Na$_2$EDTA (10 mL) was added and the mixture was stirred for 10 min. Then the reaction mixture was extracted with ethyl acetate (4×20 mL), the collected organic layers were washed with brine, dried (anhydrous Na$_2$SO$_4$) and the solvent evaporated in vacuo. Column chromatography of the residue on silica gel (gradual elution with 1% methanol in 4/2/1 hexane/methylene chloride/ethyl acetate to 2% methanol in 4/2/1 hexane/methylene chloride/ethyl acetate) afforded, after evaporation and drying, the desired product as an orange solid (76 mg, 46% yield based on 78% conversion), along with 33 mg of recovered starting material. $^1$H NMR (300 MHz, CDCl$_3$) δ, ppm: 10.64 (s, 1H), 8.58 (s, 1H), 8.29-8.16 (m, 2H), 7.02-6.95 (m, 1H), 6.74-6.60 (m, 2H), 5.88-5.82 (m, 1H), 4.66-4.62 (m, 1H), 4.38 (app t, J=11.0 Hz, 1H), 4.38-4.28 (br m, 1H, overlapping with 4.38 ppm), 2.96-2.92 (m, 1H), 2.26-2.23 (m, 1H); MS (EI) m/z 475.2 (MH)$^+$.

(R)-2-(2-amino-5-fluorophenylamino)-6-chloro-9-(8-fluorochroman-4-yl)-7H-purin-8(9H)-one. To a round bottom flask containing (R)-6-chloro-2-(5-fluoro-2-nitrophenylamino)-9-(8-fluorochroman-4-yl)-7H-purin-8(9H)-one (310 mg, 0.65 mmol) was added glacial acetic acid (15 mL), water (37.5 mL) and ethanol (75 mL), followed by iron powder (370 mg, 6.5 mmol, 10 equiv.) and the resulting mixture heated at 90° C. for 15 min (HPLC monitoring). The reaction mixture was left to cool down to room temperature, concentrated ammonium hydroxide solution (32 mL) was added to bring the pH to basic, and the mixture was stirred for 10 min. The aqueous layer was extracted with ethyl acetate (5×100 mL), the combined organic layers were washed with brine, dried (anhydrous Na$_2$SO$_4$), and the solvent removed in vacuo to give the desired product as a pink solid (yield quantitative). This material was used in the next step without further purification. MS (EI) m/z 445.2 (MH)$^+$.

6-chloro-2-(6-fluoro-1H-benzo[d]imidazol-1-yl)-9-((R)-8-fluorochroman-4-yl)-7H-purin-8(9H)-one. To a round bottom flask containing (R)-2-(2-amino-5-fluorophenylamino)-6-chloro-9-(8-fluorochroman-4-yl)-7H-purin-8(9H)-one (0.65 mmol) was added anhydrous methanol (45 mL), followed by anhydrous trimethylorthoformate (5 mL) and methane sulfonic acid (0.1 mL) and the reaction mixture was stirred under Ar at room temperature until it was complete (HPLC monitoring). Preparative HPLC purification, after evaporation of solvent and drying, provided the desired product (184 mg, 62% yield on two steps), as a white solid. $^1$H NMR (300 MHz, CDCl$_3$) δ, ppm: 9.38 (br s, 1H), 9.01 (s, 1H), 7.84-7.79 (m, 1H), 7.64-7.60 (m, 1H), 7.20-7.13 (m, 1H), 7.10-7.03 (m, 1H), 6.79-6.67 (m, 2H), 5.97-5.92 (m, 1H), 4.68-4.62 (m, 1H), 4.51-4.40 (m, 1H), 2.95-2.83 (m, 1H), 2.41-2.36 (m, 1H); MS (EI) m/z 454.9 (MH)$^+$.

Method 1

General procedure for cross-coupling reactions of 6-chloropurinones with arylboronic acids. Ethanol (1 mL) was added to an argon-purged vial containing 6-chloro-2-(6-fluoro-1H-benzo[d]imidazol-1-yl)-9-((R)-8-fluorochroman-4-yl)-7H-purin-8(9H)-one (9.2 mg, 0.02 mmol), aryl boronic acid (0.04 mmol, 2 equiv.), Pd(PPh$_3$)$_4$ (2.3 mg, 0.002 mmol, 0.1 equiv.) and a 2M aqueous solution of Na$_2$CO$_3$ (200 μL), and the mixture was heated for 30 min in the microwave oven at 150° C. After cooling to ambient temperature, the reaction mixture was diluted with a 1/1 mixture of methanol/methylene chloride, filtered through a Nylon 0.45 μm filter and the filtrate concentrated in vacuo. Preparative HPLC purification of the residue afforded, after evaporation and drying, the desired compound.

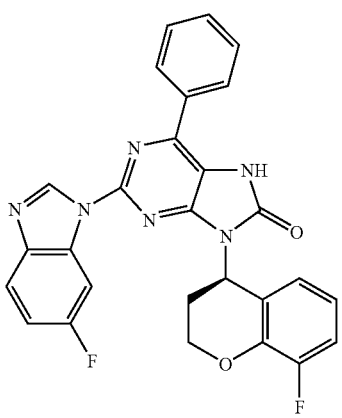

2-(6-fluoro-1H-benzo[d]imidazol-1-yl)-9-((R)-8-fluoro-chroman-4-yl)-6-phenyl-7H-purin-8(9H)-one. White solid (4.8 mg, 48% yield). Prepared from phenyl boronic acid (5 mg, 0.04 mmol, 2 equiv). $^1$H NMR (300 MHz, CDCl$_3$) δ, ppm: 10.28 (br s, 1H), 9.12 (s, 1H), 8.14-8.12 (m, 2H), 8.05-7.85 (m, 2H), 7.74-7.72 (m, 3H), 7.28-7.26 (m, 1H), 7.18-7.16 (m, 1H), 6.88-6.84 (m, 2H), 6.14-6.12 (m, 1H), 4.83-4.80 (m, 1H), 4.70-4.50 (m, 1H), 3.21-3.03 (m, 1H), 2.60-2.42 (m, 1H); MS (EI) m/z 497.1 (MH)$^+$.

Method 2

General procedure for displacement reactions of 6-chloro-purinones with aliphatic amines. To 10 mg (0.022 mmol) of 6-chloro-2-(6-fluoro-1H-benzo[d]imidazol-1-yl)-9-((R)-8-fluorochroman-4-yl)-7H-purin-8(9H)-one was added 0.6 mL of 1-butanol, followed by an aliphatic amine (0.1 mL), and the reaction mixture was stirred at 110° C. for 1-2 h (HPLC monitoring). Upon completion of the reaction, the mixture was left to cool to room temperature, was diluted with acetonitrile and filtered through a Nylon 0.45 μm filter. Preparative HPLC purification afforded, after solvent evaporation and drying, the desired product.

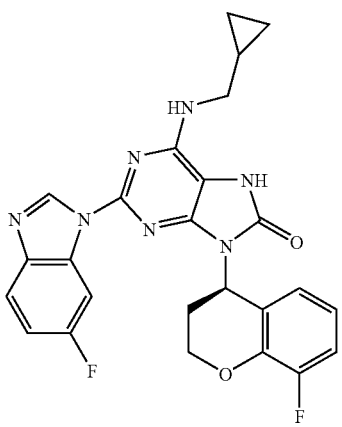

6-(cyclopropylmethylamino)-2-(6-fluoro-1H-benzo[d]imidazol-1-yl)-9-((R)-8-fluorochroman-4-yl)-7H-purin-8(9H)-one. White solid (2.4 mg, 22% yield). Prepared using aminomethyl cyclopropane (0.1 mL). Reaction time 90 min. $^1$H NMR (300 MHz, CD$_3$OD) δ, ppm: 9.01 (br s, 1H), 7.74-7.68 (m, 2H), 7.16-7.13 (m, 1H), 7.02-6.95 (m, 1H), 6.77-6.69 (m, 2H), 5.88-5.83 (m, 1H), 4.79-4.61 (m, 1H), 4.45-4.38 (m, 1H), 3.50 (d, J=6.9 Hz, 2H), 2.93-2.86 (m, 1H), 2.34-2.30 (m, 1H), 1.29-1.21 (m, 1H), 0.64-0.61 (m, 2H), 0.39-0.36 (m, 2H); MS (EI) m/z 490.1 (MH)$^+$.

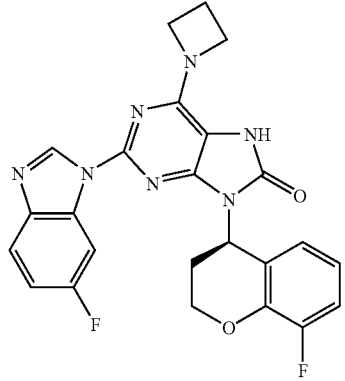

6-(azetidin-1-yl)-2-(6-fluoro-1H-benzo[d]imidazol-1-yl)-9-((R)-8-fluorochroman-4-yl)-7H-purin-8(9H)-one. White solid, 70% yield. Prepared using azetidine. $^1$H NMR (300 MHz, CDCl$_3$+CD$_3$OD) δ, ppm: 8.85 (br s, 1H), 7.75-7.67 (m, 2H), 7.13-6.90 (m, 2H), 6.78-6.67 (m, 2H), 5.90-5.84 (m, 1H), 4.73-4.67 (m, 1H), 4.45-4.41 (m, 5H), 3.00-2.95 (m, 1H), 2.63-2.55 (m, 2H), 2.36-2.30 (m, 1H); MS (EI) m/z 476.3 (MH)$^+$.

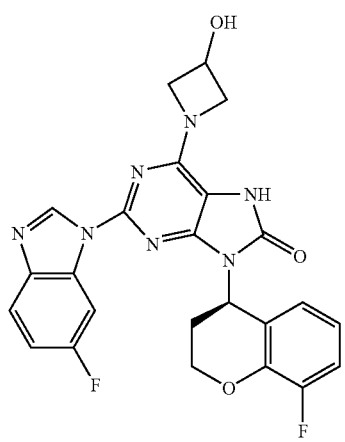

2-(6-fluoro-1H-benzo[d]imidazol-1-yl)-9-((R)-8-fluoro-chroman-4-yl)-6-(3-hydroxyazetidin-1-yl)-7H-purin-8(9H)-one. White solid, 56% yield. Prepared using 3-hydroxyazetidine. $^1$H NMR (300 MHz, CDCl$_3$+CD$_3$OD) δ, ppm: 8.92 (br s, 1H), 7.66-7.60 (m, 2H), 7.09-7.02 (m, 1H), 6.98-6.92 (m, 1H), 6.71-6.60 (m, 2H), 5.83-5.76 (m, 1H), 4.78-4.62 (m, 1H), 4.59-4.52 (m, 3H), 4.40-4.32 (m, 1H), 4.14-4.07 (m, 2H), 2.93-2.82 (m, 1H), 2.29-2.22 (m, 1H); MS (EI) m/z 492.3 (MH)$^+$.

Method 3

General procedure for cross-coupling reactions of 6-chloropurinones with organozinc halides. THF (1.5 mL) was added to an argon-purged vial containing 6-chloro-2-(6-fluoro-1H-benzo[d]imidazol-1-yl)-9-((R)-8-fluorochroman-4-yl)-7H-purin-8(9H)-one (20 mg, 0.044 mmol) and Pd(PPh₃)₄ (2.5 mg, 0.02 mmol, 0.05 equiv.). The mixture was stirred at room temperature for 10 min, and then a 0.5 M solution of an organozinc reagent in THF (132 μL, 0.066 mmol, 1.5 equiv.) was added dropwise at room temperature. The stirring at room temperature was continued for 15 min, followed by stirring at 64° C. for 1-3 days. The reaction mixture was left to cool to room temperature, the solvent was removed in vacuo, acetonitrile was added to the residue and the mixture filtered through a Nylon 0.45 μm filter. Preparative HPLC purification afforded, after evaporation and drying, the desired compound.

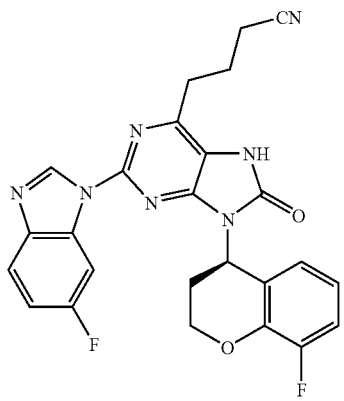

4-(2-(6-fluoro-1H-benzo[d]imidazol-1-yl)-9-((R)-8-fluorochroman-4-yl)-8-oxo-8,9-dihydro-7H-purin-6-yl)butanenitrile. White solid, 16% yield. Prepared using a 0.5 M solution of 3-cyanopropylzinc bromide in THF. ¹H NMR (300 MHz, CD₃OD) δ, ppm: 9.01 (br s, 1H), 7.89-7.79 (m, 2H), 7.27-7.13 (m, 2H), 6.91 (br m, 2H), 6.08-6.02 (m, 1H), 4.79-4.74 (m, 1H), 4.61-4.54 (m, 1H), 3.20 (t, J=7.2 Hz, 2H), 3.04-2.97 (m, 1H), 2.77 (t, J=6.93 Hz, 2H), 2.52-2.40 (m, 1H, overlapping with 2.39 ppm), 2.39 (t, J=7.1 Hz, 2H); MS (EI) m/z 488.1 (MH)⁺.

6-benzyl-2-(6-fluoro-1H-benzo[d]imidazol-1-yl)-9-((R)-8-fluorochroman-4-yl)-7H-purin-8(9H)-one. White solid, 49% yield. Prepared using a 0.5 M solution of benzylzinc bromide in THF. ¹H NMR (300 MHz, CD₃OD) δ, ppm: 9.01 (br s, 1H), 7.67-7.64 (m, 2H), 7.44-7.41 (m, 2H), 7.37-7.32 (m, 2H), 7.28-7.23 (m, 1H), 7.17-7.11 (m, 1H), 7.03-6.97 (m, 1H), 6.77-6.69 (m, 2H), 5.93-5.87 (m, 1H), 4.63-4.57 (m, 1H), 4.45-4.38 (m, 1H), 4.24 (s, 2H), 2.91-2.80 (m, 1H), 2.39-2.33 (m, 1H); MS (EI) m/z 511.1 (MH)⁺.

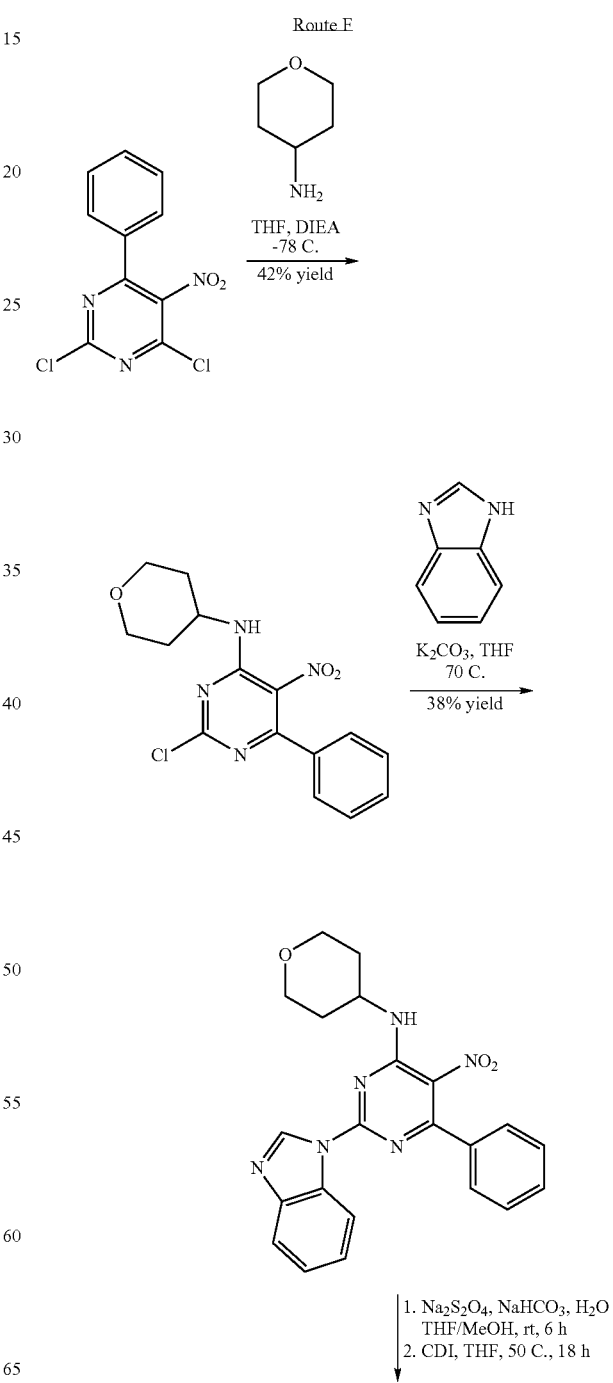

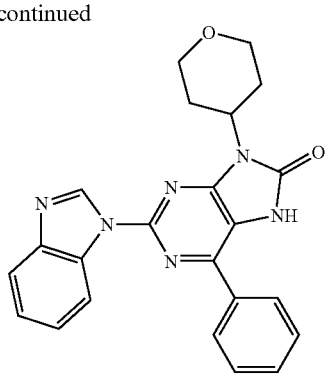

General procedure for the selective displacement of the 4-chloro substituent in 2,4-dichloro-5-nitro-6-phenylpyrimidine with an amine. To 200 mg of 2,4-dichloro-5-nitro-6-phenylpyrimidine (SPECS) (0.74 mmol) in 2 mL anhydrous THF at −78° C. under Ar was added dropwise a solution of an amine (0.74 mmol, 1.0 equiv.) and N,N-diisopropylethyl amine (284 µM, 210 mg, 1.63 mmol, 2.2 equiv.) in 2 mL of THF. The reaction mixture was stirred at −78° C. for 2 h, and then it was allowed to warm up to room temperature and stirred at ambient temperature for another 2 h (TLC monitoring). The solvent was removed in vacuo and the residue purified by column chromatography to give the desired product.

2-chloro-5-nitro-6-phenyl-N-(tetrahydro-2H-pyran-4-yl)pyrimidin-4-amine. Pale yellow solid. 104 mg, 42% yield. Synthesized using 4-aminotetrahydropyran. Purification on silica gel, elution with 5/1 hexanes/ethyl acetate. $^1$H NMR (300 MHz, CDCl$_3$+CD$_3$OD) δ, ppm: 7.41-7.32 (m, 5H), 4.35-4.29 (m, 1H), 4.02-3.92 (m, 2H), 3.51 (br t, 2H), 2.01-1.94 (m, 2H), 1.66-1.56 (m, 2H).

(R)-2-chloro-N-(6-fluorochroman-4-yl)-5-nitro-6-phenylpyrimidin-4-amine. 52% yield. Synthesized using (R)-6-fluorochroman-4-amine. Purification on silica gel, elution with 7/3 hexanes/ethyl acetate. $^1$H NMR (300 MHz, CDCl$_3$) δ, ppm: 7.62-7.43 (m, 6H), 7.01-6.93 (m, 2H), 6.88-6.82 (m, 1H), 5.61-5.53 (m, 1H), 4.37-4.28 (m, 1H), 4.26-4.17 (m, 1H), 2.45-2.33 (m, 1H), 2.22-2.13 (m, 1H); MS (EI) m/z 400.9 (MH)$^+$.

2-(1H-benzo[d]imidazol-1-yl)-5-nitro-6-phenyl-N-(tetrahydro-2H-pyran-4-yl)pyrimidin-4-amine. To 100 mg (0.3 mmol) of 2-chloro-5-nitro-6-phenyl-N-(tetrahydro-2H-pyran-4-yl)pyrimidin-4-amine in 5 mL of THF was added potassium carbonate (213 mg, 1.54 mmol, 5.1 equiv.), followed by benzimidazole (106 mg, 0.9 mmol, 3 equiv.) and the reaction mixture was stirred at 70° C. After 2.5 h, heating was discontinued; the reaction mixture was diluted with 70 mL of ethyl acetate, was washed with water and dried (anhydrous MgSO$_4$). The solvent was removed in vacuo and the residue purified by column chromatography (silica gel, elution with 4/1 hexanes/ethyl acetate) to give the desired product (48 mg, 38% yield). LC-MS: t$_R$=7.35 min, MS (EI) m/z 417.2 (MH)$^+$.

2-(1H-benzo[d]imidazol-1-yl)-N—((R)-6-fluorochroman-4-yl)-5-nitro-6-phenylpyrimidin-4-amine. Synthesized from (R)-2-chloro-N-(6-fluorochroman-4-yl)-5-nitro-6-phenylpyrimidin-4-amine. $^1$H NMR (300 MHz, CDCl$_3$) δ, ppm: 9.05 (s, 1H), 8.48-8.42 (m, 1H), 7.98 (d, 1H), 7.87-7.82 (m, 1H), 7.67-7.61 (m, 2H), 7.58-7.48 (m, 3H), 7.42-7.35 (m, 2H), 7.05-6.93 (m, 2H), 6.92-6.85 (m, 1H), 5.68-5.59 (m, 1H), 4.42-4.31 (m, 1H), 4.30-4.19 (m, 1H), 2.51-2.41 (m, 1H), 2.40-2.29 (m, 1H).

2-(1H-benzo[d]imidazol-1-yl)-6-phenyl-N$^4$-(tetrahydro-2H-pyran-4-yl)pyrimidine-4,5-diamine. To 48 mg (0.11 mmol) of 2-(1H-benzo[d]imidazol-1-yl)-5-nitro-6-phenyl-N-(tetrahydro-2H-pyran-4-yl)pyrimidin-4-amine in 10 mL THF was added a solution of 300 mg Na$_2$S$_2$O$_4$ and 100 mg NaHCO$_3$ in 30 mL of water, followed by 2 mL of methanol. The reaction mixture was stirred at room temperature (HPLC monitoring). Upon completion of the reaction, the mixture was diluted with 70 mL of ethyl acetate, the layers were separated, and the aqueous layer extracted with ethyl acetate. The combined organic layers were washed with brine, dried (anhydrous MgSO$_4$), and the solvent removed in vacuo to give 30 mg (68% yield) of desired product, which was used in the next step without further purification. MS (EI) m/z 387.4 (MH)$^+$.

2-(1H-benzo[d]imidazol-1-yl)-N$^4$—((R)-6-fluorochroman-4-yl)-6-phenylpyrimidine-4,5-diamine. Synthesized from 2-(1H-benzo[d]imidazol-1-yl)-N—((R)-6-fluorochroman-4-yl)-5-nitro-6-phenylpyrimidin-4-amine. MS (EI) m/z 453.3 (MH)$^+$.

2-(1H-benzo[d]imidazol-1-yl)-6-phenyl-9-(tetrahydro-2H-pyran-4-yl)-7H-purin-8(9H)-one. To 30 mg (0.078 mmol) of crude 2-(1H-benzo[d]imidazol-1-yl)-6-phenyl-N$^4$-(tetrahydro-2H-pyran-4-yl)pyrimidine-4,5-diamine in 3 mL THF was added CDI (38 mg, 0.233 mmol, 3 equiv.) and the reaction mixture was stirred at 50° C. for 18 h. The solvent was removed in vacuo and the residue purified by preparative TLC (silica gel, 5% methanol in methylene chloride) to afford the desired product (9.5 mg, 30% yield). $^1$H NMR (300 MHz, CDCl$_3$) δ, ppm: 9.16 (br s, 1H), 8.68 (d, 1H), 8.06 (br m, 2H), 7.90 (d, 1H), 7.71-7.62 (m, 3H), 7.52-7.33 (m, 3H), 4.82-4.68 (m, 1H), 4.31-4.20 (m, 2H), 3.64 (app t, 2H), 3.01-2.82 (m, 2H), 1.89 (br d, 2H); MS (EI) m/z 413.2 (MH)$^+$.

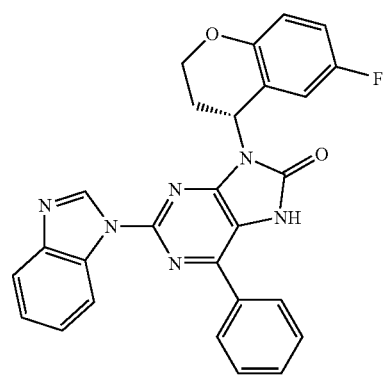

2-(1H-benzo[d]imidazol-1-yl)-9-((R)-6-fluorochroman-4-yl)-6-phenyl-7H-purin-8(9H)-one. 26% yield. Synthesized from 2-(1H-benzo[d]imidazol-1-yl)-N$^4$—((R)-6-fluorochroman-4-yl)-6-phenylpyrimidine-4,5-diamine. $^1$H NMR (300 MHz, CDCl$_3$) δ, ppm: 10.72 (br s, 1H), 8.90 (s, 1H), 8.18-8.04 (m, 3H), 7.82-7.77 (m, 1H), 7.63-7.54 (m, 3H), 7.36-7.28 (m, 2H), 7.08-7.01 (m, 1H), 6.97-6.88 (m, 1H), 6.72-6.68 (m, 1H), 6.00-5.92 (m, 1H), 4.63-4.56 (m, 1H), 4.36 (td, 1H), 3.05-2.90 (m, 1H), 2.40-2.26 (m, 1H); MS (EI) m/z 479.1 (MH)$^+$.

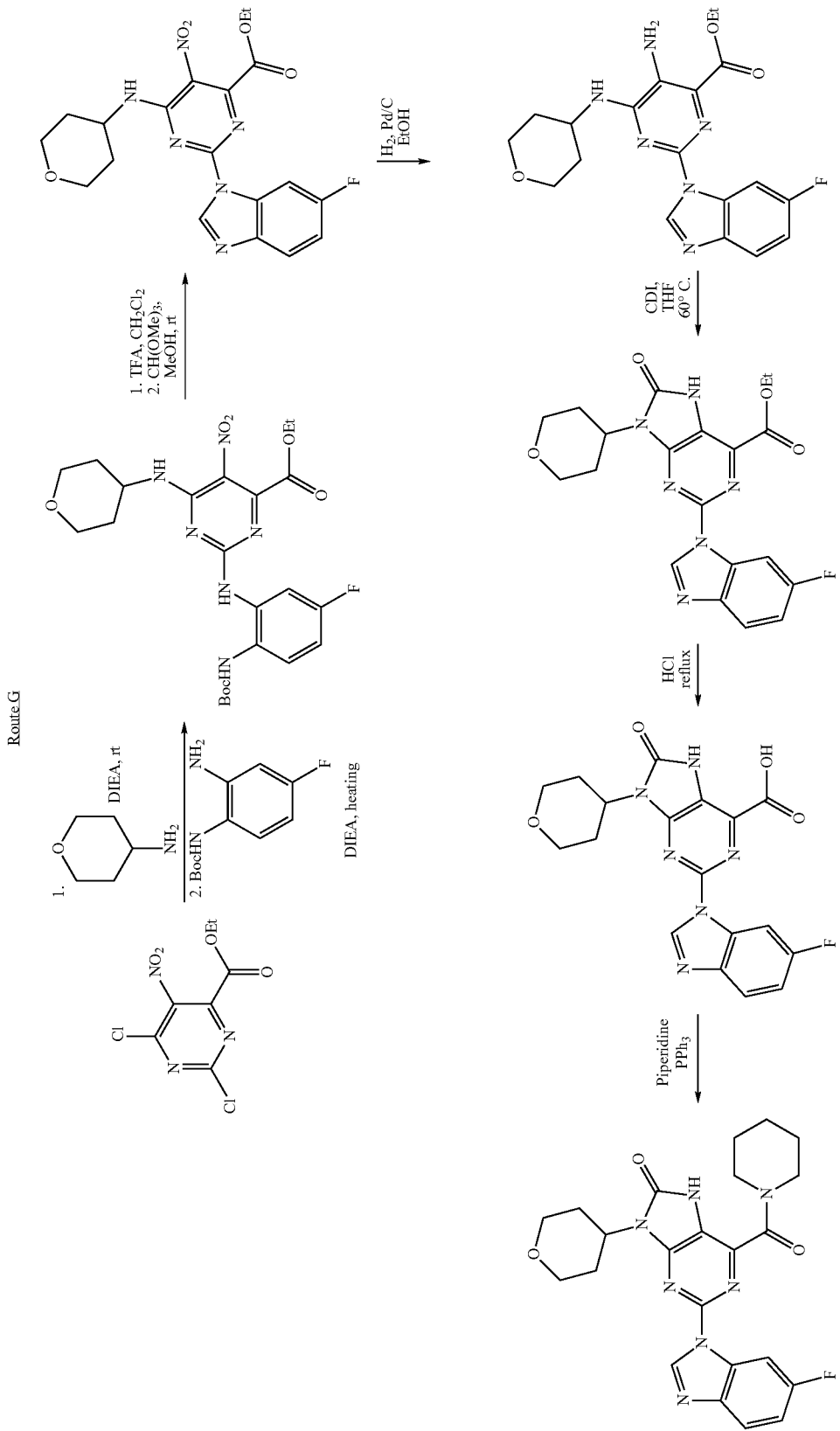

Ethyl 2-(2-(tert-butoxycarbonyl)-5-fluorophenylamino)-5-nitro-6-(tetrahydro-2H-pyran-4-ylamino)pyrimidine-4-carboxylate. To a solution of ethyl 2,6-dichloro-5-nitropyrimidine-4-carboxylate (2.0 g, 7.5 mmol) in dry dioxane (30 mL) was added N,N-diisopropylethylamine (3.9 mL, 22.5 mmol) dropwise, at 0° C. To this solution was added tetrahydro-2H-pyran-4-amine hydrochloride (1.04 g, 7.5 mmol) in aliquots, and the reaction mixture was slowly warmed to room temperature and stirred for 30 min. It was cooled to 0° C. and N,N-diisopropylethylamine (3.9 mL, 22.5 mmol) was added dropwise, followed by tert-butyl-2-amino-4-fluorophenylcarbamate (1.6 g, 7.3 mmol) and the resulting mixture was heated to 60° C. for 6 h. The reaction mixture was cooled to room temperature and concentrated in vacuo. The residue was purified using column chromatography (silica gel, gradient elution with ethyl acetate in petroleum ether) to give the desired product as a yellow solid. Yield: 530 mg, 14%. $^1$H NMR (400 MHz, DMSO-$d_6$) δ, ppm: 9.91 (s, 1H), 8.72 (s, 1H), 8.59 (d, J=7.3 Hz, 1H), 7.61 (d, J=7.7 Hz, 1H), 7.53 (t, J=7.4 Hz, 1H), 7.05 (m, 1H), 4.36 (q, J=7.1 Hz, 2H), 4.10 (m, 1H), 3.87 (d, J=11.0 Hz, 2H), 3.28 (t, J=12.2 Hz, 2H), 1.81-1.67 (m, 4H), 1.45 (s, 9H), 1.30 (t, J=7.0 Hz, 3H); LCMS (EI) m/z 521 (MH)$^+$.

Ethyl 2-(6-fluoro-1H-benzo[d]imidazol-1-yl)-5-nitro-6-(tetrahydro-2H-pyran-4-ylamino)pyrimidine-4-carboxylate. Ethyl 2-(2-(tert-butoxycarbonyl)-5-fluorophenylamino)-5-nitro-6-(tetrahydro-2H-pyran-4-ylamino)pyrimidine-4-carboxylate (530 mg, 1.02 mmol) was treated with a 30% (v) solution of TFA in methylene chloride with stirring at room temperature. TLC monitoring showed the reaction to be complete in 3 h. The solvent was evaporated and the residue treated with a solution of trimethylorthoformate in methanol (1:1 (v), 20 mL). After stirring at room temperature for 12 h, an orange solid formed. The orange solid was filtered and dried to give the desired product (310 mg, 72% yield). $^1$H NMR (400 MHz, DMSO-$d_6$) δ, ppm: 9.11 (s, 1H), 8.85 (d, J=7.6 Hz, 1H), 8.08 (d, J=2.5 Hz, 1H), 7.84 (m, 1H), 7.33-7.27 (m, 1H), 4.75 (m, 1H), 4.60 (q, J=7.0 Hz, 2H), 3.96 (d, J=11.0 Hz, 2H), 3.54 (t, J=7.3 Hz, 2H), 1.90-1.80 (m, 4H), 1.34 (t, J=7.1 Hz, 3H); LCMS (EI) m/z 431 (MH)$^+$.

Ethyl 5-amino-2-(6-fluoro-1H-benzo[d]imidazol-1-yl)-6-(tetrahydro-2H-pyran-4-ylamino)pyrimidine-4-carboxylate. Hydrogenation of ethyl 2-(6-fluoro-1H-benzo[d]imidazol-1-yl)-5-nitro-6-(tetrahydro-2H-pyran-4-ylamino)pyrimidine-4-carboxylate (310 mg, 0.717 mmol) was performed in ethanol, using Pd/C (10%), under a positive pressure of hydrogen. After 10 h, the catalyst was filtered, washed with portions of methylene chloride, and the combined filtrate concentrated to give the desired amine as a white solid (220 mg, 78% yield). $^1$H NMR (400 MHz, DMSO-$d_6$) δ, ppm: 8.97 (s, 1H), 8.47 (dd, J=2.6, 2.2 Hz, 1H), 7.74 (m, 1H), 7.60 (d, J=8.9 Hz, 2H), 7.16 (m, 1H), 6.74 (d, J=8.3 Hz, 1H), 4.37-4.32 (m, 3H), 3.94 (d, J=10.4 Hz, 2H), 3.55 (t, J=10.4 Hz, 2H), 2.01 (m, 2H), 1.58 (m, 2H), 1.42 (t, J=7.1 Hz, 3H); LCMS (EI) m/z 401 (MH)$^+$.

Ethyl 2-(6-fluoro-1H-benzo[d]imidazol-1-yl)-8-oxo-9-(tetrahydro-2H-pyran-4-yl)-8,9-dihydro-7H-purine-6-carboxylate. To a solution of ethyl 5-amino-2-(6-fluoro-1H-benzo[d]imidazol-1-yl)-6-(tetrahydro-2H-pyran-4-ylamino)pyrimidine-4-carboxylate (800 mg, 2.0 mmol) in dry THF (10 mL) was added carbonyl diimidazole (2.0 g) and the mixture was stirred at 60° C. for 48 h in a sealed tube. The solvent was evaporated and water (25 mL) was added to the residue. Filtration and drying of the white solid gave 600 mg (51% yield) of desired product. $^1$H NMR (400 MHz, DMSO-$d_6$) δ, ppm: 11.89 (s, 1H), 9.09 (s, 1H), 8.84 (dd, J=2.8, 2.4 Hz, 1H), 7.78 (dd, J=5.2, 5.2 Hz, 1H), 7.23 (m, 1H), 4.63 (m, 1H), 4.49 (q, J=6.8 Hz, 2H), 4.40 (dd, J=4.0, 3.0 Hz, 2H), 3.51 (t, J=11.6 Hz, 2H), 2.52 (m, 2H), 1.80 (d, J=2 Hz, 2H), 1.41 (t, J=7.1 Hz, 3H); LCMS (EI) m/z 427 (MH)$^+$.

2-(6-fluoro-1H-benzo[d]imidazol-1-yl)-8-oxo-9-(tetrahydro-2H-pyran-4-yl)-8,9-dihydro-7H-purine-6-carboxylic acid. A solution of ethyl 2-(6-fluoro-1H-benzo[d]imidazol-1-yl)-8-oxo-9-(tetrahydro-2H-pyran-4-yl)-8,9-dihydro-7H-purine-6-carboxylate (600 mg, 1.41 mmol) in concentrated aqueous HCl (15 mL) was heated at 100° C. for 6 h. The mixture was concentrated and the residue triturated with diethyl ether. The solid formed was filtered and dried to give 7 as an off white solid. Yield: 410 mg, 73%. $^1$H NMR (400 MHz, DMSO-$d_6$) δ, ppm: 11.84 (s, 1H), 9.20 (s, 1H), 8.47 (dd, J=2.4, 2.4 Hz, 1H), 7.82 (dd, J=5.2, 4.8 Hz, 1H), 7.26 (m, 1H), 4.63 (m, 1H), 4.04 (q, J=3.6 Hz, 2H), 3.51 (t, J=11.6 Hz, 2H), 2.60-2.54 (m, 2H), 1.80 (d, J=9.8 Hz, 2H); LCMS (EI) m/z 399 (MH)$^+$.

2-(6-fluoro-1H-benzo[d]imidazol-1-yl)-6-(piperidine-1-carbonyl)-9-(tetrahydro-2H-pyran-4-yl)-7H-purin-8(9H)-one. To a solution of 2-(6-fluoro-1H-benzo[d]imidazol-1-yl)-8-oxo-9-(tetrahydro-2H-pyran-4-yl)-8,9-dihydro-7H-purine-6-carboxylic acid (25 mg, 0.063 mmol) in THF (2 mL) at 0° C. was added piperidine (8 mg, 0.09 mmol) and triethyl amine (0.052 mL, 0.37 mmol), followed by a solution of triphenylphosphine (0.056 mL, 0.18 mmol) in ethyl acetate. The reaction mixture was allowed to reach room temperature and stirred for 24 h. The solvent was evaporated and a saturated solution of sodium bicarbonate was added to the residue. The solid formed was filtered and dried to give the desired compound as a white solid. Yield: 10 mg, 34%. $^1$H NMR (400 MHz, DMSO-$d_6$) δ, ppm: 11.89 (s, 1H), 8.20 (d, J=8.5 Hz, 1H), 7.82 (dd, J=4.8, 4.8 Hz, 1H), 7.24 (t, J=6.94 Hz, 1H), 4.58 (m, 1H), 4.03 (t, J=2.2 Hz, 2H), 3.68 (m, 2H), 3.68-3.48 (m, 4H), 2.64-2.55 (m, 2H), 1.79 (d, J=11.6 Hz, 2H), 1.66 (m, 4H), 1.55 (m, 2H); LCMS (EI) m/z 466 (MH)$^+$.

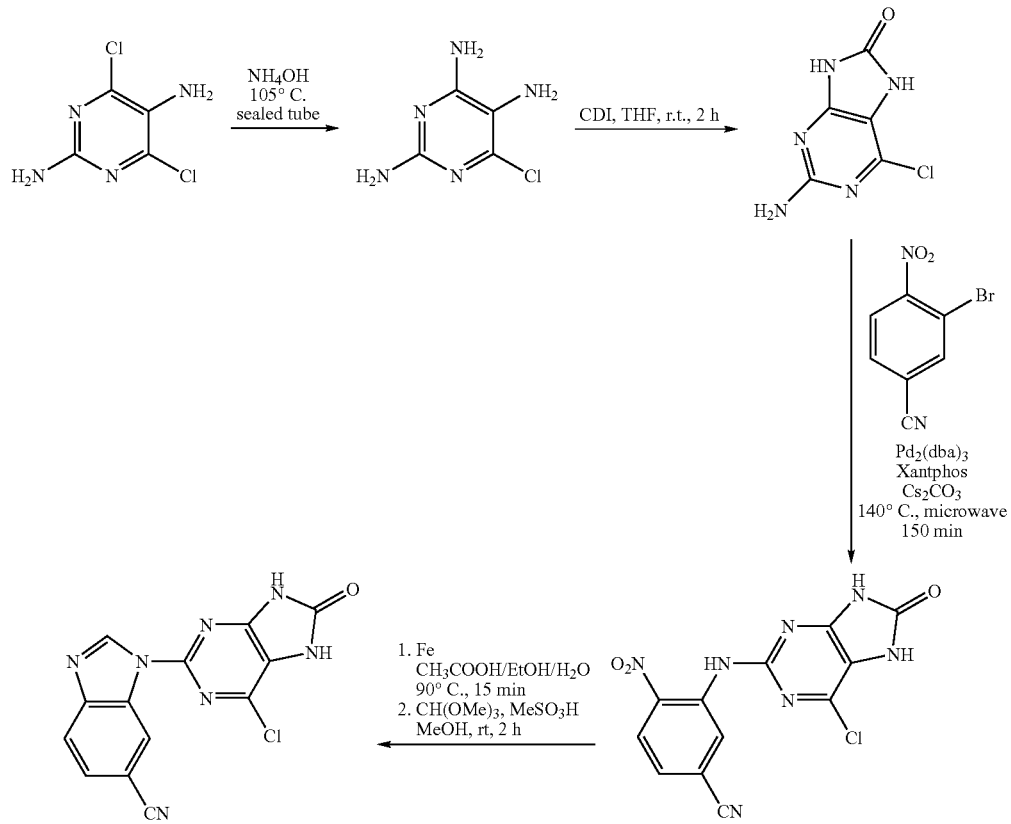

Route H 6-chloropyrimidine-2,4,5-triamine hydrochloride was prepared as described in WO 94/07892. 2,5-Diamino-4,6-dichloropyrimidine (10.8 g, 60.3 mmol) and concentrated aqueous ammonia (30 mL) were heated together in a sealed tube at 105° C. for 18 h, then cooled to room temperature. 2.34 g NaOH in water (10 mL) was added and the excess ammonia stripped out by concentrating to a low volume. Dilute HCl 2N (35 mL) and water (10 mL) were added and heated to dissolve, cooled to crystallize, then filtered to give the desired 6-chloropyrimidine-2,4,5-triamine hydrochloride (87% yield). MS (EI) m/z 160.1 (MH)$^+$.

2-amino-6-chloro-7H-purin-8(9H)-one. To a solution of 2,4,5-triamine-6-chloro-pyrimidine (6 g, 37 mmol) in 400 mL of anhydrous THF was added 1,1-carbonyldiimidazole (37 g, 226 mmol) as a solid, in portions. The reaction mixture was stirred at room temperature for 2 h (completion of the reaction checked by HPLC and MS). The solvent was removed in vacuo. Water (300 mL) was added to the residue and the mixture stirred at room temperature for 10 min. The solid formed was filtered under vacuum, and thoroughly dried to give 4.27 g (61% yield) of the desired product as a bright red solid. MS (EI) m/z 186.1 (MH)$^+$.

3-(6-chloro-8-oxo-8,9-dihydro-7H-purin-2-ylamino)-4-nitrobenzonitrile. To an oven-dried microwave flask under Ar was added 2-amino-6-chloro-7H-purin-8(9H)-one (0.64 g, 3.46 mmol, 1.0 equiv.) followed by anhydrous dioxane (10 mL) and anhydrous ethanol (4 mL); Cs$_2$CO$_3$ (Aldrich, 2.25 g, 6.92 mmol, 2 equiv.), 3-bromo-4-nitro-benzonitrile (1.02 g, 4.5 mmol, 1.3 equiv.), Xantphos (Strem, 0.6 g, 1.04 mmol, 0.3 equiv.) and Pd$_2$(dba)$_3$ (Strem, 0.32 g, 0.35 mmol, 0.1 equiv.) were all added as solids, and the mixture was stirred under Ar, at room temperature for 3 min. The flask was capped and heated in the microwave at 140° C. for 150 min (LC-MS shows reaction to be complete). The reaction mixture was cooled to room temperature, then concentrated in vacuo to give a dark brown residue, which was purified by flash chromatography (silica gel, gradual elution 3/1 ethyl acetate/hexanes, then 4/1 ethyl acetate/hexanes with 1% MeOH to 20% MeOH) to give the desired product as an orange solid in 46% yield. $^1$H NMR (300 MHz, CD$_3$COOD) δ, ppm: 9.31 (d, 1H), 8.36 (d, 1H), 7.43 (dd, 1H); MS (EI) m/z 332.0 (MH)$^+$.

4-amino-3-(6-chloro-8-oxo-8,9-dihydro-7H-purin-2-ylamino)benzonitrile. To 3-(6-chloro-8-oxo-8,9-dihydro-7H-purin-2-ylamino)-4-nitrobenzonitrile (0.41 g, 1.23 mmol) was added glacial acetic acid (30 mL), water (75 mL) and ethanol (150 mL), followed by iron powder (Aldrich, 0.69 g, 12.3 mmol, 10 equiv.) and the reaction mixture was stirred at 90° C. for 15 min (LC-MS monitoring), when it became a clear dark orange solution. It was cooled to r.t., then concentrated NH$_4$OH (50 mL) was added to bring the pH to 11. The reaction mixture was stirred at r.t. for 30 min. Repeated extractions into ethyl acetate, then into 25% isopropanol in CH$_2$Cl$_2$ (total volume 2 L), drying of the combined organic extracts, and in vacuo evaporation of the solvent provided the desired product as a brown solid, which was used in the next step without further purification. MS (EI) m/z 302.1 (MH)$^+$.

3-(6-chloro-8-oxo-8,9-dihydro-7H-purin-2-yl)-3H-benzo[d]imidazole-5-carbonitrile. To a solution of crude 4-amino-3-(6-chloro-8-oxo-8,9-dihydro-7H-purin-2-ylamino)benzonitrile (1.23 mmol) in anhydrous DMSO (10 mL) was added methanol (150 mL), followed by anhydrous trimethylorthoformate (5 mL) and p-toluene sulfonic acid (100 mg) and the reaction mixture was stirred under Ar at room temperature for 3 h (LC-MS monitoring). The solvent was removed in vacuo and the residue redissolved in 7 mL of DMSO, then 40 mL of water were added. The pink solid formed was filtered under vacuo using a fine porosity Buchner filter funnel, washed with water, then dried in the vacuum oven at 60° C. to give 0.26 g of the desired product (67% yield on 2 steps). $^1$H NMR (300 MHz, CDCl$_3$+CD$_3$OD) δ, ppm: 9.24 (s, 1H), 9.00 (s, 1H), 7.91 (d, 1H), 7.69 (d, 1H); MS (EI) m/z 312.2 (MH)$^+$.

General procedure for diversifying at the N9 position of the purinones based on a Mitsunobu reaction. A mixture of 3-(6-substituted-8-oxo-8,9-dihydro-7H-purin-2-yl)-3H-benzo[d]imidazole-5-carbonitrile (0.24 mmol, 1.0 equiv.) in CH$_2$Cl$_2$ (4 mL) and DMSO (1 mL), the corresponding benzyl alcohol or primary aliphatic alcohol (0.42 mmol, 1.75 equiv.) and resin-bound PS-triphenylphosphine (3 mmol/g, 172 mg, 0.52 mmol, 2.2 equiv.) was treated with di-t-butylazodicarboxylate (0.42 mmol, 1.75 equiv.) at room temperature. The mixture was allowed to stir at room temperature for 1-3 days. The reaction mixture was then filtered, the resin washed with CH$_2$Cl$_2$ (2×10 mL), methanol (10 mL) and CH$_2$Cl$_2$ (10 mL), and the combined filtrate and washings concentrated and subjected to preparative HPLC purification to give the desired N9-substituted purinone.

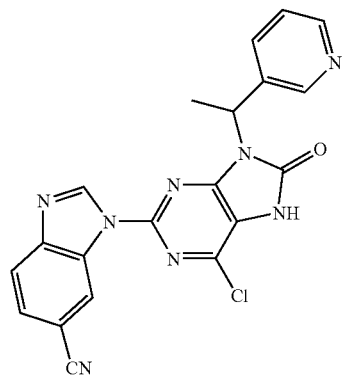

3-(6-chloro-8-oxo-9-(1-(pyridin-3-yl)ethyl)-8,9-dihydro-7H-purin-2-yl)-3H-benzo[d]imidazole-5-carbonitrile. Yellow oil (26% yield based on 73% conversion). Synthesized using 1-pyridin-3-yl-ethanol and 3-(6-chloro-8-oxo-8,9-dihydro-7H-purin-2-yl)-3H-benzo[d]imidazole-5-carbonitrile. $^1$H NMR (300 MHz, CD$_3$OD) δ, ppm: 9.27 (s, 1H), 9.20-9.00 (br m, 1H), 8.86 (d, 1H), 8.88-8.77 (m, 1H, overlapping with 8.86 ppm), 8.68 (s, 1H), 8.13 (br s, 1H), 7.87 (d, 1H), 7.68 (d, 1H), 6.17 (q, J=7.1 Hz, 1H), 2.19 (d, J=7.3 Hz, 3H); MS (EI) m/z 417.1 (MH)$^+$.

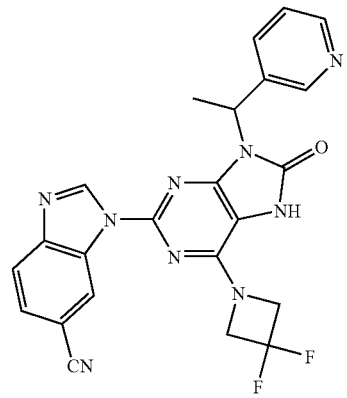

3-(6-(3,3-difluoroazetidin-1-yl)-8-oxo-9-(1-(pyridin-3-yl)ethyl)-8,9-dihydro-7H-purin-2-yl)-3H-benzo[d]imidazole-5-carbonitrile. White semi-solid. 57% yield. Synthesized from 3-(6-chloro-8-oxo-9-(1-(pyridin-3-yl)ethyl)-8,9-dihydro-7H-purin-2-yl)-3H-benzo[d]imidazole-5-carbonitrile (19 mg, 0.046 mmol) and 3,3-difluoroazetidine hydrochloride (3 equiv.) following the general procedure for displacement reactions of 6-chloropurinones with aliphatic amines. $^1$H NMR (300 MHz, CD$_3$OD) δ, ppm: 9.27 (s, 1H), 9.20-9.00 (br m, 1H), 8.78 (d, 1H), 8.88-8.77 (m, 1H, overlapping with 8.78 ppm), 8.63 (s, 1H), 8.09 (br s, 1H), 7.88 (d, 1H), 7.67 (d, 1H), 6.13 (q, J=7.1 Hz, 1H), 4.78 (t, 4H), 2.16 (d, J=7.1 Hz, 3H); MS (EI) m/z 474.0 (MH)$^+$.

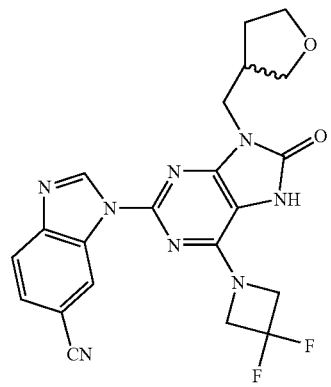

3-(6-(3,3-difluoroazetidin-1-yl)-8-oxo-9-((tetrahydrofuran-3-yl)methyl)-8,9-dihydro-7H-purin-2-yl)-3H-benzo[d]imidazole-5-carbonitrile. White solid. 18% yield. Synthesized from 3-(6-(3,3-difluoroazetidin-1-yl)-8-oxo-8,9-dihydro-7H-purin-2-yl)-3H-benzo[d]imidazole-5-carbonitrile (0.12 mmol) and tetrahydro-3-furan-methanol following the general procedure for diversifying at the N9 position of the purinones based on a Mitsunobu reaction. $^1$H NMR (300 MHz, CDCl$_3$+CD$_3$OD) δ, ppm: 9.22 (s, 1H), 8.99 (s, 1H), 7.89 (d, 1H), 7.67 (d, 1H), 4.76 (t, 4H), 4.10-3.97 (m, 3H), 3.90-3.77 (m, 3H), 3.06-2.93 (m, 1H), 2.22-2.07 (m, 1H), 1.90-1.83 (m, 1H); IR (CHCl$_3$), cm$^{-1}$: 2979 (w), 1703 (s), 1367 (m), 1167 (m); MS (EI) m/z 453.1 (MH)$^+$.

Route I
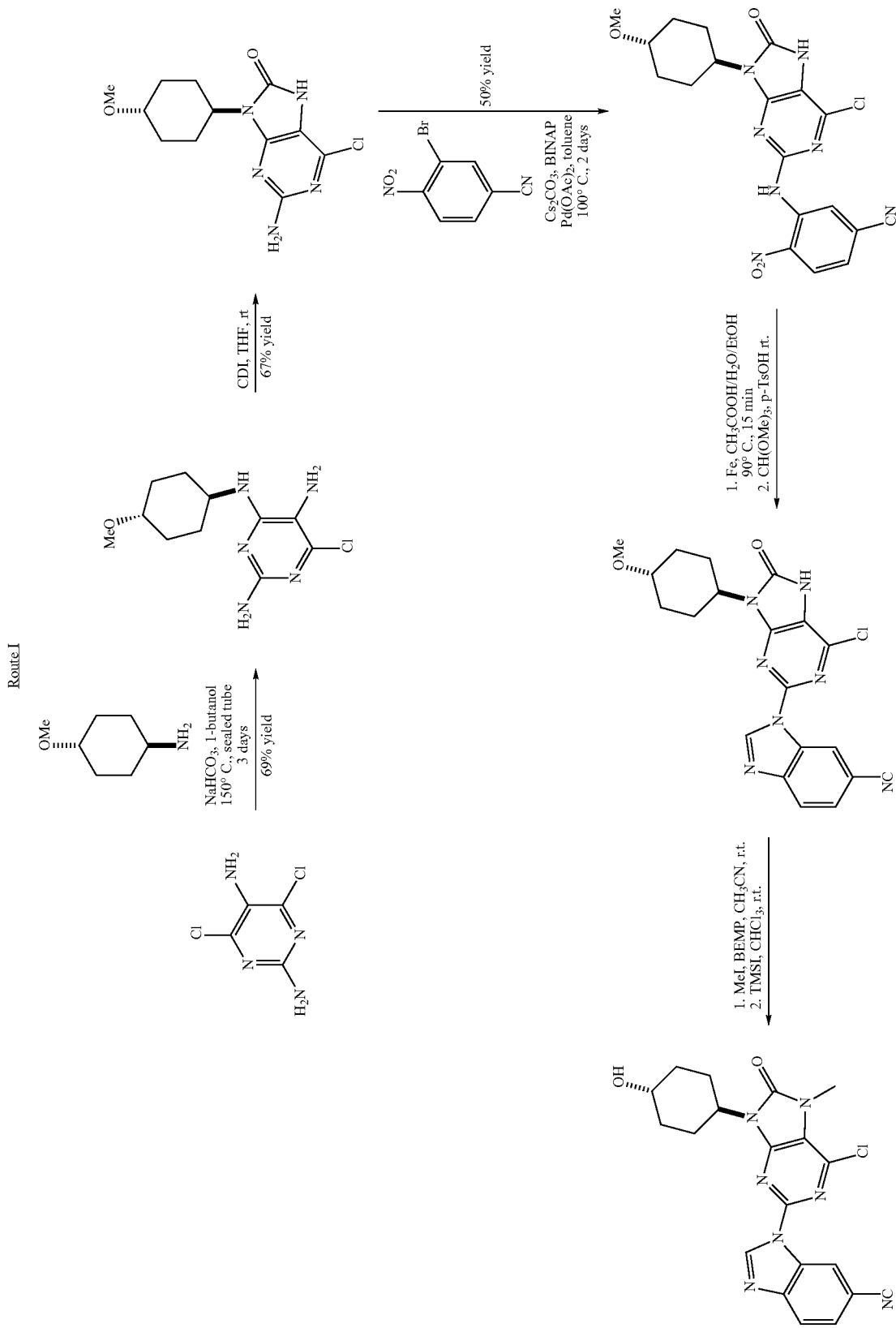

6-chloro-N⁴-(trans-4-methoxycyclohexyl)pyrimidine-2,4,5-triamine. 2,5-diamino-4,6-dichloropyrimidine (6 g, 33.5 mmol), trans-4-methoxy cyclohexyl amine (4.32 g, 33.5 mmol, 1 equiv.), sodium bicarbonate (9.85 g, 117.2 mmol, 3.5 equiv.) and 1-butanol (350 mL) were heated together at 150° C. in a sealed tube. After 3 days, when the reaction appeared to be complete (by HPLC), the reaction mixture was cooled to room temperature and the solvent was removed in vacuo. The residue was purified by flash chromatography (silica gel, gradual elution with 96/4 methylene chloride/methanol to 90/10 methylene chloride/methanol) to give the desired product as a brown solid (69% yield). MS (EI) m/z 272 (MH)⁺.

2-amino-6-chloro-9-(trans-4-methoxycyclohexyl)-7H-purin-8(9H)-one. To a solution of 6-chloro-N⁴-(trans-4-methoxycyclohexyl)pyrimidine-2,4,5-triamine (5.5 g, 20.36 mmol) in 300 mL of anhydrous THF (use oven dried glassware) was added 1,1-carbonyldiimidazole (newly opened bottle, 19.8 g, 122.2 mmol, 6 equiv.) as a solid, in portions. The reaction mixture was stirred at room temperature for 2 h (completion of the reaction checked by HPLC and MS). The solvent was removed in vacuo. Water (250 mL) was added to the residue and the mixture stirred at room temperature for 10 min. The solid formed was filtered under vacuum, washed with cold water and thoroughly dried to give the desired product as a brown solid (67% yield), which was used in the next step without further purification. MS (EI) m/z 298 (MH)⁺.

3-(6-chloro-9-(trans-4-methoxycyclohexyl)-8-oxo-8,9-dihydro-7H-purin-2-ylamino)-4-nitrobenzonitrile. To an oven-dried 250 mL round bottom flask was added 2-amino-6-chloro-9-(trans-4-methoxycyclohexyl)-7H-purin-8(9H)-one (crude, 3.65 g, 12.28 mmol, 1 equiv.) in anhydrous toluene (50 mL), then freshly grounded cesium carbonate (6 g, 18.43 mmol, 1.5 equiv.) with stirring at room temperature under Ar. Pd(OAc)₂ (1.24 g, 1.84 mmol, 0.15 equiv.), racemic BINAP (2.67 g, 4.3 mmol, 0.35 equiv.) and 3-bromo-4-nitrobenzonitrile (3.6 g, 15.96 mmol, 1.3 eq) were all added as solids. The reaction was performed under a flow of Argon, with heating at 100° C. for two days. The reaction mixture was cooled to room temperature, then concentrated in vacuo and the resulting residue was purified using flash chromatography (silica gel, gradient elution 10% EtOAc in hexanes to 50% EtOAc in hexanes) to give the desired product as an orange solid (50% yield). MS (EI) m/z 444 (MH)⁺.

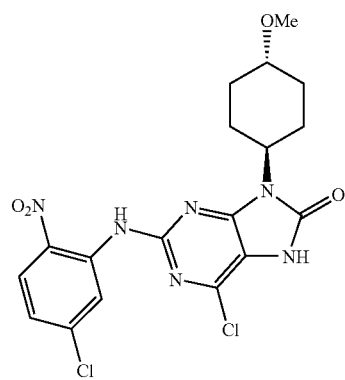

6-chloro-2-(5-chloro-2-nitrophenylamino)-9-((trans)-4-methoxycyclohexyl)-7H-purin-8(9)-one. Synthesized using the above procedure. Yield 35%. MS (EI) m/z 453 (MH)⁺.

4-amino-3-(6-chloro-9-trans-4-methoxycyclohexyl)-8-oxo-8,9-dihydro-7H-purin-2-ylamino)benzonitrile. 3-(6-chloro-9-(trans-4-methoxycyclohexyl)-8-oxo-8,9-dihydro-7H-purin-2-ylamino)-4-nitrobenzonitrile (1.3 g, 2.93 mmol) was taken in a 500 mL round bottom flask. To it was added iron powder (1.64 g, 29.3 mmol, 10 equiv.), followed by CH₃COOH:H₂O:EtOH (1:2.5:5 volume ratio) total volume 225 mL. The reaction mixture was then heated to 90° C. with continuous stirring for 30 minutes. Completion of the reaction was monitored by analytical HPLC and MS analysis (M⁺ 414). The reaction mixture was cooled to room temperature. Saturated NH₄OH was added to the cooled solution slowly, with stirring, until pH was 11-12. It was then diluted with EtOAc (250 mL). The organic layer was separated and the aqueous layer extracted with multiple portions of 200 mL of EtOAc until the aqueous layer was free of any desired compound (by HPLC). The organic layers were combined, dried over MgSO₄ and concentrated to give a light brown solid (82% yield), which was used without purification in the next step. MS (EI) m/z 414 (MH)⁺.

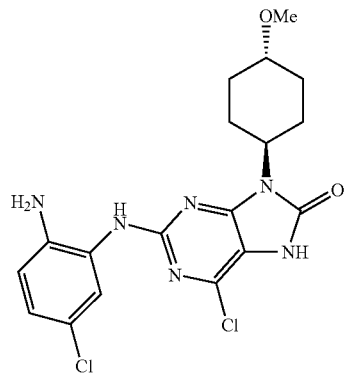

2-(2-amino-5-chlorophenylamino)-6-chloro-9-((trans)-4-methoxycyclohexyl)-7H-purin-8(9H)-one. Synthesized using the above procedure. MS (EI) m/z 423 (MH)⁺.

3-(6-chloro-9-(trans-4-methoxycyclohexyl)-8-oxo-8,9-dihydro-7H-purin-2-yl)-3H-benzo[d]imidazole-5-carbonitrile. To a solution of 4-amino-3-(6-chloro-9-trans-4-methoxycyclohexyl)-8-oxo-8,9-dihydro-7H-purin-2-ylamino)benzonitrile (1.0 g, 2.41 mmol) in 25 mL of anhydrous methanol was added trimethylorthoformate (1 mL, 10.89 mmol, 4.5 equiv.), followed by 8 to 10 drops of methane sulfonic acid. The reaction mixture was stirred at room temperature for 2 h. Completion of the reaction was checked by HPLC and MS. The reaction mixture was concentrated under high vacuum to give a dark brown solid. (97% crude yield). Preparative HPLC purification of a 50 mg sample gave pure desired compound in 20% yield. ¹HNMR (300 MHz, CDCl₃+CD₃OD) δ, ppm: 9.22 (s, 1H), 8.96 (s, 1H), 7.98 (d, 1H), 7.72 (dd, 1H), 4.54-4.40 (m, 1H), 3.58-3.40 (m, 1H, overlapping with 3.51 ppm), 3.51 (s, 3H), 2.62-2.44 (m, 2H), 2.37 (br d, 2H), 2.00 (br d, 2H), 1.59-1.41 (m, 2H); MS (EI) m/z 424.0 (MH)⁺.

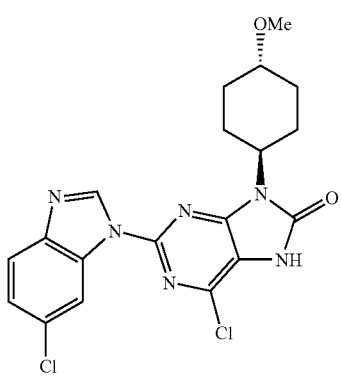

6-chloro-2-(6-chloro-1H benzo[d]imidazol-1-yl)-9-((trans-4-methoxycyclohexyl)-7H-purin-8(9H)-one. Synthesized using the above procedure. $^1$H NMR (300 MHz, CDCl$_3$+CD$_3$OD) δ, ppm: 9.03 (s, 1H), 8.58 (d, 1H), 7.72 (d, 1H), 7.38 (dd, 1H), 4.61-4.38 (m, 1H), 3.58-3.48 (m, 1H), 3.45 (s, 3H), 2.66-2.45 (m, 2H), 2.33 (br d, 2H), 1.99 (br d, 2H), 1.52-1.38 (m, 2H); MS (EI) m/z 433.1 (MH)$^+$.

General Procedure for N-7 alkylation/methylation. To a solution of 3-(6-chloro-9-(trans-4-methoxycyclohexyl)-8-oxo-8,9-dihydro-7H-purin-2-yl)-3H-benzo[d]imidazole-5-carbonitrile (1.65 mmol) in CH$_3$CN (25 mL) was added polystyrene supported BEMP (2-tert.butylimino-2-diethylamino-1,3-dimethyl-perhydro-1,3,2-diazaphosphorine (Fluka, loading 2.2 mmol/g) (4 equiv.), followed by alkyl iodide/iodomethane (6 equiv.). The reaction mixture was stirred at room temperature for 1 h. Completion of the reaction mixture was checked by HPLC and MS. The reaction mixture was filtered and the resin was washed with CH$_3$CN (10 mL×2) and MeOH (10 mL×2). The washings and the filtrate were combined and concentrated in vacuo to give the desired compound.

3-(6-chloro-9-(trans-4-methoxycyclohexyl)-7-methyl-8-oxo-8,9-dihydro-7H-purin-2-yl)-3H-benzo[d]imidazole-5-carbonitrile. Dark brown solid (76% crude yield). Synthesized using 3-(6-chloro-9-(trans-4-methoxycyclohexyl)-8-oxo-8,9-dihydro-7H-purin-2-yl)-3H-benzo[d]imidazole-5-carbonitrile (0.7 g, 1.65 mmol) and iodomethane (0.61 mL, 10 mmol, 6 equiv.). MS (EI) m/z 438 (MH)$^+$.

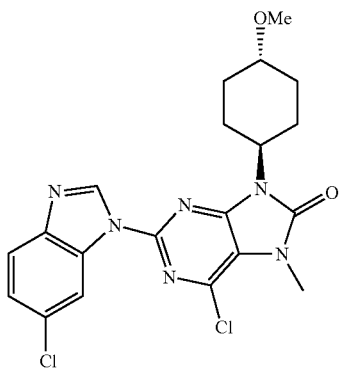

6-Chloro-2-(6-chloro-1H-benzo[d]imidazol-1-yl)-9-((trans)4-methoxycyclohexyl)-7-methyl-7H-purin-8(9H)-one. Synthesized using the above procedure. MS (EI) m/z 447 (MH)$^+$.

Typical Procedure for Selective Demethylation 3-(6-chloro-9-(trans-4-hydroxycyclohexyl)-7-methyl-8-oxo-8,9-dihydro-7H-purin-2-yl)-3H-benzo[d]/imidazole-5-carbonitrile. To an oven dried flask under Argon flow was added 3-(6-chloro-9-(trans-4-methoxycyclohexyl)-7-methyl-8-oxo-8,9-dihydro-7H-purin-2-yl)-3H-benzo[d]imidazole-5-carbonitrile (0.55 g, 1.25 mmol) in chloroform, followed by iodotrimethylsilane (0.1 mL, 1.25 mmol, 1 equiv.) The reaction mixture was stirred at room temperature for 4 h. Upon completion (HPLC monitoring), the reaction was slowly quenched with water. The organic layer was separated and the aqueous layer extracted with CHCl$_3$ (15 ml×3) and with EtOAc (15 mL×3). The combined organic layers were dried (MgSO$_4$), and concentrated in vacuo to give a dark solid (66% crude yield). MS (EI) m/z 424 (MH)$^+$.

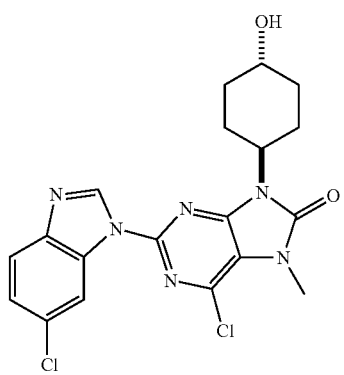

6-chloro-2-(6-chloro-1H-benzo[d]imidazol-1-yl)-9-((trans)-4-hydroxycyclohexyl)-7-methyl-7-purin-8(9H)-one. Synthesized using the above procedure. MS (EI) m/z 433 (MH)$^+$.

Typical procedure for cross-coupling reactions of 6-chloropurinones with (hetero)arylboronic acids

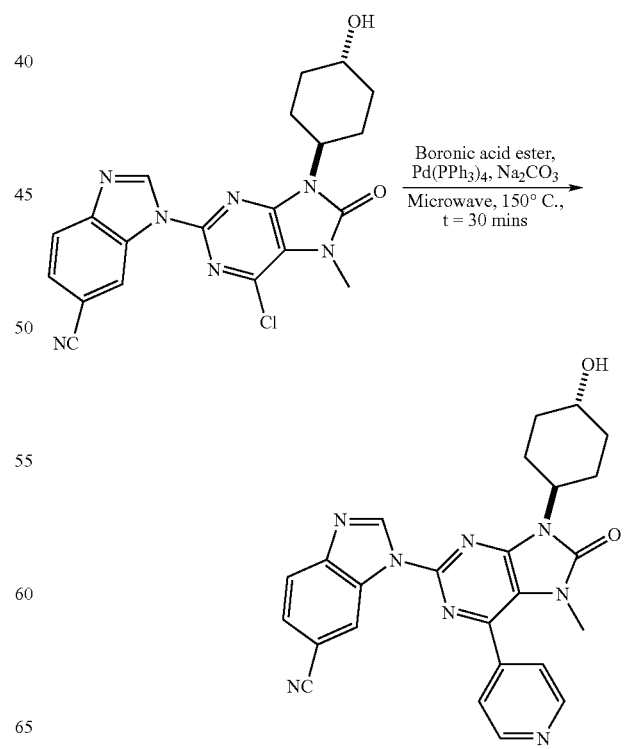

3-(9-((trans-4-hydroxycyclohexyl)-7-methyl-8-oxo-6-(pyridin-4-yl)8,9-dihydro-7H-purin-2yl)3-H-benzo[d]imidazole-5-carbonitrile. Ethanol (3 mL) was added to an argon-purged vial containing 3-(6-chloro-9-(trans-4-hydroxycyclohexyl)-7-methyl-8-oxo-8,9-dihydro-7H-purin-2-yl)-3H-benzo[d]imidazole-5-carbonitrile (100 mg, 0.236 mmol), pyridine-4-boronic acid pinacol ester (97 mg, 0.47 mmol, 2 equiv.), Pd(PPh$_3$)$_4$ (27 mg, 0.0236 mmol, 0.1 equiv.) and a 2M aqueous solution of Na$_2$CO$_3$ (200 µL). The mixture was heated for 30 min in the microwave oven at 150° C. After cooling to ambient temperature, the reaction mixture was diluted with ethanol, filtered through a Nylon 0.45 µm filter and the filtrate concentrated in vacuo. Preparative HPLC purification of the residue afforded, after evaporation and drying, the desired compound (TFA salt). $^1$HNMR (300 MHz, CDCl$_3$) δ, ppm: 9.30 (s, 1H), 9.04 (br s, 1H), 9.04-9.00 (br d, 2H, overlapping with 9.04 ppm), 8.05 (d, 1H), 7.76 (dd, 1H), 7.68 (br d, 2H), 4.74-4.60 (m, 1H), 4.20-4.08 (m, 1H), 3.33 (s, 3H), 2.84-2.67 (m, 2H), 2.42-2.31 (m, 2H), 2.17-2.04 (m, 2H), 1.82-1.64 (m, 2H), 1.36 (br s, 1H); Structure confirmed by nOe and FTIR; MS (EI) m/z 467.1 (MH)$^+$.

Typical procedure for the Displacement of Chlorine in 6-Chloropurinones with Amines

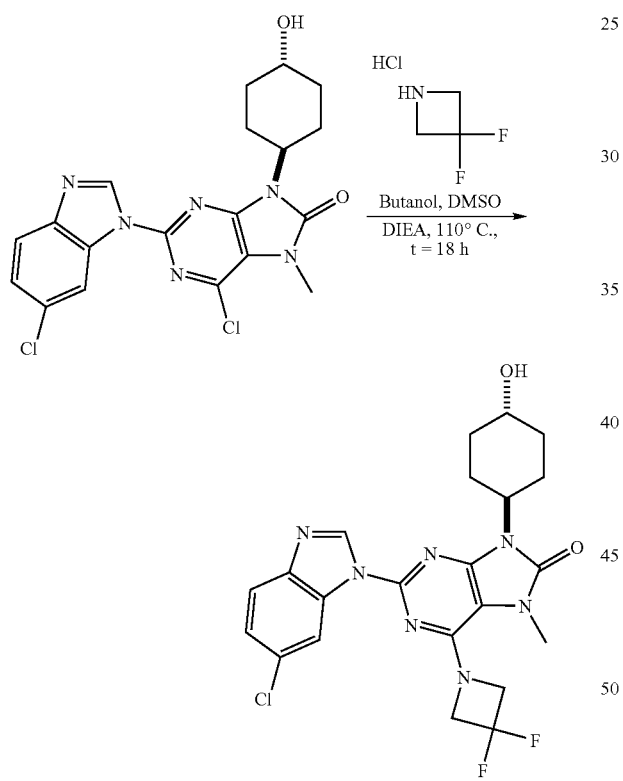

2-(6-chloro-1H-benzo[d]imidazole-1-yl)-6-(3,3-difluoroazetidin-1-yl)-9-(trans-4-hydroxy cyclohexyl)-7-methyl-7H-purin-8(9H)-one. 6-Chloro-2-(6-chloro-1H-benzo[d]imidazole-1-yl-9-((trans-4-hydroxycyclohexyl)-7-methyl-7H-purin-8(9H)-one (166 mg, 0.38 mmol) was taken in a scintillation vial with 1-butanol (2 mL), DMSO (1 mL) and DIEA (200 µL). To it was then added 3,3-difluoroazetidine hydrochloride (220 mg, 1.71 mmol, 4.5 equiv.) The reaction mixture was stirred at 110° C. for 18 h. The solvent was then removed under high vacuum. The residue was dissolved in MeOH and filtered. Preparative HPLC purification of the residue afforded, after evaporation and drying, the desired compound. White solid (no salt). $^1$HNMR (300 MHz, CDCl$_3$) δ, ppm: 8.92 (s, 1H), 8.53 (d, 1H), 7.76 (d, 1H), 7.34 (dd, 1H), 4.71 (t, 4H), 4.53-4.41 (m, 1H), 4.07-3.93 (m, 1H), 3.55 (s, 3H), 2.69-2.51 (m, 2H), 2.27-2.15 (m, 2H), 1.97-1.87 (m, 2H), 1.64-1.51 (m, 2H, overlapping with 1.56 ppm), 1.56 (br s, 1H); Structure confirmed by nOe, NOESY and FTIR; MS (EI) m/z 490.1 (MH)$^+$.

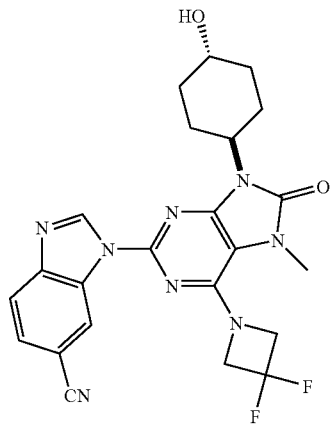

3-(6-(3,3-difluoroazetidin-1-yl)-9-(trans-4-hydroxycyclohexyl)-7-methyl-8-oxo-8,9-dihydro-7H-purin-2-yl)-3H-benzo[d]imidazole-5-carbonitrile. Synthesized using the procedure above. $^1$HNMR (300 MHz, CDCl$_3$+CD$_3$OD) δ, ppm: 9.15 (s, 1H), 8.91 (s, 1H), 7.91 (d, 1H), 7.66 (dd, 1H), 4.74 (t, 4H), 4.51-4.39 (m, 1H), 3.98-3.83 (m, 1H), 3.56 (s, 3H), 2.64-2.46 (m, 2H), 2.24-2.13 (m, 2H), 1.97-1.87 (m, 2H), 1.62-1.46 (m, 2H); Structure confirmed by nOe; MS (EI) m/z 481.2 (MH)$^+$.

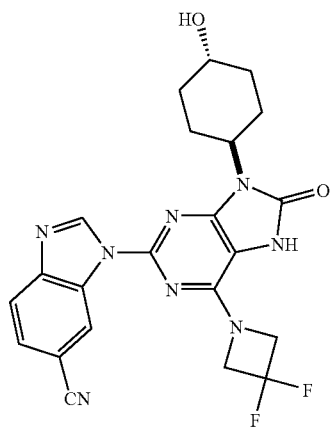

3-(6-(3,3-difluoroazetidin-1-yl)-9-(trans-4-hydroxycyclohexyl)-8-oxo-8,9-dihydro-7H-purin-2-yl)-3H-benzo[d]imidazole-5-carbonitrile. Synthesized from 3-(6-chloro-9-(trans-4-methoxycyclohexyl)-8-oxo-8,9-dihydro-7H-purin-2-yl)-3H-benzo[d]imidazole-5-carbonitrile by demethylation, followed by displacement of chlorine in the 6-chloropurinone with 3,3-difluoroazetidine. $^1$HNMR (300 MHz, CDCl$_3$+CD$_3$OD) δ, ppm: 9.12 (s, 1H), 8.92 (s, 1H), 7.90 (d, 1H), 7.64 (dd, 1H), 4.71 (t, 4H), 4.46-4.32 (m, 1H), 3.98-3.83 (m, 1H), 2.64-2.46 (m, 2H), 2.24-2.15 (m, 2H), 1.97-1.87 (m, 2H), 1.62-1.46 (m, 2H); MS (EI) m/z 467.0 (MH)$^+$.

Route J
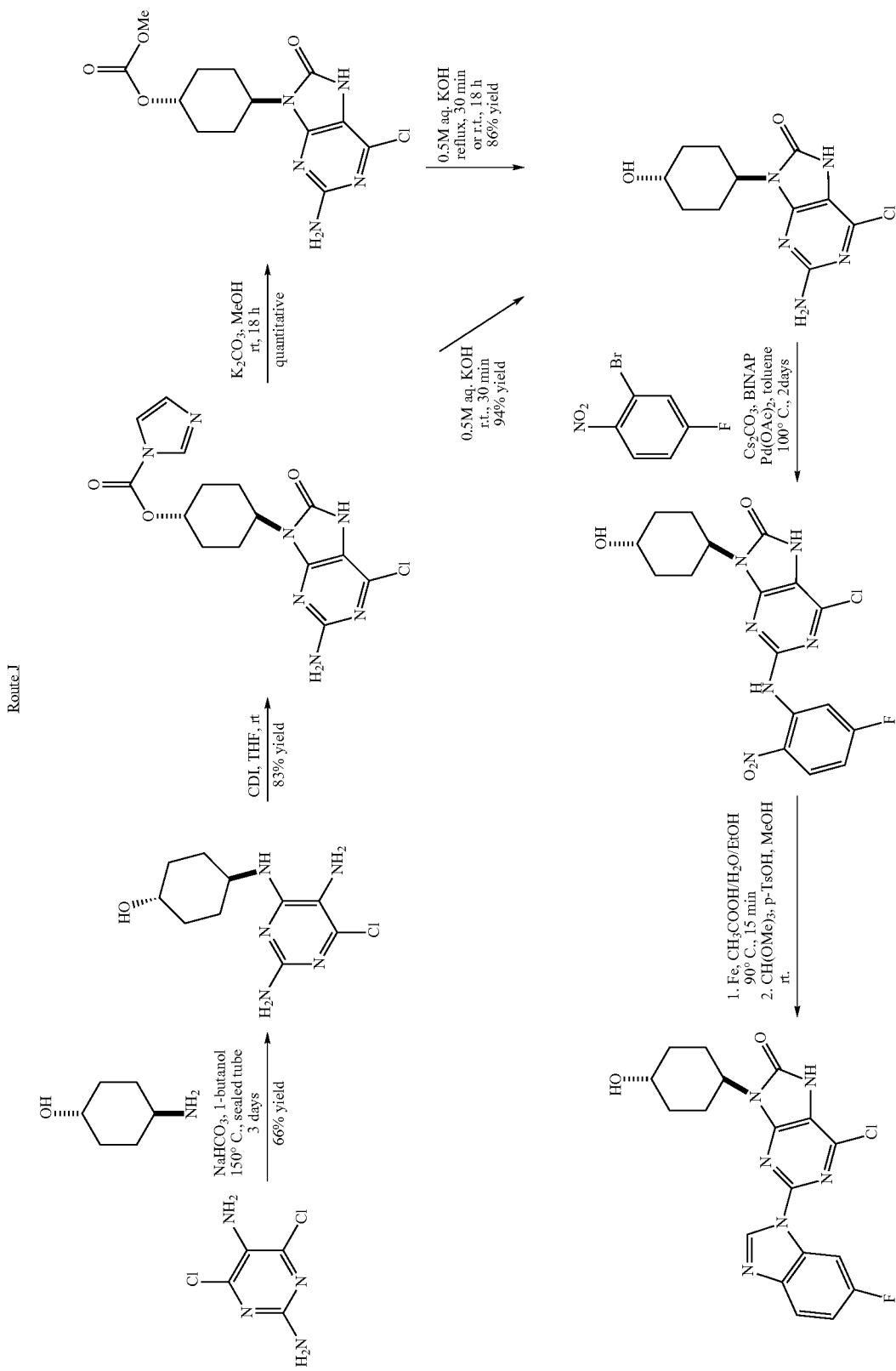

Trans-4-(2,5-diamino-6-chloropyrimidin-4-ylamino)cyclohexanol. 2,5-diamino-4,6-dichloropyrimidine (10.5 g, 58.6 mmol), trans-4-aminocyclohexanol (6.75 g, 58.6 mmol, 1 equiv.), sodium bicarbonate (17.2 g, 205 mmol, 3.5 equiv.) and 1-butanol (210 mL) were heated together at 150° C. in a sealed tube. After 3 days, when the reaction appeared to be complete (by LCMS), the reaction mixture was cooled to room temperature and the solvent was removed in vacuo. Water (150 mL) was added to the residue with stirring at room temperature for 30 min, and the dark red solid filtered under vacuo to give, after drying, 10 g (66% yield) of the desired product. $^1$H NMR (300 MHz, d$_6$-DMSO) δ, ppm: 6.14 (d, 1H), 5.57 (s, 2H), 4.54 (d, 1H), 3.90 (s, 2H), 3.81-3.76 (m, 1H), 3.40-3.32 (m, 1H), 1.86-1.82 (m, 4H), 1.28-1.20 (m, 4H); MS (EI) m/z 258.1 (MH)$^+$.

Trans-4-(2-amino-6-chloro-8-oxo-7,8-dihydropurin-9-yl)cyclohexyl-1H-imidazole-1-carboxylate. To a solution of trans-4-(2,5-diamino-6-chloropyrimidin-4-ylamino)cyclohexanol (8.7 g, 33.9 mmol) in 430 mL of anhydrous THF (use oven dried glassware) was added 1,1-carbonyldiimidazole (newly opened bottle, 33 g, 203 mmol) as a solid, in portions. The reaction mixture was stirred at room temperature for 4 h (completion of the reaction checked by HPLC and MS). The solvent was removed in vacuo. Water (1 L) was added to the residue and the mixture stirred at room temperature for 18 h. The solid was filtered under vacuum. The procedure was repeated twice and the resulting solid was thoroughly dried to give 10.6 g (83% yield) of the desired product as a pale brown solid. $^1$H NMR (300 MHz, d$_6$-DMSO) δ, ppm: 11.3 (br s, 1H), 8.27 (br s, 1H), 7.60 (br s, 1H), 7.08 (br s, 1H), 6.58 (s, 2H), 4.92-4.84 (m, 1H), 4.22-4.13 (m, 1H), 2.45-2.37 (m, 2H), 2.23-2.20 (m, 2H), 1.84-1.61 (m, 4H); MS (EI) m/z 378.4 (minor, MH)$^+$, 266.1 (fragment).

Trans-4-(2-amino-6-chloro-8-oxo-7,8-dihydropurin-9-yl)cyclohexyl methyl carbonate. To a suspension of trans-4-(2-amino-6-chloro-8-oxo-7,8-dihydropurin-9-yl)cyclohexyl-1H-imidazole-1-carboxylate (10.6 g, 28.1 mmol) in anhydrous methanol (400 mL) was added potassium carbonate (1.1 g, 10% wt) with stirring at room temperature. After 15 h, the reaction was found to be complete by LC-MS. The solvent was removed in vacuo, and water (1 L) was added with stirring at room temperature. Filtration under vacuum gave the desired product as a pink solid (yield quantitative). MS (EI) m/z 342.1 (MH)$^+$.

2-amino-6-chloro-9-(trans-4-hydroxycyclohexyl)-7H-purin-8(9H)-one. Trans-4-(2-Amino-6-chloro-8-oxo-7,8-dihydropurin-9-yl)cyclohexyl methyl carbonate (1.43 g) was dissolved in 80 mL of an aqueous solution 0.5 N KOH and the reaction mixture heated at reflux for 30 min (LC-MS analysis indicated reaction to be complete). The reaction mixture was then cooled in an ice bath, and its pH was brought to 7 by drop wise addition of a concentrated aqueous solution of HCl. A light pink solid precipitated. It was filtered under vacuum, thoroughly dried in vacuum oven at 60° C., to give the desired product in 86% yield. $^1$H NMR (300 MHz, CDCl$_3$+CD$_3$OD) δ, ppm: 8.48 (br s, 1H), 7.73 (s, 2H), 4.26-4.18 (m, 1H), 3.70-3.61 (m, 1H), 2.53-2.40 (m, 2H), 2.10-2.06 (m, 2H), 1.81-1.76 (m, 2H), 1.48-1.37 (m, 2H); MS (EI) m/z 284.1 (MH)$^+$.

Alternative one step procedure for 2-amino-6-chloro-9-(trans-4-hydroxycyclohexyl)-7H-purin-8(9H)-one. Trans-4-(2-amino-6-chloro-8-oxo-7,8-dihydropurin-9-yl)cyclohexyl-1H-imidazole-1-carboxylate (63.9 mmol) was suspended in an aqueous solution 0.5 N KOH (620 mL) with stirring at room temperature. The suspension gradually became a dark red solution. After 30 min, the reaction was found to be complete by LC-MS. The pH of the reaction mixture was brought to 7 by dropwise addition of a concentrated aqueous solution of HCl. A light pink solid precipitated. The neutralized reaction mixture was diluted with water up to a volume of 2 L, with stirring at room temperature for 10 min. The solid was filtered under vacuum, thoroughly dried in vacuum oven at 60° C., to give the desired product (17.08 g, 94% yield). $^1$H NMR (300 MHz, CDCl$_3$+CD$_3$OD) δ, ppm: 8.48 (br s, 1H), 7.73 (s, 2H), 4.26-4.18 (m, 1H), 3.70-3.61 (m, 1H), 2.53-2.40 (m, 2H), 2.10-2.06 (m, 2H), 1.81-1.76 (m, 2H), 1.48-1.37 (m, 2H); MS (EI) m/z 284.1 (MH)$^+$.

6-chloro-2-(5-fluoro-2-nitrophenylamino)-9-(trans-4-hydroxycyclohexyl)-7H-purin-8(9H)-one. All glassware was dried in vacuum oven at 60° C. for 1 day prior to reaction. Finely ground cesium carbonate and finely ground 2-amino-6-chloro-9-(trans-4-hydroxycyclohexyl)-7H-purin-8(9H)-one were dried at 60° C. under high vacuum for one day prior to experiment. To an oven-dried 2-neck flask under Ar was added 2-amino-6-chloro-9-(trans-4-hydroxycyclohexyl)-7H-purin-8(9H)-one (6.78 g, 23.9 mmol), cesium carbonate (11.71 g, 35.9 mmol, 1.5 equiv.) and anhydrous toluene (100 mL) and the mixture was stirred at room temperature for 15 min. Then, Pd(OAc)$_2$ (2.41 g, 3.59 mmol, 0.15 equiv.), racemic BINAP (5.21 g, 8.36 mmol, 0.35 equiv.) and 1-bromo-5-fluoro-2-nitrobenzene (6.84 g, 31.07 mmol, 1.3 equiv.) were added as solids, under Ar, and the reaction mixture was stirred at room temperature for 15 min, then stirred at 100° C. for 2 days (LC-MS shows ratio of desired product/starting material approx. 8/1). The reaction mixture was cooled to room temperature, and the solvent removed in vacuo. The dark brown residue was dissolved in warm CH$_3$COOH/EtOH (60 mL/60 mL), and then water (700 mL) was added. A dark yellow solid precipitated and was filtered under vacuum. A small portion of the dark yellow solid was purified by flash chromatography (silica gel, gradient elution with ethyl acetate/hexanes 1/1 to 3/1, then up to 20% methanol in 3/1 ethyl acetate/hexanes) to provide the desired compound as an orange solid. $^1$H NMR (300 MHz, CDCl$_3$+CD$_3$OD) δ, ppm: 10.67 (br s, 1H), 8.80 (dd, 1H), 8.37 (dd, 1H), 6.85-6.80 (m, 1H), 4.39-4.30 (m, 1H), 3.81-3.73 (m, 1H), 2.67-2.44 (m, 2H), 2.18-2.14 (m, 2H), 1.92-1.88 (m, 2H), 1.56-1.41 (m, 2H); MS (EI) m/z 423.3 (MH)$^+$.

2-(2-amino-5-fluorophenylamino)-6-chloro-9-(trans-4-hydroxycyclohexyl)-7H-purin-8(9H)-one. 6-chloro-2-(5-fluoro-2-nitrophenylamino)-9-(trans-4-hydroxycyclohexyl)-7H-purin-8(9H)-one (13.5 mg, 0.03 mmol) was dissolved in CH$_3$COOH:H$_2$O:EtOH (1 mL:2.5 mL:5 mL) and iron powder (18 mg, 0.32 mmol, 10 equiv.) was added. The reaction mixture was then heated to 90° C. with continuous stirring for 15 minutes. Completion of the reaction was monitored by analytical HPLC and MS analysis. The reaction mixture was cooled to room temperature. Saturated NH$_4$OH was added to the cooled solution slowly, with stirring, until pH was 11-12. It was then diluted with EtOAc (15 mL). The organic layer was separated, and the aqueous layer extracted with EtOAc (3×15 mL), the combined organic layers were washed with brine (1×15 mL), dried over MgSO$_4$ and concentrated to give a white solid (12 mg, 96% yield), which was used without purification in the next step. MS (EI) m/z 393 (MH)$^+$.

6-chloro-2-(6-fluoro-1H-benzo[d]imidazol-1-yl)-9-(trans-4-hydroxycyclohexyl)-7H-purin-8(9H)-one. To a flask containing crude 2-(2-amino-5-fluorophenylamino)-6-chloro-9-(trans-4-hydroxycyclohexyl)-7H-purin-8(9H)-one (12 mg, 0.03 mmol) was added anhydrous methanol (3 mL), followed by anhydrous trimethylorthoformate (0.5 mL) and p-toluenesulfonic acid (catalytic) and the reaction mixture was stirred under Ar at room temperature for 18 h (HPLC monitoring). A solution 10% acetonitrile in water (total volume 10 mL) was added and a pale yellow solid precipitated. Filtration under vacuum provided the desired product as a pale yellow solid (10.6 mg, 88% yield). $^1$H NMR (300 MHz, CDCl$_3$+CD$_3$OD) δ, ppm: 9.07 (br s, 1H), 8.30 (br d, 1H), 7.82-7.70 (m, 1H), 7.27-7.15 (m, 1H), 4.48-4.42 (m, 1H), 3.88-3.80 (m, 1H), 2.67-2.50 (m, 2H), 2.33-2.18 (m, 2H), 2.10-1.95 (m, 2H), 1.70-1.56 (m, 2H); MS (EI) m/z 403.1 (MH)⁺.

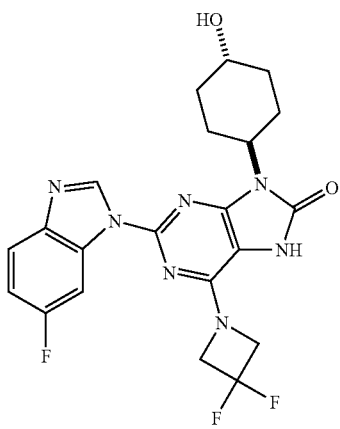

6-(3,3-difluoroazetidin-1-yl)-2-(6-fluoro-3H-benzo[d]imidazol-1-yl)-9-(trans-4-hydroxycyclohexyl)-7H-purin-8(9H)-one. Pale yellow solid. TFA salt. Synthesized following the general procedure for displacement reactions of 6-chloropurinones with aliphatic amines, using 3,3-difluoroazetidine. ¹H NMR (300 MHz, CDCl₃+CD₃OD) δ, ppm: 9.07 (br s, 1H), 8.42-8.25 (br m, 1H), 7.82-7.70 (m, 1H), 7.15 (br d, 1H), 4.71 (t, 4H), 4.48-4.38 (m, 1H), 3.88-3.80 (m, 1H), 2.67-2.50 (m, 2H), 2.27-2.15 (m, 2H), 1.97-1.87 (m, 2H), 1.62-1.50 (m, 2H); MS (EI) m/z 460.2 (MH)⁺.

Typical Procedure for Tetrahydropyranylation of Alcohols

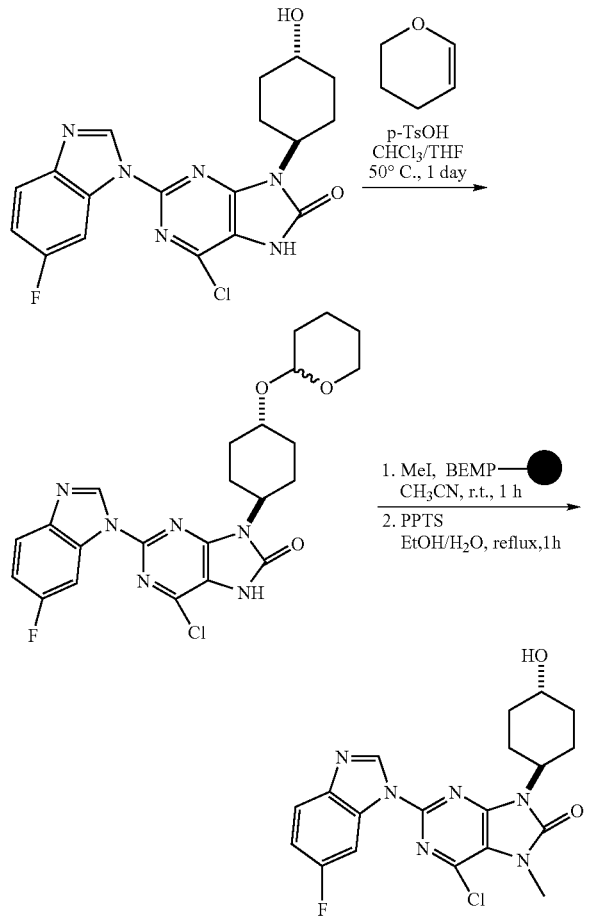

6-chloro-2-(6-fluoro-1H-benzo[d]imidazol-1-yl)-9-(trans-4-(tetrahydro-2H-pyran-2-yloxy)cyclohexyl)-7H-purin-8(9H)-one. A solution of 6-chloro-2-(6-fluoro-1H-benzo[d]imidazol-1-yl)-9-(trans-4-hydroxycyclohexyl)-7H-purin-8(9H)-one (0.8 mmol) and dihydropyran (15 equiv.) in anhydrous chloroform/THF (30 mL/15 mL) containing p-TsOH (0.1 equiv.) was stirred at 50° C. for 1 day (LCMS indicative of complete reaction). The reaction mixture was concentrated in vacuo and the residue purified by column chromatography on neutral alumina to give the desired product. MS (EI) m/z 487.3 (MH)⁺.

Typical Procedure for N7-Methylation/Alkylation 6-chloro-2-(6-fluoro-1H-benzo[d]imidazol-1-yl)-7-methyl-9-(trans-4-(tetrahydro-2H-pyran-2-yloxy)cyclohexyl)-7H-purin-8(9H)-one. To a solution of 6-chloro-2-(6-fluoro-1H-benzo[d]imidazol-1-yl)-9-(trans-4-(tetrahydro-2H-pyran-2-yloxy)cyclohexyl)-7H-purin-8(9H)-one (0.06 mmol) in anhydrous CH₃CN (10 mL) were added BEMP on polystyrene (loading 2.2 mmol/g, 4 equiv.) and iodomethane (primary alkyl iodide/benzyl iodide or bromide to be used for alkylation) (6 equiv.) with stirring at room temperature. After 1 h, LCMS showed reaction to be complete. The reaction mixture was filtered under vacuum, the resin washed with CH₃CN and methanol, and the combined filtrate and washings were concentrated in vacuo to give the desired product as a pale yellow solid, which was used in the next step without further purification. MS (EI) m/z 501.2 (MH)⁺.

Typical Procedure for the Hydrolysis of Tetrahydropyranyl Ethers 6-chloro-2-(6-fluoro-1H-benzo[d]imidazol-1-yl)-9-(trans-4-hydroxycyclohexyl)-7-methyl-7H-purin-8(9H)-one. A solution of 6-chloro-2-(6-fluoro-1H-benzo[d]imidazol-1-yl)-7-methyl-9-(trans-4-(tetrahydro-2H-pyran-2-yloxy)cyclohexyl)-7H-purin-8(9H)-one (0.06 mmol) and PPTS (5 mg) in ethanol/water (4.5 mL/0.5 mL) was stirred at reflux for 1 h. The solvent was evaporated in vacuo and the residue could be purified by chromatography or used in the next step without purification. MS (EI) m/z 417.0 (MH)⁺.

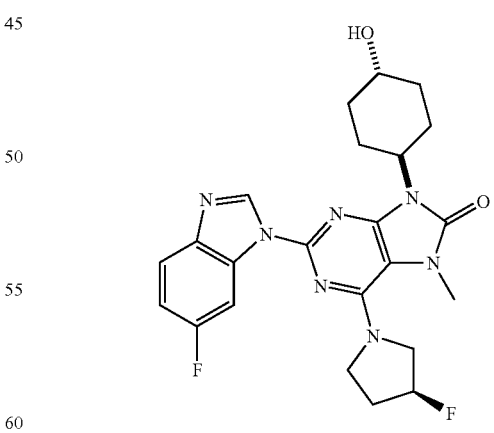

2-(6-fluoro-1H-benzo[d]imidazol-1-yl)-6-((S)-3-fluoropyrrolidin-1-yl)-9-(trans-4-hydroxycyclohexyl)-7-methyl-7H-purin-8(9H)-one. Light brown solid. TFA salt. Synthesized from 6-chloro-2-(6-fluoro-1H-benzo[d]imidazol-1-yl)-9-(trans-4-hydroxycyclohexyl)-7-methyl-7H-purin-8(9H)-one and S-(+)-3-fluoropyrrolidine hydrochloride, following the general procedure for displacement reactions of 6-chloropurinones with aliphatic amines. $^1$H NMR (300 MHz, CDCl$_3$+CD$_3$OD) δ, ppm: 8.99 (s, 1H), 8.27 (dd, 1H), 7.74 (dd, 1H), 7.15 (td, 1H), 5.47 (d, J=52.4 Hz, 1H), 4.51-4.42 (m, 1H), 4.19-3.83 (overlap of 5H), 3.65 (s, 3H), 2.68-2.42 (overlap of 3H), 2.29-2.03 (overlap of 3H), 1.97-1.90 (m, 2H), 1.62-1.49 (m, 2H); MS (EI) m/z 470.3 (MH)$^+$.

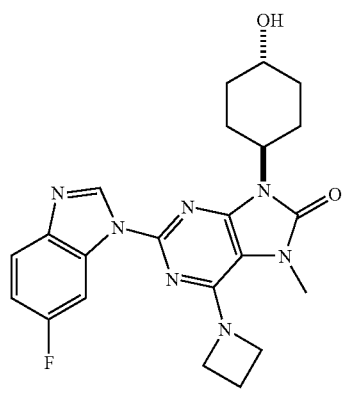

6-(azetidin-1-yl)-2-(6-fluoro-1H-benzo[d]imidazol-1-yl)-9-(trans-4-hydroxycyclohexyl)-7-methyl-7H-purin-8(9H)-one. White solid. $^1$H NMR (300 MHz, CDCl$_3$+CD$_3$OD) δ, ppm: 9.05 (s, 1H), 8.32 (br d, 1H), 7.80-7.68 (br m, 1H), 7.20-7.08 (m, 1H), 4.51-4.42 (m, 1H), 4.34 (t, 4H), 3.93-3.83 (m, 1H), 3.55 (s, 3H), 2.68-2.50 (overlap of 4H), 2.25-2.11 (m, 2H), 1.97-1.83 (m, 2H), 1.62-1.49 (m, 2H); MS (EI) m/z 438.3 (MH)$^+$.

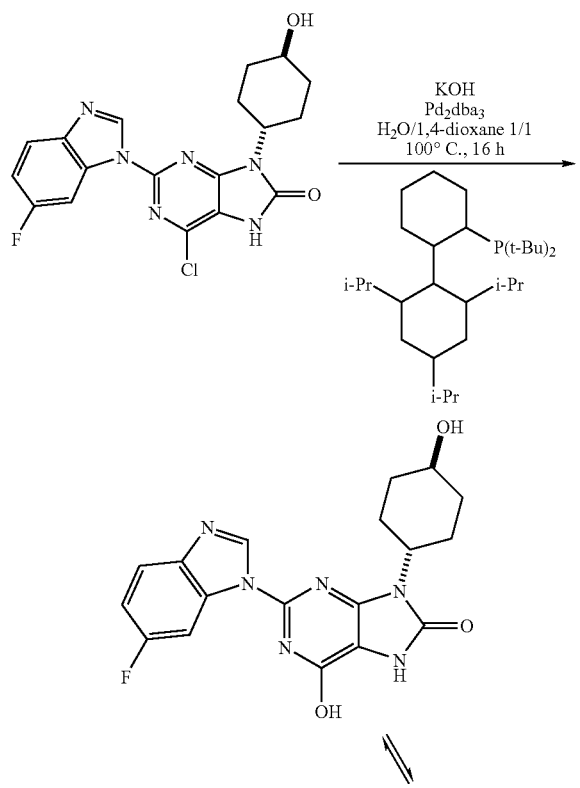

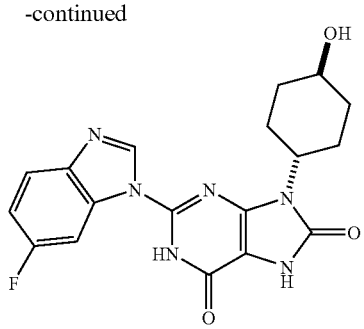

2-(6-fluoro-1H-benzo[d]imidazol-1-yl)-6-hydroxy-9-(trans-4-hydroxycyclohexyl)-7H-purin-8(9H)-one. An oven dried vial containing a stirbar was charged with Pd$_2$ dba$_3$ (2 mg, 0.002 mmol, 0.02 equiv.), 2-di-t-butylphosphino-2',4',6'-tri-isopropyl-1,1'-diphenyl (Strem, 3.5 mg, 0.008 mmol, 0.08 equiv.), KOH (17 mg, 0.3 mmol, 3 equiv.) and 6-chloro-2-(6-fluoro-1H-benzo[d]imidazol-1-yl)-9-(trans-4-hydroxycyclohexyl)-7H-purin-8(9H)-one (40 mg, 0.1 mmol, 1 equiv.), followed by 1,4-dioxane (0.3 mL) and degassed water (0.3 mL). A stream of argon was passed through the reaction mixture for 3 min; the vial was then closed and heated at 100° C. After 16 h, the reaction was found to be complete. Preparative HPLC chromatography provided, after evaporation of solvent, the desired product as a white solid. $^1$H NMR (300 MHz, CD$_3$OD+CDCl$_3$) δ, ppm: 9.04 (s, 1H), 8.45 (dd, 1H), 7.80-7.65 (m, 1H), 7.15-7.08 (m, 1H), 4.42-4.30 (m, 1H), 3.84-3.77 (m, 1H), 2.70-2.60 (m, 2H), 2.25-2.11 (m, 2H), 1.97-1.83 (m, 2H), 1.62-1.40 (m, 2H); MS (EI) m/z 385.3 (MH)$^+$.

Jak3 Kinase Assay

Human Jak3 cDNA was amplified by PCR. A fragment encoding the catalytic domain of Jak3 (508aa to 1124aa) was ligated with GST at 5' end. This fused GST-Jak3 DNA fragment was cloned into the EcoRI site of the donor plasmid pFastBac 1 (Life Technologies #10359-016). The transformation, transposition, and transfection of insect cells (Sf9) were performed according to the manufacture's instructions. The cell lysate containing recombinant GST-Jak3 was used in the kinase assay. Anti-GST antibody (10 µg/ml, Sigma #G1417) was coated onto a 384-well plate at 4° C. overnight. Cell lysate containing GST-Jak3 (1:100 dilution) was added to the anti-GST coated plates, and GST-Jak3 was captured by immobilized anti-GST antibody. Testing compounds and substrate mix (50 mM HEPES, pH 7, 0.5 mM Na$_3$VO$_4$, 25 mM MgCl$_2$, 1 mM DTT, 0.005% BSA, 1 µM ATP, and 4.5 µg/ml biotinyl poly-Glu,Ala,Tyr) were added to the plate to initiate the reaction. After a 60-min incubation, the reaction was stopped by 4 mM EDTA, and phosphorylation of biotinyl poly-Glu,Ala,Tyr was detected using 17 µg/ml Cy5-streptavidin (Amersham, #PA92005) and 2.7 µg/ml Europium-conjugated anti-phosphotyrosine antibody (PerkinElmer #AD0069) using homogeneous time-resolved fluorescence (HTRF) technology.

Jak3 Cellular Assay

The mouse F7 pre-B lymphocyte cell line was used for the cellular Jak3 assay. Human IL-2Rβc cDNA is stably expressed in F7 cells (Kawahara et al., 1995). F7 cells were maintained in RPMI 1640 medium supplemented with 10% fetal bovine serum plus IL-3. Cells (30,000 cells/well) in serum-free medium were seeded in 96-well plates for the cell proliferation assay. Testing compounds were added to cells, followed by the addition of IL-2 (final 20 ng/ml). After a 24-h incubation, the number of viable cells was determined by the CellTiter-Glo Luminescent Cell Viability Assay kit (Promega, #G7573) according to the manufacturer's instructions.

IL-2-Induced IFN-γ Production in the Mouse

Administration of IL-2 leads to an increase in serum IFN-γ in the mouse due to NK secretion of the cytokine (Thornton S, Kuhn K A, Finkelman F D and Hirsch R. NK cells secrete high levels of IFN-γ in response to in vivo administration of IL-2. Eur J Immunol 2001 31:3355-3360). The experiment is carried out essentially according to the protocol in Thornton et al. and the test compounds are administered in order to determine the level of inhibition attained. In summary, female BALB/c mice are fasted for 12-18 hours before a study but have free access to water at all times. Test compounds are administered by gavage one hour before intraperitoneal injection of IL-2 and capture antibody. At termination of the studies, the mice are sacrificed by carbon dioxide inhalation, terminal blood samples are collected by cardiac puncture and serum is generated. Serum is stored frozen until assayed for IFN-γ, as described by the kit manufacturer (BD Pharmingen™, San Diego, Calif.).

Some comparative examples are shown below. All of the IC$_{50}$'s for Jak3 are below 10 μM.

C6 Substituted Purines and Purinones

| CHEMISTRY | Jak3 Kinase, IC50 representation | Synthetic route |
|---|---|---|
| (structure) | 1 | A2 |
| (structure) | 1 | I |
| (structure) | 1 | A2 |

-continued
| CHEMISTRY | Jak3 Kinase, IC50 representation | Synthetic route |
|---|---|---|
| 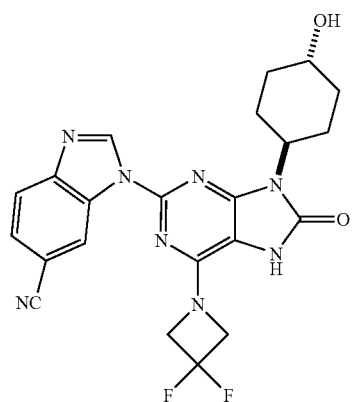 | 1 | I |
| 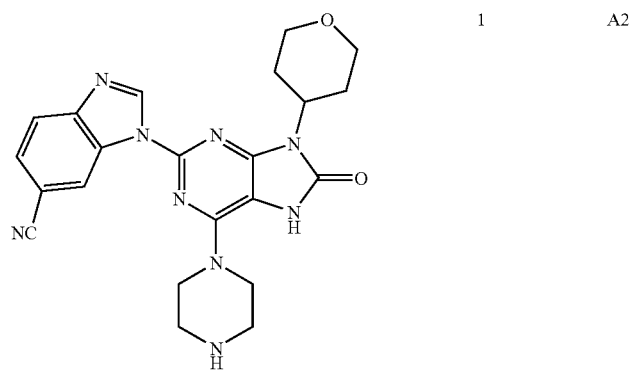 | 1 | A2 |
| 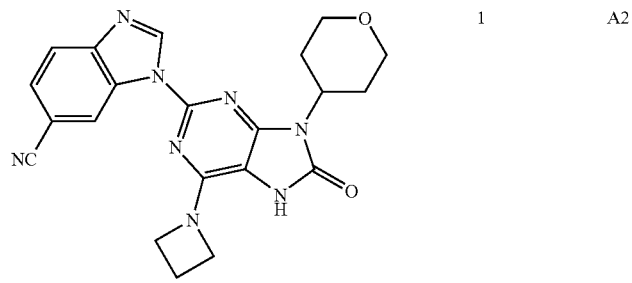 | 1 | A2 |
| 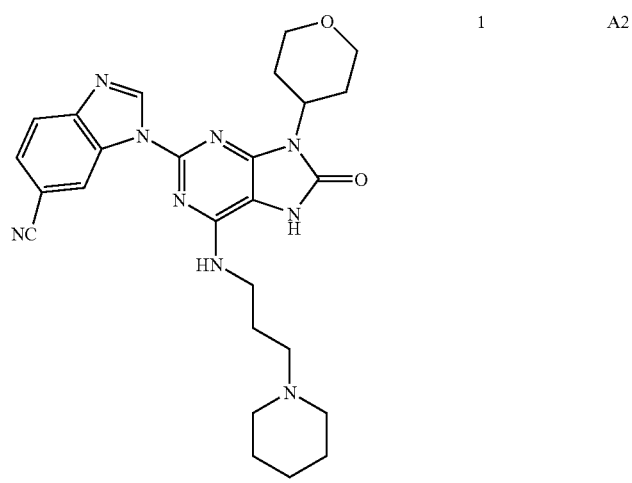 | 1 | A2 |

-continued
| CHEMISTRY | Jak3 Kinase, IC50 representation | Synthetic route |
|---|---|---|
| 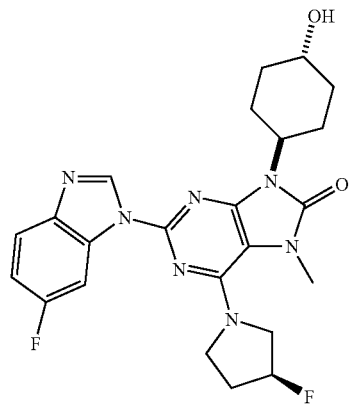 | 1 | J |
| 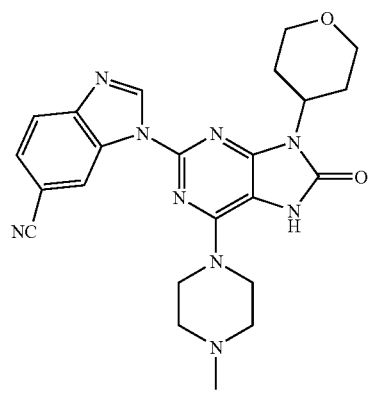 | 1 | A2 |
| 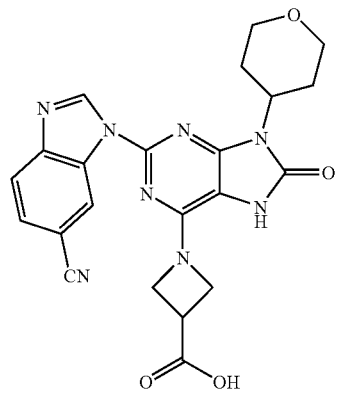 | 1 | A2 |
| 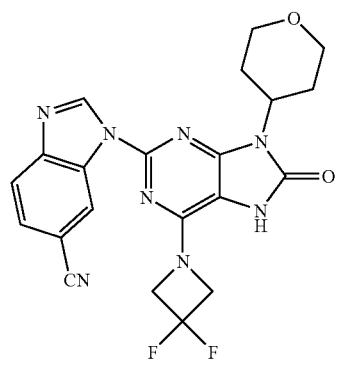 | 1 | A2 |

| CHEMISTRY | Jak3 Kinase, IC50 representation | Synthetic route |
|---|---|---|
| 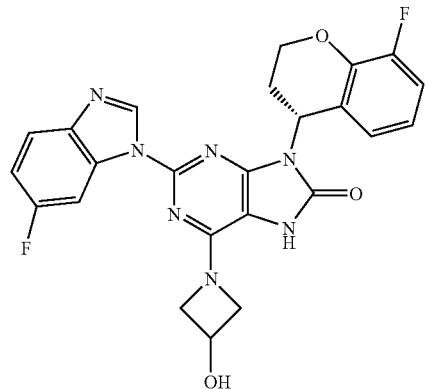 | 1 | E2 |
| 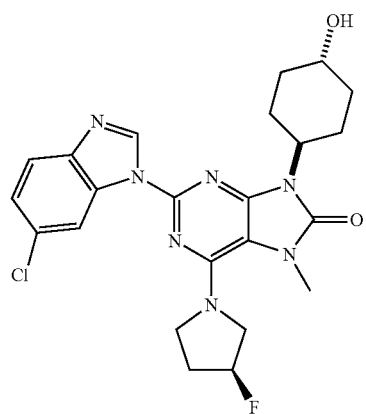 | 1 | I |
| 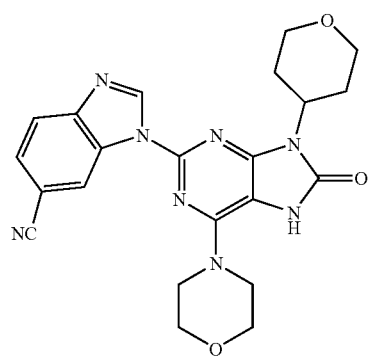 | 1 | A2 |
| 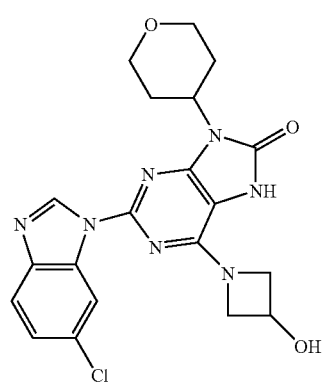 | 1 | A2 |

| CHEMISTRY | Jak3 Kinase, IC50 representation | Synthetic route |
|---|---|---|
| 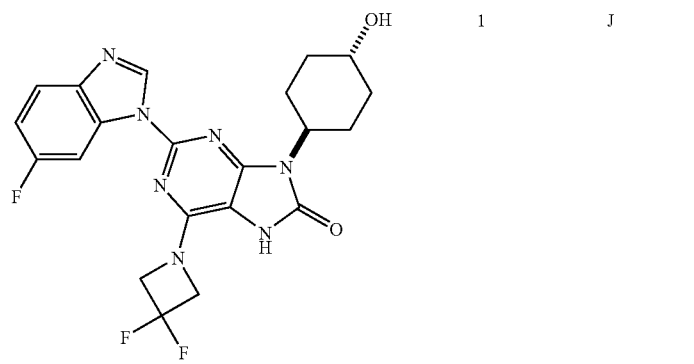 | 1 | J |
| 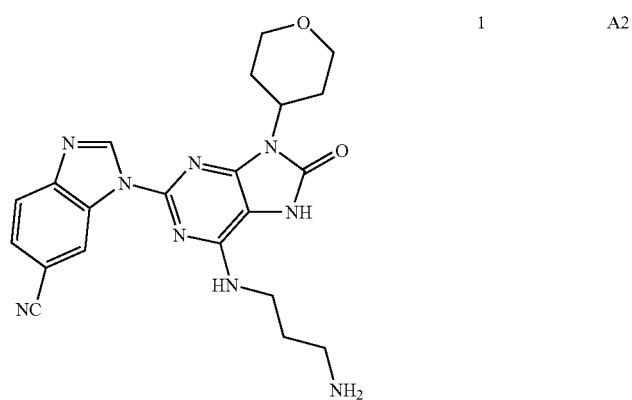 | 1 | A2 |
| 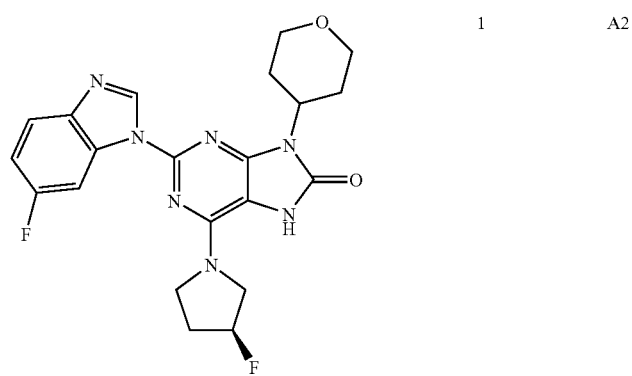 | 1 | A2 |
| 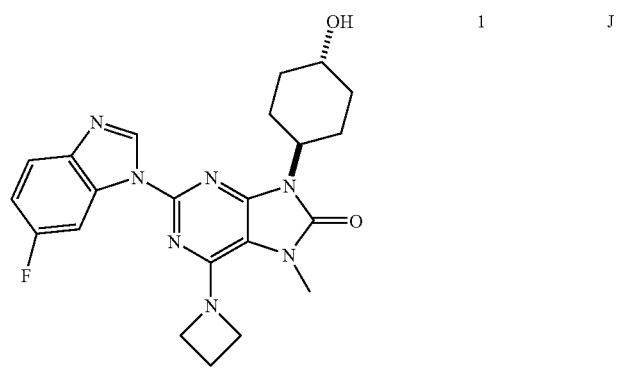 | 1 | J |

-continued
| CHEMISTRY | Jak3 Kinase, IC50 representation | Synthetic route |
|---|---|---|
| 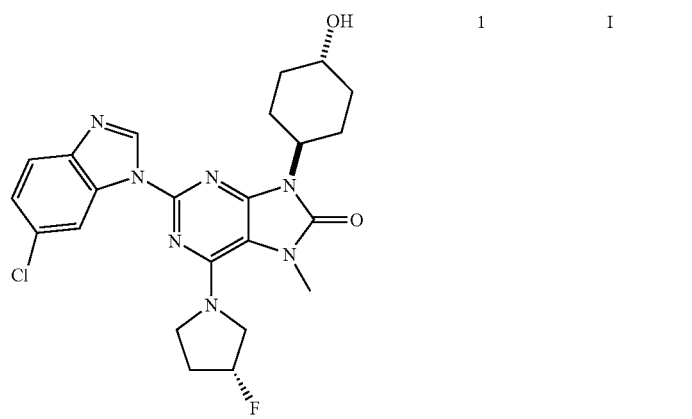 | 1 | I |
| 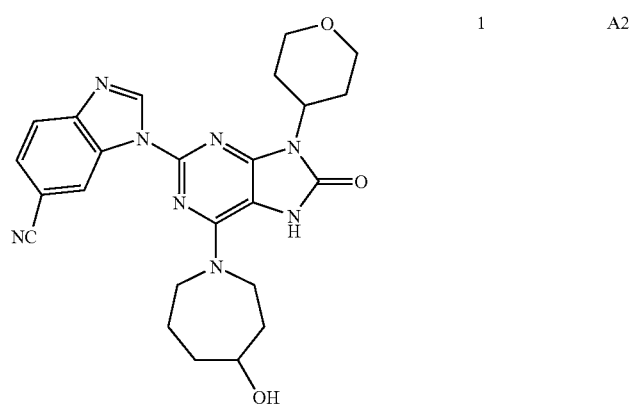 | 1 | A2 |
| 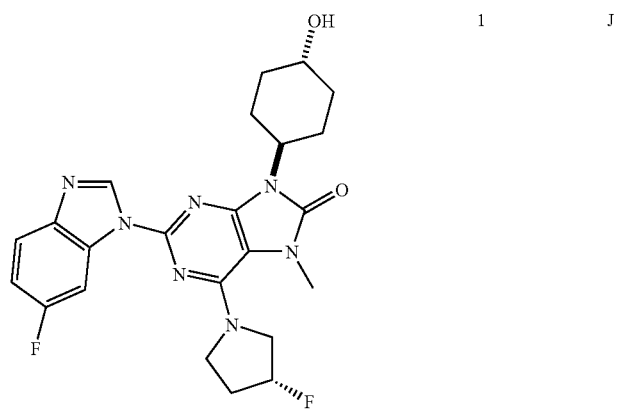 | 1 | J |

-continued
| CHEMISTRY | Jak3 Kinase, IC50 representation | Synthetic route |
|---|---|---|
| 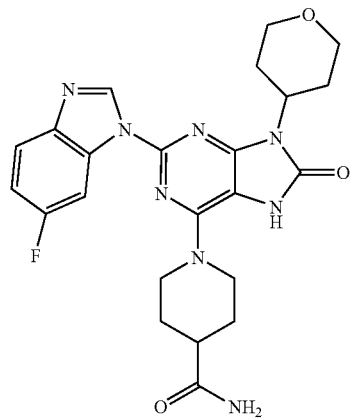 | 1 | A2 |
| 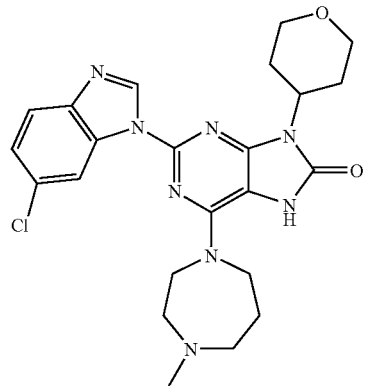 | 1 | A2 |
| 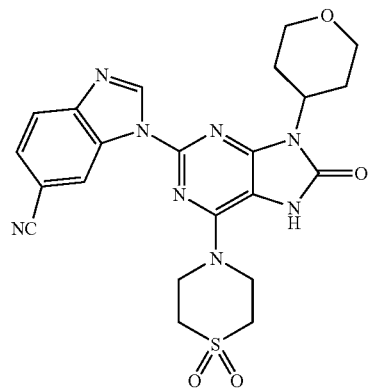 | 1 | A2 |

| CHEMISTRY | Jak3 Kinase, IC50 representation | Synthetic route |
|---|---|---|
| 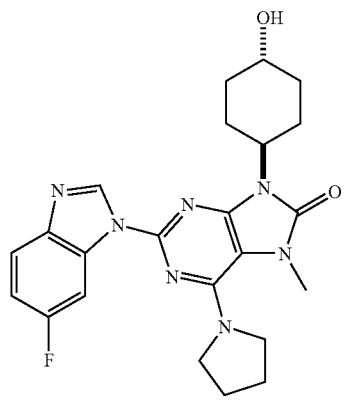 | 1 | J |
| 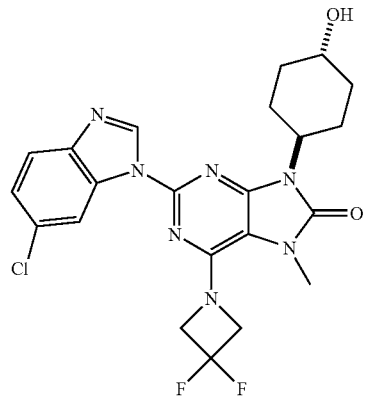 | 1 | I |
| 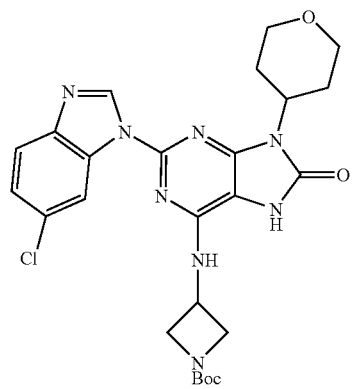 | 1 | A2 |

-continued
| CHEMISTRY | Jak3 Kinase, IC50 representation | Synthetic route |
|---|---|---|
| 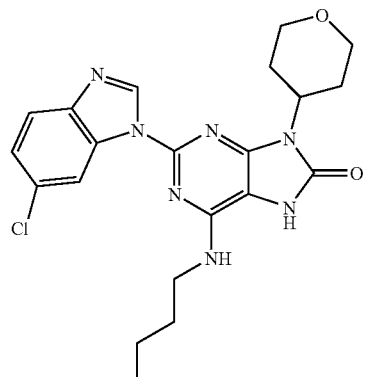 | 1 | A2 |
| 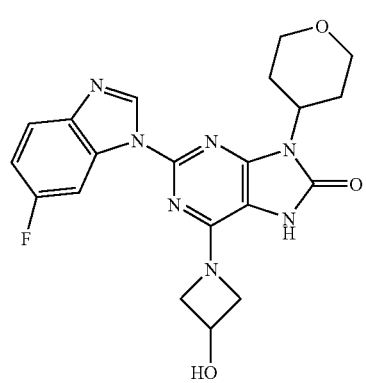 | 1 | A2 |
| 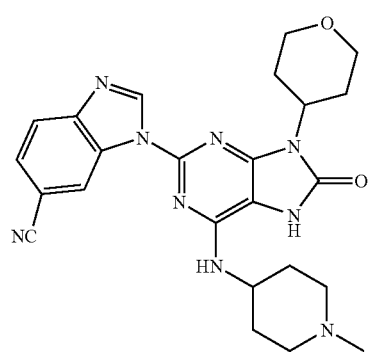 | 1 | A2 |
| 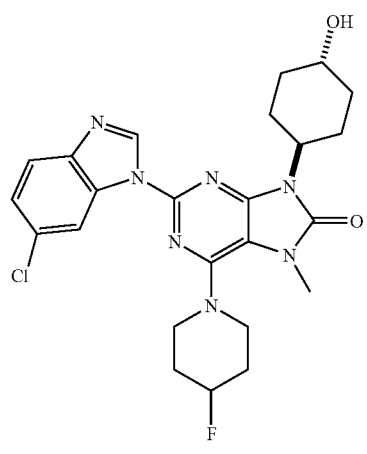 | 1 | I |

| CHEMISTRY | Jak3 Kinase, IC50 representation | Synthetic route |
|---|---|---|
| 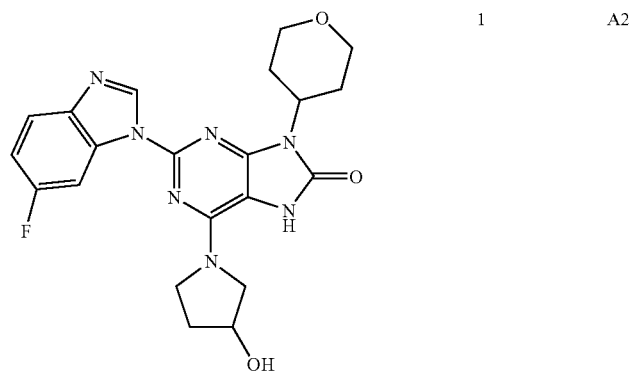 | 1 | A2 |
| 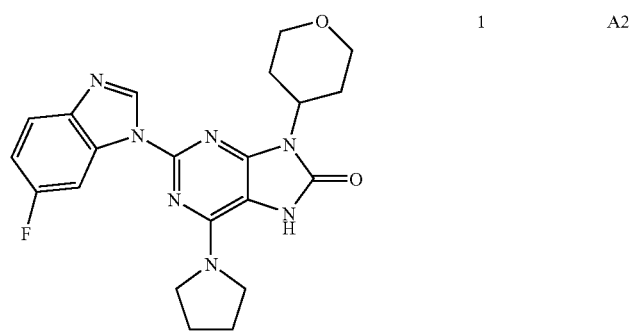 | 1 | A2 |
| 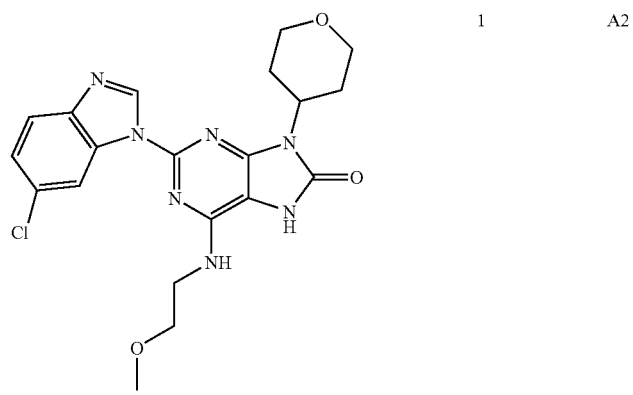 | 1 | A2 |
| 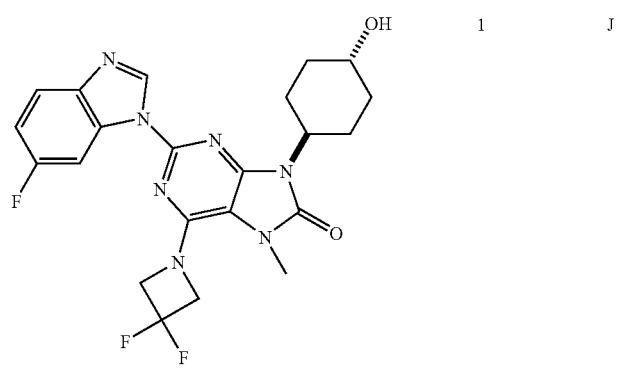 | 1 | J |

-continued
| CHEMISTRY | Jak3 Kinase, IC50 representation | Synthetic route |
|---|---|---|
| 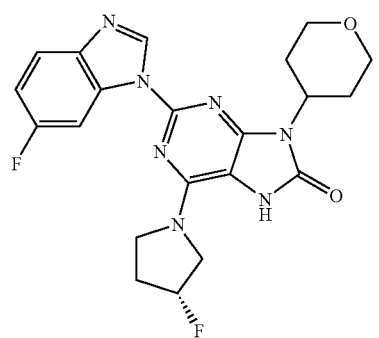 | 1 | A2 |
| 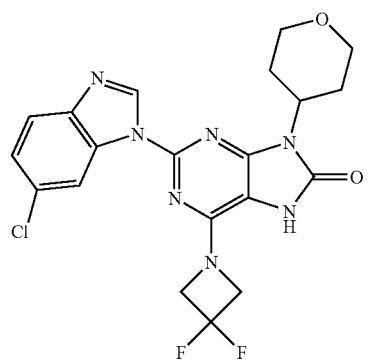 | 1 | A2 |
| 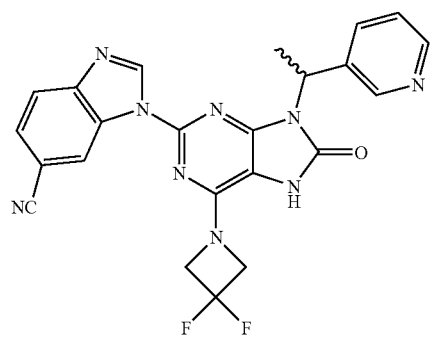 | 1 | H |
| 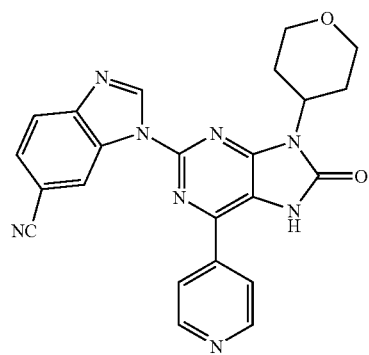 | 1 | C |

| CHEMISTRY | Jak3 Kinase, IC50 representation | Synthetic route |
|---|---|---|
| 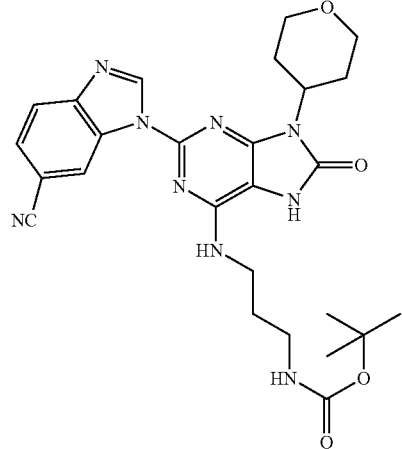 | 1 | A2 |
| 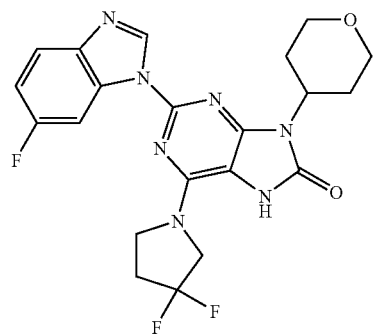 | 1 | A2 |
| 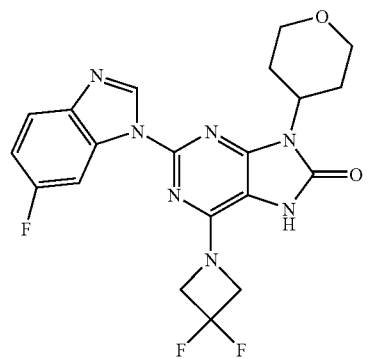 | 1 | A2 |
| 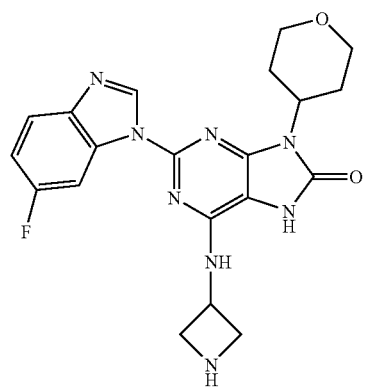 | 1 | A2 |

-continued
| CHEMISTRY | Jak3 Kinase, IC50 representation | Synthetic route |
|---|---|---|
| 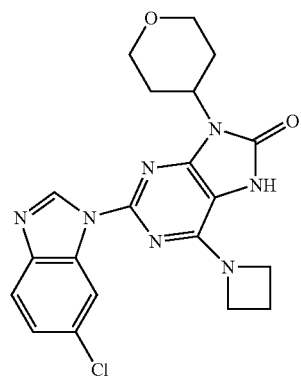 | 1 | A2 |
| 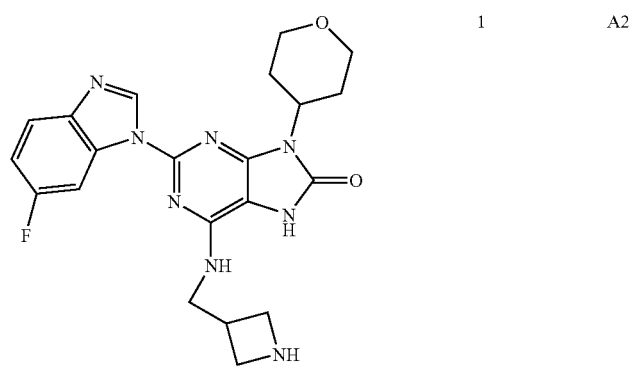 | 1 | A2 |
| 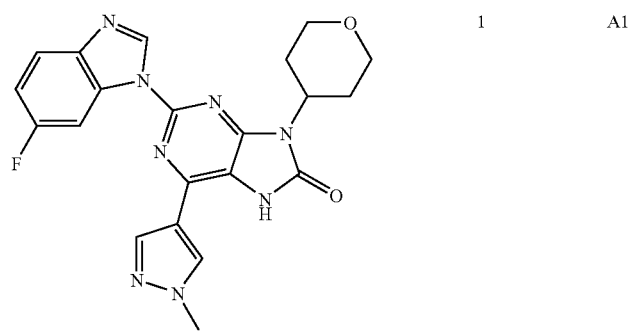 | 1 | A1 |
| 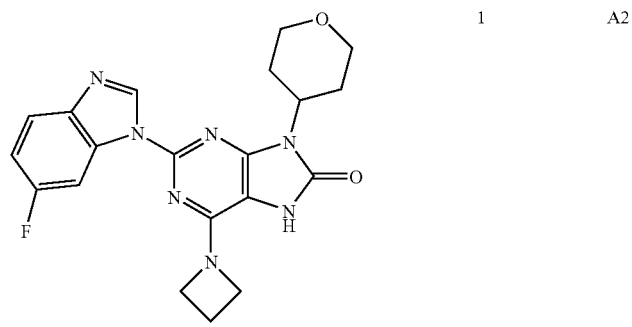 | 1 | A2 |

| CHEMISTRY | Jak3 Kinase, IC50 representation | Synthetic route |
|---|---|---|
| 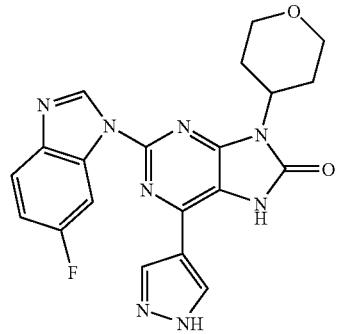 | 1 | A1 |
| 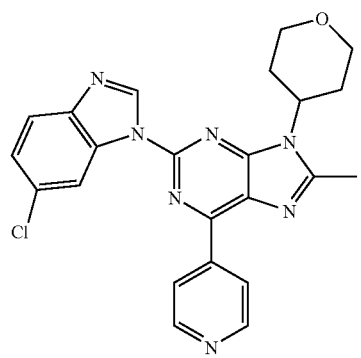 | 1 | D |
| 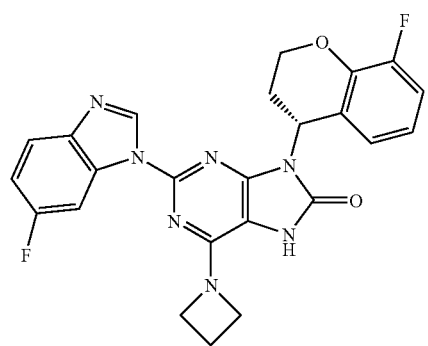 | 1 | E2 |
| 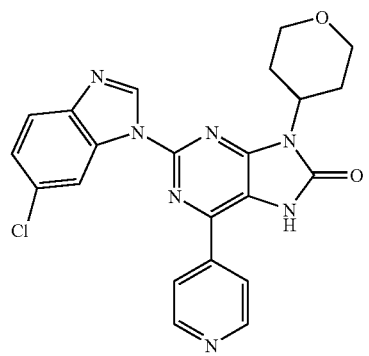 | 1 | C |

| CHEMISTRY | Jak3 Kinase, IC50 representation | Synthetic route |
|---|---|---|
| 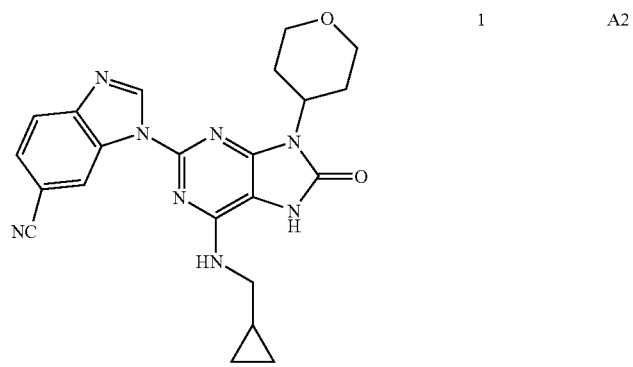 | 1 | A2 |
| 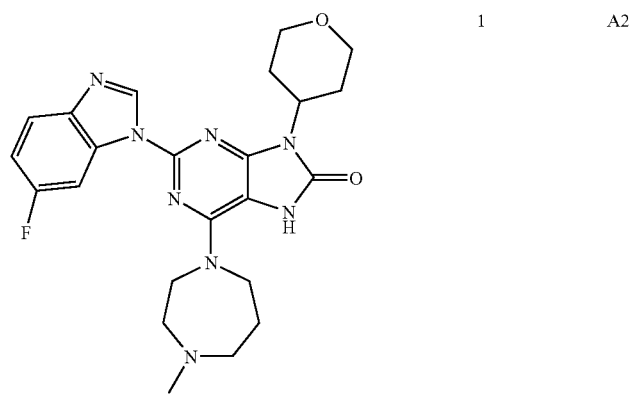 | 1 | A2 |
| 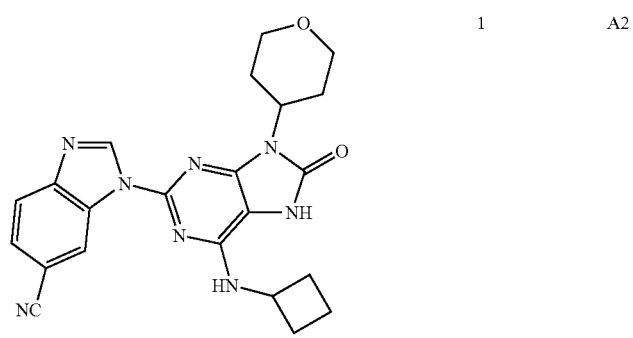 | 1 | A2 |
| 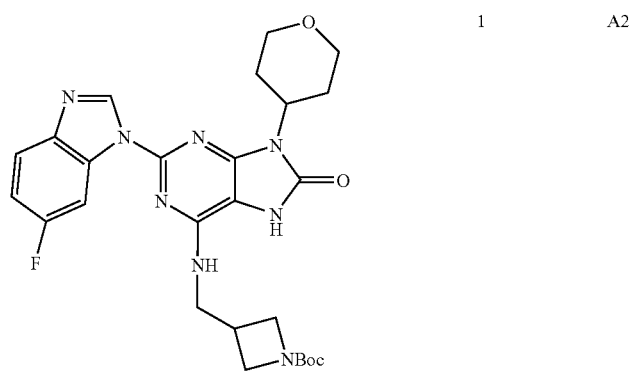 | 1 | A2 |

| CHEMISTRY | Jak3 Kinase, IC50 representation | Synthetic route |
|---|---|---|
| 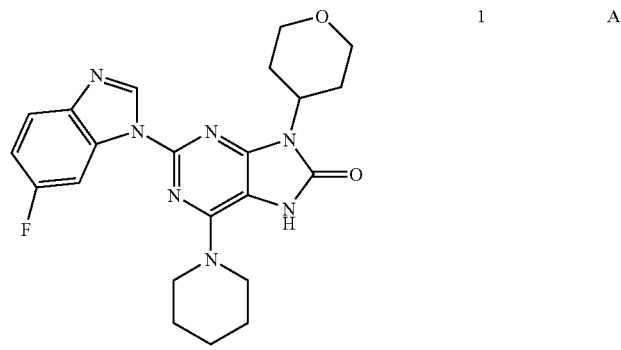 | 1 | A2 |
| 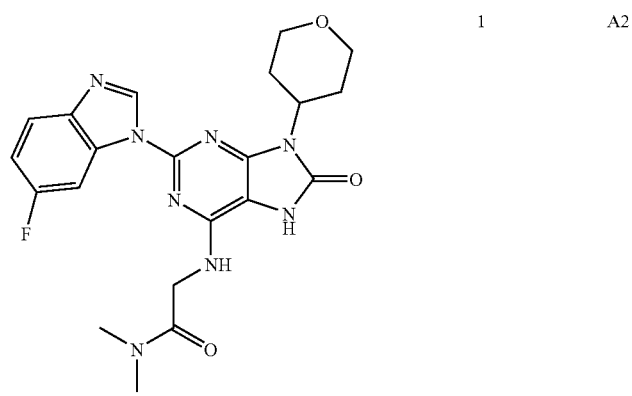 | 1 | A2 |
| 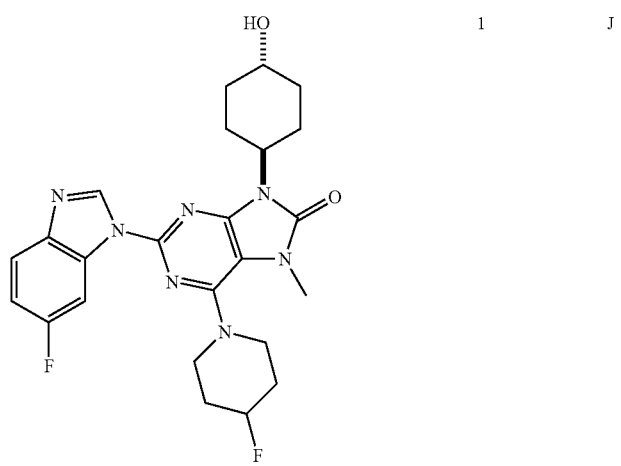 | 1 | J |

| CHEMISTRY | Jak3 Kinase, IC50 representation | Synthetic route |
|---|---|---|
| 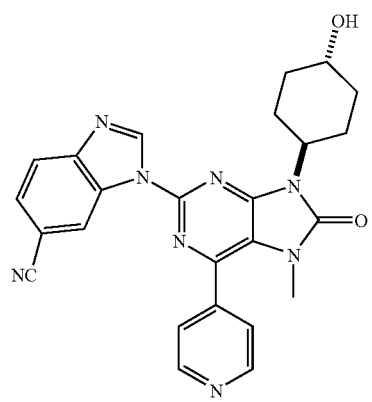 | 1 | I |
| 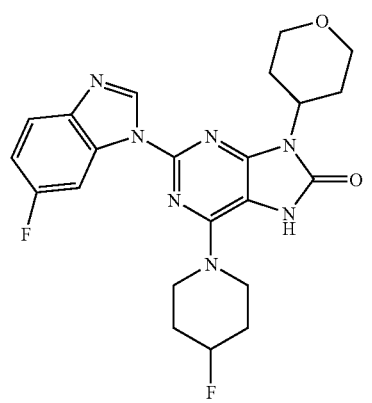 | 1 | A2 |
| 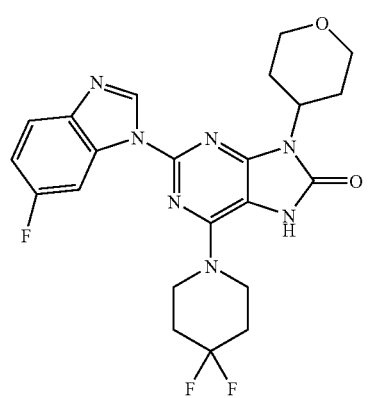 | 1 | A2 |

| CHEMISTRY | Jak3 Kinase, IC50 representation | Synthetic route |
|---|---|---|
| 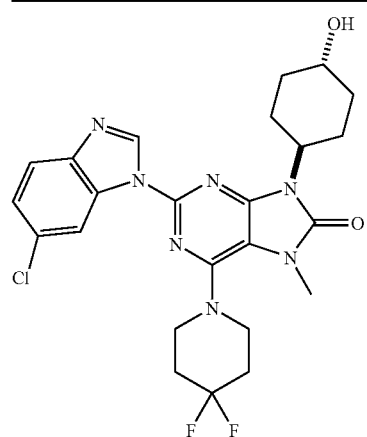 | 1 | I |
| 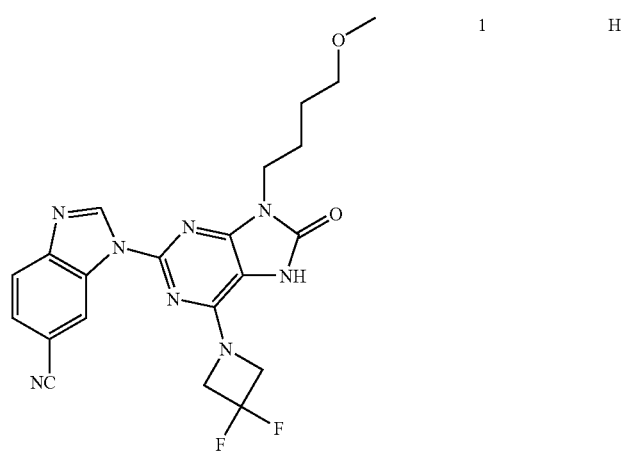 | 1 | H |
| 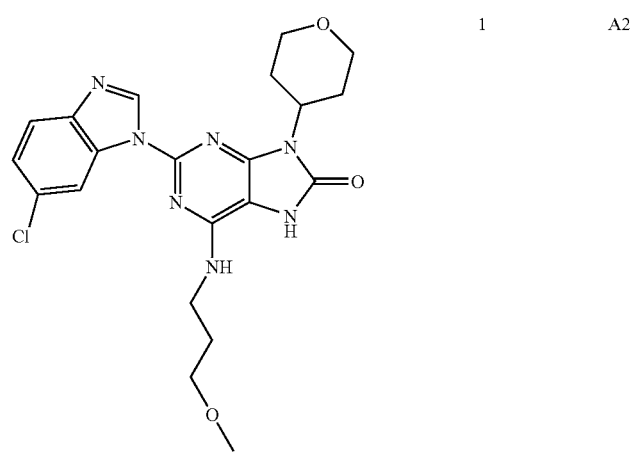 | 1 | A2 |

-continued
| CHEMISTRY | Jak3 Kinase, IC50 representation | Synthetic route |
|---|---|---|
| 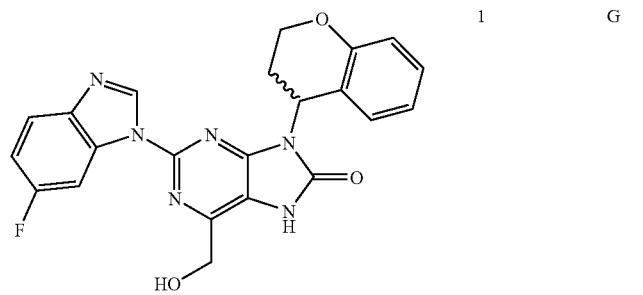 | 1 | G |
| 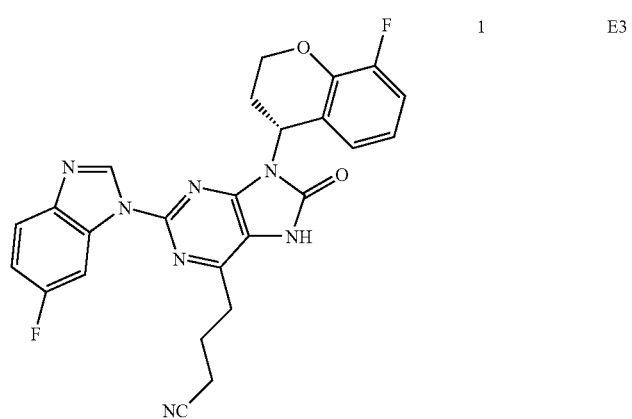 | 1 | E3 |
| 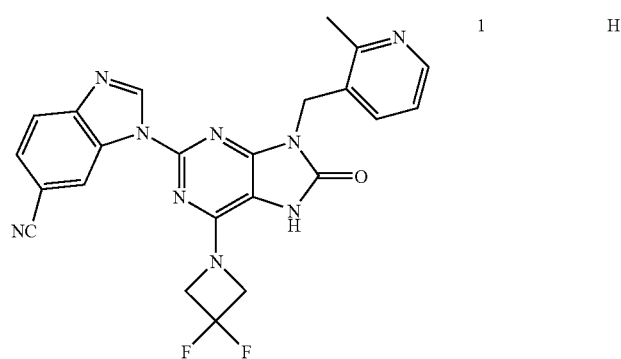 | 1 | H |
| 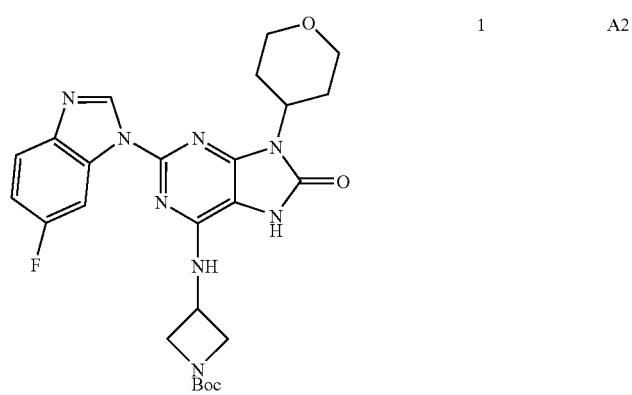 | 1 | A2 |

-continued
| CHEMISTRY | Jak3 Kinase, IC50 representation | Synthetic route |
|---|---|---|
| 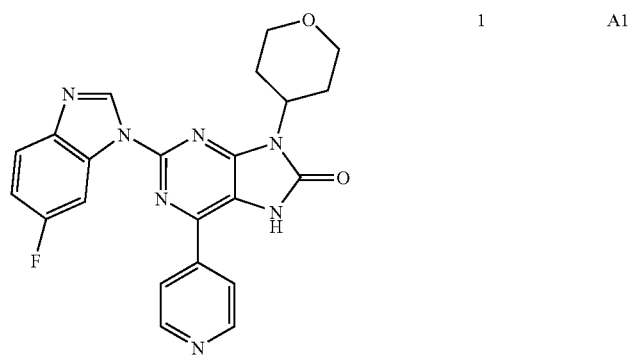 | 1 | A1 |
| 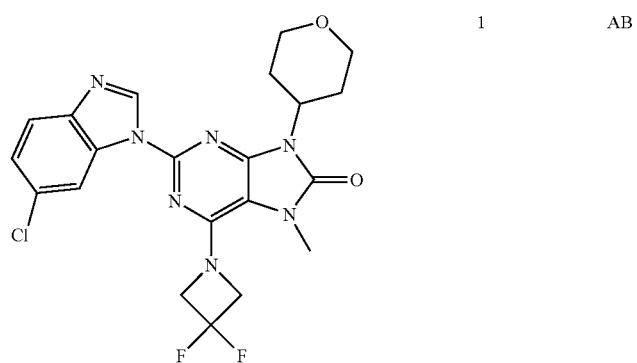 | 1 | AB |
| 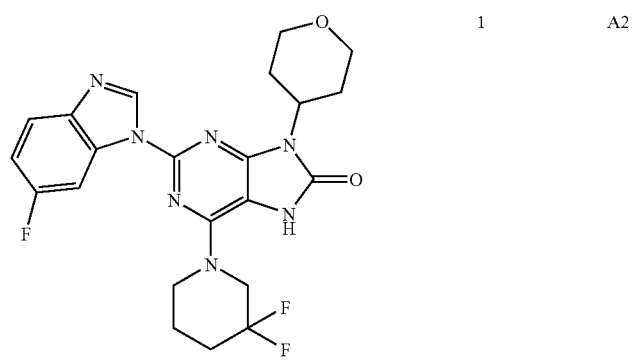 | 1 | A2 |
| 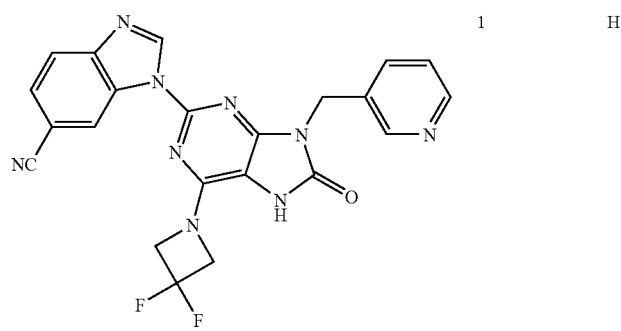 | 1 | H |

-continued
| CHEMISTRY | Jak3 Kinase, IC50 representation | Synthetic route |
|---|---|---|
| 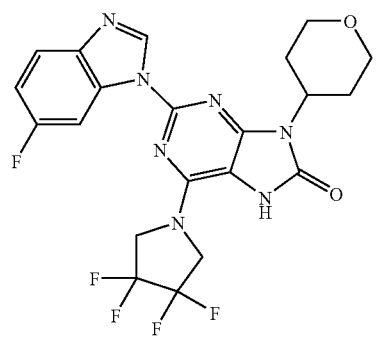 | 1 | A2 |
| 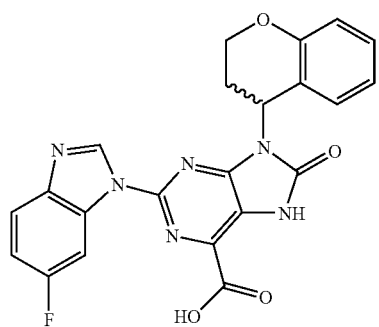 | 1 | G |
| 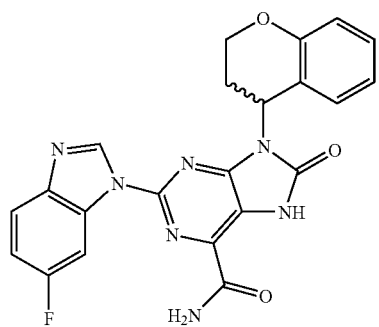 | 1 | G |
| 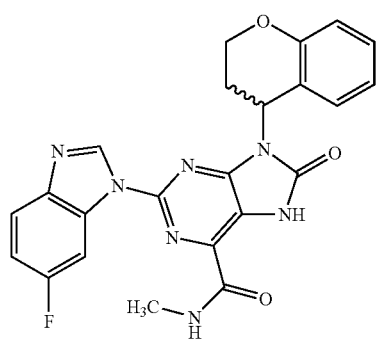 | 1 | G |

| CHEMISTRY | Jak3 Kinase, IC50 representation | Synthetic route |
|---|---|---|
| 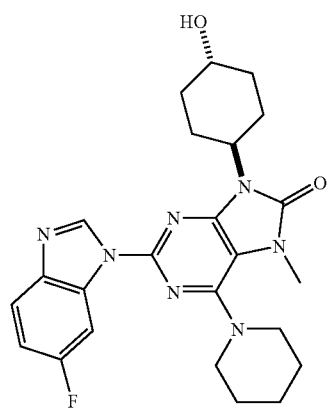 | 1 | J |
| 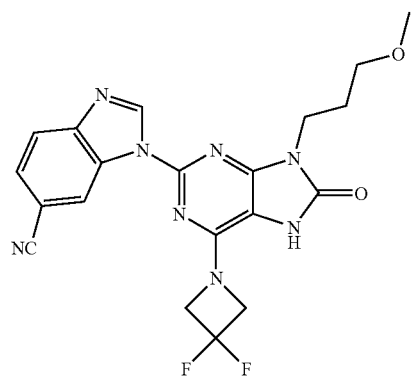 | 1 | H |
| 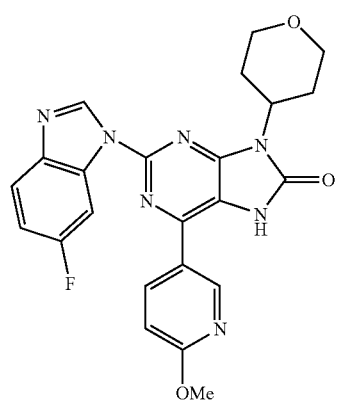 | 1 | A1 |

-continued
| CHEMISTRY | Jak3 Kinase, IC50 representation | Synthetic route |
|---|---|---|
| 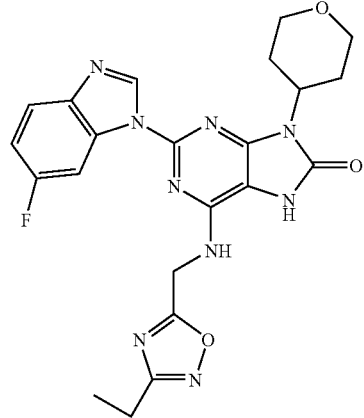 | 1 | A2 |
| 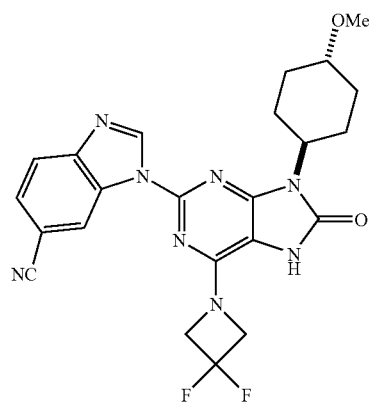 | 1 | I |
| 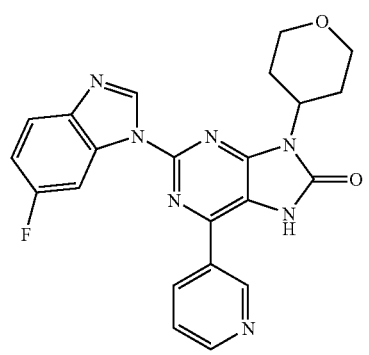 | 1 | A1 |
| 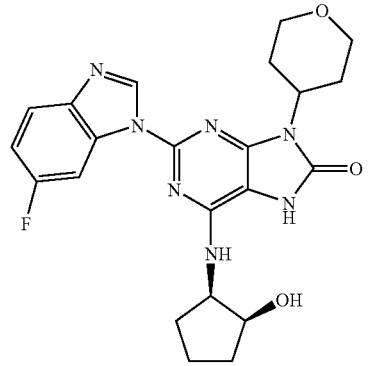 | 1 | A2 |

| CHEMISTRY | Jak3 Kinase, IC50 representation | Synthetic route |
|---|---|---|
| 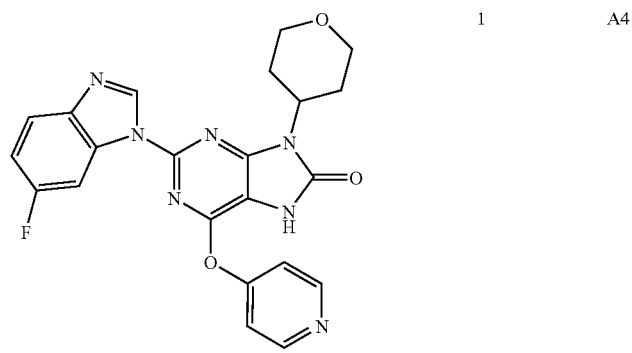 | 1 | A4 |
| 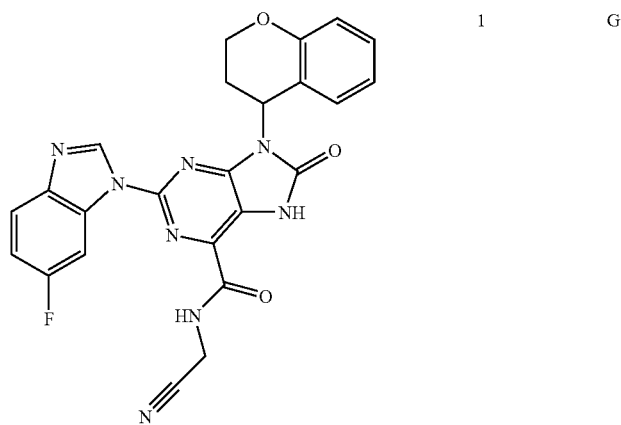 | 1 | G |
| 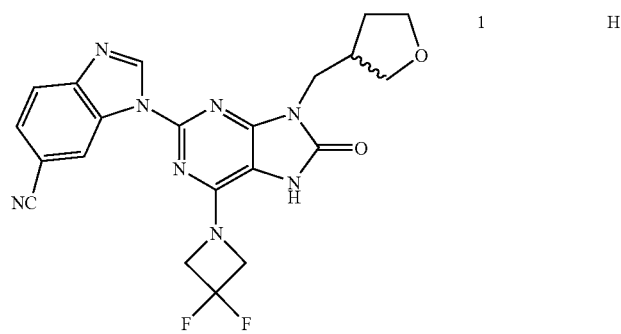 | 1 | H |
| 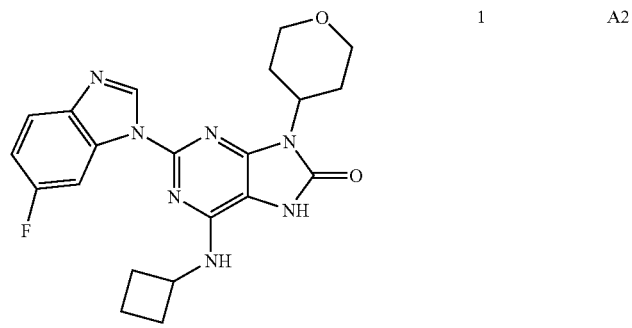 | 1 | A2 |

| CHEMISTRY | Jak3 Kinase, IC50 representation | Synthetic route |
|---|---|---|
| 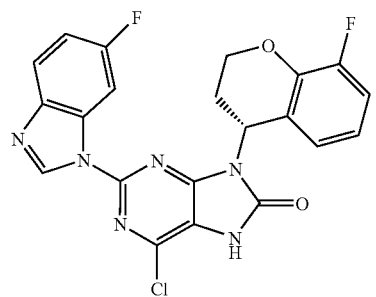 | 1 | E |
| 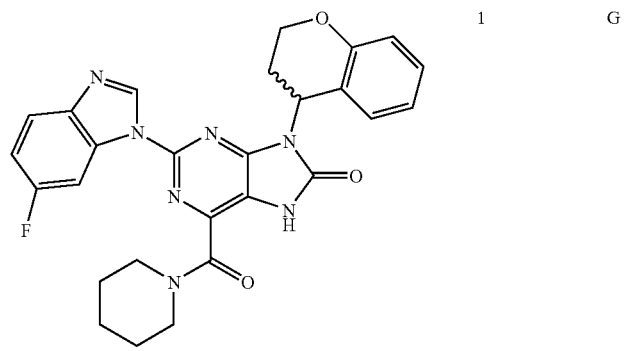 | 1 | G |
| 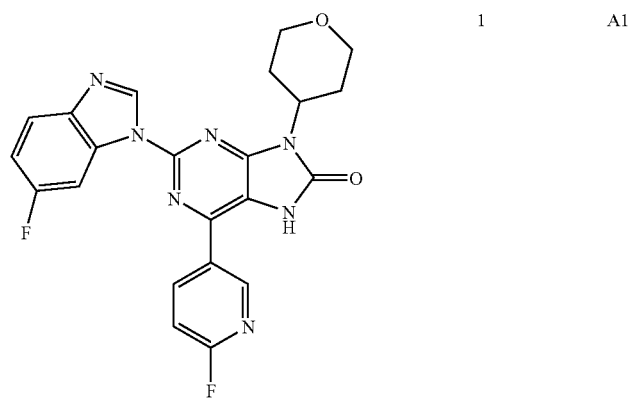 | 1 | A1 |
| 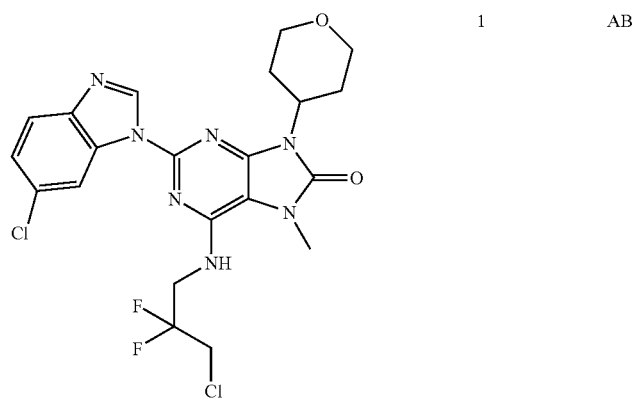 | 1 | AB |

-continued
| CHEMISTRY | Jak3 Kinase, IC50 representation | Synthetic route |
|---|---|---|
| 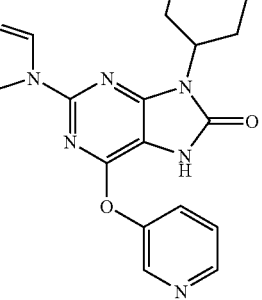 | 1 | A4 |
| 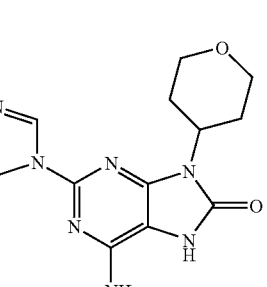 | 1 | A2 |
| 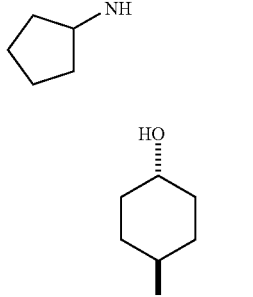 | 1 | J |
| 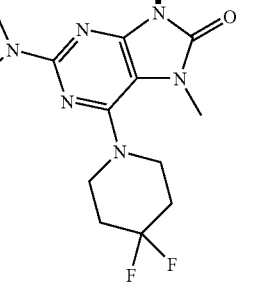 | 1 | G |

-continued
| CHEMISTRY | Jak3 Kinase, IC50 representation | Synthetic route |
|---|---|---|
| 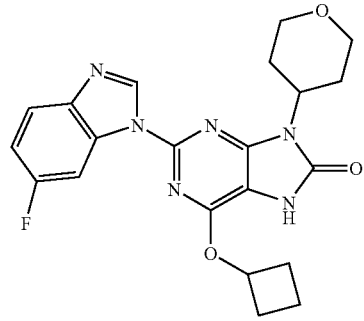 | 1 | A4 |
| 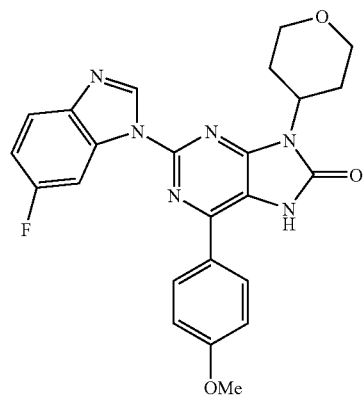 | 1 | A1 |
| 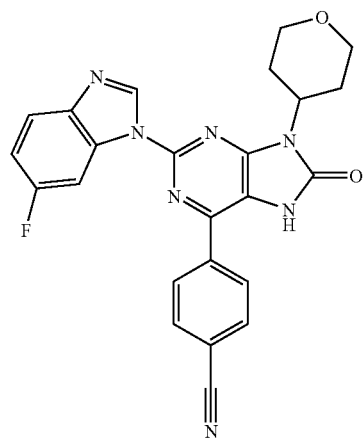 | 1 | B |
| 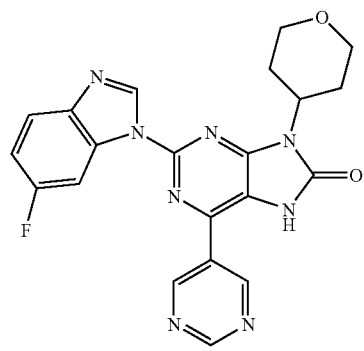 | 1 | A1 |

| CHEMISTRY | Jak3 Kinase, IC50 representation | Synthetic route |
|---|---|---|
| 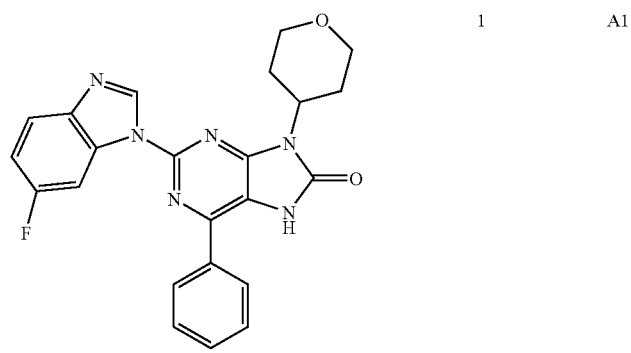 | 1 | A1 |
| 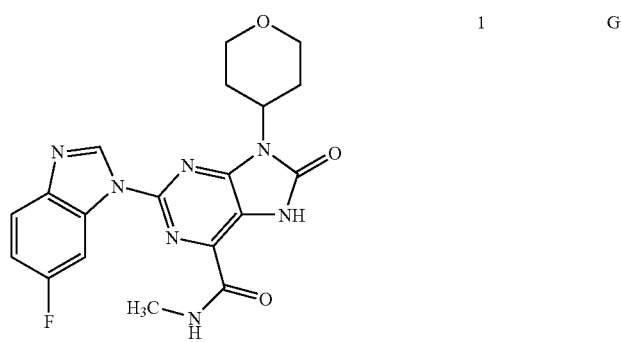 | 1 | G |
| 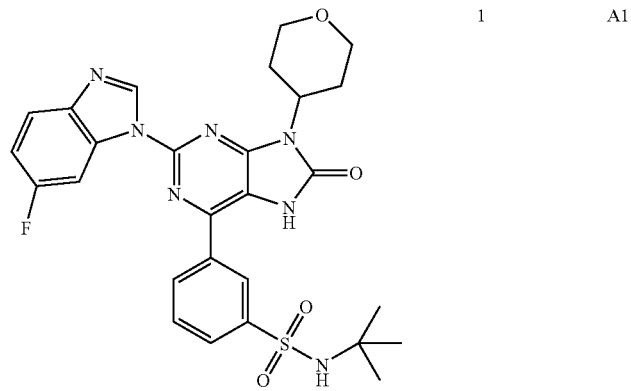 | 1 | A1 |
| 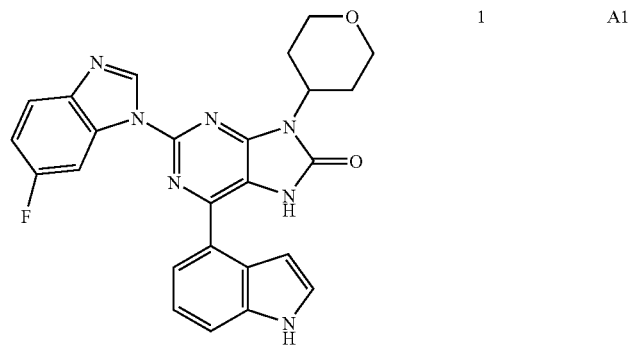 | 1 | A1 |

| CHEMISTRY | Jak3 Kinase, IC50 representation | Synthetic route |
|---|---|---|
| 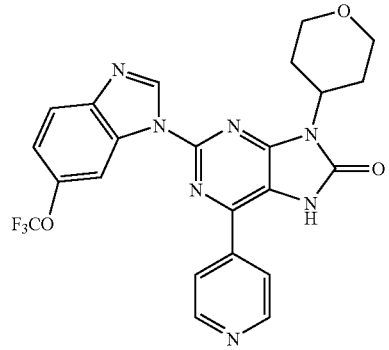 | 2 | C1 |
| 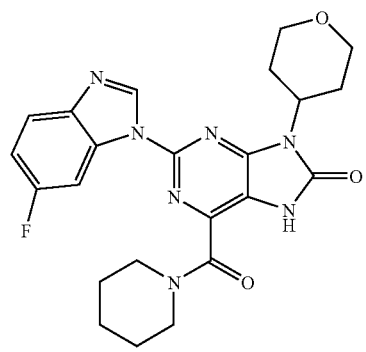 | 2 | G |
| 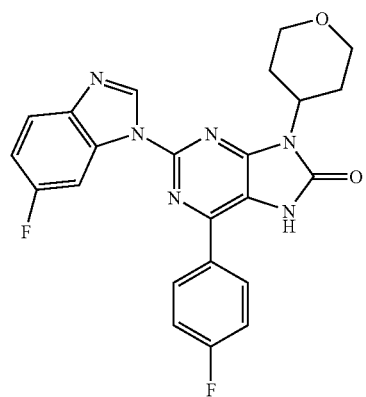 | 2 | A1 |
| 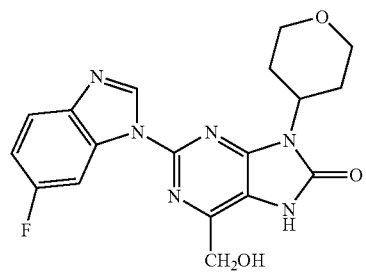 | 2 | G |

| CHEMISTRY | Jak3 Kinase, IC50 representation | Synthetic route |
|---|---|---|
| 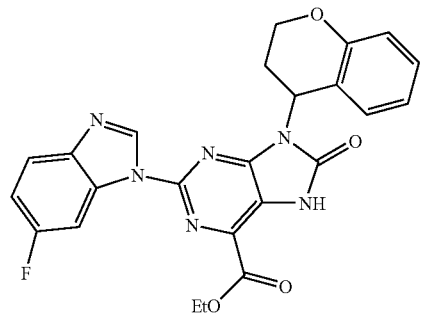 | 2 | G |
| 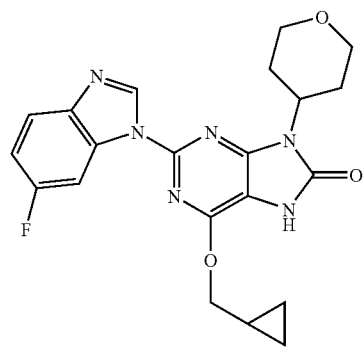 | 2 | A4 |
| 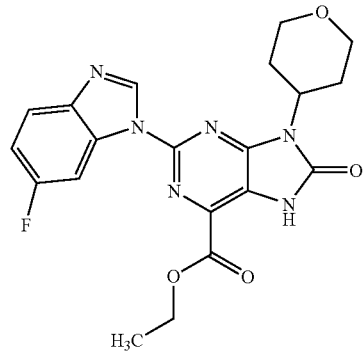 | 2 | G |
| 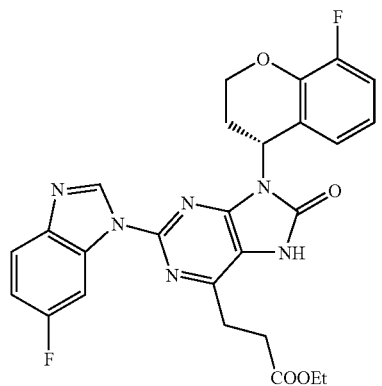 | 2 | E3 |

-continued

| CHEMISTRY | Jak3 Kinase, IC50 representation | Synthetic route |
|---|---|---|
| (structure) | 2 | G |
| (structure) | 2 | A4 |
| (structure) | 2 | I |
| (structure) | 2 | E1 |

-continued
| CHEMISTRY | Jak3 Kinase, IC50 representation | Synthetic route |
|---|---|---|
| 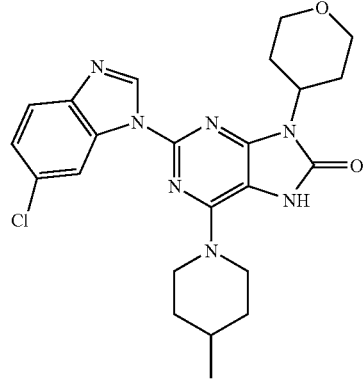 | 2 | A2 |
| 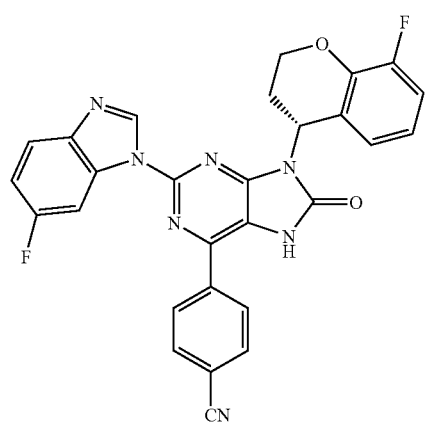 | 2 | E1 |
| 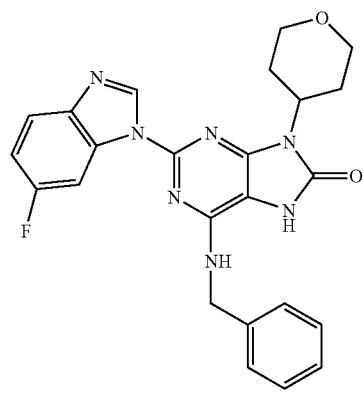 | 2 | A2 |
| 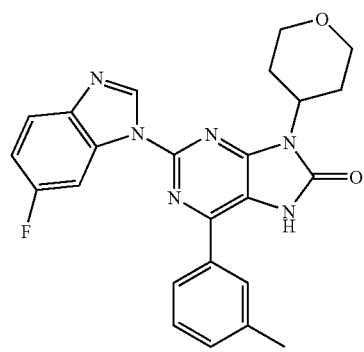 | 2 | A1 |

-continued
| CHEMISTRY | Jak3 Kinase, IC50 representation | Synthetic route |
|---|---|---|
| 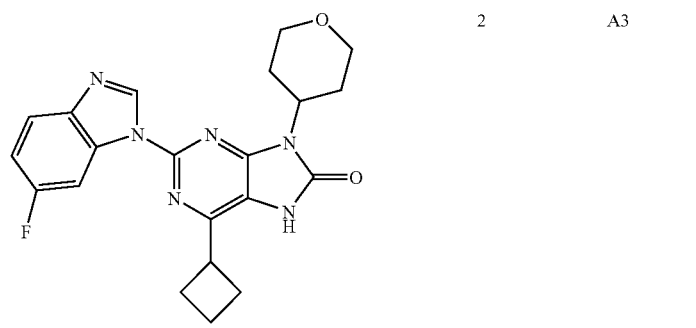 | 2 | A3 |
| 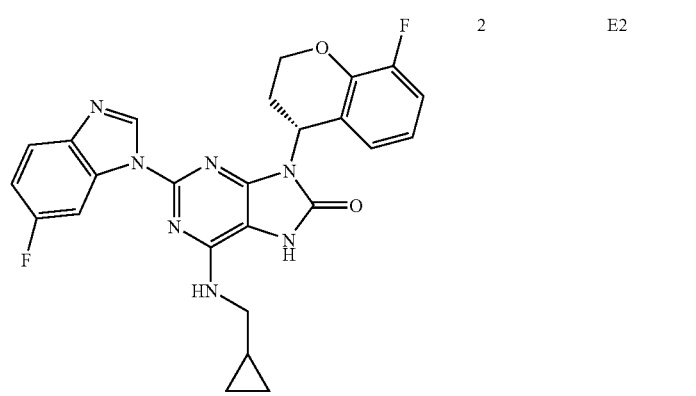 | 2 | E2 |
| 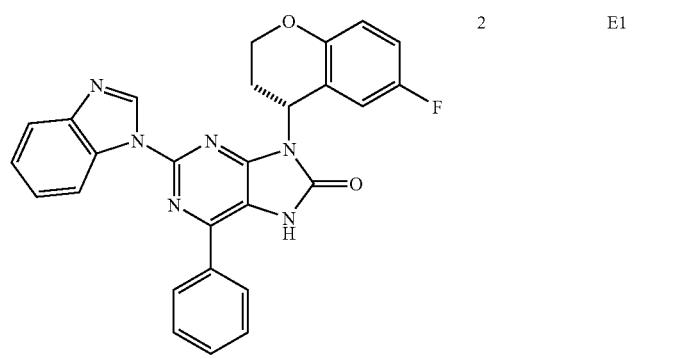 | 2 | E1 |
| 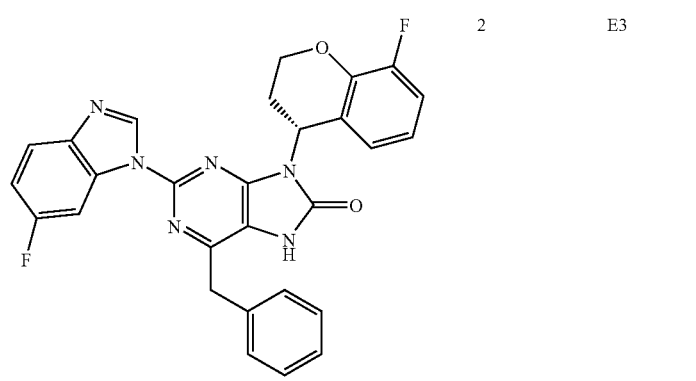 | 2 | E3 |

-continued
| CHEMISTRY | Jak3 Kinase, IC50 representation | Synthetic route |
|---|---|---|
| 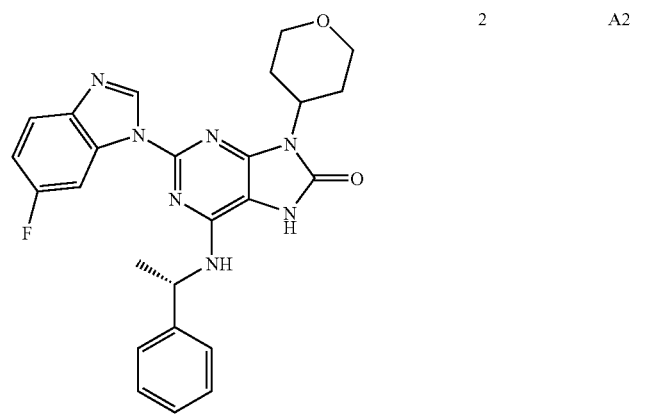 | 2 | A2 |
| 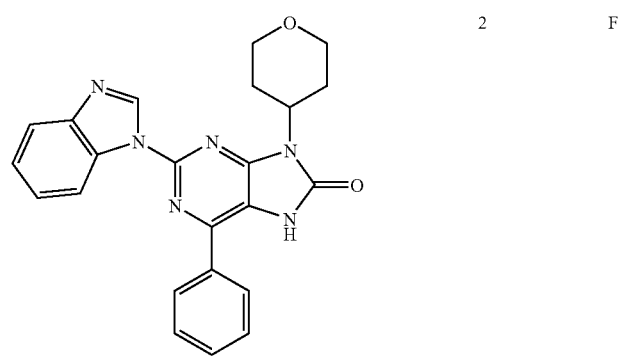 | 2 | F |
| 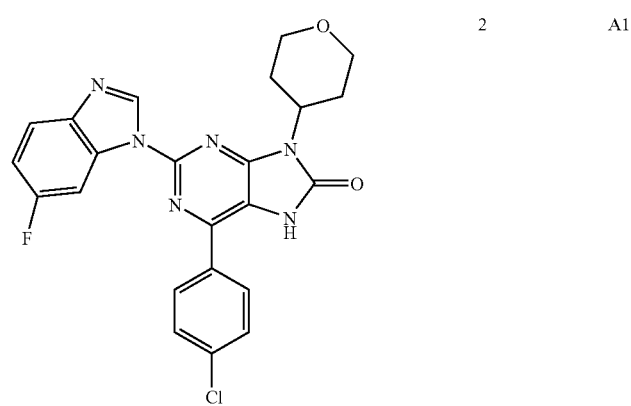 | 2 | A1 |

-continued
| CHEMISTRY | Jak3 Kinase, IC50 representation | Synthetic route |
|---|---|---|
| 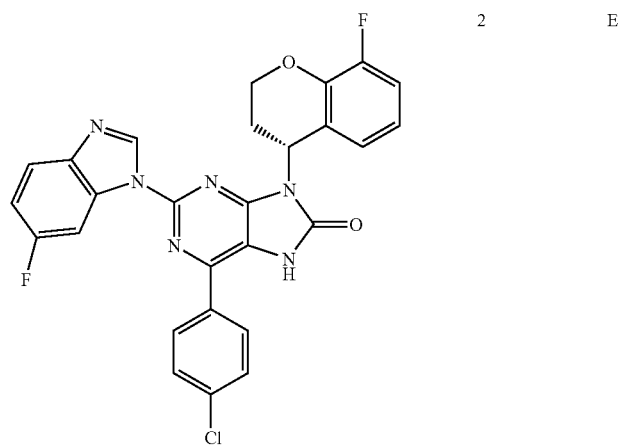 | 2 | E1 |
| 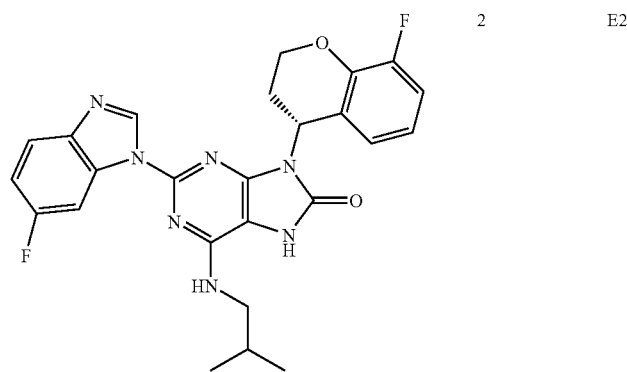 | 2 | E2 |
| 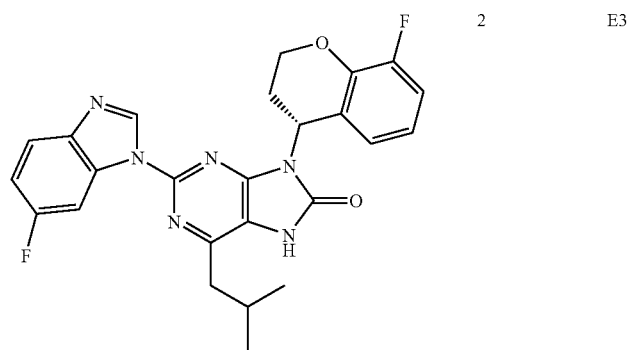 | 2 | E3 |
| 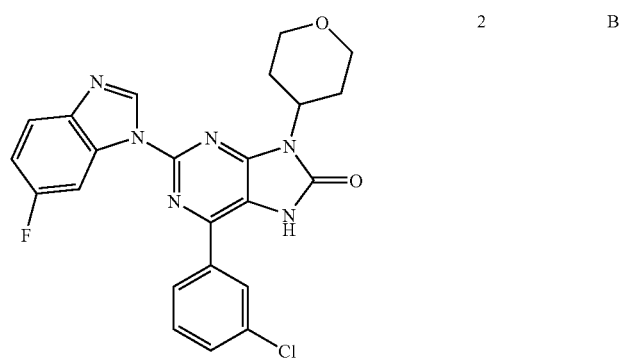 | 2 | B |

| CHEMISTRY | Jak3 Kinase, IC50 representation | Synthetic route |
|---|---|---|
| 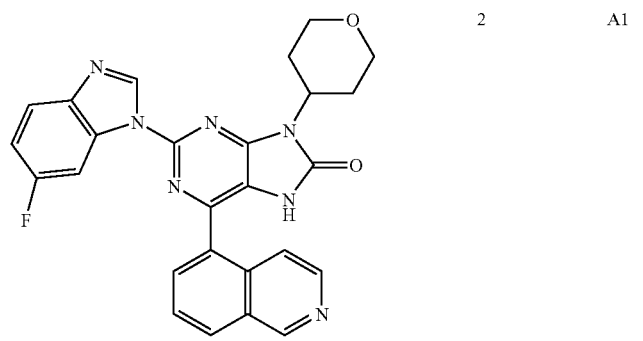 | 2 | A1 |
| 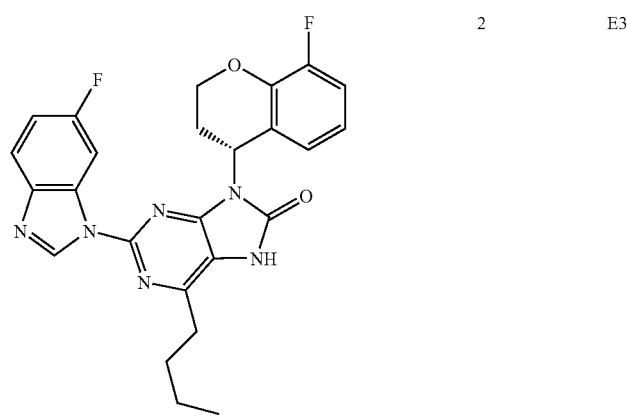 | 2 | E3 |
| 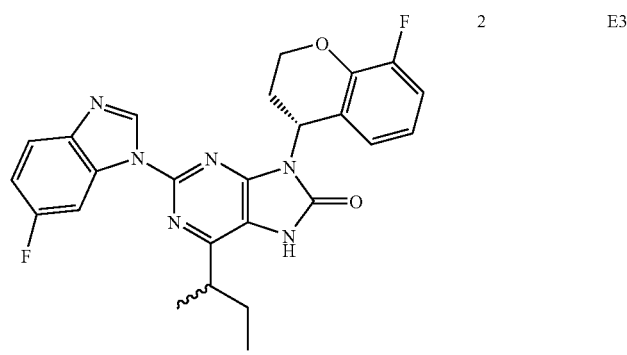 | 2 | E3 |
| 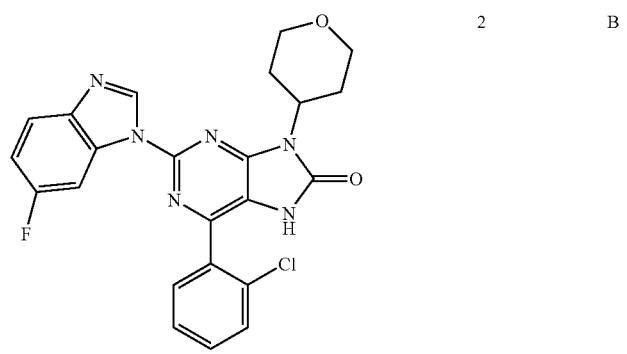 | 2 | B |

-continued

| CHEMISTRY | Jak3 Kinase, IC50 representation | Synthetic route |
|---|---|---|
| 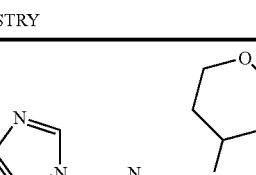 | 3 | A2 |

In the foregoing table, an IC$_{50}$ less than 100 nM is represented as 1; an IC$_{50}$ between 100 nM and 1 μM is represented as 2; and an IC$_{50}$ greater than 1 μM is represented as 3.

The invention claimed is:

1. A compound of formula I or II

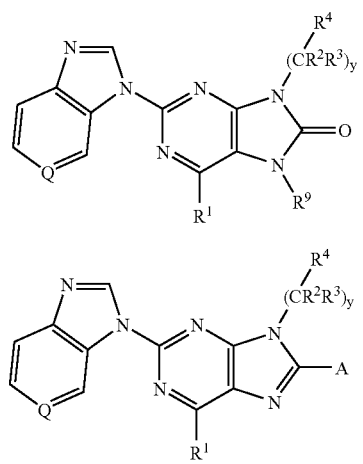

wherein

Q is selected from the group consisting of CX and nitrogen;
X is selected from the group consisting of hydrogen, halogen, and an electron-withdrawing group;
A is chosen from the group consisting of H, (C$_1$-C$_6$) alkyl, heteroaryl, and aryl;
R$^1$ is selected from the group consisting of halogen, CN, (C$_2$-C$_6$) alkyl, substituted (C$_1$-C$_6$) alkyl, aryl, substituted aryl, azetidinyl, piperidinyl, piperazinyl, pyridinyl, pyrimidinyl, morpholinyl, thiomorpholinyl, pyrrolyl, pyrazolyl, indolyl, isoquinolinyl, azepinyl, diazepinyl, cyclobutyl, substituted azetidinyl, substituted piperidinyl, substituted piperazinyl, substituted pyridinyl, substituted pyrimidinyl, substituted morpholinyl, substituted thiomorpholinyl, substituted pyrrolyl, substituted pyrazolyl, substituted indolyl, substituted isoquinolinyl, substituted azepinyl, substituted diazepinyl, substituted cyclobutyl, and —V—R$^7$;

R$^2$ and R$^3$ are selected independently for each occurrence of (CR$^2$R$^3$) from the group consisting of hydrogen and (C$_1$-C$_6$) alkyl;
R$^4$ is selected from a group consisting of alkyl, OH, alkoxy, pyranyl, benzopyranyl, furanyl, pyridinyl, cyclohexyl, aryl, substituted alkyl, substituted pyranyl, substituted benzopyranyl, substituted furanyl, substituted pyridinyl, substituted cyclohexyl, and substituted aryl;
R$^7$ is chosen from H, (C$_1$-C$_6$) alkyl, substituted (C$_1$-C$_6$) alkyl, aryl, substituted aryl, pyridinyl, piperidinyl, furanyl, oxadiazolyl, azetidinyl, cyclopropyl, cyclobutyl, cyclopentyl, and substituted pyridinyl, substituted piperidinyl, substituted furanyl, substituted oxadiazolyl, substituted azetidinyl, substituted cyclopropyl, substituted cyclobutyl, substituted cyclopentyl;
V is chosen from —C(=O)O—, —C(=O)NR$^8$—, —O—, and —NR$^8$—;
R$^8$ is chosen from H and (C$_1$-C$_6$) alkyl, or, azetidinyl, piperidinyl, oxadiazolyl, cyclopropyl, cyclobutyl, cyclopentyl, substituted azetidinyl, substituted piperidinyl, substituted oxadiazolyl, substituted cyclopropyl, substituted cyclobutyl, substituted cyclopentyl;
R$^9$ is chosen from hydrogen, alkyl, and substituted alkyl; and
y is zero or an integer selected from 1, 2, and 3.

2. A compound according to claim 1, wherein R$^9$ is hydrogen and R$^1$ is chosen from aryl, substituted aryl, azetidinyl, piperidinyl, piperazinyl, pyridinyl, pyrimidinyl, morpholinyl, thiomorpholinyl, pyrrolyl, pyrazolyl, indolyl, isoquinolinyl, azepinyl, diazepinyl, cyclobutyl, and substituted azetidinyl, substituted piperidinyl, substituted piperazinyl, substituted pyridinyl, substituted pyrimidinyl, substituted morpholinyl, substituted thiomorpholinyl, substituted pyrrolyl, substituted pyrazolyl, substituted indolyl, substituted isoquinolinyl, substituted azepinyl, substituted diazepinyl, substituted cyclobutyl.

3. A compound according to claim 2, wherein R$^1$ is chosen from pyridinyl, pyrazolyl, pyrimidinyl, isoquinolinyl, azetidinyl, piperidinyl, piperizinyl, pyrrolidinyl, morpholinyl, azepanyl, diazepanyl, and phenyl optionally substituted with hydroxy, halogen, carboxamido, alkyl, carboxy, sulfone, alkoxy, and cyano.

4. A compound according to claim 1, wherein R$^1$ is chosen from aryl, substituted aryl, (C$_1$-C$_6$) alkyl, and substituted (C$_1$-C$_6$) alkyl.

5. A compound according to claim 1, wherein $R^1$ is —V—$R^7$.

6. A compound according to claim 5, wherein V is —C(=O)O— or —C(=O)$NR^8$—, and $R^7$ is chosen from —$CH_2CN$, ($C_1$-$C_6$) alkyl, and H, or $VR^7$ is

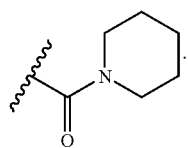

7. A compound according to claim 5, wherein V is chosen from —O— and —$NR^8$—; $R^7$ is ($C_1$-$C_6$) alkyl; and $R^8$ is H.

8. A compound according to claim 1, wherein $R^9$ is hydrogen, y is zero and $R^4$ is a residue selected from a monocycle, a bicycle, a substituted monocycle, and a substituted bicycle said residue containing at least one oxygen atom.

9. A compound according to claim 8, wherein $R^4$ is chosen from pyranyl, benzopyranyl, furanyl, substituted pyranyl, substituted benzopyranyl, substituted furanyl, a hydroxyl-substituted cycloalkyl, an alkoxy-substituted aryl, and a hydroxyl-substituted aryl.

10. A compound according to claim 9, wherein $R^4$ is chosen from

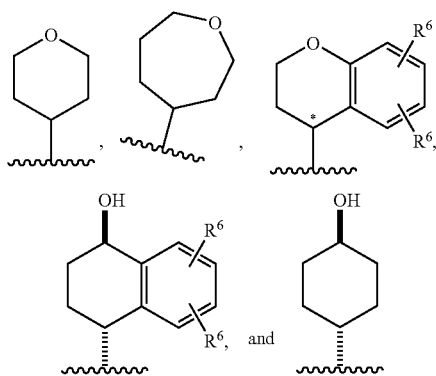

wherein $R^6$ is hydrogen or fluorine, and the carbon marked with an asterisk is of the R absolute configuration.

11. A compound according to claim 1, wherein $R^9$ is hydrogen, y is 1-3, $R^2$ and $R^3$ are hydrogen in all occurrences, and $R^4$ is alkoxy or OH of formula Ib or IIb:

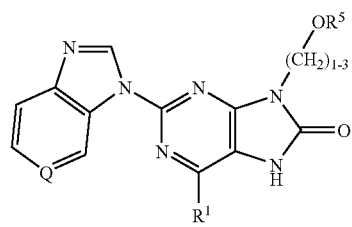

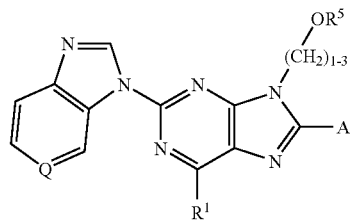

wherein $R^5$ is hydrogen or ($C_1$-$C_6$) alkyl.

12. A compound according to claim 1, wherein $R^9$ is hydrogen, Q is CX, and y is zero of formula Ic or IIc:

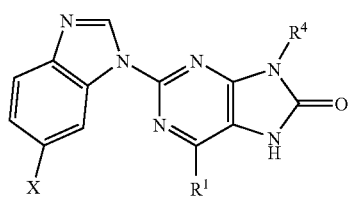

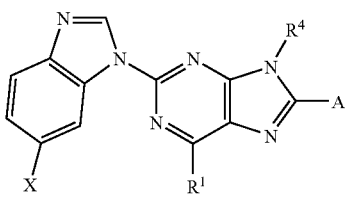

13. A compound according to claim 12, wherein $R^1$ is chosen from halogen, substituted ($C_1$-$C_6$) alkyl, azetidinyl, piperidinyl, piperazinyl, pyridinyl, pyrimidinyl, morpholinyl, thiomorpholinyl, pyrrolyl, pyrazolyl, indolyl, isoquinolinyl, azepinyl, diazepinyl, cyclobutyl, substituted azetidinyl, substituted piperidinyl, substituted piperazinyl, substituted pyridinyl, substituted pyrimidinyl, substituted morpholinyl, substituted thiomorpholinyl, substituted pyrrolyl, substituted pyrazolyl, substituted indolyl, substituted isoquinolinyl, substituted azepinyl, substituted diazepinyl, substituted cyclobutyl, aryl, substituted aryl, and —V—$R^7$.

14. A compound according to claim 13, wherein
V is —$NR^8$—, —C(=O)O—, —C(=O)$NR^8$, or O;
$R^7$ is H, ($C_1$-$C_6$) alkyl, substituted ($C_1$-$C_6$) alkyl, pyridinyl, piperidinyl, furanyl, oxadiazolyl, azetidinyl, cyclopropyl, cyclobutyl, cyclopentyl, substituted pyridinyl, substituted piperidinyl, substituted furanyl, substituted oxadiazolyl, substituted azetidinyl, substituted cyclopropyl, substituted cyclobutyl, substituted cyclopentyl, or aryl; and
$R^8$ is hydrogen or ($C_1$-$C_6$) alkyl, or azetidinyl, piperidinyl, oxadiazolyl, cyclopropyl, cyclobutyl, cyclopentyl, substituted azetidinyl, substituted piperidinyl, substituted oxadiazolyl, substituted cyclopropyl, substituted cyclobutyl, substituted cyclopentyl.

15. A compound according to claim 12, wherein
$R^4$ is chosen from tetrahydrofuranyl, pyranyl, benzopyranyl, hydroxytetralinyl, oxepanyl, hydroxycyclohexyl, and their halogenated congeners;
$R^1$ is chosen from halogen, ($C_2$-$C_6$) alkyl, substituted ($C_1$-$C_6$) alkyl, azetidinyl, phenyl, piperidinyl, piperizinyl, pyrrolidinyl, morpholinyl, azepanyl, diazepanyl, pyridinyl, pyrimidinyl, and pyrazolyl optionally substituted with hydroxy, halogen, carboxamido, alkyl, carboxy, sulfonyl, alkoxy, and cyano; and
X is chosen from halogen, cyano, substituted alkoxy, and hydrogen.
16. A compound according to claim 15 selected from the group consisting of:
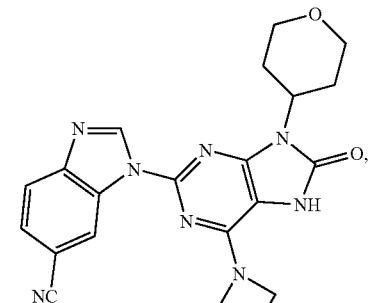
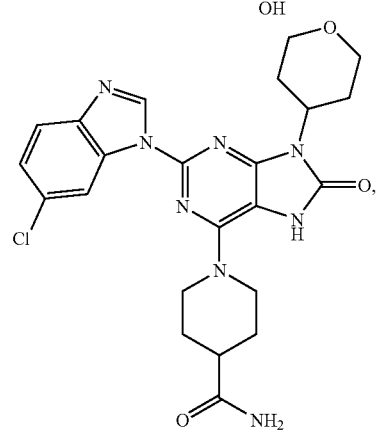
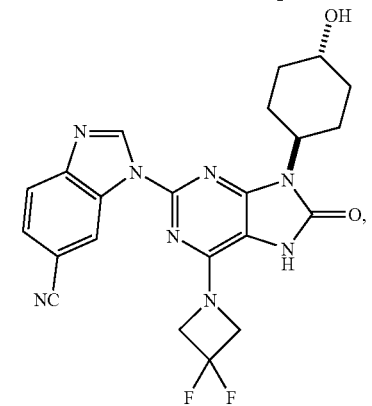
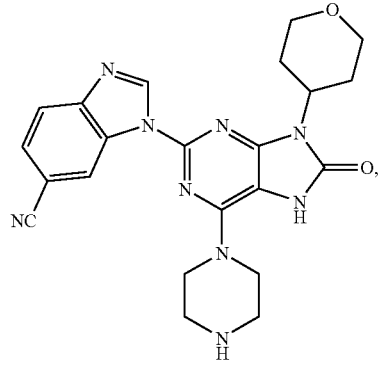
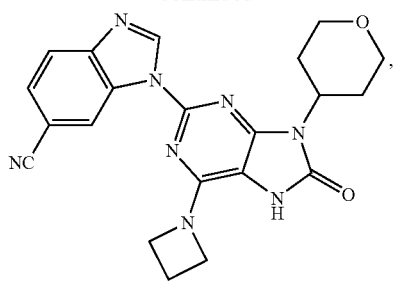
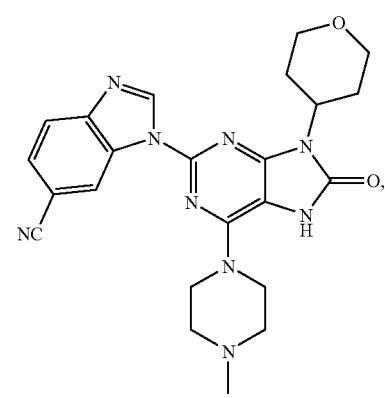
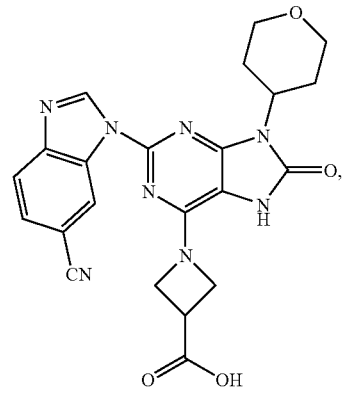
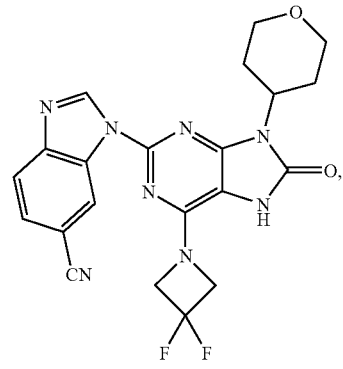

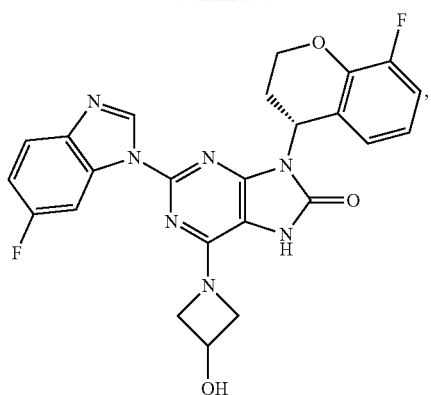
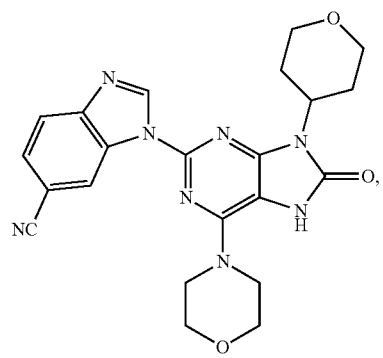
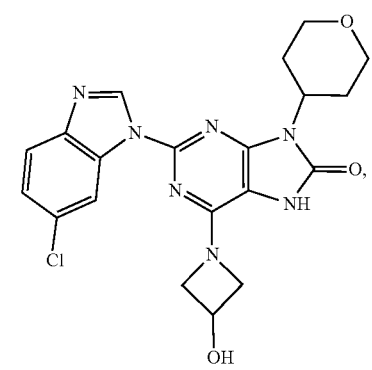
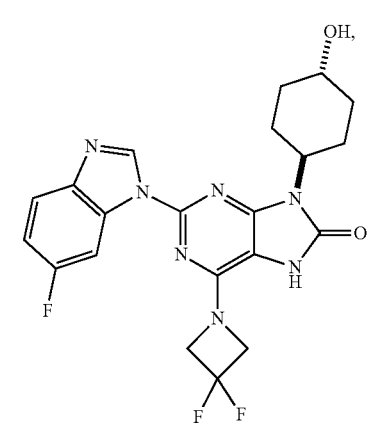
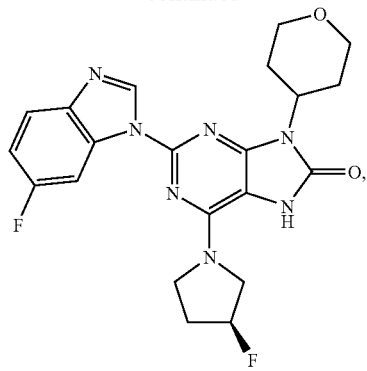
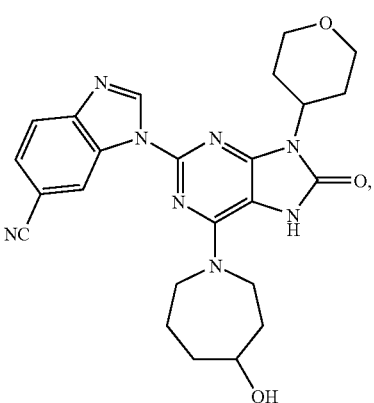
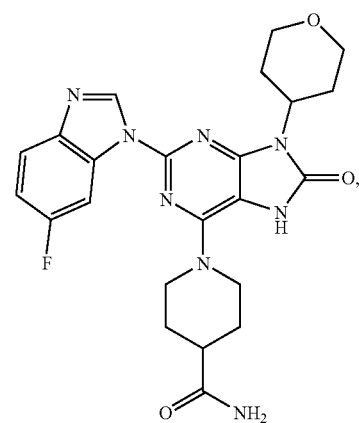
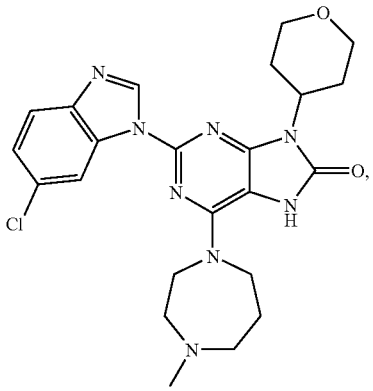

183
-continued
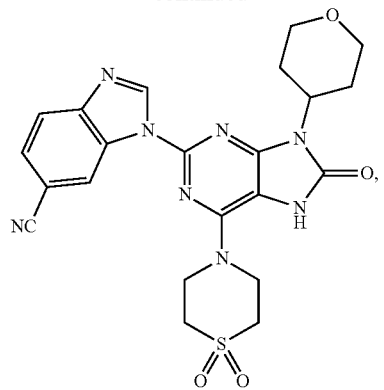
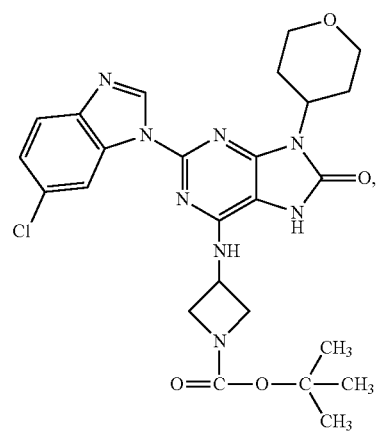
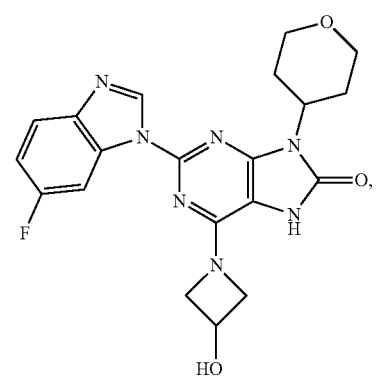
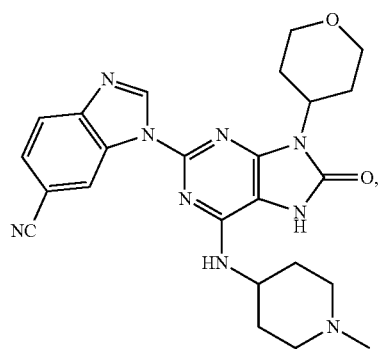
184
-continued
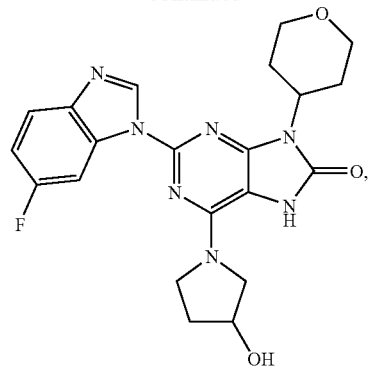
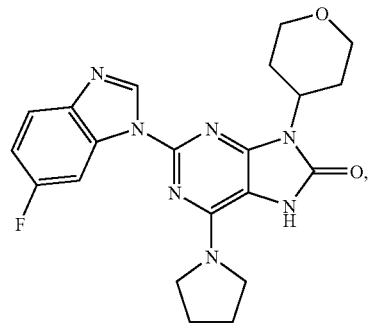
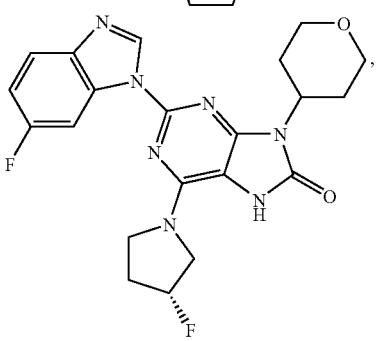
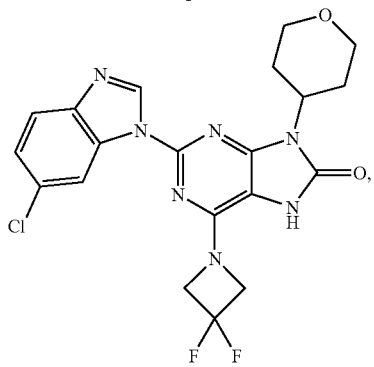
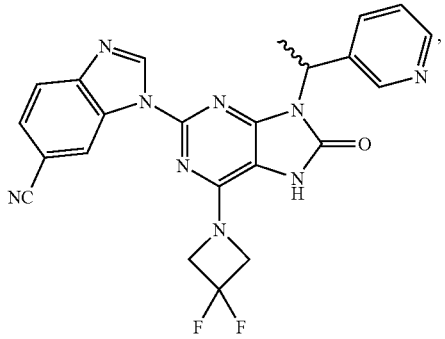

-continued
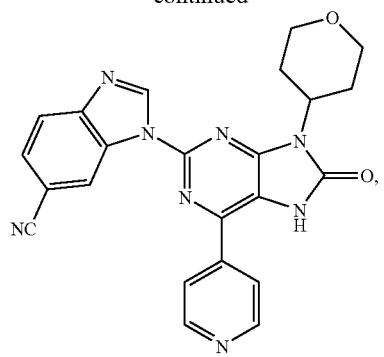
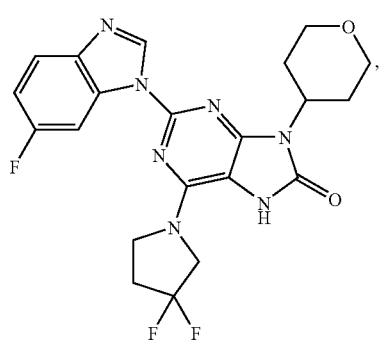
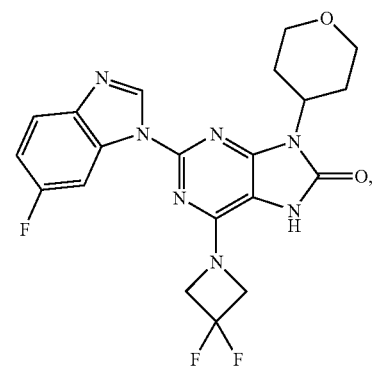
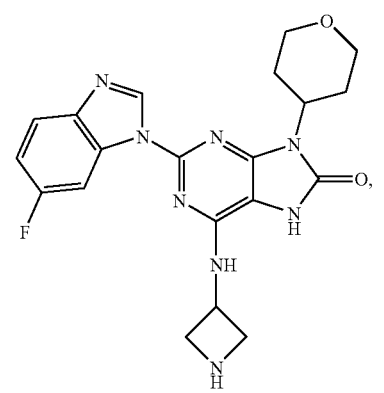
-continued
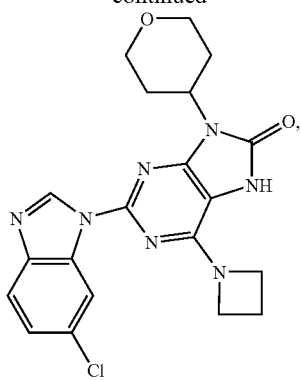
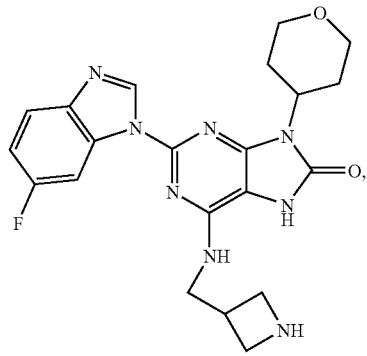
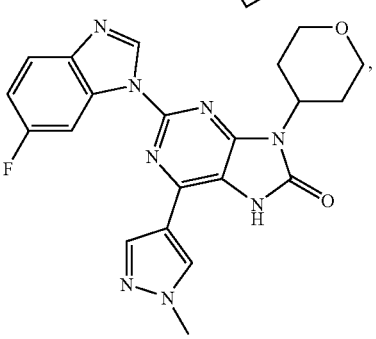
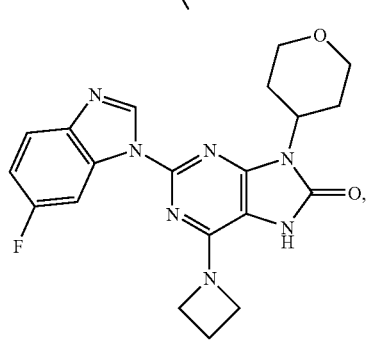
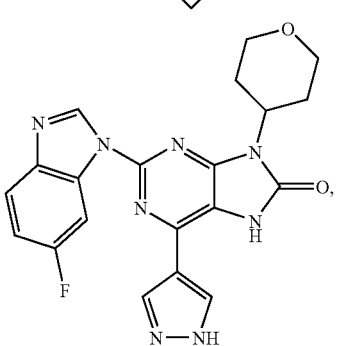

187
-continued
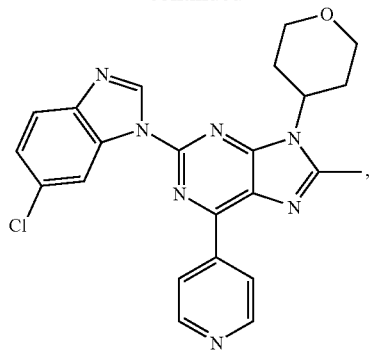
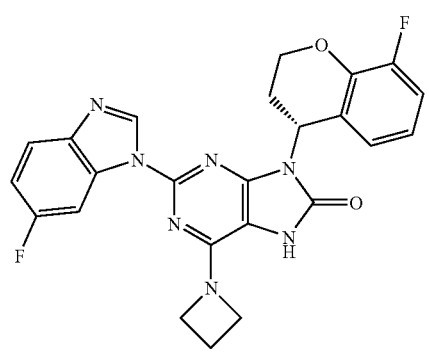
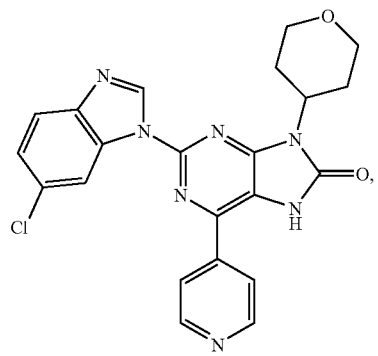
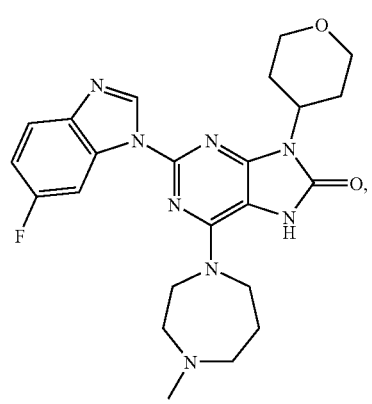
188
-continued
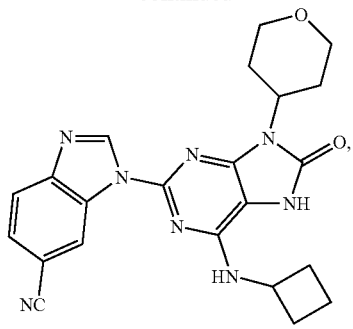
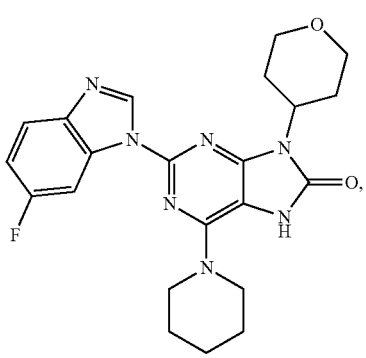
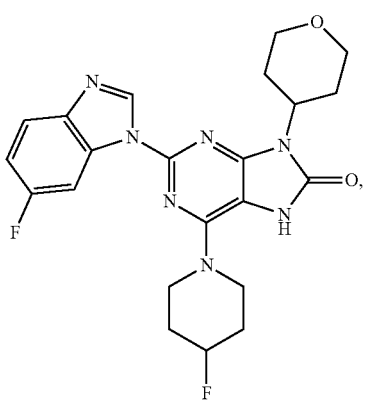
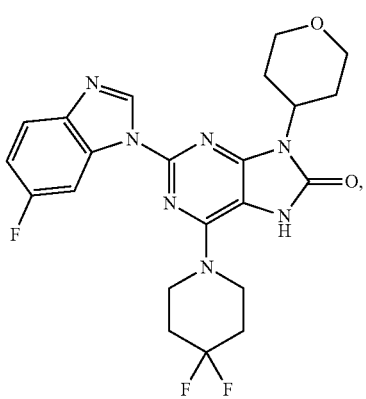

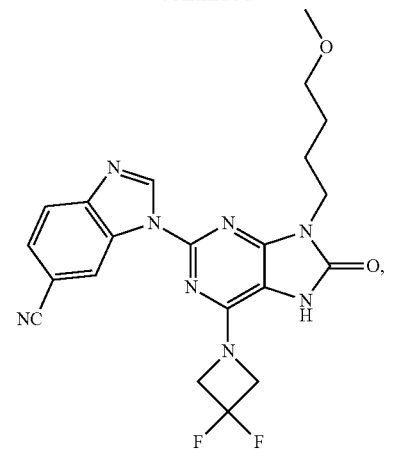
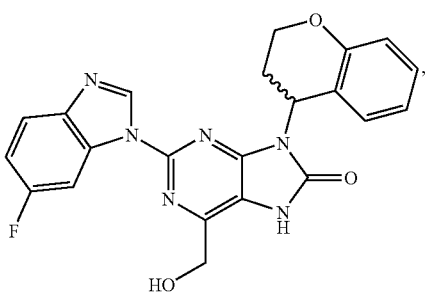
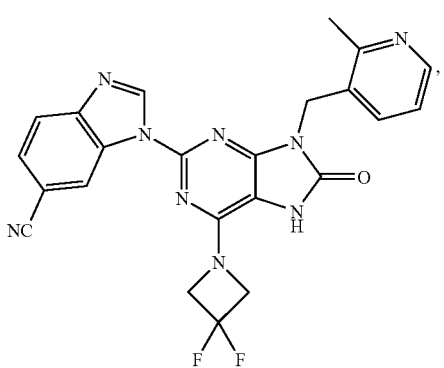
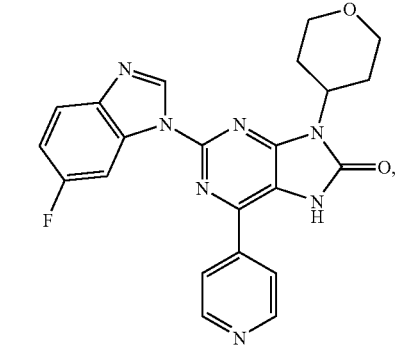
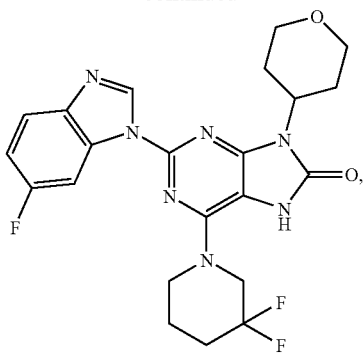
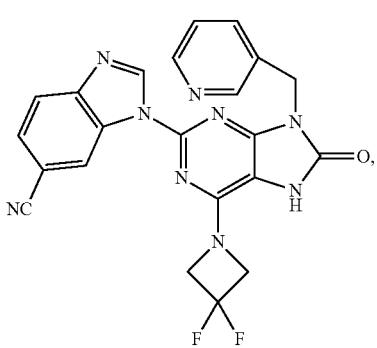
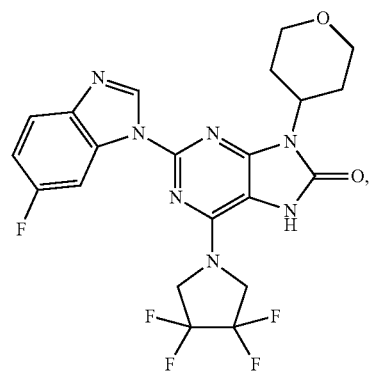
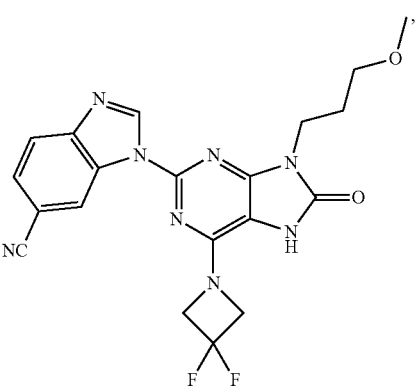

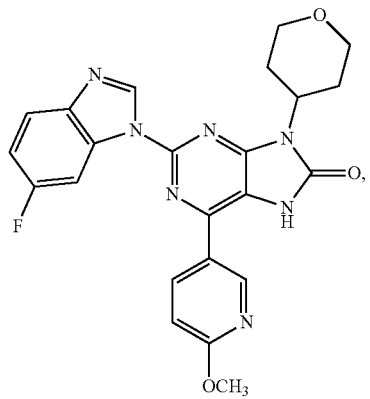
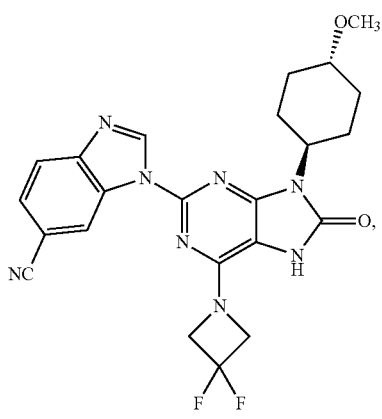
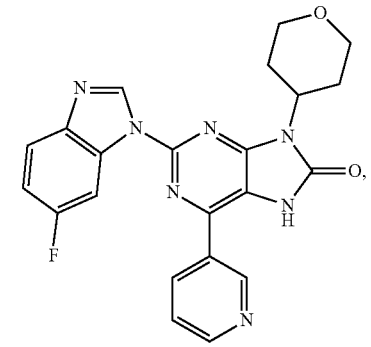
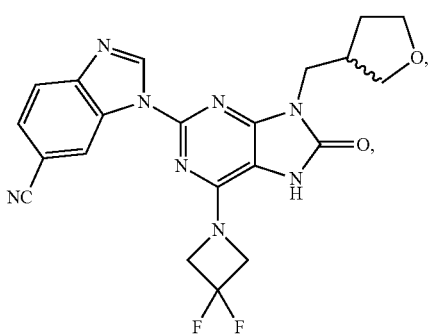
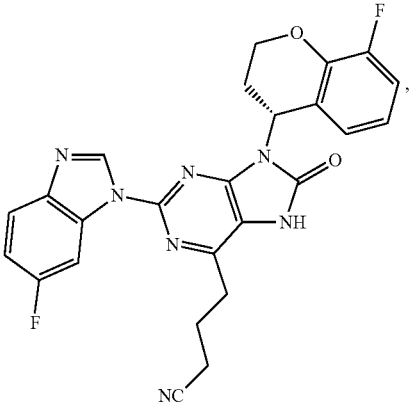
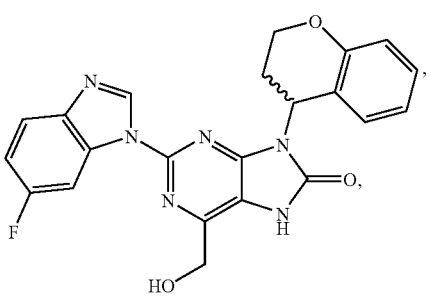
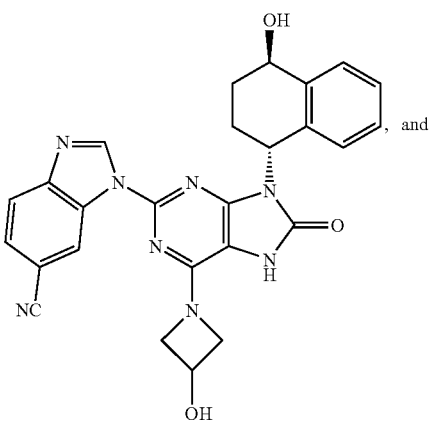
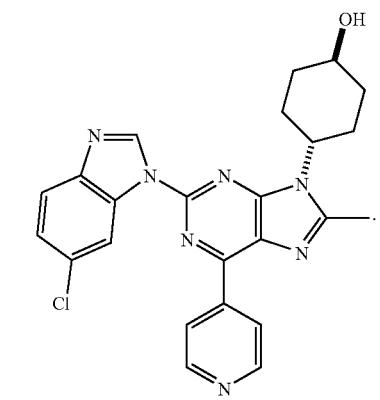

17. A compound according to claim 14 selected from the group consisting of:
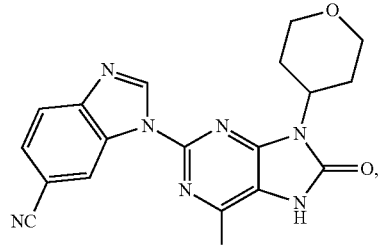
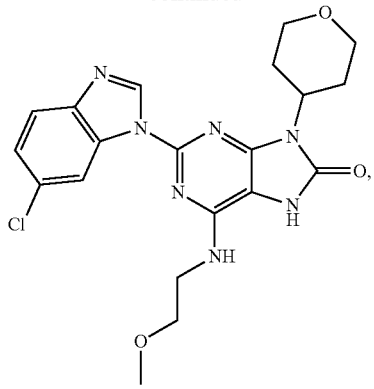
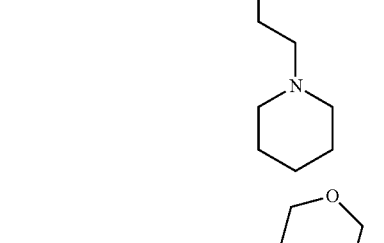
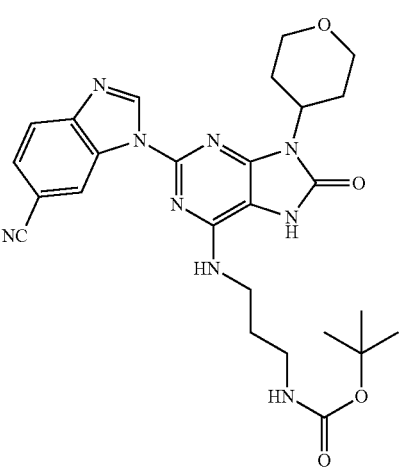
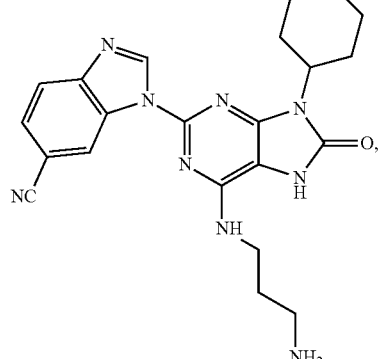
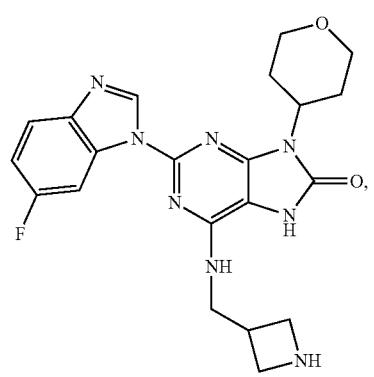
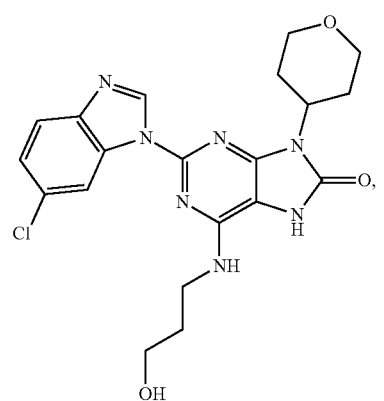
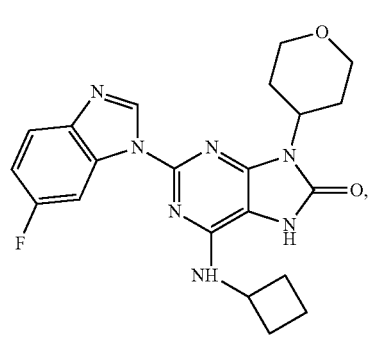
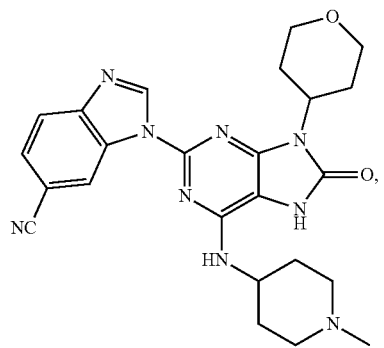

195
-continued
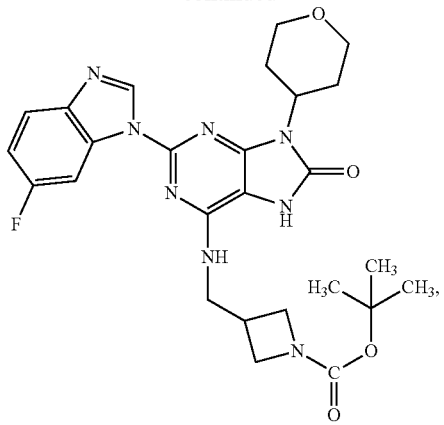
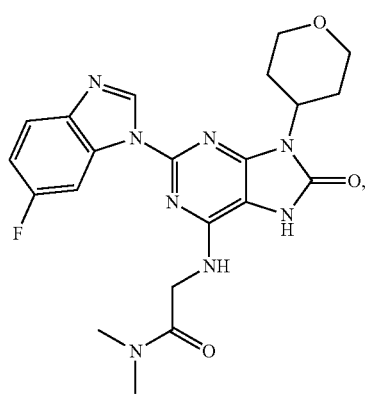
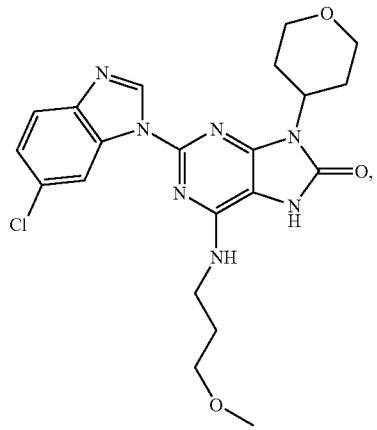
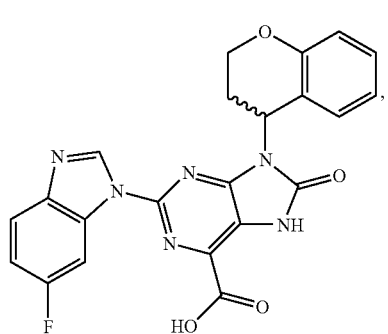
196
-continued
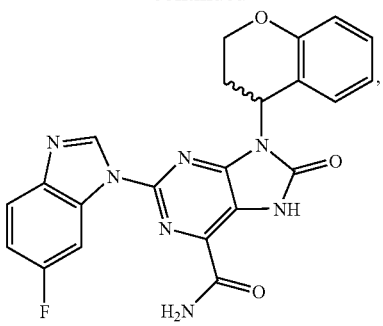
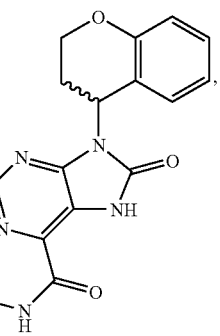
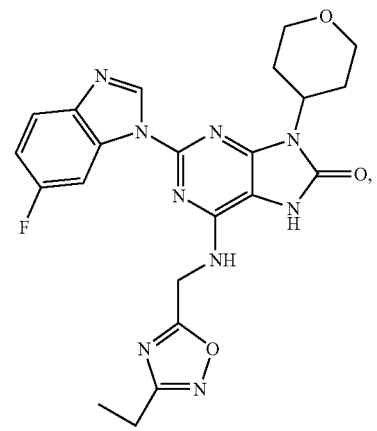
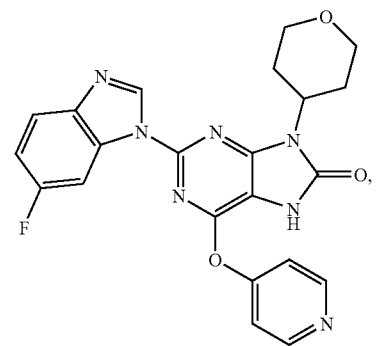

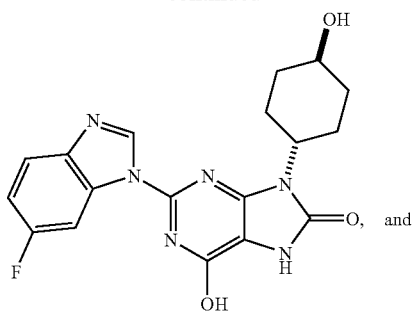

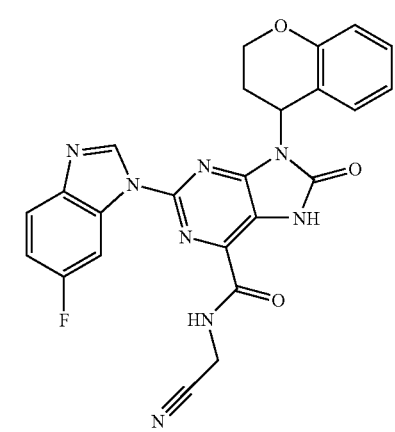

18. A compound according to claim 1, wherein R⁹ is hydrogen, Q is CX, y is zero, and R⁴ is hydroxytetralinyl and hydroxycyclohexyl of formula Id or IId:

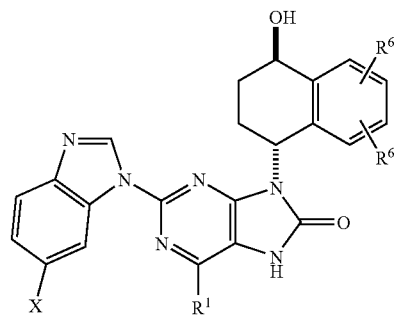

Id

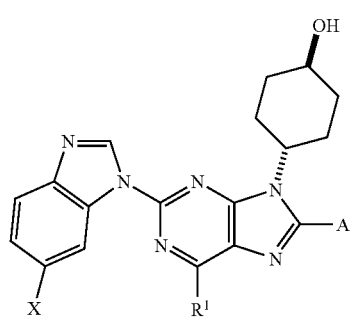

IId wherein R⁶ is H or halogen, and R¹ is chosen from halogen, azetidinyl, piperidinyl, piperizinyl, pyrrolidinyl, phenyl, morpholinyl, azepanyl, diazepanyl, pyridinyl pyrimidinyl, and pyrazolyl optionally substituted with hydroxy, halogen, carboxamido, alkyl, carboxy, sulfonyl, alkoxy, and cyano; and X is halogen, cyano, substituted alkoxy, and hydrogen.

19. A compound according to claim 18 selected from

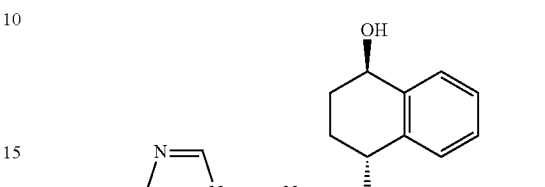

and

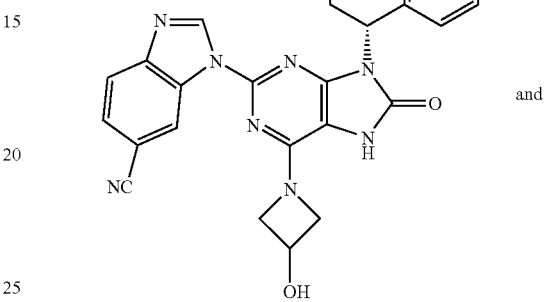

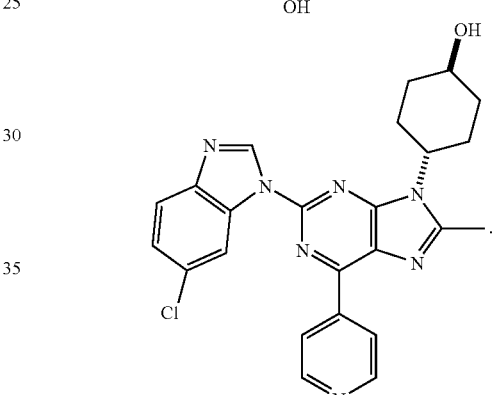

20. A compound according to claim 1, wherein Q is CX, y is zero, and R⁹ is alkyl or substituted alkyl of formula Ie:

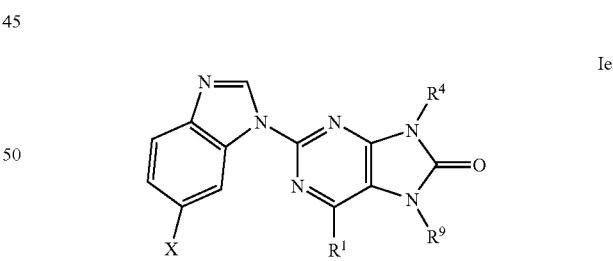

Ie

21. A compound according to claim 20, wherein R⁴ is chosen from tetrahydrofuran, benzopyran, hydroxytetralin, oxepane, hydroxycyclohexane, and their halogenated congeners.

22. A compound according to claim 21, wherein R¹ is chosen from halogen, heteroaryl, heterocyclyl, substituted ($C_1$-$C_6$) alkyl, aryl, substituted aryl, cyano, carboxy, carboalkoxy, carboxamido, and amidino; and X is chosen from halogen, cyano, hydrogen, or alkoxy.

23. A compound according to claim 22 selected from the group consisting of:

199
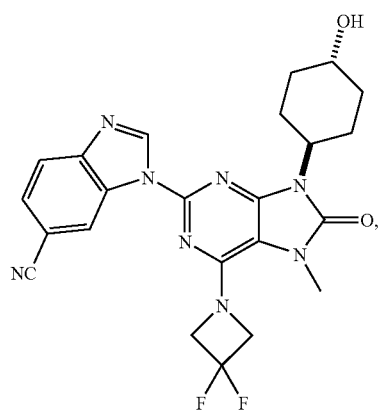
200
-continued
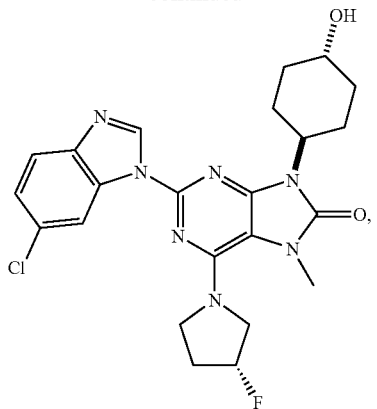
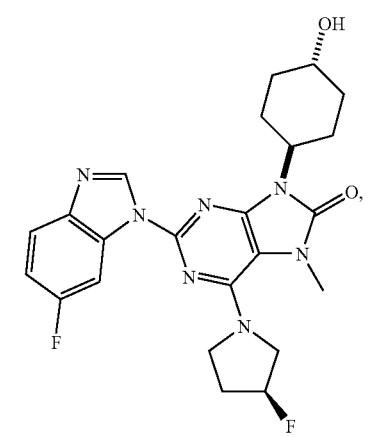
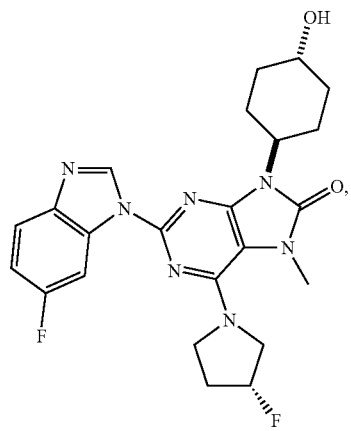
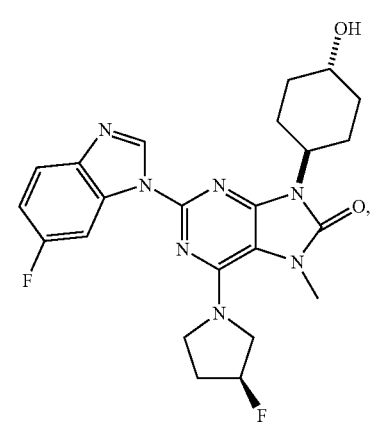
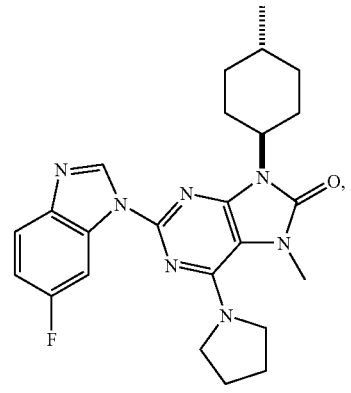
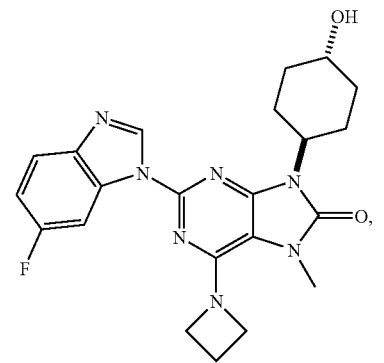
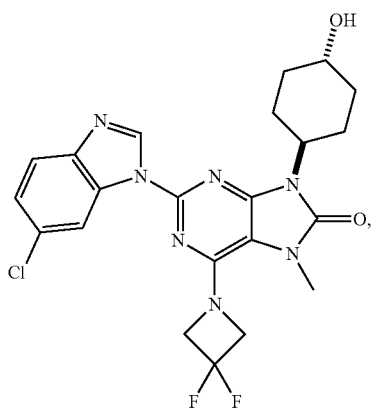

201
-continued
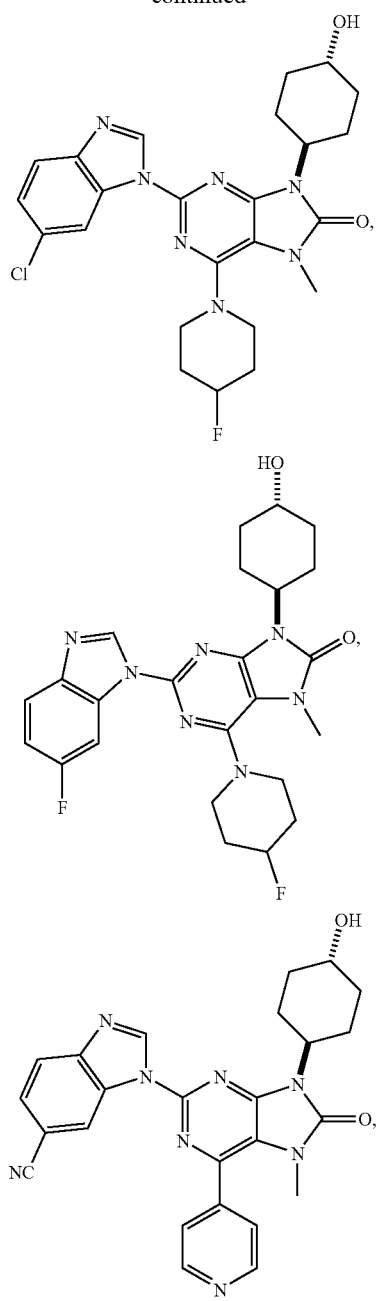
202
-continued
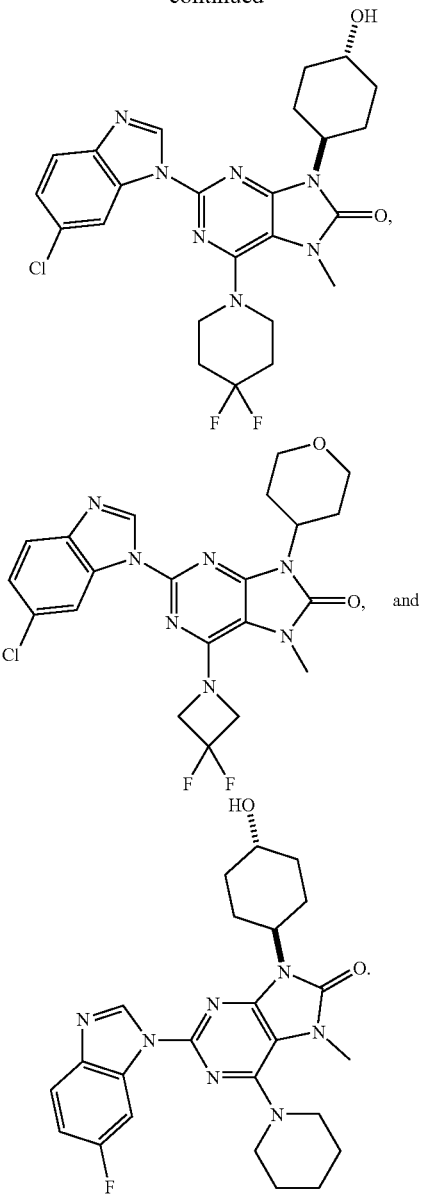
24. A pharmaceutical composition comprising a pharmaceutically acceptable carrier and a therapeutically effective amount of a compound according to claim 1.
* * * * *